US009067893B2

(12) United States Patent
Sun et al.

(10) Patent No.: US 9,067,893 B2
(45) Date of Patent: Jun. 30, 2015

(54) DIHYDROPYRIMIDIN-2(1H)-ONE COMPOUNDS AS S-NITROSOGLUTATHIONE REDUCTASE INHIBITORS

(71) Applicant: N30 Pharmaceuticals, Inc., Boulder, CO (US)

(72) Inventors: Xicheng Sun, Broomfield, CO (US); Jian Qiu, Longmont, CO (US)

(73) Assignee: Nivalis Therapeutics, Inc., Boulder, CO (US)

( * ) Notice: Subject to any disclaimer, the term of this patent is extended or adjusted under 35 U.S.C. 154(b) by 0 days.

(21) Appl. No.: 14/262,915

(22) Filed: Apr. 28, 2014

(65) Prior Publication Data
US 2014/0235640 A1 Aug. 21, 2014

Related U.S. Application Data

(62) Division of application No. 13/496,799, filed as application No. PCT/US2010/050164 on Sep. 24, 2010, now Pat. No. 8,741,915.

(60) Provisional application No. 61/245,859, filed on Sep. 25, 2009.

(51) Int. Cl.
| | |
|---|---|
| *A01N 43/54* | (2006.01) |
| *C07D 239/42* | (2006.01) |
| *C07D 401/04* | (2006.01) |
| *C07D 233/32* | (2006.01) |
| *C07D 239/36* | (2006.01) |
| *C07D 239/40* | (2006.01) |
| *C07D 401/14* | (2006.01) |
| *C07D 403/04* | (2006.01) |
| *C07D 403/10* | (2006.01) |
| *C07D 405/04* | (2006.01) |
| *C07D 409/04* | (2006.01) |
| *C07D 409/14* | (2006.01) |
| *C07D 413/04* | (2006.01) |
| *C07D 413/10* | (2006.01) |
| *C07D 417/04* | (2006.01) |
| *A61K 31/513* | (2006.01) |
| *C07D 233/42* | (2006.01) |
| *A61K 31/505* | (2006.01) |
| *A61K 31/506* | (2006.01) |
| *C07D 239/32* | (2006.01) |
| *C07D 239/34* | (2006.01) |
| *C07D 239/38* | (2006.01) |

(52) U.S. Cl.
CPC ............ *C07D 233/32* (2013.01); *C07D 239/36* (2013.01); *C07D 239/40* (2013.01); *C07D 401/04* (2013.01); *C07D 401/14* (2013.01); *C07D 403/04* (2013.01); *C07D 403/10* (2013.01); *C07D 405/04* (2013.01); *C07D 409/04* (2013.01); *C07D 409/14* (2013.01); *C07D 413/04* (2013.01); *C07D 413/10* (2013.01); *C07D 417/04* (2013.01); *A61K 31/505* (2013.01); *A61K 31/506* (2013.01); *A61K 31/513* (2013.01); *C07D 239/32* (2013.01); *C07D 239/34* (2013.01); *C07D 239/38* (2013.01); *C07D 233/42* (2013.01)

(58) Field of Classification Search
USPC ................. 544/315, 316, 318, 330, 331, 332; 514/256, 259
See application file for complete search history.

(56) References Cited

U.S. PATENT DOCUMENTS

| | | | |
|---|---|---|---|
| 6,268,369 | B1 | 7/2001 | Nagarathnam et al. |
| 7,566,723 | B2 | 7/2009 | Gielen-Haertwig et al. |
| 8,741,915 | B2 | 6/2014 | Sun et al. |
| 8,906,933 | B2 | 12/2014 | Sun et al. |
| 2002/0128205 | A1 | 9/2002 | Stamler et al. |
| 2005/0014697 | A1 | 1/2005 | Stamler et al. |
| 2005/0187166 | A1 | 8/2005 | Stamler et al. |
| 2009/0163545 | A1 | 6/2009 | Goldfarb |
| 2010/0286174 | A1 | 11/2010 | Stamler et al. |
| 2012/0208817 | A1 | 8/2012 | Sun et al. |
| 2013/0096161 | A1 | 4/2013 | Sun et al. |
| 2013/0131093 | A1 | 5/2013 | Sun et al. |

FOREIGN PATENT DOCUMENTS

| | | |
|---|---|---|
| JP | 2007001104 | 1/2007 |
| WO | WO 96/35677 | 11/1996 |
| WO | WO 99/65315 | 12/1999 |
| WO | WO 2004/009560 | 1/2004 |
| WO | WO 2004/101742 | 11/2004 |
| WO | WO 2006/097617 | 9/2006 |
| WO | WO 2006/131676 | 12/2006 |
| WO | WO 2007104034 | 9/2007 |
| WO | WO 2008/103068 | 8/2008 |
| WO | WO 2008/118391 | 10/2008 |
| WO | WO 2009/076665 | 6/2009 |

(Continued)

OTHER PUBLICATIONS

M.W. Foster et al., 9 Trends in Molecular Medicine, 160-168 (2003).*

(Continued)

Primary Examiner — Alexander R Pagano
(74) Attorney, Agent, or Firm — Swanson & Bratschun, L.L.C.

(57) ABSTRACT

The present invention is directed to novel dihydropyrimidin-2(1H)-one compounds useful as S-nitrosoglutathione reductase (GSNOR) inhibitors, pharmaceutical compositions comprising such compounds, and methods of making and using the same.

8 Claims, No Drawings

(56) References Cited

FOREIGN PATENT DOCUMENTS

| WO | WO 2009/150668 | 12/2009 |
|---|---|---|
| WO | WO 2010/019905 | 2/2010 |
| WO | WO 2010/046780 | 4/2010 |
| WO | WO 2010/107476 | 9/2010 |
| WO | WO 2011/038204 | 3/2011 |
| WO | WO 2012/009227 | 1/2012 |
| WO | WO 2012/039718 | 3/2012 |

OTHER PUBLICATIONS

M.W. Foster et al., 15 Trends in Molecular Medicine, 391-404 (2009).*
A.E. Redington, 533 European Journal of Pharmacology, 263-276 (2006).*
Fabio L.M. Ricciardolo et al., 533 European Journal of Pharmacology, 240-252 (2006).*
A.H. Synder et al., 165 American Journal of Respiratory and Critical Care Medicine, 922-926 (2002).*
Bruno et al. (1993) "3,5-diphenyl-1H-pyrazole derivatives. XI. N-aryl-5(3)-phenyl-4-(3,5-diphenyl-1-pyrazolyl)-3(5)-pyrazole amines, 5-substituted 4,5-dihydro-3-phenyl-4-(3,5-diphenyl-1-pyrazolyl)-1H-pyrazoles and 2,6-disubstituted 1,6-dihydro-4-phenyl-5-(3,5-diphenyl-1-pyrazolyl)pyrimidines with antipyretic, antiinflammatory and other activities." Il Farmaco 48(7):949-966.
Chemical Abstracts Service, Columbus, Ohio, US; Aug. 21, 2004, XP002690644, retrieved from STN—Registry No. 729560-89-8 *abstract* Database Registry [Online].
Chemical Abstracts Service, Columbus, Ohio, US; Jan. 4, 2002, XP002690645, retrieved from STN—Registry No. 380467-43-6 *abstract* Database Registry [Online].
Chemical Abstracts Service, Columbus, Ohio, US; Mar. 14, 2001, XP002690646, retrieved from STN—Registry No. 327091-97-4 *abstract* Database Registry [Online].
Chemical Abstracts Service, Columbus, Ohio, US; Mar. 7, 2001, XP002690647—retrieved from STN—Registry No. 326024-49-1 *Registry Nos. 326024-49-1, 326010-63-3 and 326010-60-0 Database Registry [Online].
Chemical Abstracts Service. Columbus, Ohio. US; Mar. 6, 2001. XP002690648, retrieved from STN—Registry No. 325823-34-5 *abstract* Database Registry [Online].
Chemical Abstracts Service. Columbus, Ohio. US; Mar. 5, 2001 XP002690649 retrieved from STN—Registry No. 325763-84-6 *CAS Registry Nos. 325763-84-6. 325751-72-2 and 325749-34-6*.
de Belder et al. (May 1994) "Effects of S-nitroso-glutathione in the human forearm circulation; evidence for selective inhibition of platelet activation", Cardiovasc Res., 28(5):691-694.
de Jesus-Berrios et al. (Nov. 2003) "Enzymes that Counteract Nitrosative Stress Promot Fungal Virulence", Curr. Biol., 13:1963-1968.
Dzvinchuk, I. B. et al. (2002) "2-phenacylbenzothiazole in the Biginelli reaction", Chemistry of Heterocyclic Compounds, 38(8), 1000-1007.
Dzvinchuk, I. B. et al. (2003) "2-Acylmethyl-1H-benzimidazoles in the Biginelli reaction", Chemistry of Heterocyclic Compounds, 39(4), 455-460.
European Search Report issued Feb. 20, 2013 in European Patent Application Serial No. 10819517.3.
Foster et al. (Apr. 2003) "S-nitrosylation in health and disease", Trends in Molecular Medicine, 9(4):160-168.
Gaston et al. (Dec. 1993) "Endogenous nitrogen oxides and bronchodilator S-nitrosolthiols in human airways", Proc. Natl. Acad. Sci. USA, 90:10957-10961.
International Preliminary Report on Patentability issued in PCT/US2010/050164 mailed Apr. 5, 2012.
International Preliminary Report on Patentability issued in PCT/US2010/050186 issued Mar. 26, 2013.
International Search Report and Written Opinion issued in PCT/US2010/050164 mailed Nov. 15, 2010.
International Search Report and Written Opinion issued in PCT/US2010/050186 mailed Nov. 18, 2010.
Jensen et al. (1998) "S-Nitrosoglutathione is a substrate for rat alcohol dehydrognease class III isoenzyme", Biochem J., 331:659-668.
Kaposzta et al. (Dec. 2002) "S-Nitrosoglutathione Reduces Asymptomatic Embolization After Carotid Angioplasty", Circulation, 106(24):3057-3062.
Kefayati et al. (2009) "An efficient synthesis of new 3,4-dihydropyrimidin-2(1H)-ones incorporating a phenyl moiety at C-5 and C-6 catalyzed by TMSCl and Co(OAc)2.4H2O" Phosphorus, Sulfur and Silicon and the Related Elements, 184(7), 1796-1804.
Lipton et al. (Sep. 2001) "S-Nitrosothiols signal the ventilatory response to hypoxia", Nature, 413:171-174.
Liu et al. (Feb. 2004) "Essential Roles of S-Nitrosothiols in Vascular Homeostatsis and Endotoxic Shock", Cell, 116(4):617-628.
Liu et al. (Mar. 2001) "A metabolic enzyme for S-nitrosothiol conserved from bacterial to humans", Nature, 410:490-494.
Que et al. (Jun. 2005) "Protection from Experimental Asthma by an Endogenous Bronchodilator", Science, 308(5728):1618-1621.
Sanghani et al. (2000) "Kinetic Mechanism of Human Glutathioone-Dependent Formaldehyde Dehydrogenase", Biochemistry, 39:10720-10729.
Sanghani et al. (2002) "Human Glutathione-Dependent Formaldehyde Dehydrognease. Structures of Apo, Binary, and Inhibitory Ternary Complexes", Biochemistry,41:10778-10786.
Shen et al. (2010) "Bronsted Base-Catalyzed One-Pot Three-Component Biginelli-Type Reaction: An Efficient Synthesis of 4,5,6-Triaryl-3,4-dihydropyrimidin-2(1H)-one and Mechanistic Study" Journal of Organic Chemistry, 75(4), 1162-1167.
Staab et al. (2008) "Dual functions of alcohol dehydrogenase 3: implications with focus on formaldehyde dehydrogenase and S-nitroglutathione reductase activities", Cell Mol. Life Sci, 65:3950-3960.
Staab et al. (Jun. 15, 2009) "Medium-chain fatty acids and glutathione derivatives as inhibitors of S-nitrosoglutathione reduction mediated by alcohol dehydrogenase 3", Chemico-Biological Interactions 180(1):113-118.
Stamler et al. (Aug. 1992) "Nitric oxide circulates in mammalian plasma primarily as an S-nitrose adduct of serium albumin", Proc. Natl. Acad. Sci. USA, 89:7674-7677.
Uotila and Koivusalo (1989) Coenzymes and Cofactors vol. 3: Glutathione, part A., D. Dolphin, ed. pp. 517-551 (New York, John Wiley & Sons).
Zaman et al. (2001) "S-Nitrosoglutathione Increases Cystic Fibrosis Transmembrane Regulator Maturation", Biochem Biophys Res Commun., 284:65-70.

* cited by examiner

DIHYDROPYRIMIDIN-2(1H)-ONE COMPOUNDS AS S-NITROSOGLUTATHIONE REDUCTASE INHIBITORS

RELATED APPLICATIONS

This application is a divisional application of U.S. application Ser. No. 13/496,799, filed Apr. 27, 2012. U.S. application Ser. No. 13/496,799 is a 35 U.S.C. §371 national phase application of PCT/US2010/050164, filed Sep. 24, 2010 (WO 2011/038204), which claims the benefit of U.S. Provisional Application Ser. No. 61/245,859, filed Sep. 25, 2009. Each of these applications is incorporated herein by reference in its entirety.

FIELD OF THE INVENTION

The present invention is directed to novel dihydropyrimidin-2(1H)-one compounds, pharmaceutical compositions comprising such compounds, and methods of making and using the same. These compounds are useful as inhibitors of S-nitrosoglutathione reductase (GSNOR).

BACKGROUND

The chemical compound nitric oxide is a gas with chemical formula NO. NO is one of the few gaseous signaling molecules known in biological systems, and plays an important role in controlling various biological events. For example, the endothelium uses NO to signal surrounding smooth muscle in the walls of arterioles to relax, resulting in vasodilation and increased blood flow to hypoxic tissues. NO is also involved in regulating smooth muscle proliferation, platelet function, neurotransmission, and plays a role in host defense. Although nitric oxide is highly reactive and has a lifetime of a few seconds, it can both diffuse freely across membranes and bind to many molecular targets. These attributes make NO an ideal signaling molecule capable of controlling biological events between adjacent cells and within cells.

NO is a free radical gas, which makes it reactive and unstable, thus NO is short lived in vivo, having a half life of 3-5 seconds under physiologic conditions. In the presence of oxygen, NO can combine with thiols to generate a biologically important class of stable NO adducts called S-nitrosothiols (SNO's). This stable pool of NO has been postulated to act as a source of bioactive NO and as such appears to be critically important in health and disease, given the centrality of NO in cellular homeostasis (Stamler et al., *Proc. Natl. Acad. Sci. USA,* 89:7674-7677 (1992)). Protein SNO's play broad roles in cardiovascular, respiratory, metabolic, gastrointestinal, immune and central nervous system function (Foster et al., 2003, Trends in Molecular Medicine Volume 9, Issue 4, April 2003, pages 160-168). One of the most studied SNO's in biological systems is S-nitrosoglutathione (GSNO) (Gaston et al., *Proc. Natl. Acad. Sci. USA* 90:10957-10961 (1993)), an emerging key regulator in NO signaling since it is an efficient trans-nitrosating agent and appears to maintain an equilibrium with other S-nitrosated proteins (Liu et al., *Nature,* 410:490-494 (2001)) within cells. Given this pivotal position in the NO—SNO continuum, GSNO provides a therapeutically promising target to consider when NO modulation is pharmacologically warranted.

In light of this understanding of GSNO as a key regulator of NO homeostasis and cellular SNO levels, studies have focused on examining endogenous production of GSNO and SNO proteins, which occurs downstream from the production of the NO radical by the nitric oxide synthetase (NOS) enzymes. More recently there has been an increasing understanding of enzymatic catabolism of GSNO which has an important role in governing available concentrations of GSNO and consequently available NO and SNO's.

Central to this understanding of GSNO catabolism, researchers have recently identified a highly conserved S-nitrosoglutathione reductase (GSNOR) (Jensen et al., *Biochem J.,* 331:659-668 (1998); Liu et al., (2001)). GSNOR is also known as glutathione-dependent formaldehyde dehydrogenase (GS-FDH), alcohol dehydrogenase 3 (ADH-3) (Uotila and Koivusalo, *Coenzymes and Cofactors.,* D. Dolphin, ed. pp. 517-551 (New York, John Wiley & Sons, 1989)), and alcohol dehydrogenase 5 (ADH-5). Importantly GSNOR shows greater activity toward GSNO than other substrates (Jensen et al., 1998; Liu et al., 2001) and appears to mediate important protein and peptide denitrosating activity in bacteria, plants, and animals. GSNOR appears to be the major GSNO-metabolizing enzyme in eukaryotes (Liu et al., 2001). Thus, GSNO can accumulate in biological compartments where GSNOR activity is low or absent (e.g. airway lining fluid) (Gaston et al., 1993).

Yeast deficient in GSNOR accumulate S-nitrosylated proteins which are not substrates of the enzyme, which is strongly suggestive that GSNO exists in equilibrium with SNO-proteins (Liu et al., 2001). Precise enzymatic control over ambient levels of GSNO and thus SNO-proteins raises the possibility that GSNO/GSNOR may play roles across a host of physiological and pathological functions including protection against nitrosative stress wherein NO is produced in excess of physiologic needs. Indeed, GSNO specifically has been implicated in physiologic processes ranging from the drive to breathe (Lipton et al., *Nature,* 413:171-174 (2001)) to regulation of the cystic fibrosis transmembrane regulator (Zaman et al., *Biochem Biophys Res Commun,* 284: 65-70 (2001), to regulation of vascular tone, thrombosis and platelet function (de Belder et al., *Cardiovasc Res.* 1994 May; 28(5):691-4. (1994); Z. Kaposzta, A et al., *Circulation;* 106 (24): 3057-3062, 2002) as well as host defense (de Jesus-Berrios et al., *Curr. Biol.,* 13:1963-1968 (2003)). Other studies have found that GSNOR protects yeast cells against nitrosative stress both in vitro (Liu et al., 2001) and in vivo (de Jesus-Berrios et al., 2003).

Collectively data suggest GSNOR as a primary physiological ligand for the enzyme S-nitrosoglutathione reductase (GSNOR), which catabolizes GSNO and consequently reduces available SNO's and NO in biological systems (Liu et al., 2001), (Liu et al., *Cell,* (2004), 116(4), 617-628), and (Que et al., *Science,* 2005, 308, (5728):1618-1621). As such, this enzyme plays a central role in regulating local and systemic bioactive NO. Since perturbations in NO bioavailability has been linked to the pathogenesis of numerous disease states, including hypertension, atherosclerosis, thrombosis, asthma, gastrointestinal disorders, inflammation and cancer, agents that regulate GSNOR activity are candidate therapeutic agents for treating diseases associated with nitric oxide imbalance.

Currently, there is a great need in the art for diagnostics, prophylaxis, ameliorations, and treatments for medical conditions relating to increased NO synthesis and/or increased NO bioactivity. In addition, there is a significant need for novel compounds, compositions and methods for preventing, ameliorating, or reversing other NO-associated disorders. The present invention satisfies these needs.

SUMMARY

The present invention provides novel dihydropyrimidin-2 (1H)-one compounds. These compounds are useful as S-nitrosoglutathione reductase ("GSNOR") inhibitors. The invention encompasses pharmaceutically acceptable salts, prodrugs, and metabolites of the described compounds. Also encompassed by the invention are pharmaceutical compositions comprising at least one compound of the invention and at least one pharmaceutically acceptable carrier.

The compositions of the present invention can be prepared in any suitable pharmaceutically acceptable dosage form.

The present invention provides a method for inhibiting S-nitrosoglutathione reductase in a subject in need thereof. Such a method comprises administering a therapeutically effective amount of a pharmaceutical composition comprising at least one GSNOR inhibitor or a pharmaceutically acceptable salt thereof, a prodrug or metabolite thereof, in combination with at least one pharmaceutically acceptable carrier. The GSNOR inhibitor can be a novel compound according to the invention, or it can be a known compound which previously was not known to be an inhibitor of GSNOR.

The present invention also provides a method of treating a disorder ameliorated by NO donor therapy in a subject in need thereof. Such a method comprises administering a therapeutically effective amount of a pharmaceutical composition comprising at least one GSNOR inhibitor or a pharmaceutically acceptable salt thereof, a prodrug, or metabolite thereof, in combination with at least one pharmaceutically acceptable carrier. The GSNOR inhibitor can be a novel compound according to the invention, or it can be a known compound which previously was not known to be an inhibitor of GSNOR.

The present invention also provides a method of treating a cell proliferative disorder in a subject in need thereof. Such a method comprises administering a therapeutically effective amount of a pharmaceutical composition comprising at least one GSNOR inhibitor or a pharmaceutically acceptable salt thereof, a prodrug, or metabolite thereof, in combination with at least one pharmaceutically acceptable carrier. The GSNOR inhibitor can be a novel compound according to the invention, or it can be a known compound which previously was not known to be an inhibitor of GSNOR.

The methods of the invention encompass administration with one or more secondary active agents. Such administration can be sequential or in a combination composition.

Although methods and materials similar or equivalent to those described herein can be used in the practice or testing of the present invention, suitable methods and materials are described below. All publicly available publications, patent applications, patents, and other references mentioned herein are incorporated by reference in their entirety. In the case of conflict, the present specification, including definitions, will control.

Both the foregoing summary and the following detailed description are exemplary and explanatory and are intended to provide further details of the compositions and methods as claimed. Other objects, advantages, and novel features will be readily apparent to those skilled in the art from the following detailed description.

DETAILED DESCRIPTION

A. Overview of the Invention

Until recently, S-nitrosoglutathione reductase (GSNOR) was known to oxidize the formaldehyde glutathione adduct, S-hydroxymethylglutathione. GSNOR has since been identified in a variety of bacteria, yeasts, plants and animals and is well conserved. The proteins from *E. coli, S. cerevisiae* and mouse macrophages share over 60% amino acid sequence identity. GSNOR activity (i.e., decomposition of S-nitrosoglutathione when NADH is present as a required cofactor) has been detected in *E. coli*, in mouse macrophages, in mouse endothelial cells, in mouse smooth muscle cells, in yeasts, and in human HeLa, epithelial and monocyte cells. Human GSNOR nucleotide and amino acid sequence information can be obtained from the National Center for Biotechnology Information (NCBI) databases under Accession Nos. M29872, NM_000671. Mouse GSNOR nucleotide and amino acid sequence information can be obtained from NCBI databases under Accession Nos. NM_007410. In the nucleotide sequence, the start site and stop site are underlined. CDS designates coding sequence. SNP designates single nucleotide polymorphism. Other related GSNOR nucleotide and amino acid sequences, including those of other species, can be found in U.S. Patent Application 2005/0014697.

In accord with the present invention, GSNOR has been shown to function in vivo and in vitro to metabolize S-nitrosoglutathione (GSNO) and protein S-nitrosothiols (SNOs) to modulate NO bioactivity, by controlling the intracellular levels of low mass NO donor compounds and preventing protein nitrosylation from reaching toxic levels.

Based on this, it follows that inhibition of this enzyme potentiates bioactivity in all diseases in which NO donor therapy is indicated, inhibits the proliferation of pathologically proliferating cells, and increases NO bioactivity in diseases where this is beneficial.

The present invention provides pharmaceutical agents that are potent inhibitors of GSNOR. In particular, provided are substituted dihydropyrimidin-2(1H)-one analogs having the structures depicted below (Formula I), or a pharmaceutically acceptable salt, stereoisomer, or prodrug thereof.

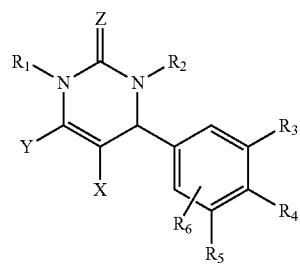

I wherein
X is selected from the group consisting of aryl, substituted aryl, heteroaryl, substituted heteroaryl, cycloalkyl, substituted cycloalkyl, heterocyclyl, and substituted heterocyclyl, each having 6 members or less in the ring;
Y is selected from the group consisting of aryl, substituted aryl, heteroaryl, substituted heteroaryl, $C_4$-$C_6$ cycloalkyl, substituted $C_4$-$C_6$ cycloalkyl, heterocyclyl, and substituted heterocyclyl;
Z is selected from the group consisting of O, S and $NR_7$;
$R_1$, $R_2$ and $R_7$ are independently selected from the group consisting of hydrogen, and $C_1$-$C_6$ alkyl;
$R_3$ is selected from the group consisting of hydrogen, nitro, cyano, carboxy, carbamoyl, methylsulfonamido, fluoro, chloro, bromo, hydroxy, methylsulfonyl, and methylsulfinyl, isoxazol-4-yl, $C_1$-$C_6$ alkoxy, —C(NH)NHOH, sulfonic acid, and acetyl;
$R_4$ is selected from the group consisting of hydroxy, carboxy, and tetrazol-5-yl;

or optionally $R_3$ and $R_4$, taken together can form a heterocycle;

$R_5$ is selected from the group consisting of hydrogen, hydroxy, carboxy, chloro, fluoro, cyano, —O(CH$_2$)$_{1-6}$NMe$_2$, C$_1$-C$_6$ alkyl, —O(CH$_2$)$_{1-6}$OCH$_3$, —O(CH$_2$)$_{1-6}$OH, acetyl, CF$_3$, and C$_1$-C$_6$ alkoxy;

or optionally $R_4$ and $R_5$, taken together can form a heterocycle; and $R_6$ is selected from the group consisting of hydrogen and hydroxy.

As used in this context, the term "analog" refers to a compound having similar chemical structure and function as compounds of Formula I that retains the dihydropyrimidin-2(1H)-one ring.

Some dihydropyrimidin-2(1H)-one analogs of the invention can also exist in various isomeric forms, including configurational, geometric and conformational isomers, as well as existing in various tautomeric forms, particularly those that differ in the point of attachment of a hydrogen atom. As used herein, the term "isomer" is intended to encompass all isomeric forms of a compound including tautomeric forms of the compound.

Illustrative compounds having asymmetric centers can exist in different enantiomeric and diastereomeric forms. A compound can exist in the form of an optical isomer or a diastereomer. Accordingly, the invention encompasses compounds in the forms of their optical isomers, diastereomers and mixtures thereof, including racemic mixtures.

It should be noted that if there is a discrepancy between a depicted structure and a name given to that structure, the depicted structure controls. In addition, if the stereochemistry of a structure or a portion of a structure is not indicated with, for example, bold, wedged, or dashed lines, the structure or portion of the structure is to be interpreted as encompassing all stereoisomers of the described compound.

B. S-Nitrosoglutathione Reductase Inhibitors

1. Inventive Compounds

In one of its aspects the present invention provides a compound having a structure shown in Formula I, or a pharmaceutically acceptable salt, stereoisomer, or prodrug thereof:

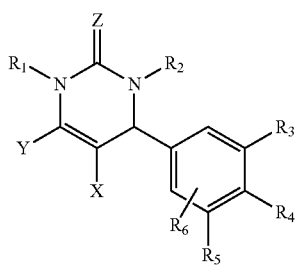

I wherein

X is selected from the group consisting of aryl, substituted aryl, heteroaryl, substituted heteroaryl, cycloalkyl, substituted cycloalkyl, heterocyclyl, and substituted heterocyclyl, each having 6 members or less in the ring;

Y is selected from the group consisting of aryl, substituted aryl, heteroaryl, substituted heteroaryl, C$_4$-C$_6$ cycloalkyl, substituted C$_4$-C$_6$ cycloalkyl, heterocyclyl, and substituted heterocyclyl;

Z is selected from the group consisting of O, S and NR$_7$;

$R_1$, $R_2$ and $R_7$ are independently selected from the group consisting of hydrogen, and C$_1$-C$_6$ alkyl;

$R_3$ is selected from the group consisting of hydrogen, nitro, cyano, carboxy, carbamoyl, methylsulfonamido, fluoro, chloro, bromo, hydroxy, methylsulfonyl, and methylsulfinyl, isoxazol-4-yl, C$_1$-C$_6$ alkoxy, —C(NH)NHOH, sulfonic acid, and acetyl;

$R_4$ is selected from the group consisting of hydroxy, carboxy, and tetrazol-5-yl;

or optionally $R_3$ and $R_4$, taken together can form a heterocycle;

$R_5$ is selected from the group consisting of hydrogen, hydroxy, carboxy, chloro, fluoro, cyano, —O(CH$_2$)$_{1-6}$NMe$_2$, C$_1$-C$_6$ alkyl, —O(CH$_2$)$_{1-6}$OCH$_3$, —O(CH$_2$)$_{1-6}$OH, acetyl, CF$_3$, and C$_1$-C$_6$ alkoxy;

or optionally $R_4$ and $R_5$, taken together can form a heterocycle; and $R_6$ is selected from the group consisting of hydrogen and hydroxy.

In a further aspect of the invention, $R_1$, $R_2$ and $R_7$ are independently selected from the group consisting of hydrogen and methyl; $R_3$ is selected from the group consisting of hydrogen, nitro, cyano, carboxy, carbamoyl, methylsulfonamido, fluoro, chloro, bromo, hydroxy, methylsulfonyl, and methylsulfinyl, isoxazol-4-yl, C$_1$-C$_6$ alkoxy, —C(NH)NHOH, sulfonic acid, and acetyl; $R_4$ is selected from the group consisting of hydroxy, carboxy, and tetrazol-5-yl; $R_5$ is selected from the group consisting of hydrogen, hydroxy, carboxy, chloro, fluoro, cyano, —O(CH$_2$)$_2$NMe$_2$, C$_1$-C$_6$ alkyl, —O(CH$_2$)$_2$OCH$_3$, —O(CH$_2$)$_2$OH, acetyl, CF$_3$, methoxy, ethoxy, isopropoxy, and n-propoxy; and $R_6$ is hydrogen.

In a further aspect of the invention, $R_1$, $R_2$ and $R_7$ are independently selected from the group consisting of hydrogen and methyl; $R_3$ is selected from the group consisting of nitro, cyano, carboxy, carbamoyl, methylsulfonamido, fluoro, chloro, bromo, hydroxy, methylsulfonyl, and methylsulfinyl, isoxazol-4-yl, C$_1$-C$_6$ alkoxy, —C(NH)NHOH, sulfonic acid, and acetyl; $R_4$ is selected from the group consisting of hydroxy, carboxy, and tetrazol-5-yl; $R_5$ is selected from the group consisting of hydrogen, hydroxy, carboxy, chloro, fluoro, cyano, —O(CH$_2$)$_2$NMe$_2$, C$_1$-C$_6$ alkyl, —O(CH$_2$)$_2$OCH$_3$, —O(CH$_2$)$_2$OH, acetyl, CF$_3$, methoxy, ethoxy, isopropoxy, and n-propoxy; and $R_6$ is hydrogen.

In a further aspect of the invention, suitable identities for X include, but are not limited to phenyl, substituted phenyl, thiophen-yl, substituted thiophen-yl, thiazol-yl, substituted thiazol-yl, pyrazin-yl, substituted pyrazin-yl, pyridin-yl, and substituted pyridin-yl, cyclohexyl, and substituted cyclohexyl.

In a further aspect of the invention, suitable identities for X include, but are not limited to, phenyl, thiophen-2-yl, thiophen-3-yl, thiazol-2-yl, 2-fluorophenyl, p-tolyl, m-tolyl, biphenyl-4-yl, 4-methoxyphenyl, 3-chlorophenyl, 3,4-dichlorophenyl, 3-methoxyphenyl, 3,4-dimethoxyphenyl, 4-bromophenyl, o-tolyl, 4-chlorophenyl, 2-chlorophenyl, 3-cyanophenyl, 3,4-difluorophenyl, 4-cyanophenyl, 3-carbamoylphenyl, pyrazin-2-yl, biphenyl-3-yl, 2-cyanophenyl, pyridin-4-yl, and pyridin-3-yl, 4-(dimethylamino)phenyl, 3-fluorophenyl, 3-ethylphenyl, and cyclohexyl.

In a further aspect of the invention, suitable identities for Y include, but are not limited to phenyl, substituted phenyl, thiophen-yl, substituted thiophen-yl, thiazol-yl, substituted thiazol-yl, pyrazin-yl, substituted pyrazin-yl, pyridin-yl, substituted pyridin-yl, furan-yl, substituted furan-yl, benzo[d][1,3]dioxol-yl, substituted benzo[d][1,3]dioxol-yl, imidazol-yl, substituted imidazol-yl, naphthalen-yl, substituted naphthalen-yl, pyrrol-yl, substituted pyrrol-yl, pyrazol-yl, substituted pyrazol-yl, tetrahydrofuran-yl, substituted tetrahydrofuran-yl, cyclopentyl, substituted cyclopentyl, cyclohexyl, and substituted cyclohexyl.

In a further aspect of the invention, suitable identities for Y include, but are not limited to, phenyl, 3-methoxyphenyl, p-tolyl, 4-methoxyphenyl, 3,5-dichlorophenyl, 3-fluorophenyl, 4-bromophenyl, biphenyl-4-yl, 4-fluorophenyl, 4-chlorophenyl, 3-chlorophenyl, 3,4-dimethoxyphenyl, 3-fluoro-4-methoxyphenyl, 4-chloro-3-fluorophenyl, 3-chloro-4-fluorophenyl, 3,4-difluorophenyl, 3,5-difluorophenyl, 3,4-dichlorophenyl, 4-hydroxyphenyl, 2,4-difluorophenyl, furan-3-yl, 2-chlorophenyl, 3-cyanophenyl, 4-(dimethylamino)phenyl, 2-fluorophenyl, 4-morpholinophenyl, 4-aminophenyl, naphthal-2-yl, benzo[d][1,3]dioxol-5-yl, 4-cyanophenyl, naphthal-3-yl, naphthal-4-yl, 4-acetamidophenyl, thiophen-2-yl, thiophen-3-yl, 1-methyl-1H-imidazol-4-yl, naphthalene-1-yl, methyl phenylcarbamate, and naphthalene-2-yl, 4-(methanesulfonamido)phenyl, 1H-pyrrol-3-yl, 1-(phenylsulfonyl)-1H-pyrrol-3-yl, furan-2-yl, 4-(trifluoromethyl)phenyl, o-tolyl, 1-methyl-1H-pyrazol-4-yl, 1-methyl-1H-pyrazol-3-yl, 3-chloro-5-fluorophenyl, 3-hydroxyphenyl, pyrazin-2-yl, quinolin-6-yl, isoquinolin-6-yl, 1-methyl-1H-pyrazol-5-yl, tetrahydrofuran-2-yl, cyclopentyl, tetrahydrofuran-3-yl, and cyclohexyl.

In a further aspect of the invention, suitable compounds of formula I include, but are not limited to:
4-(3-ethoxy-4-hydroxy-5-nitrophenyl)-5,6-diphenyl-3,4-dihydropyrimidin-2(1H)-one;
(S)-4-(3-ethoxy-4-hydroxy-5-nitrophenyl)-5,6-diphenyl-3,4-dihydropyrimidin-2(1H)-one;
4-(3-ethoxy-4-hydroxy-5-nitrophenyl)-6-phenyl-5-(thiophen-2-yl)-3,4-dihydropyrimidin-2(1H)-one;
4-(3-ethoxy-4-hydroxy-5-nitrophenyl)-6-phenyl-5-(thiophen-3-yl)-3,4-dihydropyrimidin-2(1H)-one;
(S)-4-(3-ethoxy-4-hydroxy-5-nitrophenyl)-6-phenyl-5-(thiophen-3-yl)-3,4-dihydropyrimidin-2(1H)-one;
4-(3-ethoxy-4-hydroxy-5-nitrophenyl)-5,6-diphenyl-3,4-dihydropyrimidine-2(1H)-thione;
4-(4-hydroxy-3-methoxy-5-nitrophenyl)-5,6-diphenyl-3,4-dihydropyrimidin-2(1H)-one;
4-(3,4-dihydroxy-5-nitrophenyl)-5,6-diphenyl-3,4-dihydropyrimidin-2(1H)-one;
4-(3-ethoxy-4-hydroxy-5-nitrophenyl)-1-methyl-5,6-diphenyl-3,4-dihydropyrimidin-2(1H)-one;
4-(3-ethoxy-4-hydroxy-5-nitrophenyl)-6-phenyl-5-(thiazol-2-yl)-3,4-dihydropyrimidin-2(1H)-one;
4-(3-ethoxy-4-hydroxy-5-nitrophenyl)-5-(2-fluorophenyl)-6-phenyl-3,4-dihydropyrimidin-2(1H)-one;
4-(3-ethoxy-4-hydroxy-5-nitrophenyl)-6-phenyl-5-p-tolyl-3,4-dihydropyrimidin-2(1H)-one;
4-(3-ethoxy-4-hydroxy-5-nitrophenyl)-6-(3-methoxyphenyl)-5-phenyl-3,4-dihydropyrimidin-2(1H)-one;
4-(3-ethoxy-4-hydroxy-5-nitrophenyl)-5-phenyl-6-p-tolyl-3,4-dihydropyrimidin-2(1H)-one;
4-(3-ethoxy-4-hydroxy-5-nitrophenyl)-6-phenyl-5-m-tolyl-3,4-dihydropyrimidin-2(1H)-one;
5-(biphenyl-4-yl)-4-(3-ethoxy-4-hydroxy-5-nitrophenyl)-6-phenyl-3,4-dihydropyrimidin-2(1H)-one;
4-(3-ethoxy-4-hydroxy-5-nitrophenyl)-5-(4-methoxyphenyl)-6-phenyl-3,4-dihydropyrimidin-2(1H)-one;
4-(3-ethoxy-4-hydroxy-5-nitrophenyl)-6-(4-methoxyphenyl)-5-phenyl-3,4-dihydropyrimidin-2(1H)-one;
5-(3-chlorophenyl)-4-(3-ethoxy-4-hydroxy-5-nitrophenyl)-6-phenyl-3,4-dihydropyrimidin-2(1H)-one;
5-(3,4-dichlorophenyl)-4-(3-ethoxy-4-hydroxy-5-nitrophenyl)-6-phenyl-3,4-dihydropyrimidin-2(1H)-one;
4-(3-ethoxy-4-hydroxy-5-nitrophenyl)-5-(3-methoxyphenyl)-6-phenyl-3,4-dihydropyrimidin-2(1H)-one;
5-(3,4-dimethoxyphenyl)-4-(3-ethoxy-4-hydroxy-5-nitrophenyl)-6-phenyl-3,4-dihydropyrimidin-2(1H)-one;
5-(4-bromophenyl)-4-(3-ethoxy-4-hydroxy-5-nitrophenyl)-6-phenyl-3,4-dihydropyrimidin-2(1H)-one;
4-(3-ethoxy-4-hydroxy-5-nitrophenyl)-6-phenyl-5-o-tolyl-3,4-dihydropyrimidin-2(1H)-one;
5-(4-chlorophenyl)-4-(3-ethoxy-4-hydroxy-5-nitrophenyl)-6-phenyl-3,4-dihydropyrimidin-2(1H)-one;
5-(2-chlorophenyl)-4-(3-ethoxy-4-hydroxy-5-nitrophenyl)-6-phenyl-3,4-dihydropyrimidin-2(1H)-one;
3-(4-(3-ethoxy-4-hydroxy-5-nitrophenyl)-2-oxo-6-phenyl-1,2,3,4-tetrahydropyrimidin-5-yl)benzonitrile;
5-(3,4-difluorophenyl)-4-(3-ethoxy-4-hydroxy-5-nitrophenyl)-6-phenyl-3,4-dihydropyrimidin-2(1H)-one;
6-(3,5-dichlorophenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-(3-fluorophenyl)-5-phenyl-3,4-dihydropyrimidin-2(1H)-one;
6-(4-bromophenyl)-4-(3-ethoxy-4-hydroxy-5-nitrophenyl)-5-phenyl-3,4-dihydropyrimidin-2(1H)-one;
6-(biphenyl-4-yl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-(4-fluorophenyl)-5-phenyl-3,4-dihydropyrimidin-2(1H)-one;
6-(4-chlorophenyl)-4-(3-ethoxy-4-hydroxy-5-nitrophenyl)-5-phenyl-3,4-dihydropyrimidin-2(1H)-one;
6-(3-chlorophenyl)-4-(3-ethoxy-4-hydroxy-5-nitrophenyl)-5-phenyl-3,4-dihydropyrimidin-2(1H)-one;
6-(3,4-dimethoxyphenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-(3-fluoro-4-methoxyphenyl)-5-phenyl-3,4-dihydropyrimidin-2(1H)-one;
4-(3-ethoxy-4-hydroxy-5-nitrophenyl)-1,3-dimethyl-5,6-diphenyl-3,4-dihydropyrimidin-2(1H)-one;
4-(4-(3-ethoxy-4-hydroxy-5-nitrophenyl)-2-oxo-6-phenyl-1,2,3,4-tetrahydropyrimidin-5-yl)benzonitrile;
6-(4-chloro-3-fluorophenyl)-4-(3-ethoxy-4-hydroxy-5-nitrophenyl)-5-phenyl-3,4-dihydropyrimidin-2(1H)-one;
6-(3-chloro-4-fluorophenyl)-4-(3-ethoxy-4-hydroxy-5-nitrophenyl)-5-phenyl-3,4-dihydropyrimidin-2(1H)-one;
6-(3,4-difluorophenyl)-4-(3-ethoxy-4-hydroxy-5-nitrophenyl)-5-phenyl-3,4-dihydropyrimidin-2(1H)-one;
6-(3,5-difluorophenyl)-4-(3-ethoxy-4-hydroxy-5-nitrophenyl)-5-phenyl-3,4-dihydropyrimidin-2(1H)-one;
6-(3,4-dichlorophenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-(4-hydroxyphenyl)-5-phenyl-3,4-dihydropyrimidin-2(1H)-one;
6-(2,4-difluorophenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-(furan-3-yl)-5-phenyl-3,4-dihydropyrimidin-2(1H)-one;
6-(2-chlorophenyl)-4-(3-ethoxy-4-hydroxy-5-nitrophenyl)-5-phenyl-3,4-dihydropyrimidin-2(1H)-one;
3-(4-(3-ethoxy-4-hydroxy-5-nitrophenyl)-2-oxo-6-phenyl-1,2,3,4-tetrahydropyrimidin-5-yl)benzamide;
3-(6-(3-ethoxy-4-hydroxy-5-nitrophenyl)-2-oxo-5-phenyl-1,2,3,6-tetrahydropyrimidin-4-yl)benzonitrile;
6-(4-(dimethylamino)phenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-(2-fluorophenyl)-5-phenyl-3,4-dihydropyrimidin-2(1H)-one;
4-(3-ethoxy-4-hydroxy-5-nitrophenyl)-6-(4-morpholinophenyl)-5-phenyl-3,4-dihydropyrimidin-2(1H)-one;

6-(4-aminophenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-phenyl-5-(pyrazin-2-yl)-3,4-dihydropyrimidin-2(1H)-one;
4-(3-ethoxy-4-hydroxy-5-nitrophenyl)-5-phenyl-6-(pyridin-2-yl)-3,4-dihydropyrimidin-2(1H)-one;
5-(biphenyl-3-yl)-4-(3-ethoxy-4-hydroxy-5-nitrophenyl)-6-phenyl-3,4-dihydropyrimidin-2(1H)-one;
6-(benzo[d][1,3]dioxol-5-yl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-3-methyl-5,6-diphenyl-3,4-dihydropyrimidin-2(1H)-one;
4-(6-(3-ethoxy-4-hydroxy-5-nitrophenyl)-2-oxo-5-phenyl-1,2,3,6-tetrahydropyrimidin-4-yl)benzonitrile;
4-(3-ethoxy-5-fluoro-4-hydroxyphenyl)-5,6-diphenyl-3,4-dihydropyrimidin-2(1H)-one;
4-(3-ethoxy-4-hydroxy-5-nitrophenyl)-5-phenyl-6-(pyridin-3-yl)-3,4-dihydropyrimidin-2(1H)-one;
(R)-4-(3-ethoxy-4-hydroxy-5-nitrophenyl)-5-phenyl-6-(pyridin-3-yl)-3,4-dihydropyrimidin-2(1H)-one;
(S)-4-(3-ethoxy-4-hydroxy-5-nitrophenyl)-5-phenyl-6-(pyridin-3-yl)-3,4-dihydropyrimidin-2(1H)-one;
4-(3-fluoro-4-hydroxy-5-methoxyphenyl)-5,6-diphenyl-3,4-dihydropyrimidin-2(1H)-one;
3-ethoxy-2-hydroxy-5-(2-oxo-5,6-diphenyl-1,2,3,4-tetrahydropyrimidin-4-yl)benzonitrile;
2-(4-(3-ethoxy-4-hydroxy-5-nitrophenyl)-2-oxo-6-phenyl-1,2,3,4-tetrahydropyrimidin-5-yl)benzonitrile;
4-(3-ethoxy-4-hydroxy-5-nitrophenyl)-5-phenyl-6-(pyridin-4-yl)-3,4-dihydropyrimidin-2(1H)-one;
7-ethoxy-5-(2-oxo-5,6-diphenyl-1,2,3,4-tetrahydropyrimidin-4-yl)benzo[d]oxazol-2(3H)-one;
N-(4-(6-(3-ethoxy-4-hydroxy-5-nitrophenyl)-2-oxo-5-phenyl-1,2,3,6-tetrahydropyrimidin-4-yl)phenyl)acetamide;
4-(3-ethoxy-4-hydroxy-5-nitrophenyl)-6-phenyl-5-(pyridin-4-yl)-3,4-dihydropyrimidin-2(1H)-one;
N-(3-ethoxy-2-hydroxy-5-(2-oxo-5,6-diphenyl-1,2,3,4-tetrahydropyrimidin-4-yl)phenyl)methanesulfonamide;
N-(2-hydroxy-3-methoxy-5-(2-oxo-5,6-diphenyl-1,2,3,4-tetrahydropyrimidin-4-yl)phenyl)methanesulfonamide;
3-ethoxy-2-hydroxy-5-(2-oxo-5,6-diphenyl-1,2,3,4-tetrahydropyrimidin-4-yl)benzoic acid;
4-(3-ethoxy-4-hydroxy-5-nitrophenyl)-5-phenyl-6-(thiophen-2-yl)-3,4-dihydropyrimidin-2(1H)-one;
4-(3-ethoxy-4-hydroxy-5-nitrophenyl)-5-phenyl-6-(thiophen-3-yl)-3,4-dihydropyrimidin-2(1H)-one;
4-(3-ethoxy-4-hydroxy-5-nitrophenyl)-6-(1-methyl-1H-imidazol-4-yl)-5-phenyl-3,4-dihydropyrimidin-2(1H)-one;
4-(3-ethoxy-4-hydroxy-5-nitrophenyl)-6-(naphthalen-1-yl)-5-phenyl-3,4-dihydropyrimidin-2(1H)-one;
3-ethoxy-2-hydroxy-5-(2-oxo-5,6-diphenyl-1,2,3,4-tetrahydropyrimidin-4-yl)benzamide;
methyl 4-(6-(3-ethoxy-4-hydroxy-5-nitrophenyl)-2-oxo-5-phenyl-1,2,3,6-tetrahydropyrimidin-4-yl)phenylcarbamate;
4-(3-ethoxy-4-hydroxy-5-nitrophenyl)-6-phenyl-5-(pyridin-3-yl)-3,4-dihydropyrimidin-2(1H)-one;
4-(3-ethoxy-4-hydroxy-5-nitrophenyl)-6-(naphthalen-2-yl)-5-phenyl-3,4-dihydropyrimidin-2(1H)-one;
2-hydroxy-5-(2-oxo-5,6-diphenyl-1,2,3,4-tetrahydropyrimidin-4-yl)benzoic acid;
4-(4-hydroxy-3-methoxyphenyl)-5,6-diphenyl-3,4-dihydropyrimidin-2(1H)-one;
5-(4-(dimethylamino)phenyl)-4-(3-ethoxy-4-hydroxy-5-nitrophenyl)-6-phenyl-3,4-dihydropyrimidin-2(1H)-one;
4-(8-nitro-2,3-dihydrobenzo[b][1,4]dioxin-6-yl)-5,6-diphenyl-3,4-dihydropyrimidin-2(1H)-one;
4-(2-oxo-5,6-diphenyl-1,2,3,4-tetrahydropyrimidin-4-yl)benzoic acid;
1,1'-(2-hydroxy-5-(2-oxo-5,6-diphenyl-1,2,3,4-tetrahydropyrimidin-4-yl)-1,3-phenylene)diethanone;
4-(4-hydroxy-3-nitrophenyl)-5,6-diphenyl-3,4-dihydropyrimidin-2(1H)-one;
2-hydroxy-5-(2-oxo-5,6-diphenyl-1,2,3,4-tetrahydropyrimidin-4-yl)benzonitrile;
2-ethoxy-4-(2-oxo-5,6-diphenyl-1,2,3,4-tetrahydropyrimidin-4-yl)benzoic acid;
4-(3-bromo-5-ethoxy-4-hydroxyphenyl)-5,6-diphenyl-3,4-dihydropyrimidin-2(1H)-one;
N-(4-(6-(3-ethoxy-4-hydroxy-5-nitrophenyl)-2-oxo-5-phenyl-1,2,3,6-tetrahydropyrimidin-4-yl)phenyl)methanesulfonamide;
4-(4-hydroxy-3-isopropoxy-5-nitrophenyl)-5,6-diphenyl-3,4-dihydropyrimidin-2(1H)-one;
4-(3-ethoxy-4-hydroxy-5-(methylsulfonyl)phenyl)-5,6-diphenyl-3,4-dihydropyrimidin-2(1H)-one;
4-(3-ethoxy-4-hydroxy-5-(methylsulfinyl)phenyl)-5,6-diphenyl-3,4-dihydropyrimidin-2(1H)-one;
3-ethoxy-2-hydroxy-5-(2-oxo-6-phenyl-5-(thiophen-3-yl)-1,2,3,4-tetrahydropyrimidin-4-yl)benzonitrile;
4-(3-ethoxy-4-hydroxy-5-nitrophenyl)-5-phenyl-6-(1H-pyrrol-3-yl)-3,4-dihydropyrimidin-2(1H)-one;
4-(3-ethoxy-4-hydroxy-5-nitrophenyl)-5-phenyl-6-(1-(phenylsulfonyl)-1H-pyrrol-3-yl)-3,4-dihydropyrimidin-2(1H)-one;
4-(3-ethoxy-4-hydroxy-5-nitrophenyl)-6-(4-fluorophenyl)-5-(3-methoxyphenyl)-3,4-dihydropyrimidin-2(1H)-one;
4-(3-ethoxy-4-hydroxy-5-nitrophenyl)-6-(4-fluorophenyl)-5-(thiophen-3-yl)-3,4-dihydropyrimidin-2(1H)-one;
2-hydroxy-3-nitro-5-(2-oxo-5,6-diphenyl-1,2,3,4-tetrahydropyrimidin-4-yl)benzoic acid;
4-(3-ethoxy-4-hydroxy-5-nitrophenyl)-6-(furan-2-yl)-5-phenyl-3,4-dihydropyrimidin-2(1H)-one;
2-ethoxy-4-(2-imino-5,6-diphenyl-1,2,3,4-tetrahydropyrimidin-4-yl)-6-nitrophenol;
4-(3-ethoxy-4-hydroxy-5-nitrophenyl)-5-phenyl-6-(4-(trifluoromethyl)phenyl)-3,4-dihydropyrimidin-2(1H)-one;
4-(3-ethoxy-4-hydroxy-5-nitrophenyl)-5-phenyl-6-o-tolyl-3,4-dihydropyrimidin-2(1H)-one;
4-(3-ethoxy-4-hydroxy-5-nitrophenyl)-5-(3-fluorophenyl)-6-phenyl-3,4-dihydropyrimidin-2(1H)-one;
4-(3-ethoxy-4-hydroxy-5-nitrophenyl)-6-(pyridin-3-yl)-5-(thiophen-3-yl)-3,4-dihydropyrimidin-2(1H)-one;
(Z)-2-ethoxy-4-(2-(methylimino)-5,6-diphenyl-1,2,3,4-tetrahydropyrimidin-4-yl)-6-nitrophenol;
4-(3-ethoxy-4-hydroxy-5-nitrophenyl)-6-(1-methyl-1H-pyrazol-4-yl)-5-(thiophen-3-yl)-3,4-dihydropyrimidin-2(1H)-one;
4-(3-ethoxy-4-hydroxy-5-nitrophenyl)-6-(1-methyl-1H-pyrazol-3-yl)-5-(thiophen-3-yl)-3,4-dihydropyrimidin-2(1H)-one;
4-(3-chloro-4-hydroxy-5-nitrophenyl)-5,6-diphenyl-3,4-dihydropyrimidin-2(1H)-one;
6-(3-chloro-5-fluorophenyl)-4-(3-ethoxy-4-hydroxy-5-nitrophenyl)-5-phenyl-3,4-dihydropyrimidin-2(1H)-one;
2-hydroxy-3-nitro-5-(2-oxo-5,6-diphenyl-1,2,3,4-tetrahydropyrimidin-4-yl)benzonitrile;
2-hydroxy-5-(2-oxo-5,6-diphenyl-1,2,3,4-tetrahydropyrimidin-4-yl)benzenesulfonic acid;
(S)-3-ethoxy-2-hydroxy-5-(2-oxo-6-(pyridin-3-yl)-5-(thiophen-3-yl)-1,2,3,4-tetrahydropyrimidin-4-yl)benzoic acid;
3-ethoxy-2-hydroxy-5-(2-oxo-6-(pyridin-3-yl)-5-(thiophen-3-yl)-1,2,3,4-tetrahydropyrimidin-4-yl)benzoic acid;

4-(3-fluoro-4-hydroxy-5-nitrophenyl)-5,6-diphenyl-3,4-dihydropyrimidin-2(1H)-one;
3-ethoxy-2-hydroxy-5-(2-oxo-6-(pyridin-3-yl)-5-(thiophen-3-yl)-1,2,3,4-tetrahydropyrimidin-4-yl)benzonitrile;
4-(3-ethoxy-4-hydroxy-5-nitrophenyl)-6-(3-hydroxyphenyl)-5-phenyl-3,4-dihydropyrimidin-2(1H)-one;
4-(4-hydroxy-3-nitro-5-propoxyphenyl)-5,6-diphenyl-3,4-dihydropyrimidin-2(1H)-one;
4-(3-ethoxy-4-hydroxy-5-nitrophenyl)-6-(pyrazin-2-yl)-5-(thiophen-3-yl)-3,4-dihydropyrimidin-2(1H)-one;
4-(3-ethoxy-4-hydroxy-5-nitrophenyl)-5-phenyl-6-(quinolin-6-yl)-3,4-dihydropyrimidin-2(1H)-one;
4-(3-ethoxy-4-hydroxy-5-nitrophenyl)-6-(isoquinolin-6-yl)-5-phenyl-3,4-dihydropyrimidin-2(1H)-one;
4-(3-ethoxy-4-hydroxy-5-nitrophenyl)-5-(3-methoxyphenyl)-6-(pyridin-3-yl)-3,4-dihydropyrimidin-2(1H)-one;
3-ethoxy-2-hydroxy-5-(5-(3-methoxyphenyl)-2-oxo-6-(pyridin-3-yl)-1,2,3,4-tetrahydropyrimidin-4-yl)benzoic acid;
4-(3-ethoxy-4-hydroxy-5-nitrophenyl)-6-(pyridin-4-yl)-5-(thiophen-3-yl)-3,4-dihydropyrimidin-2(1H)-one;
4-(4-hydroxy-3-(2-hydroxyethoxy)-5-nitrophenyl)-5,6-diphenyl-3,4-dihydropyrimidin-2(1H)-one;
2-hydroxy-4-(2-oxo-5,6-diphenyl-1,2,3,4-tetrahydropyrimidin-4-yl)benzoic acid;
4-(3-ethoxy-4-hydroxy-5-nitrophenyl)-6-(1-methyl-1H-pyrazol-5-yl)-5-(thiophen-3-yl)-3,4-dihydropyrimidin-2(1H)-one;
2-nitro-4-(2-oxo-5,6-diphenyl-1,2,3,4-tetrahydropyrimidin-4-yl)benzoic acid;
4-(3-ethoxy-4-hydroxy-5-nitrophenyl)-5-(3-ethylphenyl)-6-phenyl-3,4-dihydropyrimidin-2(1H)-one;
3-ethoxy-2-hydroxy-5-(6-(1-methyl-1H-pyrazol-4-yl)-2-oxo-5-(thiophen-3-yl)-1,2,3,4-tetrahydropyrimidin-4-yl)benzoic acid;
(S)-4-(3-ethoxy-4-hydroxy-5-nitrophenyl)-6-(pyridin-3-yl)-5-(thiophen-3-yl)-3,4-dihydropyrimidin-2(1H)-one;
2-chloro-4-(2-oxo-5,6-diphenyl-1,2,3,4-tetrahydropyrimidin-4-yl)benzoic acid;
(S)-3-ethoxy-2-hydroxy-5-(6-(1-methyl-1H-pyrazol-4-yl)-2-oxo-5-(thiophen-3-yl)-1,2,3,4-tetrahydropyrimidin-4-yl)benzoic acid;
(S)-4-(3-ethoxy-4-hydroxy-5-nitrophenyl)-6-(1-methyl-1H-pyrazol-3-yl)-5-(thiophen-3-yl)-3,4-dihydropyrimidin-2(1H)-one;
4-ethoxy-6-(2-oxo-5,6-diphenyl-1,2,3,4-tetrahydropyrimidin-4-yl)benzo[d]oxazol-2(3H)-one;
3-fluoro-2-hydroxy-5-(2-oxo-5,6-diphenyl-1,2,3,4-tetrahydropyrimidin-4-yl)benzoic acid;
2-fluoro-4-(2-oxo-5,6-diphenyl-1,2,3,4-tetrahydropyrimidin-4-yl)benzoic acid;
2-ethoxy-6-nitro-4-(2-oxo-5,6-diphenyl-1,2,3,4-tetrahydropyrimidin-4-yl)benzoic acid;
4-(4-hydroxy-3-nitro-5-(trifluoromethyl)phenyl)-5,6-diphenyl-3,4-dihydropyrimidin-2(1H)-one;
4-(4-hydroxy-3-(2-methoxyethoxy)-5-nitrophenyl)-5,6-diphenyl-3,4-dihydropyrimidin-2(1H)-one;
4-(4-hydroxy-3-nitro-5-propylphenyl)-5,6-diphenyl-3,4-dihydropyrimidin-2(1H)-one;
4-(2-oxo-5,6-diphenyl-1,2,3,4-tetrahydropyrimidin-4-yl)-2-(trifluoromethyl)benzoic acid;
2-fluoro-6-hydroxy-4-(2-oxo-5,6-diphenyl-1,2,3,4-tetrahydropyrimidin-4-yl)benzoic acid;
2-hydroxy-4-(6-(1-methyl-1H-pyrazol-4-yl)-2-oxo-5-(thiophen-3-yl)-1,2,3,4-tetrahydropyrimidin-4-yl)benzoic acid;
2-hydroxy-4-(2-oxo-5-phenyl-6-(pyridin-3-yl)-1,2,3,4-tetrahydropyrimidin-4-yl)benzoic acid;
2-ethoxy-6-hydroxy-4-(2-oxo-5,6-diphenyl-1,2,3,4-tetrahydropyrimidin-4-yl)benzoic acid;
4-(4-(2H-tetrazol-5-yl)phenyl)-5-phenyl-6-(pyridin-3-yl)-3,4-dihydropyrimidin-2(1H)-one;
2-chloro-6-hydroxy-4-(2-oxo-5,6-diphenyl-1,2,3,4-tetrahydropyrimidin-4-yl)benzoic acid;
4-(4-(2H-tetrazol-5-yl)phenyl)-5,6-diphenyl-3,4-dihydropyrimidin-2(1H)-one;
2-hydroxy-6-methoxy-4-(2-oxo-5,6-diphenyl-1,2,3,4-tetrahydropyrimidin-4-yl)benzoic acid;
4-(4-(2H-tetrazol-5-yl)phenyl)-6-(pyridin-3-yl)-5-(thiophen-3-yl)-3,4-dihydropyrimidin-2(1H)-one;
2-hydroxy-4-(6-(1-methyl-1H-pyrazol-4-yl)-2-oxo-5-phenyl-1,2,3,4-tetrahydropyrimidin-4-yl)benzoic acid;
(S)-2-hydroxy-4-(6-(1-methyl-1H-pyrazol-4-yl)-2-oxo-5-(thiophen-3-yl)-1,2,3,4-tetrahydropyrimidin-4-yl)benzoic acid;
4-(3-(2-(dimethylamino)ethoxy)-4-hydroxy-5-nitrophenyl)-5,6-diphenyl-3,4-dihydropyrimidin-2(1H)-one;
4-(3-ethoxy-4-hydroxy-5-nitrophenyl)-5-phenyl-6-(tetrahydrofuran-2-yl)-3,4-dihydropyrimidin-2(1H)-one;
6-cyclopentyl-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-5-phenyl-6-(tetrahydrofuran-3-yl)-3,4-dihydropyrimidin-2(1H)-one;
6-cyclohexyl-4-(3-ethoxy-4-hydroxy-5-nitrophenyl)-5-(thiophen-3-yl)-3,4-dihydropyrimidin-2(1H)-one;
4-(3-ethoxy-4-hydroxy-5-nitrophenyl)-5-phenyl-6-((S)-tetrahydrofuran-2-yl)-3,4-dihydropyrimidin-2(1H)-one;
4-(3-ethoxy-4-hydroxy-5-nitrophenyl)-5-phenyl-6-((R)-tetrahydrofuran-2-yl)-3,4-dihydropyrimidin-2(1H)-one; and
5-cyclohexyl-4-(3-ethoxy-4-hydroxy-5-nitrophenyl)-6-phenyl-3,4-dihydropyrimidin-2(1H)-one.

Also provided are compounds having a structure shown in Formula II, or a pharmaceutically acceptable salt, stereoisomer, or prodrug thereof:

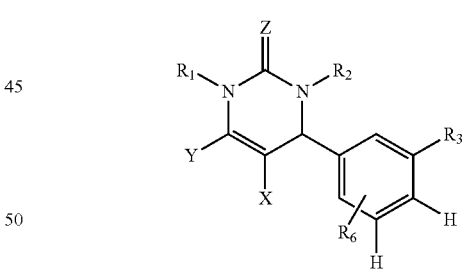

II wherein
X is selected from the group consisting of aryl, substituted aryl, heteroaryl, substituted heteroaryl, cycloalkyl, substituted cycloalkyl, heterocyclyl, and substituted heterocyclyl, each having 6 members or less in the ring;
Y is selected from the group consisting of aryl, substituted aryl, heteroaryl, substituted heteroaryl, $C_4$-$C_6$ cycloalkyl, substituted $C_4$-$C_6$ cycloalkyl, heterocyclyl, and substituted heterocyclyl;
Z is selected from the group consisting of O, S and $NR_7$;
$R_1$, $R_2$ and $R_7$ are independently selected from the group consisting of hydrogen, and $C_1$-$C_6$ alkyl;
$R_3$ is selected from the group consisting of cyano, carboxy, carbamoyl, isoxazol-4-yl, and C(NH)NHOH; and $R_6$ is selected from the group consisting of hydrogen and hydroxy.

In a further aspect of the invention, $R_1$, $R_2$ and $R_7$ are independently selected from the group consisting of hydrogen and methyl; $R_3$ is selected from the group consisting of hydrogen, nitro, cyano, carboxy, carbamoyl, methylsulfonamido, fluoro, chloro, bromo, hydroxy, methylsulfonyl, and methylsulfinyl, isoxazol-4-yl, $C_1$-$C_6$ alkoxy, —C(NH)NHOH, sulfonic acid, and acetyl; and $R_6$ is hydrogen. In a further aspect of the invention, $R_1$, $R_2$ and $R_7$ are independently selected from the group consisting of hydrogen and methyl; $R_3$ is selected from the group consisting of nitro, cyano, carboxy, carbamoyl, methylsulfonamido, fluoro, chloro, bromo, hydroxy, methylsulfonyl, and methylsulfinyl, isoxazol-4-yl, $C_1$-$C_6$ alkoxy, —C(NH)NHOH, sulfonic acid, and acetyl and $R_6$ is hydrogen. In a further aspect of the invention, suitable identities for X include, but are not limited to phenyl, substituted phenyl, thiophen-yl, substituted thiophen-yl, thiazol-yl, substituted thiazol-yl, pyrazin-yl, substituted pyrazin-yl, pyridin-yl, and substituted pyridin-yl, cyclohexyl, and substituted cyclohexyl. In a further aspect of the invention, suitable identities for X include, but are not limited to, phenyl, thiophen-2-yl, thiophen-3-yl, thiazol-2-yl, 2-fluorophenyl, p-tolyl, m-tolyl, biphenyl-4-yl, 4-methoxyphenyl, 3-chlorophenyl, 3,4-dichlorophenyl, 3-methoxyphenyl, 3,4-dimethoxyphenyl, 4-bromophenyl, o-tolyl, 4-chlorophenyl, 2-chlorophenyl, 3-cyanophenyl, 3,4-difluorophenyl, 4-cyanophenyl, 3-carbamoylphenyl, pyrazin-2-yl, biphenyl-3-yl, 2-cyanophenyl, pyridin-4-yl, and pyridin-3-yl, 4-(dimethylamino)phenyl, 3-fluorophenyl, 3-ethylphenyl, and cyclohexyl. In a further aspect of the invention, suitable identities for Y include, but are not limited to phenyl, substituted phenyl, thiophen-yl, substituted thiophen-yl, thiazol-yl, substituted thiazol-yl, pyrazin-yl, substituted pyrazin-yl, pyridin-yl, substituted pyridin-yl, furan-yl, substituted furan-yl, benzo[d][1,3]dioxol-yl, substituted benzo[d][1,3]dioxol-yl, imidazol-yl, substituted imidazol-yl, naphthalen-yl, substituted naphthalen-yl, pyrrol-yl, substituted pyrrol-yl, pyrazol-yl, substituted pyrazol-yl, tetrahydrofuran-yl, substituted tetrahydrofuran-yl, cyclopentyl, substituted cyclopentyl, cyclohexyl, and substituted cyclohexyl. In a further aspect of the invention, suitable identities for Y include, but are not limited to, phenyl, 3-methoxyphenyl, p-tolyl, 4-methoxyphenyl, 3,5-dichlorophenyl, 3-fluorophenyl, 4-bromophenyl, biphenyl-4-yl, 4-fluorophenyl, 4-chlorophenyl, 3-chlorophenyl, 3,4-dimethoxyphenyl, 3-fluoro-4-methoxyphenyl, 4-chloro-3-fluorophenyl, 3-chloro-4-fluorophenyl, 3,4-difluorophenyl, 3,5-difluorophenyl, 3,4-dichlorophenyl, 4-hydroxyphenyl, 2,4-difluorophenyl, furan-3-yl, 2-chlorophenyl, 3-cyanophenyl, 4-(dimethylamino)phenyl, 2-fluorophenyl, 4-morpholinophenyl, 4-aminophenyl, naphthal-2-yl, benzo[d][1,3]dioxol-5-yl, 4-cyanophenyl, naphthal-3-yl, naphthal-4-yl, 4-acetamidophenyl, thiophen-2-yl, thiophen-3-yl, 1-methyl-1H-imidazol-4-yl, naphthalene-1-yl, methyl phenylcarbamate, and naphthalene-2-yl, 4-(methanesulfonamido)phenyl, 1H-pyrrol-3-yl, 1-(phenylsulfonyl)-1H-pyrrol-3-yl, furan-2-yl, 4-(trifluoromethyl)phenyl, o-tolyl, 1-methyl-1H-pyrazol-4-yl, 1-methyl-1H-pyrazol-3-yl, 3-chloro-5-fluorophenyl, 3-hydroxyphenyl, pyrazin-2-yl, quinolin-6-yl, isoquinolin-6-yl, 1-methyl-1H-pyrazol-5-yl, tetrahydrofuran-2-yl, cyclopentyl, tetrahydrofuran-3-yl, and cyclohexyl.

In a further aspect of the invention, suitable compounds of Formula II include, but are not limited to:
4-(3-(isoxazol-4-yl)phenyl)-5,6-diphenyl-3,4-dihydropyrimidin-2(1H)-one;
3-(2-oxo-5,6-diphenyl-1,2,3,4-tetrahydropyrimidin-4-yl)benzoic acid;
2-hydroxy-3-(2-oxo-5,6-diphenyl-1,2,3,4-tetrahydropyrimidin-4-yl)benzonitrile;
3-(2-oxo-5,6-diphenyl-1,2,3,4-tetrahydropyrimidin-4-yl)benzamide; and
N-hydroxy-3-(2-oxo-5,6-diphenyl-1,2,3,4-tetrahydropyrimidin-4-yl)benzimidamide.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

The compounds described herein may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic, and geometric isomeric forms of a structure are intended, unless the specific stereochemistry or isomeric form is specifically indicated. All tautomers of shown or described compounds are also considered to be part of the present invention.

It is to be understood that isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

2. Representative Compounds

Examples 1-177 list representative novel dihydropyrimidin-2(1H)-one analogs of Formula I. The synthetic methods that can be used to prepare each compound are detailed in Examples 1-177, with reference to intermediates described in Example 178. Supporting mass spectrometry data and proton NMR data for each compound is also included in Examples 1-177. Optical rotation data is included when available for enantiomer pairs.

GSNOR inhibitor activity was determined by the assay described in Example 179 and $IC_{50}$ values were obtained. GSNOR inhibitor compounds in Examples 1-87, 89-91, 93, 95-103, 105-170, 172-177 had an $IC_{50}$ of about <100 µM. GSNOR inhibitor compounds in Examples 1, 2, 4-13, 15-17, 20-23, 26, 28-39, 43-61, 63, 65, 67, 69, 71, 73, 77-81, 83-86, 95, 101-102, 105-116, 118-121, 125-139, 141-143, 146-148, 150-152, 154-156, 158-161, 163, 165, 167, 169, 170, 172-175, and 177 had an $IC_{50}$ of about <1.0 µM. GSNOR inhibitor compounds in Examples 1, 2, 4-6, 9, 13, 15-17, 20-21, 23, 29, 31-39, 43-51, 53, 55-57, 61, 63, 65, 67, 71, 73, 78-79, 81, 83, 101-102, 107-109, 111, 113, 115-116, 118-121, 125, 129-139, 141-143, 146, 148, 155-156, 158-159, 161, 163, 165, 167, 169, 172, 174, and 177 had an $IC_{50}$ of about less than 0.1 µM.

In certain embodiments of the invention it has been demonstrated that racemic mixtures have GSNOR inhibitor activity and in some instances when the separated enantiomers are produced, one of the enantiomers has the majority of the GSNOR inhibitor activity and the other enantiomer is significantly less active as a GSNOR inhibitor. For example the following Table 1 shows racemates and separated enantiomers and their $IC_{50}$ data. Without being bound by theory, it is believed that when the enantiomers of a GSNOR inhibitor are separated, the enantiomer which demonstrates significantly better GSNOR inhibitor activity is of the S configuration. For example, Example 2 (the separated enantiomer of Example 1 with significantly better activity as a GSNOR inhibitor) has been shown by X-ray crystallography to have an S configuration when crystallized with GSNOR. See Table 1 below for GSNOR $IC_{50}$ data (procedure for obtaining GSNOR $IC_{50}$ is detailed in Example 179).

TABLE 1

| Example # | Configuration | GSNOR $IC_{50}$ (nM) |
|---|---|---|
| 1 | racemic | 29 |
| 2 | S | 11 |
| 3 | R | 19720 |
| 5 | racemic | 19 |
| 6 | S | 18 |
| 7 | R | 1820 |
| 65 | racemic | 43 |
| 67 | S | 28 |
| 66 | R | 6020 |
| 126 | racemic | 150 |
| 125 | S | 67 |
| 124 | R | 3170 |
| 116 | racemic | 24 |
| 143 | S | 16 |
| 144 | R | 1900 |
| 142 | racemic | 27 |
| 146 | S | 13 |
| 147 | R | 580 |
| 119 | racemic | 40 |
| 148 | S | 35 |
| 149 | R | 31000 |
| 159 | racemic | 39 |
| 169 | S | 23 |
| 168 | R | 4250 |

C. Definitions

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The term "acyl" includes compounds and moieties that contain the acetyl radical ($CH_3CO—$) or a carbonyl group to which a straight or branched chain lower alkyl residue is attached.

The term "alkyl" as used herein refers to a straight or branched chain, saturated hydrocarbon having the indicated number of carbon atoms. For example, ($C_1$-$C_6$)alkyl is meant to include, but is not limited to methyl, ethyl, propyl, isopropyl, butyl, sec-butyl, tert-butyl, pentyl, isopentyl, neopentyl, hexyl, isohexyl, and neohexyl. An alkyl group can be unsubstituted or optionally substituted with one or more substituents as described herein.

The term "alkenyl" as used herein refers to a straight or branched chain unsaturated hydrocarbon having the indicated number of carbon atoms and at least one double bond. Examples of a ($C_2$-$C_8$)alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene. An alkenyl group can be unsubstituted or optionally substituted with one or more substituents as described herein.

The term "alkynyl" as used herein refers to a straight or branched chain unsaturated hydrocarbon having the indicated number of carbon atoms and at least one triple bond. Examples of a ($C_2$-$C_8$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein.

The term "alkoxy" as used herein refers to an —O-alkyl group having the indicated number of carbon atoms. For example, a ($C_1$-$C_6$)alkoxy group includes —O-methyl, —O-ethyl, —O-propyl, —O-isopropyl, —O-butyl, —O-sec-butyl, —O-tert-butyl, —O-pentyl, —O— isopentyl, —O-neopentyl, —O-hexyl, —O-isohexyl, and —O-neohexyl.

The term "aminoalkyl" as used herein, refers to an alkyl group (typically one to six carbon atoms) wherein one or more of the $C_1$-$C_6$ alkyl group's hydrogen atoms is replaced with an amine of formula —N($R^c$)$_2$, wherein each occurrence of $R^c$ is independently —H or ($C_1$-$C_6$)alkyl. Examples of aminoalkyl groups include, but are not limited to, —$CH_2NH_2$, —$CH_2CH_2NH_2$, —$CH_2CH_2CH_2NH_2$, —$CH_2CH_2CH_2CH_2NH_2$, —$CH_2CH_2CH_2CH_2CH_2NH_2$, —$CH_2CH_2CH_2CH_2CH_2CH_2NH_2$, —$CH_2CH_2CH_2N(CH_3)_2$, t-butylaminomethyl, isopropylaminomethyl and the like.

The term "aryl" as used herein refers to a 5- to 14-membered monocyclic, bicyclic or tricyclic aromatic ring system. Examples of an aryl group include phenyl and naphthyl. An aryl group can be unsubstituted or optionally substituted with one or more substituents as described herein below. Examples of aryl groups include phenyl or aryl heterocycles such as, pyrrole, furan, thiophene, thiazole, isothiazole, imidazole, triazole, tetrazole, pyrazole, oxazole, isoxazole, pyridine, pyrazine, pyridazine, and pyrimidine, and the like.

As used herein, the term "bioactivity" indicates an effect on one or more cellular or extracellular process (e.g., via binding, signaling, etc.) which can impact physiological or pathophysiological processes.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxy" or "carboxyl" means a —COOH group or carboxylic acid.

The term "$C_m$-$C_n$" means "m" number of carbon atoms to "n" number of carbon atoms. For example, the term "$C_1$-$C_6$" means one to six carbon atoms ($C_1$, $C_2$, $C_3$, $C_4$, $C_5$ or $C_6$). The term "$C_2$-$C_6$" includes two to six carbon atoms ($C_2$, $C_3$, $C_4$, $C_5$ or $C_6$). The term "$C_3$-$C_6$" includes three to six carbon atoms ($C_3$, $C_4$, $C_5$ or $C_6$).

The term "cycloalkyl" as used herein refers to a 3- to 14-membered saturated or unsaturated non-aromatic monocyclic, bicyclic or tricyclic hydrocarbon ring system. Included in this class are cycloalkyl groups which are fused to a benzene ring. Representative cycloalkyl groups include, but are not limited to, cyclopropyl, cyclobutyl, cyclobutenyl, cyclopentyl, cyclopentenyl, cyclopentadienyl, cyclohexyl, cyclohexenyl, 1,3-cyclohexadienyl, cycloheptyl, cycloheptenyl, 1,3-cycloheptadienyl, 1,4-cycloheptadienyl, -1,3,5-cycloheptatrienyl, cyclooctyl, cyclooctenyl, 1,3-cyclooctadienyl, 1,4-cyclooctadienyl, -1,3,5-cyclooctatrienyl, decahydronaphthalene, octahydronaphthalene, hexahydronaphthalene, octahydroindene, hexahydroindene, tetrahydroinden, decahydrobenzocycloheptene, octahydrobenzocycloheptene, hexahydrobenzocycloheptene, tetrahydrobenzocyclopheptene, dodecahydroheptalene, decahydroheptalene, octahydroheptalene, hexahydroheptalene, and tetrahydroheptalene, (1s,3s)-bicyclo[1.1.0]butane, bicyclo[1.1.1]pentane, bicyclo[2.1.1]hexane, Bicyclo[2.2.1]heptane, bicyclo[2.2.2]octane, bicyclo[3.1.1]heptane, bicyclo[3.2.1]octane, bicyclo[3.3.1]nonane, bicyclo[3.3.2]decane, bicyclo[3.3.]undecane, bicyclo[4.2.2]decane, bicyclo[4.3.1]decane. A cycloalkyl group can be unsubstituted or optionally substituted with one or more substituents as described herein below.

The term "halogen" includes fluorine, bromine, chlorine, iodine, etc.

The term "haloalkyl," as used herein, refers to a $C_1$-$C_6$ alkyl group wherein from one or more of the $C_1$-$C_6$ alkyl group's hydrogen atom is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl.

The term "heteroalkyl," by itself or in combination with another term, means, unless otherwise stated, a stable straight or branched chain alkyl, or combinations thereof, consisting of carbon atoms and from one to three heteroatoms selected from the group consisting of O, N and S, and wherein the nitrogen and sulfur atoms may optionally be oxidized and the nitrogen heteroatom may optionally be quaternized. The heteroatom(s) O, N and S can be placed at any position of the heteroalkyl group. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, and —$CH_2$—CH=N—$OCH_3$. Up to two heteroatoms can be consecutive, such as, for example, —$CH_2$—NH—$OCH_3$. When a prefix such as ($C_2$-$C_8$) is used to refer to a heteroalkyl group, the number of carbons (2 to 8, in this example) is meant to include the heteroatoms as well. For example, a $C_2$-heteroalkyl group is meant to include, for example, —$CH_2$OH (one carbon atom and one heteroatom replacing a carbon atom) and —$CH_2$SH.

To further illustrate the definition of a heteroalkyl group, where the heteroatom is oxygen, a heteroalkyl group can be an oxyalkyl group. For instance, ($C_2$-$C_5$)oxyalkyl is meant to include, for example —$CH_2$—O—$CH_3$ (a $C_3$-oxyalkyl group with two carbon atoms and one oxygen replacing a carbon atom), —$CH_2CH_2CH_2CH_2$OH, —$OCH_2CH_2OCH_2CH_2$OH, —$OCH_2CH(OH)CH_2$OH, and the like.

The term "heteroaryl" as used herein refers to an aromatic heterocycle ring of 5 to 14 members and having at least one heteroatom selected from nitrogen, oxygen and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thienyl, benzothienyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, quinoxalinyl and oxazolyl. A heteroaryl group can be unsubstituted or optionally substituted with one or more substituents as described herein below.

As used herein, the term "heteroatom" is meant to include oxygen (O), nitrogen (N), and sulfur (S).

As used herein, the term "heterocycle" refers to 3- to 14-membered ring systems which are either saturated, unsaturated, or aromatic, and which contains from 1 to 4 heteroatoms independently selected from nitrogen, oxygen and sulfur, and wherein the nitrogen and sulfur heteroatoms can be optionally oxidized, and the nitrogen heteroatom can be optionally quaternized, including, including monocyclic, bicyclic, and tricyclic ring systems. The bicyclic and tricyclic ring systems may encompass a heterocycle or heteroaryl fused to a benzene ring. The heterocycle can be attached via any heteroatom or carbon atom, where chemically acceptable. Heterocycles include heteroaryls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, dioxanyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thienyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl and quinazolinyl. A heterocycle group can be unsubstituted or optionally substituted with one or more substituents as described herein below.

The term "heterocycloalkyl," by itself or in combination with other terms, represents, unless otherwise stated, cyclic versions of "heteroalkyl." Additionally, a heteroatom can occupy the position at which the heterocycle is attached to the remainder of the molecule. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "hydroxyalkyl," as used herein, refers to an alkyl group having the indicated number of carbon atoms wherein one or more of the hydrogen atoms in the alkyl group is replaced with an —OH group. Examples of hydroxyalkyl groups include, but are not limited to, —$CH_2$OH, —$CH_2CH_2$OH, —$CH_2CH_2CH_2$OH, —$CH_2CH_2CH_2CH_2$OH, —$CH_2CH_2CH_2CH_2CH_2$OH, —$CH_2CH_2CH_2CH_2CH_2CH_2$OH, and branched versions thereof.

The term "hydroxy" or "hydroxyl" includes groups with an —OH or —O$^-$.

As used herein and unless otherwise indicated, the term "stereoisomer" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. In some embodiments, a stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

As used herein, "protein" is used synonymously with "peptide," "polypeptide," or "peptide fragment". A "purified" polypeptide, protein, peptide, or peptide fragment is substantially free of cellular material or other contaminating proteins from the cell, tissue, or cell-free source from which the amino acid sequence is obtained, or substantially free from chemical precursors or other chemicals when chemically synthesized.

As used herein, "modulate" is meant to refer to an increase or decrease in the levels of a peptide or a polypeptide, or to increase or decrease the stability or activity of a peptide or a polypeptide. The term "inhibit" is meant to refer to a decrease in the levels of a peptide or a polypeptide or to decrease in the stability or activity of a peptide or a polypeptide. In preferred embodiments, the peptide which is modulated or inhibited is S-nitrosoglutathione (GSNO) or protein S-nitrosothiols (SNOs).

As used here, the terms "nitric oxide" and "NO" encompass uncharged nitric oxide and charged nitric oxide species, particularly including nitrosonium ion ($NO^+$) and nitroxyl ion ($NO^-$). The reactive form of nitric oxide can be provided by gaseous nitric oxide. Compounds having the structure $X-NO_y$, wherein X is a nitric oxide releasing, delivering or transferring moiety, including any and all such compounds which provide nitric oxide to its intended site of action in a form active for their intended purpose, and Y is 1 or 2.

As utilized herein, the term "pharmaceutically acceptable" means approved by a regulatory agency of a federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils.

A "pharmaceutically acceptable salt" or "salt" of a compound of the invention is a product of the disclosed compound that contains an ionic bond, and is typically produced by reacting the disclosed compound with either an acid or a base, suitable for administering to a subject. A pharmaceutically acceptable salt can include, but is not limited to, acid addition salts including hydrochlorides, hydrobromides, phosphates, sulphates, hydrogen sulphates, alkylsulphonates, arylsulphonates, arylalkylsulfonates, acetates, benzoates, citrates, maleates, fumarates, succinates, lactates, and tartrates; alkali metal cations such as Li, Na, K, alkali earth metal salts such as Mg or Ca, or organic amine salts.

A "pharmaceutical composition" is a formulation comprising the disclosed compounds in a form suitable for administration to a subject. A pharmaceutical composition of the invention is preferably formulated to be compatible with its intended route of administration. Examples of routes of administration include, but are not limited to, oral and parenteral, e.g., intravenous, intradermal, subcutaneous, inhalation, topical, transdermal, transmucosal, and rectal administration.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Ring double bonds, as used herein, are double bonds that are formed between two adjacent ring atoms (e.g., C=C, C=N, or N=N).

Substituents for the groups referred to as alkyl, heteroalkyl, alkylene, alkenyl, alkynyl, cycloalkyl, heterocycloalkyl, cycloalkenyl and heterocycloalkenyl can be selected from a variety of groups including $-OR^{d'}$, $=O$, $=NR^{d'}$, $=N-OR^{d'}$, $-NR^{d'}R^{d''}$, $-SR^{d'}$, -halo, $-SiR^{d'}R^{d''}R^{d'''}$, $-OC(O)R^{d'}$, $-C(O)R^{d'}$, $-CO_2R^{d'}$, $-CONR^{d'}R^{d''}$, $-OC(O)NR^{d'}R^{d''}$, $-NR^{d''}C(O)R^{d'}$, $-NR^{d''}C(O)NR^{d'}R^{d''}$, $-NR^{d'''}SO_2NR^{d'}R^{d''}$, $-NR^{d''}CO_2R^{d'}$, $-NHC(NH_2)=NH$, $-NR^{a'}C(NH_2)=NH$, $-NHC(NH_2)=NR^{d'}$, $-S(O)R^{d'}$, $-SO_2R^{d'}$, $-SO_2NR^{d'}R^{d''}$, $-NR^{d''}SO_2R^{d'}$, $-CN$ and $-NO_2$, in a number ranging from zero to three, with those groups having zero, one or two substituents being exemplary.

$R^{d'}$, $R^{d''}$ and $R^{d'''}$ each independently refer to hydrogen, unsubstituted ($C_1$-$C_8$)alkyl, unsubstituted hetero($C_1$-$C_8$) alkyl, unsubstituted aryl and aryl substituted with one to three substituents selected from -halo, unsubstituted alkyl, unsubstituted alkoxy, unsubstituted thioalkoxy and unsubstituted aryl($C_1$-$C_4$)alkyl. When $R^{d'}$ and $R^{d''}$ are attached to the same nitrogen atom, they can be combined with the nitrogen atom to form a 5-, 6- or 7-membered ring. For example, $-NR^{d'}R^{d''}$ can represent 1-pyrrolidinyl or 4-morpholinyl.

Typically, an alkyl or heteroalkyl group will have from zero to three substituents, with those groups having two or fewer substituents being exemplary of the present invention. An alkyl or heteroalkyl radical can be unsubstituted or monosubstituted. In some embodiments, an alkyl or heteroalkyl radical will be unsubstituted.

Exemplary substituents for the alkyl and heteroalkyl radicals include but are not limited to $-OR^{d'}$, $=O$, $=NR^{d'}$, $=N-OR^{d'}$, $-NR^{d'}R^{d''}$, $-SR^{d'}$, -halo, $-SiR^{d'}R^{d''}R^{d'''}$, $-OC(O)R^{d'}$, $-C(O)R^{d'}$, $-CO_2R^{d'}$, $-CONR^{d'}R^{d''}$, $-OC(O)NR^{d'}R^{d''}$, $-NR^{d''}C(O)R^{d'}$, $-NR^{d''}C(O)NR^{d'}R^{d''}$, $-NR^{d'''}SO_2NR^{d'}R^{d''}$, $-NR^{d''}CO_2R^{d'}$, $-NHC(NH_2)=NH$, $-NR^{a'}C(NH_2)=NH$, $-NHC(NH_2)=NR^{d'}$, $-S(O)R^{d'}$, $-SO_2R^{d'}$, $-SO_2NR^{d'}R^{d''}$, $-NR^{d''}SO_2R^{d'}$, $-CN$ and $-NO_2$, where $R^{d'}$, $R^{d''}$ and $R^{d'''}$ are as defined above. Typical substituents can be selected from: $-OR^{d'}$, $=O$, $-NR^{d'}R^{d''}$, -halo, $-OC(O)R^{d'}$, $-CO_2R^{d'}$, $-C(O)NR^{d'}R^{d''}$, $-OC(O)NR^{d'}R^{d''}$, $-NR^{d''}C(O)R^{d'}$, $-NR^{d''}CO_2R^{d'}$, $-NR^{d'''}SO_2NR^{d'}R^{d''}$, $-SO_2R^{d'}$, $-SO_2NR^{d'}R^{d''}$, $-NR^{d''}SO_2R^{d'}$ $-CN$ and $-NO_2$.

Similarly, substituents for the aryl and heteroaryl groups are varied and selected from: -halo, $-OR^{e'}$, $-OC(O)R^{e'}$, $-NR^{e'}R^{e''}$, $-SR^{e'}$, $-R^{e'}$, $-CN$, $-NO_2$, $-CO_2R^{e'}$, $-C(O)NR^{e'}R^{e''}$, $-C(O)R^{e'}$, $-OC(O)NR^{e'}R^{e''}$, $-NR^{e''}C(O)R^{e'}$, $-NR^{e''}CO_2R^{e'}$, $-NR^{e'''}C(O)NR^{e'}R^{e''}$, $-NR^{e'''}SO_2NR^{e'}R^{e''}$, $-NHC(NH_2)=NH$, $-NR^{e'}C(NH_2)=NH$, $-NH-C(NH_2)=NR^{e'}$, $-S(O)R^{e'}$, $-SO_2R^{e'}$, $-SO_2NR^{e'}R^{e''}$, $-NR^{e''}SO_2R^{e'}$, $-N_3$, $-CH(Ph)_2$, perfluoroalkoxy and perfluoro($C_1$-$C_4$)alkyl, in a number ranging from zero to the total number of open valences on the aromatic ring system.

$R^{e'}$, $R^{e''}$ and $R^{e'''}$ are independently selected from hydrogen, unsubstituted ($C_1$-$C_8$)alkyl, unsubstituted hetero($C_1$-$C_8$) alkyl, unsubstituted aryl, unsubstituted heteroaryl, unsubstituted aryl($C_1$-$C_4$)alkyl and unsubstituted aryloxy($C_1$-$C_4$) alkyl. Typically, an aryl or heteroaryl group will have from zero to three substituents, with those groups having two or fewer substituents being exemplary in the present invention. In one embodiment of the invention, an aryl or heteroaryl group will be unsubstituted or monosubstituted. In another embodiment, an aryl or heteroaryl group will be unsubstituted.

Two of the substituents on adjacent atoms of an aryl or heteroaryl ring in an aryl or heteroaryl group as described herein may optionally be replaced with a substituent of the formula -T-C(O)-$(CH_2)_q$-U-, wherein T and U are independently $-NH-$, $-O-$, $-CH_2-$ or a single bond, and q is an integer of from 0 to 2. Alternatively, two of the substituents on adjacent atoms of the aryl or heteroaryl ring may optionally be replaced with a substituent of the formula -J-$(CH_2)_r$—K—, wherein J and K are independently —$CH_2$—, —O—, —NH—, —S—, —S(O)—, —S(O)$_2$—, —S(O)$_2$NR$^{fi}$— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —$(CH_2)_s$—X—$(CH_2)_t$—, where s and t are independently integers of from 0 to 3, and X is —O—, —NR$^{fi}$—, —S—, —S(O)—, —S(O)$_2$—, or —S(O)$_2$NR$^{an}$—. The substituent R$^{fi}$ in —NR$^{fi}$— and —S(O)$_2$NR$^{fi}$— is selected from hydrogen or unsubstituted ($C_1$-$C_6$)alkyl.

"Stable compound" and "stable structure" are meant to indicate a compound that is sufficiently robust to survive isolation to a useful degree of purity from a reaction mixture, and formulation into an efficacious therapeutic agent.

As used herein the term "therapeutically effective amount" generally means the amount necessary to ameliorate at least one symptom of a disorder to be prevented, reduced, or treated as described herein. The phrase "therapeutically effective amount" as it relates to the GSNOR inhibitors of the present invention shall mean the GSNOR inhibitor dosage that provides the specific pharmacological response for which the GSNOR inhibitor is administered in a significant number of subjects in need of such treatment. It is emphasized that a therapeutically effective amount of a GSNOR inhibitor that is administered to a particular subject in a particular instance will not always be effective in treating the conditions/diseases described herein, even though such dosage is deemed to be a therapeutically effective amount by those of skill in the art.

The term "biological sample" includes, but is not limited to, samples of blood (e.g., serum, plasma, or whole blood), urine, saliva, sweat, breast milk, vaginal secretions, semen, hair follicles, skin, teeth, bones, nails, or other secretions, body fluids, tissues, or cells. In accordance with the invention, the levels of the S-nitrosoglutathione reductase in the biological sample can be determined by the methods described in U.S. Patent Application Publication No. 2005/0014697.

D. Pharmaceutical Compositions

The invention encompasses pharmaceutical compositions comprising at least one compound of the invention described herein and at least one pharmaceutically acceptable carrier. Suitable carriers are described in "Remington: The Science and Practice, Twentieth Edition," published by Lippincott Williams & Wilkins, which is incorporated herein by reference. Pharmaceutical compositions according to the invention may also comprise one or more non-inventive compound active agents.

The pharmaceutical compositions of the invention can comprise novel compounds described herein, the pharmaceutical compositions can comprise known compounds which previously were not known to have GSNOR inhibitor activity, or a combination thereof.

The compounds of the invention can be utilized in any pharmaceutically acceptable dosage form, including but not limited to injectable dosage forms, liquid dispersions, gels, aerosols, ointments, creams, lyophilized formulations, dry powders, tablets, capsules, controlled release formulations, fast melt formulations, delayed release formulations, extended release formulations, pulsatile release formulations, mixed immediate release and controlled release formulations, etc. Specifically, the compounds of the invention described herein can be formulated: (a) for administration selected from the group consisting of oral, pulmonary, intravenous, intra-arterial, intrathecal, intra-articular, rectal, ophthalmic, colonic, parenteral, intracisternal, intravaginal, intraperitoneal, local, buccal, nasal, and topical administration; (b) into a dosage form selected from the group consisting of liquid dispersions, gels, aerosols, ointments, creams, tablets, sachets and capsules; (c) into a dosage form selected from the group consisting of lyophilized formulations, dry powders, fast melt formulations, controlled release formulations, delayed release formulations, extended release formulations, pulsatile release formulations, and mixed immediate release and controlled release formulations; or (d) any combination thereof.

For respiratory infections, an inhalation formulation can be used to achieve high local concentrations. Formulations suitable for inhalation include dry power or aerosolized or vaporized solutions, dispersions, or suspensions capable of being dispensed by an inhaler or nebulizer into the endobronchial or nasal cavity of infected patients to treat upper and lower respiratory bacterial infections.

Solutions or suspensions used for parenteral, intradermal, or subcutaneous application can comprise one or more of the following components: (1) a sterile diluent such as water for injection, saline solution, fixed oils, polyethylene glycols, glycerine, propylene glycol or other synthetic solvents; (2) antibacterial agents such as benzyl alcohol or methyl parabens; (3) antioxidants such as ascorbic acid or sodium bisulfite; (4) chelating agents such as ethylenediaminetetraacetic acid; (5) buffers such as acetates, citrates or phosphates; and (5) agents for the adjustment of tonicity such as sodium chloride or dextrose. The pH can be adjusted with acids or bases, such as hydrochloric acid or sodium hydroxide. A parenteral preparation can be enclosed in ampoules, disposable syringes or multiple dose vials made of glass or plastic.

Pharmaceutical compositions suitable for injectable use may comprise sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringability exists. The pharmaceutical composition should be stable under the conditions of manufacture and storage and should be preserved against the contaminating action of microorganisms such as bacteria and fungi.

The carrier can be a solvent or dispersion medium comprising, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol or sorbitol, and inorganic salts such as sodium chloride in the composition. Prolonged absorption of the injectable compositions can be brought about by including in the composition an agent which delays absorption, for example, aluminum monostearate and gelatin.

Sterile injectable solutions can be prepared by incorporating the active reagent in the required amount in an appropriate solvent with one or a combination of ingredients enumerated above, as required, followed by filtered sterilization. Generally, dispersions are prepared by incorporating at least one compound of the invention into a sterile vehicle that contains a basic dispersion medium and any other required ingredients. In the case of sterile powders for the preparation of sterile injectable solutions, exemplary methods of preparation include vacuum drying and freeze-drying, both of which yield a powder of a compound of the invention plus any additional desired ingredient from a previously sterile-filtered solution thereof.

Oral compositions generally include an inert diluent or an edible carrier. They can be enclosed, for example, in gelatin capsules or compressed into tablets. For the purpose of oral therapeutic administration, the compound of the invention can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

For administration by inhalation, the compounds are delivered in the form of an aerosol spray from pressured container or dispenser that contains a suitable propellant, e.g., a gas such as carbon dioxide, a nebulized liquid, or a dry powder from a suitable device. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active reagents are formulated into ointments, salves, gels, or creams as generally known in the art. The reagents can also be prepared in the form of suppositories (e.g., with conventional suppository bases such as cocoa butter and other glycerides) or retention enemas for rectal delivery.

In one embodiment, the compounds of the invention are prepared with carriers that will protect against rapid elimination from the body. For example, a controlled release formulation can be used, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, suspensions of the compounds of the invention may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also include suitable stabilizers or agents to increase the solubility of the compounds and allow for the preparation of highly concentrated solutions.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of the compound of the invention calculated to produce the desired therapeutic effect in association with the required pharmaceutical carrier. The specification for the dosage unit forms of the invention are dictated by and directly dependent on the unique characteristics of the compound of the invention and the particular therapeutic effect to be achieved, and the limitations inherent in the art of compounding such an active agent for the treatment of individuals.

Pharmaceutical compositions according to the invention comprising at least one compound of the invention can comprise one or more pharmaceutical excipients. Examples of such excipients include, but are not limited to binding agents, filling agents, lubricating agents, suspending agents, sweeteners, flavoring agents, preservatives, buffers, wetting agents, disintegrants, effervescent agents, and other excipients. Such excipients are known in the art. Exemplary excipients include: (1) binding agents which include various celluloses and cross-linked polyvinylpyrrolidone, microcrystalline cellulose, such as Avicel® PH101 and Avicel® PH102, silicified microcrystalline cellulose (ProSolv SMCC™), gum tragacanth and gelatin; (2) filling agents such as various starches, lactose, lactose monohydrate, and lactose anhydrous; (3) disintegrating agents such as alginic acid, Primogel, corn starch, lightly crosslinked polyvinyl pyrrolidone, potato starch, maize starch, and modified starches, croscarmellose sodium, cross-povidone, sodium starch glycolate, and mixtures thereof; (4) lubricants, including agents that act on the flowability of a powder to be compressed, include magnesium stearate, colloidal silicon dioxide, such as Aerosil® 200, talc, stearic acid, calcium stearate, and silica gel; (5) glidants such as colloidal silicon dioxide; (6) preservatives, such as potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride; (7) diluents such as pharmaceutically acceptable inert fillers, such as microcrystalline cellulose, lactose, dibasic calcium phosphate, saccharides, and/or mixtures of any of the foregoing; examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose; (8) sweetening agents, including any natural or artificial sweetener, such as sucrose, saccharin sucrose, xylitol, sodium saccharin, cyclamate, aspartame, and acesulfame; (9) flavoring agents, such as peppermint, methyl salicylate, orange flavoring, Magnasweet® (trademark of MAFCO), bubble gum flavor, fruit flavors, and the like; and (10) effervescent agents, including effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

E. Kits Comprising the Compositions of the Invention

The present invention also encompasses kits comprising the compositions of the invention. Such kits can comprise, for example, (1) at least one compound of the invention; and (2) at least one pharmaceutically acceptable carrier, such as a solvent or solution. Additional kit components can optionally include, for example: (1) any of the pharmaceutically acceptable excipients identified herein, such as stabilizers, buffers, etc., (2) at least one container, vial or similar apparatus for holding and/or mixing the kit components; and (3) delivery apparatus, such as an inhaler, nebulizer, syringe, etc.

F. Methods of Preparing Compounds of the Invention

The compounds of the invention can readily be synthesized using known synthetic methodologies or via a modification of known synthetic methodologies. As would be readily recognized by a skilled artisan, the methodologies described below allow the synthesis of dihydropyrimidin-2(1H)-ones having a variety of substituents. Exemplary synthetic methods are described in the examples below.

If needed, further purification and separation of enantiomers and diastereomers can be achieved by routine procedures known in the art. Thus, for example, the separation of enantiomers of a compound can be achieved by the use of chiral HPLC and related chromatographic techniques. Diastereomers can be similarly separated. In some instances, however, diastereomers can simply be separated physically, such as, for example, by controlled precipitation or crystallization.

The process of the invention, when carried out as prescribed herein, can be conveniently performed at temperatures that are routinely accessible in the art. In one embodiment, the process is performed at a temperature in the range of about 25° C. to about 110° C. In another embodiment, the temperature is in the range of about 40° C. to about 100° C. In yet another embodiment, the temperature is in the range of about 50° C. to about 95° C.

Synthetic steps that require a base are carried out using any convenient organic or inorganic base. Typically, the base is not nucleophilic. Thus, in one embodiment, the base is selected from carbonates, phosphates, hydroxides, alkoxides, salts of disilazanes, and tertiary amines.

The process of the invention, when performed as described herein, can be substantially complete after several minutes to after several hours depending upon the nature and quantity of reactants and reaction temperature. The determination of when the reaction is substantially complete can be conveniently evaluated by ordinary techniques known in the art such as, for example, HPLC, LCMS, TLC, and $^1$H NMR.

G. Methods of Treatment

The invention encompasses methods of preventing or treating (e.g., alleviating one or more symptoms of) medical conditions through use of one or more of the disclosed compounds. The methods comprise administering a therapeutically effective amount of a compound of the invention to a patient in need. The compositions of the invention can also be used for prophylactic therapy.

The compound of the invention used in the methods of treatment according to the invention can be: (1) a novel compound described herein, or a pharmaceutically acceptable salt thereof, a prodrug thereof, or a metabolite thereof; (2) a compound which was known prior to the present invention, but wherein it was not known that the compound is a GSNOR inhibitor, or a pharmaceutically acceptable salt thereof, a prodrug thereof, or a metabolite thereof; or (3) a compound which was known prior to the present invention, and wherein it was known that the compound is a GSNOR inhibitor, but wherein it was not known that the compound is useful for the methods of treatment described herein, or a pharmaceutically acceptable salt thereof, a prodrug thereof, or a metabolite thereof.

The patient can be any animal, domestic, livestock or wild, including, but not limited to cats, dogs, horses, pigs and cattle, and preferably human patients. As used herein, the terms patient and subject may be used interchangeably.

As used herein, "treating" describes the management and care of a patient for the purpose of combating a disease, condition, or disorder and includes the administration of a compound of the present invention to prevent the onset of the symptoms or complications, alleviating the symptoms or complications, or eliminating the disease, condition or disorder. More specifically, "treating" includes reversing, attenuating, alleviating, minimizing, suppressing or halting at least one deleterious symptom or effect of a disease (disorder) state, disease progression, disease causative agent (e.g., bacteria or viruses), or other abnormal condition. Treatment is continued as long as symptoms and/or pathology ameliorate.

In general, the dosage, i.e., the therapeutically effective amount, ranges from 1 µg to 10 g/kg and often ranges from 10 µg to 1 g/kg or 10 µg to 100 mg/kg body weight of the subject being treated, per day.

H. GSNOR Uses

In subjects with deleteriously high levels of GSNOR or GSNOR activity, modulation may be achieved, for example, by administering one or more of the disclosed compounds that disrupts or down-regulates GSNOR function, or decreases GSNOR levels. These compounds may be administered with other GSNOR inhibitor agents, such as anti-GSNOR antibodies or antibody fragments, GSNOR antisense, iRNA, or small molecules, or other inhibitors, alone or in combination with other agents as described in detail herein.

The present invention provides a method of treating a subject afflicted with a disorder ameliorated by NO donor therapy. Such a method comprises administering to a subject a therapeutically effective amount of a GSNOR inhibitor.

The disorders can include pulmonary disorders associated with hypoxemia and/or smooth muscle constriction in the lungs and airways and/or lung infection and/or lung inflammation and/or lung injury (e.g., pulmonary hypertension, ARDS, asthma, pneumonia, pulmonary fibrosis/interstitial lung diseases, cystic fibrosis, COPD); cardiovascular disease and heart disease (e.g., hypertension, ischemic coronary syndromes, atherosclerosis, heart failure, glaucoma); diseases characterized by angiogenesis (e.g., coronary artery disease); disorders where there is risk of thrombosis occurring; disorders where there is risk of restenosis occurring; inflammatory diseases (e.g., AIDS related dementia, inflammatory bowel disease (IBD), Crohn's disease, and psoriasis); functional bowel disorders (e.g., irritable bowel syndrome (IBS)); diseases where there is risk of apoptosis occurring (e.g., heart failure, atherosclerosis, degenerative neurologic disorders, arthritis and liver injury (ischemic or alcoholic)); impotence; sleep apnea; diabetic wound healing; cutaneous infections; treatment of psoriasis; obesity caused by eating in response to craving for food; stroke; reperfusion injury (e.g., traumatic muscle injury in heart or lung or crush injury); and disorders where preconditioning of heart or brain for NO protection against subsequent ischemic events is beneficial, central nervous system (CNS) disorders (e.g., anxiety, depression, psychosis, and schizophrenia); and infections caused by bacteria (e.g., tuberculosis, *c. difficile* infections, among others).

In one embodiment, the compounds of the present invention or a pharmaceutically acceptable salt thereof, or a prodrug or metabolite thereof, can be administered in combination with an NO donor. An NO donor donates nitric oxide or a related redox species and more generally provides nitric oxide bioactivity, that is activity which is identified with nitric oxide, e.g., vasorelaxation or stimulation or inhibition of a receptor protein, e.g., ras protein, adrenergic receptor, NFκB. NO donors including S-nitroso, O-nitroso, C-nitroso and N-nitroso compounds and nitro derivatives thereof and metal NO complexes, but not excluding other NO bioactivity generating compounds, useful herein are described in "Methods in Nitric Oxide Research," Feelisch et al. eds., pages 71-115 (J. S., John Wiley & Sons, New York, 1996), which is incorporated herein by reference. NO donors which are C-nitroso compounds where nitroso is attached to a tertiary carbon which are useful herein include those described in U.S. Pat. No. 6,359,182 and in WO 02/34705. Examples of S-nitroso compounds, including S-nitrosothiols useful herein, include, for example, S-nitrosoglutathione, S-nitroso-N-acetylpenicillamine, S-nitroso-cysteine and ethyl ester thereof, S-nitroso cysteinyl glycine, S-nitroso-gamma-methyl-L-homocysteine, S-nitroso-L-homocysteine, S-nitroso-gamma-thio-L-leucine, S-nitroso-delta-thio-L-leucine, and S-nitrosoalbumin. Examples of other NO donors useful herein are sodium nitroprusside (nipride), ethyl nitrite, isosorbide, nitroglycerin, SIN 1 which is molsidomine, furoxamines, N-hydroxy (N-nitrosamine) and perfluorocarbons that have been saturated with NO or a hydrophobic NO donor.

The combination of a GSNOR inhibitor with R(+) enantiomer of amlodipine, a known NO releaser (Zhang X. P at al. 2002 J. Cardiovascular Pharmacology 39, 208-214) is also an embodiment of the present invention.

The present invention also provides a method of treating a subject afflicted with pathologically proliferating cells where the method comprises administering to said subject a therapeutically effective amount of an inhibitor of GSNOR. The inhibitors of GSNOR are the compounds as defined above, or a pharmaceutically acceptable salt thereof, or a prodrug or metabolite thereof, in combination with a pharmaceutically acceptable carrier. Treatment is continued as long as symptoms and/or pathology ameliorate.

In another embodiment, the pathologically proliferating cells can be pathologically proliferating microbes. The microbes involved can be those where GSNOR is expressed to protect the microbe from nitrosative stress or where a host cell infected with the microbe expresses the enzyme, thereby protecting the microbe from nitrosative stress. The term "pathologically proliferating microbes" is used herein to mean pathologic microorganisms including but not limited to pathologic bacteria, pathologic viruses, pathologic *Chlamydia*, pathologic protozoa, pathologic *Rickettsia*, pathologic fungi, and pathologic mycoplasmata. More detail on the applicable microbes is set forth at columns 11 and 12 of U.S. Pat. No. 6,057,367. The term "host cells infected with pathologic microbes" includes not only mammalian cells infected with pathologic viruses but also mammalian cells containing intracellular bacteria or protozoa, e.g., macrophages containing *Mycobacterium tuberculosis, Mycobacterium leper* (leprosy), or *Salmonella typhi* (typhoid fever).

In another embodiment, the pathologically proliferating cells can be pathologic helminths. The term "pathologic helminths" is used herein to refer to pathologic nematodes, pathologic trematodes and pathologic cestodes. More detail on the applicable helminths is set forth at column 12 of U.S. Pat. No. 6,057,367.

In another embodiment, the pathologically proliferating cells can be pathologically proliferating mammalian cells. The term "pathologically proliferating mammalian cells" as used herein means cells of the mammal that grow in size or number in said mammal so as to cause a deleterious effect in the mammal or its organs. The term includes, for example, the pathologically proliferating or enlarging cells causing restenosis, the pathologically proliferating or enlarging cells causing benign prostatic hypertrophy, the pathologically proliferating cells causing myocardial hypertrophy and proliferating cells at inflammatory sites such as synovial cells in arthritis or cells associated with a cell proliferation disorder.

As used herein, the term "cell proliferative disorder" refers to conditions in which the unregulated and/or abnormal growth of cells can lead to the development of an unwanted condition or disease, which can be cancerous or non-cancerous, for example a psoriatic condition. As used herein, the term "psoriatic condition" refers to disorders involving keratinocyte hyperproliferation, inflammatory cell infiltration, and cytokine alteration. The cell proliferative disorder can be a precancerous condition or cancer. The cancer can be primary cancer or metastatic cancer, or both.

As used herein, the term "cancer" includes solid tumors, such as lung, breast, colon, ovarian, pancreas, prostate, adenocarcinoma, squamous carcinoma, sarcoma, malignant glioma, leiomyosarcoma, hepatoma, head and neck cancer, malignant melanoma, non-melanoma skin cancers, as well as hematologic tumors and/or malignancies, such as leukemia, childhood leukemia and lymphomas, multiple myeloma, Hodgkin's disease, lymphomas of lymphocytic and cutaneous origin, acute and chronic leukemia such as acute lymphoblastic, acute myelocytic or chronic myelocytic leukemia, plasma cell neoplasm, lymphoid neoplasm and cancers associated with AIDS.

In addition to psoriatic conditions, the types of proliferative diseases which may be treated using the compositions of the present invention are epidermic and dermoid cysts, lipomas, adenomas, capillary and cutaneous hemangiomas, lymphangiomas, nevi lesions, teratomas, nephromas, myofibromatosis, osteoplastic tumors, and other dysplastic masses and the like. In one embodiment, proliferative diseases include dysplasias and disorders of the like.

In one embodiment, the treating cancer comprises a reduction in tumor size, decrease in tumor number, a delay of tumor growth, decrease in metastaic lesions in other tissues or organs distant from the primary tumor site, an improvement in the survival of patients, or an improvement in the quality of patient life, or at least two of the above.

In another embodiment, the treating a cell proliferative disorder comprises a reduction in the rate of cellular proliferation, reduction in the proportion of proliferating cells, a decrease in size of an area or zone of cellular proliferation, or a decrease in the number or proportion of cells having an abnormal appearance or morphology, or at least two of the above.

In yet another embodiment, the compounds of the present invention or a pharmaceutically acceptable salt thereof, a prodrug thereof, or metabolite thereof, can be administered in combination with a second chemotherapeutic agent. In a further embodiment, the second chemotherapeutic agent is selected from the group consisting of tamoxifen, raloxifene, anastrozole, exemestane, letrozole, cisplatin, carboplatin, paclitaxel, cyclophosphamide, lovastatin, minosine, gemcitabine, araC, 5-fluorouracil, methotrexate, docetaxel, goserelin, vincristin, vinblastin, nocodazole, teniposide, etoposide, epothilone, navelbine, camptothecin, daunonibicin, dactinomycin, mitoxantrone, amsacrine, doxorubicin, epirubicin, idarubicin imatanib, gefitinib, erlotinib, sorafenib, sunitinib malate, trastuzumab, rituximab, cetuximab, and bevacizumab.

In one embodiment, the compounds of the present invention or a pharmaceutically acceptable salt thereof, a prodrug thereof, or metabolite thereof, can be administered in combination with an agent that imposes nitrosative or oxidative stress. Agents for selectively imposing nitrosative stress to inhibit proliferation of pathologically proliferating cells in combination therapy with GSNOR inhibitors herein and dosages and routes of administration therefor include those disclosed in U.S. Pat. No. 6,057,367, which is incorporated herein. Supplemental agents for imposing oxidative stress (i.e., agents that increase GSSG (oxidized glutathione) over GSH (glutathione) ratio or NAD(P) over NAD(P)H ratio or increase thiobarbituric acid derivatives) in combination therapy with GS-FDH inhibitors herein include, for example, L-buthionine-S-sulfoximine (BSO), glutathione reductase inhibitors (e.g., BCNU), inhibitors or uncouplers of mitochondrial respiration and drugs that increase reactive oxygen species (ROS), e.g., adriamycin, in standard dosages with standard routes of administration.

GSNOR inhibitors may also be co-administered with a phosphodiesterase inhibitor (e.g., rolipram, cilomilast, roflumilast, Viagra® (sildenifil citrate), Cialis® (tadalafil), Levitra® (vardenifil), etc.), a β-agonist, a steroid, or a leukotriene antagonist (LTD-4). Those skilled in the art can readily determine the appropriate therapeutically effective amount depending on the disorder to be ameliorated.

GSNOR inhibitors may be used as a means to improve β-adrenergic signaling. In particular, inhibitors of GSNOR alone or in combination with β-agonists could be used to treat or protect against heart failure, or other vascular disorders such as hypertension and asthma. GSNOR inhibitors can also be used to modulate G protein coupled receptors (GPCRs) by potentiating Gs G-protein, leading to smooth muscle relaxation (e.g., airway and blood vessels), and by attenuating Gq G-protein, and thereby preventing smooth muscle contraction (e.g., in airway and blood vessels).

The therapeutically effective amount for the treatment of a subject afflicted with a disorder ameliorated by NO donor therapy is the GSNOR inhibiting amount in vivo that causes amelioration of the disorder being treated or protects against a risk associated with the disorder. For example, for asthma, a therapeutically effective amount is a bronchodilating effective amount; for cystic fibrosis, a therapeutically effective amount is an airway obstruction ameliorating effective amount; for ARDS, a therapeutically effective amount is a hypoxemia ameliorating effective amount; for heart disease, a therapeutically effective amount is an angina relieving or angiogenesis inducing effective amount; for hypertension, a therapeutically effective amount is a blood pressure reducing effective amount; for ischemic coronary disorders, a therapeutic amount is a blood flow increasing effective amount; for atherosclerosis, a therapeutically effective amount is an endothelial dysfunction reversing effective amount; for glaucoma, a therapeutic amount is an intraocular pressure reducing effective amount; for diseases characterized by angiogenesis, a therapeutically effective amount is an angiogenesis inhibiting effective amount; for disorders where there is risk of thrombosis occurring, a therapeutically effective amount is a thrombosis preventing effective amount; for disorders where there is risk of restenosis occurring, a therapeutically effective amount is a restenosis inhibiting effective amount; for chronic inflammatory diseases, a therapeutically effective amount is an inflammation reducing effective amount; for disorders where there is risk of apoptosis occurring, a therapeutically effective amount is an apoptosis preventing effective amount; for impotence, a therapeutically effective is an erection attaining or sustaining effective amount; for obesity, a therapeutically effective amount is a satiety causing effective amount; for stroke, a therapeutically effective amount is a blood flow increasing or a TIA protecting effective amount; for reperfusion injury, a therapeutically effective amount is a function increasing effective amount; and for preconditioning of heart and brain, a therapeutically effective amount is a cell protective effective amount, e.g., as measured by triponin or CPK.

The therapeutically effective amount for the treatment of a subject afflicted with pathologically proliferating cells means a GSNOR inhibiting amount in vivo which is an antiproliferative effective amount. Such antiproliferative effective amount as used herein means an amount causing reduction in rate of proliferation of at least about 20%, at least about 10%, at least about 5%, or at least about 1%.

I. Uses in an Apparatus

The compounds of the present invention or a pharmaceutically acceptable salt thereof, or a prodrug or metabolite thereof, can be applied to various apparatus in circumstances when the presence of such compounds would be beneficial. Such apparatus can be any device or container, for example, implantable devices in which a compound of the invention can be used to coat a surgical mesh or cardiovascular stent prior to implantation in a patient. The compounds of the invention can also be applied to various apparatus for in vitro assay purposes or for culturing cells.

The compounds of the present invention or a pharmaceutically acceptable salt thereof, or a prodrug or metabolite thereof, can also be used as an agent for the development, isolation or purification of binding partners to compounds of the invention, such as antibodies, natural ligands, and the like. Those skilled in the art can readily determine related uses for the compounds of the present invention.

EXAMPLES

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

Examples 1-177 list representative novel dihydropyrimidin-2(1H)-one analogs of Formula I useful as GSNOR inhibitors of the invention. The synthetic methods that can be used to prepare each compound are detailed in Examples 1-177. Corresponding Intermediates are detailed in Example 178.

A general scheme for preparing dihydropyrimidin-2(1H)-one analogs is shown here.

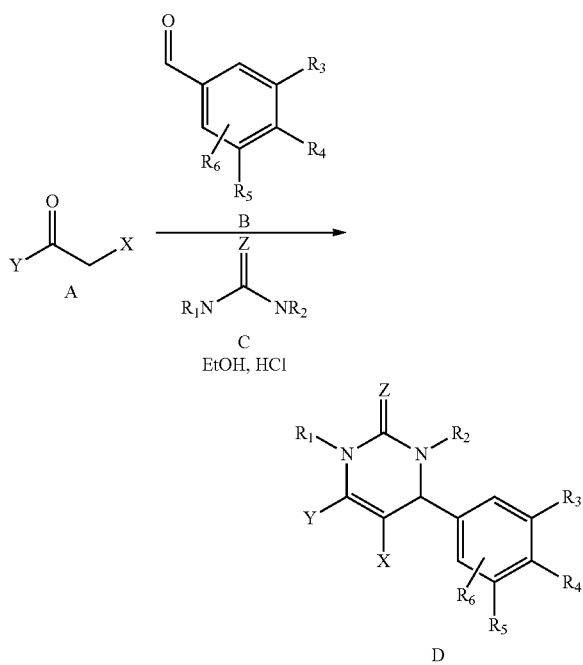

The di-cyclic ethanone (A) is combined with the aldehyde (B) and the urea (or thiourea or guanidine) (C), in EtOH with concentrated HCl. The reaction is refluxed for 1-5 days. Typically the crude is purified by column chromatography (silica gel) or reverse phase prep HPLC to give the desired dihydropyrimidin-2(1H)-one compound (D). In some cases, the di-cyclic ethanone or the aldehyde is not commercially available. In these cases, the synthesis of the intermediates is described in Example 178. Supporting mass spectrometry data and proton NMR data for each compound is also included in Examples 1-177. Optical rotation data is included when available for enantiomer pairs.

Example 1

Compound 1, 4-(3-ethoxy-4-hydroxy-5-nitrophenyl)-5,6-diphenyl-3,4-dihydropyrimidin-2(1H)-one

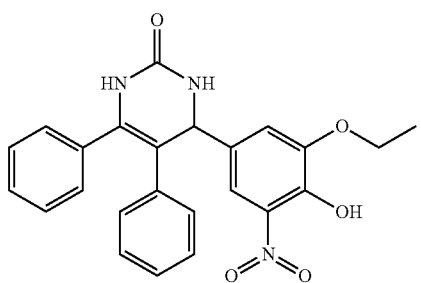 [SMILES: CCOc1cc(C2NC(=O)NC(c3ccccc3)=C2c2ccccc2)cc([N+](=O)[O-])c1O]

To a mixture of compound 1,2-diphenylethanone (557 mg, 2.8 mmol), 3-ethoxy-4-hydroxy-5-nitrobenzaldehyde (500 mg, 2.4 mmol), and urea (427 mg, 7.1 mmol) in EtOH (50 mL) was added concentrated HCl (0.24 mL), and the reaction mixture was heated at reflux for three days. TLC (EtOAc:MeOH=10:1) showed that the starting materials were consumed. The reaction mixture was concentrated and purified by column chromatography (EtOAc:MeOH=30:1) to afford Compound 1 as a yellow solid (500 mg, yield: 49.0%). $^1$H NMR (DMSO-$d_6$ 400 MHz): δ 10.25 (s, 1H), 8.70 (s, 1H), 7.50 (s, 1H), 7.42 (d, J=2.0 Hz, 1H), 7.15-7.25 (m, 6H), 6.95-7.05 (m, 3H), 6.80 (d, J=6.4 Hz, 2H), 5.15 (d, J=2.8 Hz, 1H), 4.05 (m, 2H), 1.30 (t, J=6.8 Hz, 3H); MS (ESI): m/z 432.2 [M+1]$^+$.

Example 2

Compound 2, (S)-4-(3-ethoxy-4-hydroxy-5-nitrophenyl)-5,6-diphenyl-3,4-dihydropyrimidin-2(1H)-one (Single Enantiomer of Compound 1)

1.6 g of Compound 1 (racemic) was separated by chiral supercritical chromatography (SFC separation condition: Column: OD-10 UM, 250*20 mm, 10 UM, Mobile phase: Supercritical Fluid $CO_2$=50:50, 70 mL/MIN, Detector Wavelength: 220 nm), and the eluting solution for the first peak was collected and evaporated to give one enantiomer as Compound 2 (500 mg, 62.5% separation yield). $^1$H NMR (DMSO-$d_6$ 400 MHz): δ 10.30 (s, 1H), 8.72 (s, 1H), 7.54 (s, 1H), 7.46 (s, 1H), 7.20-7.27 (m, 6H), 7.02-7.06 (m, 3H), 6.80 (d, J=7.5 Hz, 2H), 5.20 (s, 1H), 4.04-4.12 (m, 2H), 1.32-1.36 (m, 3H); MS (ESI): m/z 432.1 [M+1]$^+$; $[\alpha]^{20}_D$=−0.128 (c=0.0103 g/mL, MeOH).

Example 3

Compound 3, (R)-4-(3-ethoxy-4-hydroxy-5-nitrophenyl)-5,6-diphenyl-3,4-dihydropyrimidin-2(1H)-one (Single Enantiomer of Compound 1)

1.6 g of Compound 1 (racemic) was separated by chiral supercritical chromatography (SFC separation condition: Column: OD-10 UM, 250*20 mm, 10 UM, Mobile phase: Supercritical Fluid $CO_2$=50:50, 70 mL/MIN, Detector Wavelength: 220 nm), the eluting solution for the second peak was collected and evaporated to give another enantiomer as Compound 3 (500 mg, 62.5% separation yield). $^1$H NMR (DMSO-$d_6$ 400 MHz): δ 10.30 (s, 1H), 8.72 (s, 1H), 7.54 (s, 1H), 7.46 (s, 1H), 7.20-7.27 (m, 6H), 7.02-7.06 (m, 3H), 6.80 (d, J=7.5 Hz, 2H), 5.20 (s, 1H), 4.04-4.12 (m, 2H), 1.32-1.36 (m, 3H); MS (ESI): m/z 432.1 [M+1]$^+$; $[\alpha]^{20}_D$=+0.134 (c=0.01047 g/mL, MeOH).

Example 4

Compound 4, 4-(3-ethoxy-4-hydroxy-5-nitrophenyl)-6-phenyl-5-(thiophen-2-yl)-3,4-dihydropyrimidin-2(1H)-one

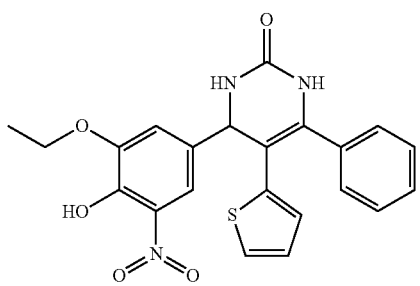 [SMILES: CCOc1cc(C2NC(=O)NC(c3ccccc3)=C2c2cccs2)cc([N+](=O)[O-])c1O]

A mixture of 1-phenyl-2-(thiophen-2-yl)ethanone (Intermediate 1, see Example 178 for synthesis of all Intermediates) (200 mg, 0.99 mmol), 3-ethoxy-4-hydroxy-5-nitrobenzaldehyde (200 mg, 0.94 mmol), and urea (175 mg, 2.82 mmol) in anhydrous EtOH (20 mL) was added concentrated HCl solution (0.1 mL), and the reaction mixture was refluxed for three days. When TLC (EtOAc:MeOH=10:1) showed that about 50% of starting materials were consumed, the reaction mixture was concentrated, and the crude product was purified by column chromatography (EtOAc:MeOH=40:1) and preparative HPLC to afford Compound 4 as a yellow solid (27 mg, yield 6.2%). $^1$H NMR (DMSO-$d_6$ 400 MHz): δ 10.30 (s, 1H), 8.89 (s, 1H), 7.65 (s, 1H), 7.53 (s, 1H), 7.40 (s, 3H), 7.34 (s, 3H), 7.10 (d, J=5.2 Hz, 1H), 6.71-6.73 (m, 1H), 6.56 (s, 1H), 5.24 (s, 1H), 4.10 (q, J=7.2 Hz, 2H); 1.37 (t, J=7.2 Hz, 3H); MS (ESI): m/z 438.2 [M+1]$^+$.

Example 5

Compound 5, 4-(3-ethoxy-4-hydroxy-5-nitrophenyl)-6-phenyl-5-(thiophen-3-yl)-3,4-dihydropyrimidin-2(1H)-one

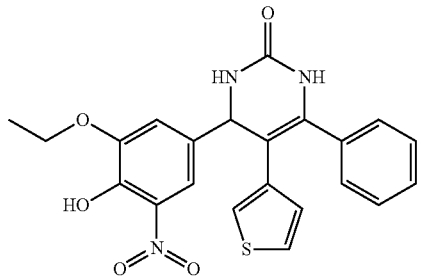 [SMILES: CCOc1cc(C2NC(=O)NC(c3ccccc3)=C2c2ccsc2)cc([N+](=O)[O-])c1O]

A mixture of 1-phenyl-2-(thiophen-3-yl)ethanone (Intermediate 2) (100 mg, 0.50 mmol), 3-ethoxy-4-hydroxy-5-nitrobenzaldehyde (100 mg, 0.47 mmol), and urea (90 mg, 1.4 mmol) in anhydrous EtOH (10 mL) was added concentrated HCl solution (0.1 mL), and the reaction mixture was refluxed for three days. When TLC (EtOAc:MeOH=10:1) showed that about 50% of starting materials were consumed, the reaction mixture was concentrated and purified by column chromatography (EtOAc:MeOH=40:1) and preparative HPLC to afford Compound 5 as a yellow solid (51 mg, yield 24.8%). $^1$H NMR (DMSO-$d_6$ 400 MHz TMS): δ 10.30 (s, 1H), 8.73 (s, 1H), 7.57 (s, 1H), 7.51 (s, 1H), 7.37 (s, 3H), 7.29 (s, 3H), 7.16 (s, 1H), 6.86 (s, 1H), 6.23 (d, J=4.8 Hz, 1H), 5.21 (s, 1H), 4.10 (q, J=7.2 Hz, 2H); 1.37 (t, J=7.2 Hz, 3H); MS (ESI): m/z 438.1 [M+1]$^+$.

Example 6

Compound 6, (S)-4-(3-ethoxy-4-hydroxy-5-nitrophenyl)-6-phenyl-5-(thiophen-3-yl)-3,4-dihydropyrimidin-2(1H)-one (Single Enantiomer of Compound 5)

The two enantiomers of Compound 5 (racemic) were separated by chiral supercritical fluid chromatography (SFC separation condition: Column: AD-SUM, 150*300 mm, SUM, Mobile phase:Supercritical Fluid $CO_2$:IPA (0.25% DEA)= 70:30, 60 mL/MIN, Detector Wavelength: 220 nm), and the eluting solution for the first peak was collected and evaporated to afford one enantiomer as Compound 6 (235 mg, yield 10.8%). $^1$H NMR (DMSO-$d_6$ 400 MHz): δ 10.30 (s, 1H), 8.73 (s, 1H), 7.57 (s, 1H), 7.51 (s, 1H), 7.37 (s, 3H), 7.29 (s, 3H), 7.16 (s, 1H), 6.86 (s, 1H), 6.23 (d, J=4.8 Hz, 1H), 5.21 (s, 1H), 4.10 (q, J=7.2 Hz, 2H); 1.37 (t, J=7.2 Hz, 3H); MS (ESI): m/z 438.1 [M+1]$^+$; $[α]^{20}_D$=−0.606 (c=0.0095 g/mL, MeOH).

Example 7

Compound 7, (R)-4-(3-ethoxy-4-hydroxy-5-nitrophenyl)-6-phenyl-5-(thiophen-3-yl)-3,4-dihydropyrimidin-2(1H)-one (Single Enantiomer of Compound 5)

The two enantiomers of Compound 5 (racemic) were separated by chiral supercritical fluid chromatography (SFC separation condition: Column: AD-SUM, 150*300 mm, SUM, Mobile phase: Supercritical Fluid $CO_2$:IPA (0.25% DEA)= 70:30, 60 mL/MIN, Detector Wavelength: 220 nm), the eluting solution for the second peak was collected and evaporated to afford another enantiomer as Compound 7 (265 mg, yield, 12.17%). $^1$H NMR (DMSO-$d_6$ 400 MHz): δ 10.30 (s, 1H), 8.73 (s, 1H), 7.57 (s, 1H), 7.51 (s, 1H), 7.37 (s, 3H), 7.29 (s, 3H), 7.16 (s, 1H), 6.86 (s, 1H), 6.23 (d, J=4.8 Hz, 1H), 5.21 (s, 1H), 4.10 (q, J=7.2 Hz, 2H); 1.37 (t, J=7.2 Hz, 3H); MS (ESI): m/z 438.1 [M+1]$^+$; $[α]^{20}_D$=+0.346 (c=0.0098 g/mL, MeOH).

Example 8

Compound 8, 4-(3-ethoxy-4-hydroxy-5-nitrophenyl)-5,6-diphenyl-3,4-dihydropyrimidine-2(1H)-thione

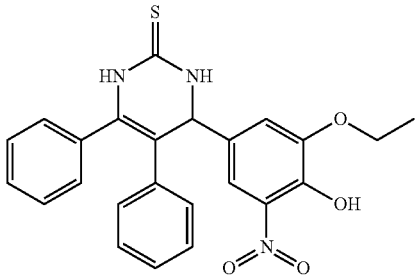

A mixture of 3-ethoxy-4-hydroxy-5-nitrobenzaldehyde (323 mg, 1.53 mmol), 1,2-diphenylethanone (300 mg, 1.53 mmol), thiourea (349.16 mg, 4.59 mmol), concentrated HCl solution (0.8 mL) in ethanol (10 mL) was refluxed at 78° C. for 76 h. After being cooled down to room temperature, the mixture was evaporated under reduced pressure, and the residue was purified by preparative HPLC to give Compound 8 (20 mg, yield 2.9%). 1H NMR ($CD_3CN$): δ 7.68 (s, 1H), 7.65 (s, 1H), 7.31 (m, 4H), 7.21 (s, 1H), 7.09 (m, 3H), 6.94 (m, 2H), 5.34 (s, 1H), 4.11 (q, J=7.2 Hz, 2H), 1.43-1.40 (t, J=7.2 Hz, 3H); MS (ESI): m/z 447.9 [M+1]$^+$.

Example 9

Compound 9, 4-(4-hydroxy-3-methoxy-5-nitrophenyl)-5,6-diphenyl-3,4-dihydropyrimidin-2(1H)-one

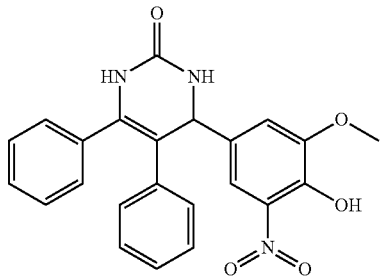 [SMILES: COc1cc(C2NC(=O)NC(c3ccccc3)=C2c2ccccc2)cc([N+](=O)[O-])c1O]

A mixture of 1,2-diphenylethanone (300 mg, 1.53 mmol), 4-hydroxy-3-methoxy-5-nitrobenzaldehyde (301 mg, 1.53 mmol), urea (275 mg, 4.587 mmol), and concentrated HCl (0.3 mL) in ethanol (10 mL) was refluxed for 80 h. After being cooled down to room temperature, the mixture was evaporated. The residue was purified by HPLC to give Compound 9 (262 mg, yield 41.1%). $^1$H NMR (DMSO-$d_6$ 400 MHz): δ 10.45 (s, 1H), 8.73 (s, 1H), 7.54 (s, 1H), 7.46 (s, 1H), 7.27-7.25 (m, 3H), 7.23-7.21 (m, 3H), 7.06-7.00 (m, 3H), 6.83 (d, J=6.8 Hz, 2H), 5.2 (d, J=2.4 Hz, 1H), 3.80 (s, 3H); MS (ESI): m/z 417.9 [M+1]$^+$.

Example 10

Compound 10, 4-(3,4-dihydroxy-5-nitrophenyl)-5,6-diphenyl-3,4-dihydropyrimidin-2(1H)-one

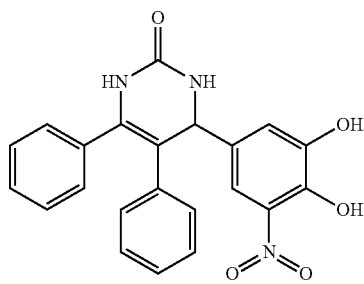 [SMILES: O=C1NC(c2ccccc2)=C(c2ccccc2)C(c2cc(O)c(O)c([N+](=O)[O-])c2)N1]

To a mixture of 3,4-dihydroxy-5-nitrobenzaldehyde (196 mg, 1.0 mmol), 1,2-diphenylethanone (183 mg, 1.0 mmol) and urea (180 mg, 3.0 mmol) in ethanol (50 mL) was added concentrated HCl (0.2 mL) and the reaction solution was heated to reflux for three days. The reaction solution was concentrated in vacuo and purified by silica gel column chromatography (DCM:THF=20:1) to afford Compound 10 as a yellow solid (49.7 mg, 12.3%). $^1$H NMR (DMSO-$d_6$ 500 MHz): δ 10.23 (br, 1H), 8.72 (s, 1H), 7.51 (s, 1H), 7.20-7.28 (m, 7H), 6.81-7.04 (m, 3H), 6.80 (d, J=6.5 Hz, 2H), 5.08 (s, 1H); MS (ESI): m/z 404 [M+1]$^+$.

Example 11

Compound 11, 4-(3-ethoxy-4-hydroxy-5-nitrophenyl)-1-methyl-5,6-diphenyl-3,4-dihydropyrimidin-2(1H)-one

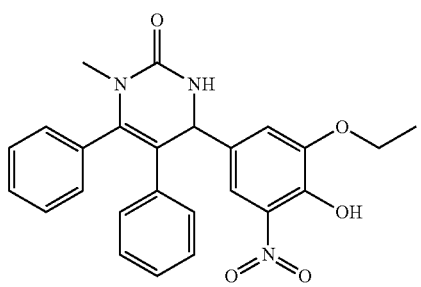 [SMILES: CCOc1cc(C2NC(=O)N(C)C(c3ccccc3)=C2c2ccccc2)cc([N+](=O)[O-])c1O]

A mixture of 1,2-diphenylethanone (400 mg, 2.04 mmol), 3-ethoxy-4-hydroxy-5-nitrobenzaldehyde (430 mg, 2.04 mmol), and 1-methylurea (454 mg, 6.12 mmol) in anhydrous EtOH was added concentrated HCl (204 mg, 2.04 mmol), and the reaction mixture was refluxed for 3 days. When TLC (EtOAc:MeOH=10:1) showed that the starting materials were consumed, the reaction mixture was concentrated, and purified by preparative HPLC to afford Compound 11 as a yellow solid (138 mg, yield: 15.2%). $^1$H NMR (DMSO-$d_6$ 400 MHz TMS): δ 10.25 (s, 1H), 7.68 (d, J=2.8 Hz, 1H), 7.45 (s, 1H), 7.20-7.28 (m, 3H), 7.15-7.20 (m, 3H), 6.85-6.95 (m, 3H), 6.70 (d, J=6.4 Hz, 1H), 5.00 (d, J=2.4 Hz, 1H), 4.02 (m, 2H), 2.60 (s, 3H), 1.30 (t, J=7.0 Hz, 3H); MS (ESI): m/z 446.2 [M+1]$^+$.

Example 12

Compound 12, 4-(3-ethoxy-4-hydroxy-5-nitrophenyl)-6-phenyl-5-(thiazol-2-yl)-3,4-dihydropyrimidin-2(1H)-one

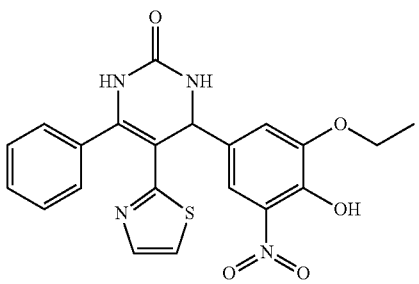 [SMILES: CCOc1cc(C2NC(=O)NC(c3ccccc3)=C2c2nccs2)cc([N+](=O)[O-])c1O]

To a mixture of 1-phenyl-2-(thiazol-2-yl)ethanone (Intermediate 3) (170 mg, 0.84 mmol), 3-ethoxy-4-hydroxy-5-nitrobenzaldehyde (212 mg, 1.00 mmol), and urea (151 mg, 2.52 mmol) in anhydrous EtOH (20 mL) was added concentrated HCl solution (0.1 mL), and the reaction mixture was refluxed for three days. When TLC (EtOAc:MeOH=10:1) showed that about 30% of the starting materials were consumed, the reaction mixture was concentrated, and the crude product was purified by column chromatography and preparative HPLC to afford Compound 12 as a yellow solid (12.5 mg, yield: 3.4%). $^1$H NMR (DMSO-$d_6$ 400 MHz TMS): δ 10.25 (s, 1H), 9.25 (s, 1H), 7.82 (s, 1H), 7.50-7.56 (m, 4H), 7.48 (s, 1H), 7.36-7.40 (m, 3H), 7.22 (d, J=3.6 Hz, 1H), 5.68 (d, J=3.6 Hz, 1H), 4.10 (q, J=6.0 Hz, 2H), 1.35 (t, J=7.2 Hz, 3H); MS (ESI): m/z 439.1 [M+1]$^+$.

Example 13

Compound 13, 4-(3-ethoxy-4-hydroxy-5-nitrophenyl)-5-(2-fluorophenyl)-6-phenyl-3,4-dihydropyrimidin-2(1H)-one

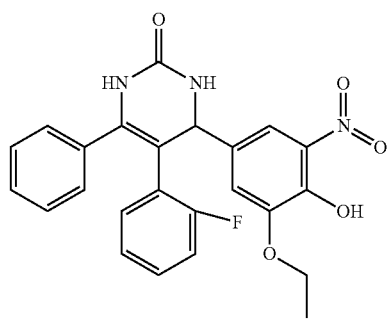 [SMILES: CCOc1cc(C2NC(=O)NC(c3ccccc3)=C2c2ccccc2F)cc([N+](=O)[O-])c1O]

To a solution of 2-(2-fluorophenyl)-1-phenylethanone (200 mg, 0.93 mmol), 3-ethoxy-4-hydroxy-5-nitrobenzaldehyde (196 mg, 0.93 mmol) and urea (846 mg, 1.4 mmol) in 20 mL of ethanol was added 0.2 mL of concentrated HCl, the mixture was stirred at reflux for 2 days. After the solvent was removed under reduced pressure, the residue was purified by reverse-phase preparatory HPLC (26-53% acetonitrile+0.1% trifluoroacetic acid in water+0.1% trifluoroacetic acid, over 15 min.) to give Compound 13 (100 mg, yield 23.8%). $^1$H NMR (DMSO-$d_6$ 400 MHz): δ 10.26 (s, 1H), 8.81 (s, 1H), 7.53 (s, 1H), 7.35 (d, J=1.6 Hz, 1H), 7.22-6.87 (m, 7H), 5.22 (s, 1H), 4.00 (m, 2H), 1.31 (t, J=7.2 Hz, 3H); MS (ESI): m/z 450.2 [M+1]$^+$.

Example 14

Compound 14, 4-(3-ethoxy-4-hydroxy-5-nitrophenyl)-6-phenyl-5-p-tolyl-3,4-dihydropyrimidin-2(1H)-one

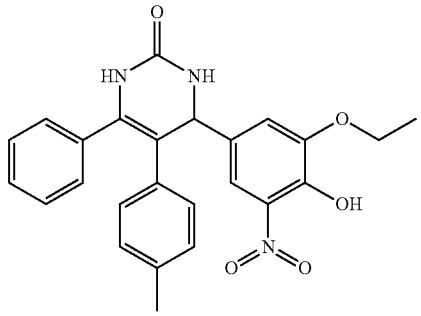 [SMILES: CCOc1cc(C2NC(=O)NC(c3ccccc3)=C2c2ccc(C)cc2)cc([N+](=O)[O-])c1O]

To a solution of 1-phenyl-2-p-tolylethanone (70 mg, 0.33 mmol), 3-ethoxy-4-hydroxy-5-nitrobenzaldehyde (65 mg, 0.33 mmol) and urea (60 mg, 1.0 mmol) in 20 mL of ethanol was added 0.2 mL of concentrated HCl, the mixture was stirred at reflux for 2 days. After the solvent was removed under reduced pressure, the residue was purified by reverse-phase preparatory HPLC (26-53% acetonitrile+0.1% trifluoroacetic acid in water+0.1% trifluoroacetic acid, over 15 min.) to give Compound 14 (21 mg, yield 14.9%). $^1$H NMR (DMSO-$d_6$ 400 MHz TMS): δ 10.30 (s, 1H), 8.67 (s, 1H), 7.52 (s, 1H), 7.44 (s, 1H), 7.26-7.19 (m, 6H), 6.85-6.70 (m, 4H), 5.16 (s, 1H), 4.05 (s, 2H), 2.12 (s, 3H), 1.33 (t, J=6.4 Hz, 3H); MS (ESI): m/z 446.0 [M+1]$^+$.

Example 15

Compound 15, 4-(3-ethoxy-4-hydroxy-5-nitrophenyl)-6-(3-methoxyphenyl)-5-phenyl-3,4-dihydropyrimidin-2(1H)-one

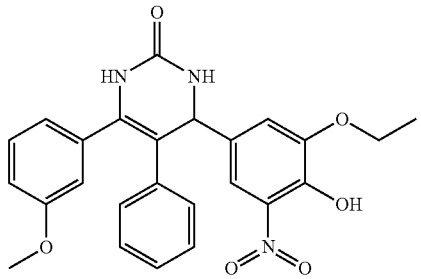

A mixture of 1-(3-methoxyphenyl)-2-phenylethanone (100 mg, 0.44 mmol), 3-ethoxy-4-hydroxy-5-nitrobenzaldehyde (72 mg, 0.34 mmol), urea (80 mg, 1.33 mmol), and concentrated HCl solution (0.04 mL, 0.44 mmol) in EtOH (5 mL) was refluxed overnight. The mixture was evaporated in vacuo and the residue was purified by preparative HPLC to give Compound 15 (42.57 mg, yield 21%). $^1$H NMR (DMSO-$d_6$ 400 MHz): δ 10.29 (s, 1H), 8.72 (s, 1H), 7.54 (s, 1H), 7.44 (s, 1H), 7.18-7.12 (m, 2H), 7.08-7.02 (m, 3H), 6.86-6.81 (m, 3H), 6.77-6.74 (m, 2H), 5.20 (d, J=2.8 Hz, 1H), 4.05 (q, J=6.8 Hz, 2H), 3.63 (s, 3H), 1.33 (t, J=6.8 Hz, 3H); MS (ESI): m/z 462.1 [M+1]$^+$.

Example 16

Compound 16, 4-(3-ethoxy-4-hydroxy-5-nitrophenyl)-5-phenyl-6-p-tolyl-3,4-dihydropyrimidin-2(1H)-one

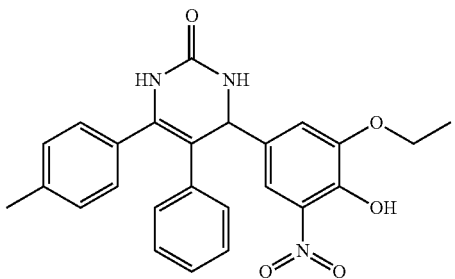 [SMILES: CCOc1cc(C2NC(=O)NC(c3ccc(C)cc3)=C2c2ccccc2)cc([N+](=O)[O-])c1O]

A mixture of 2-phenyl-1-p-tolylethanone (65 mg, 0.31 mmol), 3-ethoxy-4-hydroxy-5-nitrobenzaldehyde (54 mg, 0.26 mmol), urea (56 mg, 0.93 mmol), and concentrated HCl solution (0.03 mL, 0.31 mmol) in EtOH (5 mL) was refluxed overnight. The mixture was evaporated in vacuo and the residue was purified by preparative HPLC to give compound 16 (455.19 mg, yield 40%). $^1$H NMR (DMSO-$d_6$ 400 MHz): δ 10.28 (s, 1H), 8.64 (s, 1H), 7.51 (s, 1H), 7.42 (s, 1H), 7.17 (s, 1H), 7.08-6.96 (m, 7H), 6.80 (d, J=6.8 Hz, 2H), 5.14 (d, J=2.4 Hz, 1H), 4.05-3.98 (m, 2H), 2.23 (s, 3H), 1.31 (t, J=6.8 Hz, 3H); MS (ESI): m/z 446.2 [M+1]$^+$.

Example 17

Compound 17, 4-(3-ethoxy-4-hydroxy-5-nitrophenyl)-6-phenyl-5-m-tolyl-3,4-dihydropyrimidin-2(1H)-one

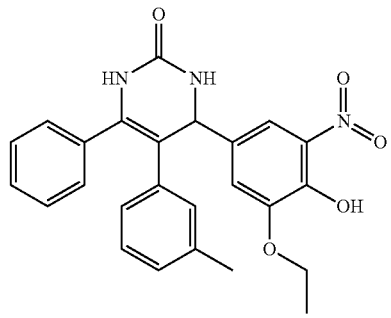 [SMILES: CCOc1cc(C2NC(=O)NC(c3ccccc3)=C2c2cccc(C)c2)cc([N+](=O)[O-])c1O]

To a solution of 1-phenyl-2-m-tolylethanone (Intermediate 4) (460 mg, 2.18 mmol), 3-ethoxy-4-hydroxy-5-nitrobenzaldehyde (460 mg, 2.18 mmol) and urea (300 mg, 6.54 mmol) in 20 mL of ethanol was added 0.2 mL of concentrated HCl, the mixture was stirred at reflux for 4 days. After the solvent was removed under reduced pressure, the residue was purified by HPLC (38-68% acetonitrile+0.1% trifluoroacetic acid in water, over 15 min.) and thin layer chromatography (PE: EtOAc=1:2) to give Compound 17 (25 mg, yield 2.6%). $^1$H NMR (CD$_3$OD 400 MHz): δ 7.62 (s, 1H), 7.27 (s, 5H), 7.18 (d, J=1.6 Hz, 1H), 6.95 (t, J=7.6 Hz, 1H), 6.88 (d, J=7.6 Hz, 1H), 6.74 (s, 1H), 6.67 (d, J=7.6 Hz, 1H), 5.36 (s, 1H), 4.07 (m, 2H), 2.10 (s, 3H), 1.41 (t, J=6.8 Hz, 3H); MS (ESI): m/z 446.2 [M+1]$^+$.

Example 18

Compound 18, 5-(biphenyl-4-yl)-4-(3-ethoxy-4-hydroxy-5-nitrophenyl)-6-phenyl-3,4-dihydropyrimidin-2(1H)-one

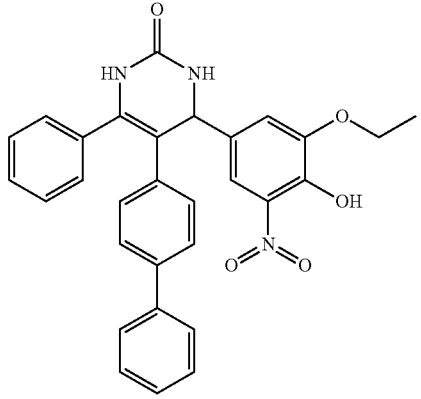 [SMILES: CCOc1cc(C2NC(=O)NC(c3ccccc3)=C2c2ccc(-c3ccccc3)cc2)cc([N+](=O)[O-])c1O]

To a solution of 2-(biphenyl-4-yl)-1-phenylethanone (Intermediate 5) (430 mg, 1.57 mmol), 3-ethoxy-4-hydroxy-5-nitrobenzaldehyde (333 mg, 1.57 mmol), and urea (217 mg, 4.71 mmol) in 20 mL of ethanol was added 0.2 mL of concentrated HCl, the mixture was stirred at reflux for 4 days. After the solvent was removed under reduced pressure, the residue was purified by column chromatography on silica gel (PE:EtOAc=3:1-0:1) and thin layer chromatography (PE:EtOAc=1:2) to give Compound 18 (23 mg, yield 2.9%). $^1$H NMR (CD$_3$OD 400 MHz TMS): δ 7.61 (d, J=2.0 Hz, 1H), 7.49 (d, J=7.2 Hz, 2H), 7.38-7.27 (m, 10H), 7.02 (s, 1H), 6.98 (d, J=8.0 Hz, 2H), 5.23 (s, 1H), 4.02-3.99 (m, 2H), 1.38 (t, J=6.8 Hz, 3H); MS (ESI): m/z 508.2 [M+1]$^+$.

Example 19

Compound 19, 4-(3-ethoxy-4-hydroxy-5-nitrophenyl)-5-(4-methoxyphenyl)-6-phenyl-3,4-dihydropyrimidin-2(1H)-one

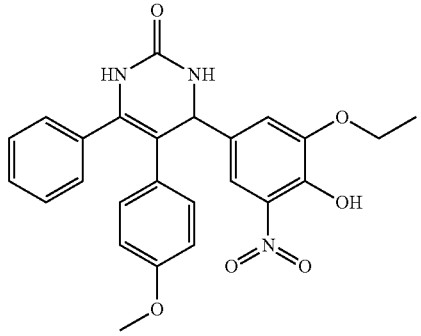 [SMILES: CCOc1cc(C2NC(=O)NC(c3ccccc3)=C2c2ccc(OC)cc2)cc([N+](=O)[O-])c1O]

To a solution of 2-(4-methoxyphenyl)-1-phenylethanone (100 mg, 0.44 mmol), 3-ethoxy-4-hydroxy-5-nitrobenzaldehyde (93 mg, 0.44 mmol), and urea (60 mg, 1.32 mmol) in 20 mL of ethanol was added 0.2 mL of concentrated HCl, the mixture was stirred at reflux for 4 days. After the solvent was removed under reduced pressure, the residue was purified by thin layer chromatography (PE:EtOAc=1:2) to give Compound 19 (22 mg, yield 10.8%). $^1$H NMR (CD$_3$OD 400 MHz): δ 7.55 (s, 1H), 7.20 (s, 5H), 7.12 (s, 1H), 6.73 (d, J=8.4 Hz, 2H), 6.57 (d, J=8.8 Hz, 2H), 5.25 (s, 1H), 4.05-4.00 (m, 2H), 3.61 (s, 3H), 1.35 (t, J=6.8 Hz, 3H); MS (ESI): m/z 462.2 [M+1]$^+$.

Example 20

Compound 20, 4-(3-ethoxy-4-hydroxy-5-nitrophenyl)-6-(4-methoxyphenyl)-5-phenyl-3,4-dihydropyrimidin-2(1H)-one

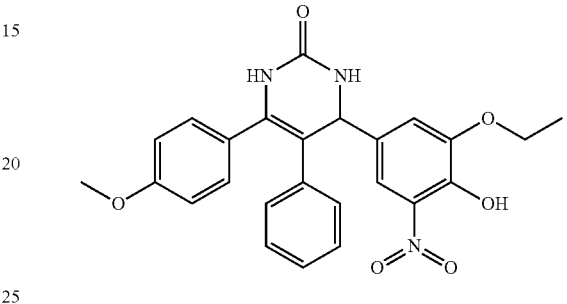

To a mixture of 1-(4-methoxyphenyl)-2-phenylethanone (200 mg, 0.88 mmol), 3-ethoxy-4-hydroxy-5-nitrobenzaldehyde (187 mg, 0.89 mmol), and urea (159 mg, 2.65 mmol) in anhydrous EtOH (20 mL) was added concentrated HCl solution (0.1 mL). The reaction mixture was refluxed for two days. When TLC (EtOAc:MeOH=10:1) showed that about 30% of the starting materials were consumed, the reaction mixture was concentrated. The residue was purified by column chromatography (EtOAc:MeOH=40:1) and preparative HPLC to afford Compound 20 as a yellow solid (30 mg, yield: 7.5%). $^1$H NMR (DMSO-d$_6$ 300 MHz): δ 10.30 (s, 1H), 8.65 (s, 1H), 7.52 (s, 1H), 7.45 (s, 1H), 7.20 (s, 1H), 7.09-7.15 (m, 2H), 6.96-7.08 (m, 3H), 6.75-6.82 (m, 4H), 5.12 (s, 1H), 4.00-4.10 (m, 2H), 3.70 (s, 3H), 1.34 (t, J=6.9 Hz, 3H); MS (ESI): m/z 462.0 [M+1]$^+$.

Example 21

Compound 21, 5-(3-chlorophenyl)-4-(3-ethoxy-4-hydroxy-5-nitrophenyl)-6-phenyl-3,4-dihydropyrimidin-2(1H)-one

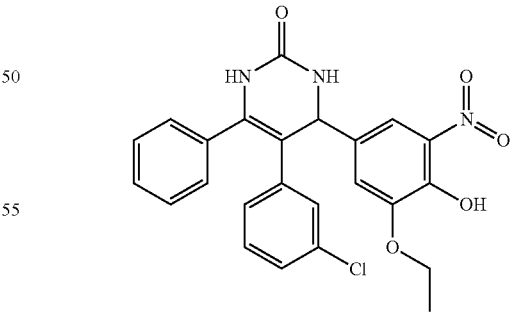

To a mixture of 2-(3-chlorophenyl)-1-phenylethanone (200 mg, 0.88 mmol), 3-ethoxy-4-hydroxy-5-nitrobenzaldehyde (220 mg, 1.04 mmol), and urea (159 mg, 2.65 mmol) in anhydrous EtOH (20 mL) was added concentrated HCl solution (0.1 mL), and the reaction mixture was refluxed for three days. When TLC (EtOAc:MeOH=10:1) showed that about 50% of starting materials were consumed, the reaction mixture was concentrated and purified by column chromatography (EtOAc:MeOH=40:1) and preparative HPLC to afford Compound 21 as a yellow solid (90 mg, yield 22.3%). $^1$H NMR (DMSO-d$_6$ 400 MHz): δ 10.30 (s, 1H), 8.81 (s, 1H), 7.60 (s, 1H), 7.45 (s, 1H), 7.25 (d, J=4.0 Hz, 3H), 7.15-7.25 (m, 3H), 7.03 (d, J=4.8 Hz, 2H), 6.71-6.81 (m, 2H), 5.25 (s, 1H), 4.00-4.10 (m, 2H), 1.33 (t, J=6.8 Hz, 3H); MS (ESI): m/z 466.0 [M+1]$^+$.

Example 22

Compound 22, 5-(3,4-dichlorophenyl)-4-(3-ethoxy-4-hydroxy-5-nitrophenyl)-6-phenyl-3,4-dihydropyrimidin-2(1H)-one

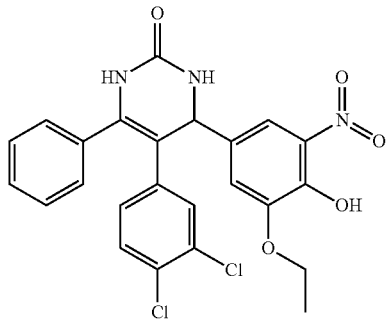 [SMILES: CCOc1cc(C2NC(=O)NC(c3ccccc3)=C2c2ccc(Cl)c(Cl)c2)cc([N+](=O)[O-])c1O]

To a solution of 2-(3,4-dichlorophenyl)-1-phenylethanone (Intermediate 6) (400 mg, 1.5 mmol), 3-ethoxy-4-hydroxy-5-nitrobenzaldehyde (317 mg, 1.5 mmol), and urea (207 mg, 4.5 mmol) in 20 mL of ethanol was added 0.2 mL of concentrated HCl, the mixture was stirred at reflux for 4 days. After the solvent was removed under reduced pressure, the residue was purified by HPLC (48-78% acetonitrile+0.1% trifluoroacetic acid in water, over 15 min.) and thin layer chromatography (PE:EtOAc=1:2) to give Compound 22 (17.8 mg, yield 2.4%). $^1$H NMR (CD$_3$OD 400 MHz): δ 7.64 (s, 1H), 7.35-7.31 (m, 5H), 7.23-7.19 (m, 2H), 7.03 (s, 1H), 6.79 (d, J=8.0 Hz, 1H), 5.37 (s, 1H), 4.12 (m, 2H), 1.43 (t, J=6.8 Hz, 3H); MS (ESI): m/z 500.2 [M+1]$^+$.

Example 23

Compound 23, 4-(3-ethoxy-4-hydroxy-5-nitrophenyl)-5-(3-methoxyphenyl)-6-phenyl-3,4-dihydropyrimidin-2(1H)-one

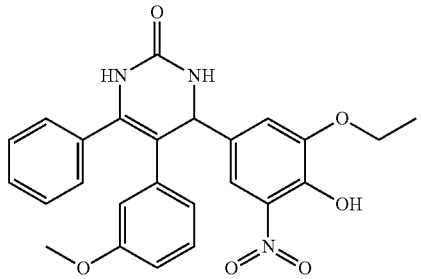 [SMILES: CCOc1cc(C2NC(=O)NC(c3ccccc3)=C2c2cccc(OC)c2)cc([N+](=O)[O-])c1O]

To a solution of 2-(3-methoxyphenyl)-1-phenylethanone (400 mg, 1.77 mmol), 3-ethoxy-4-hydroxy-5-nitrobenzaldehyde (374 mg, 1.77 mmol) and urea (244 mg, 5.31 mmol) in 20 mL of ethanol was added 0.2 mL of concentrated HCl, then the mixture was stirred at reflux for 4 days. After the solvent was removed under reduced pressure, the residue was purified by HPLC (35-65% acetonitrile+0.1% trifluoroacetic acid in water, over 15 min.) and then purified by thin layer chromatography (PE:EtOAc=1:2) further to give Compound 23 (20 mg, yield 2.5%). $^1$H NMR (CD$_3$OD 400 MHz): δ 7.43 (s, 1H), 7.17 (s, 5H), 6.86-6.82 (m, 2H), 6.48 (d, J=6.4 Hz, 1H), 6.40 (d, J=8.0 Hz, 1H), 6.30 (s, 1H), 5.03 (s, 1H), 3.91-3.89 (m, 2H), 3.37 (s, 3H), 1.30 (t, J=7.2 Hz, 3H); MS (ESI): m/z 462.3 [M+1]$^+$.

Example 24

Compound 24, 5-(3,4-dimethoxyphenyl)-4-(3-ethoxy-4-hydroxy-5-nitrophenyl)-6-phenyl-3,4-dihydropyrimidin-2(1H)-one

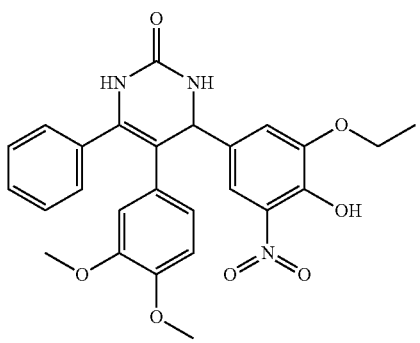 [SMILES: CCOc1cc(C2NC(=O)NC(c3ccccc3)=C2c2ccc(OC)c(OC)c2)cc([N+](=O)[O-])c1O]

To a solution of 2-(3,4-dimethoxyphenyl)-1-phenylethanone (Intermediate 7) (130 mg, 0.5 mmol), 3-ethoxy-4-hydroxy-5-nitrobenzaldehyde (106 mg, 0.5 mmol) and urea (69 mg, 1.5 mmol) in 20 mL of ethanol was added 0.2 mL of concentrated HCl, then the mixture was stirred at reflux for 4 days. After the solvent was removed under reduced pressure, the residue was purified by thin layer chromatography (PE:EtOAc=1:2) to give Compound 24 (24.3 mg, yield 9.8%). $^1$H NMR (CD$_3$OD 400 MHz): δ 7.62 (d, J=1.6 Hz, 1H), 7.30 (s, 5H), 7.17 (s, 1H), 6.68 (d, J=8.0 Hz, 1H), 6.51 (dd, J=2.0 Hz, 8.0 Hz, 1H), 6.38 (d, J=2.0 Hz, 1H), 5.30 (s, 1H), 4.09-4.06 (m, 2H), 3.71 (s, 3H), 3.41 (s, 3H), 1.40 (t, J=7.2 Hz, 3H); MS (ESI): m/z 492.3 [M+1]$^+$.

Example 25

Compound 25, 5-(4-bromophenyl)-4-(3-ethoxy-4-hydroxy-5-nitrophenyl)-6-phenyl-3,4-dihydropyrimidin-2(1H)-one

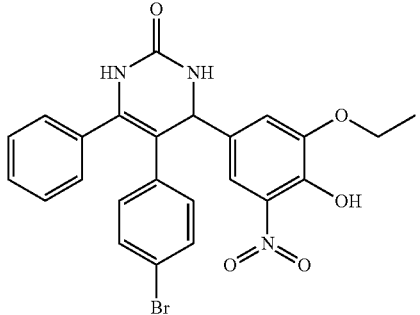

To a solution of 2-(4-bromophenyl)-1-phenylethanone (Intermediate 8) (140 mg, 0.5 mmol), 3-ethoxy-4-hydroxy-5-nitrobenzaldehyde (108 mg, 0.5 mmol), and urea (69 mg, 1.5 mmol) in 20 mL of ethanol was added 0.2 mL of concentrated HCl, the mixture was stirred at reflux for 3 days. After the solvent was removed under reduced pressure, the residue was purified by HPLC (46-76% acetonitrile+0.1% trifluoroacetic acid in water, over 15 min.) to give Compound 25 (43 mg, yield 16.5%). $^1$H NMR (CD$_3$OD 400 MHz): δ 7.52 (s, 1H), 7.20-7.17 (m, 5H), 7.11-7.08 (m, 3H), 6.69 (d, J=8.4 Hz, 2H), 5.23 (s, 1H), 3.40-3.95 (m, 2H), 1.30 (t, J=6.8 Hz, 3H); MS (ESI): m/z 510.2 [M+1]$^+$.

Example 26

Compound 26, 4-(3-ethoxy-4-hydroxy-5-nitrophenyl)-6-phenyl-5-o-tolyl-3,4-dihydropyrimidin-2(1H)-one

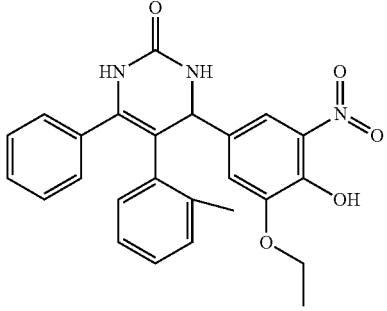 [SMILES: CCOc1cc(C2NC(=O)NC(c3ccccc3)=C2c2ccccc2C)cc([N+](=O)[O-])c1O]

To a solution of 1-phenyl-2-o-tolylethanone (Intermediate 9) (100 mg, 0.47 mmol), 3-ethoxy-4-hydroxy-5-nitrobenzaldehyde (93.8 mg, 0.47 mmol), and urea (84.7 mg, 1.41 mmol) in 20 mL of ethanol was added 0.2 ml con HCl solution. The mixture was stirred at reflux for 2 days. After the solvent was removed under reduced pressure, the residue was purified by reverse-phase preparatory HPLC (26-53% acetonitrile+0.1% trifluoroacetic acid in water+0.1% trifluoroacetic acid, over 15 min.) to give Compound 26 (22 mg, yield 10.4%). $^1$H NMR (DMSO-d$_6$ 400 MHz): δ 8.60 (m, 1H), 7.47-6.36 (m, 11H), 4.87 (m, 1H), 4.03-3.70 (m, 2H), 2.24 (m, 3H), 1.41-1.20 (m, 3H); MS (ESI): m/z 446.0 [M+1]$^+$.

Example 27

Compound 27, 5-(4-chlorophenyl)-4-(3-ethoxy-4-hydroxy-5-nitrophenyl)-6-phenyl-3,4-dihydropyrimidin-2(1H)-one

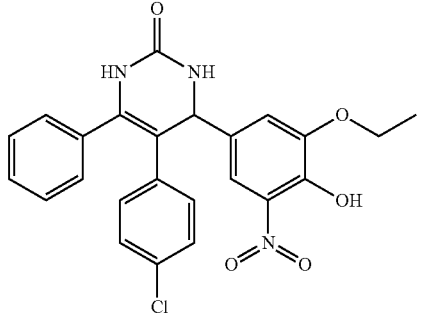 [SMILES: CCOc1cc(C2NC(=O)NC(c3ccccc3)=C2c2ccc(Cl)cc2)cc([N+](=O)[O-])c1O]

To a mixture of 2-(4-chlorophenyl)-1-phenylethanone (200 mg, 0.88 mmol), 3-ethoxy-4-hydroxy-5-nitrobenzaldehyde (200 mg, 0.95 mmol), and urea (156 mg, 2.65 mmol) in anhydrous EtOH (20 mL) was added concentrated HCl solution (0.1 mL), and the reaction mixture was refluxed for three days. When TLC (EtOAc:MeOH=10:1) showed that about 50% of starting materials were consumed, the reaction mixture was concentrated, and the residue was purified by column chromatography (EtOAc:MeOH=40:1) and preparative HPLC to afford Compound 27 as a yellow solid (25 mg, yield: 6.25%). $^1$H NMR (DMSO-d$_6$ 400 MHz TMS): δ 10.30 (s, 1H), 8.81 (s, 1H), 7.60 (s, 1H), 7.45 (s, 1H), 7.25-7.30 (m, 3H), 7.17-7.24 (m, 3H), 7.10 (d, J=8.8 Hz, 2H), 6.80 (d, J=8.4 Hz, 2H), 5.20 (d, J=2.8 Hz, 1H), 4.00-4.11 (m, 2H), 1.33 (t, J=6.8 Hz, 3H); MS (ESI): m/z 466.0 [M+1]$^+$.

Example 28

Compound 28, 5-(2-chlorophenyl)-4-(3-ethoxy-4-hydroxy-5-nitrophenyl)-6-phenyl-3,4-dihydropyrimidin-2(1H)-one

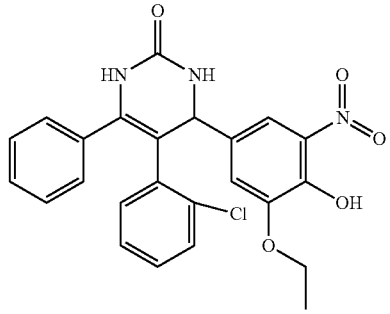 [SMILES: CCOc1cc(C2NC(=O)NC(c3ccccc3)=C2c2ccccc2Cl)cc([N+](=O)[O-])c1O]

To a mixture of 2-(2-chlorophenyl)-1-phenylethanone (Intermediate 10) (85 mg, 0.37 mmol), 3-ethoxy-4-hydroxy-5-nitrobenzaldehyde (94 mg, 0.45 mmol), and urea (67 mg, 1.1 mmol) in anhydrous EtOH (20 mL) was added concentrated HCl solution (0.1 mL), and the reaction mixture was refluxed for three days. TLC (EtOAc:MeOH=10:1) showed that about 50% of starting materials were consumed, and the reaction mixture was concentrated. The residue was purified by column chromatography (EtOAc:MeOH=40:1) and preparative HPLC to afford Compound 28 as a yellow solid (12 mg, yield: 7.0%). $^1$H NMR (CD$_3$OD 400 MHz): δ 7.47 (s, 1H), 7.34-7.40 (m, 1H), 7.20 (s, 5H), 7.10-7.13 (m, 1H), 7.05 (s, 1H), 6.80-6.87 (m, 1H), 6.40-6.45 (m, 1H), 5.45 (s, 1H), 3.95-4.10 (m, 2H), 1.37-1.42 (m, 3H); MS (ESI): m/z 466.2 [M+1]$^+$.

Example 29

Compound 29, 3-(4-(3-ethoxy-4-hydroxy-5-nitrophenyl)-2-oxo-6-phenyl-1,2,3,4-tetrahydropyrimidin-5-yl)benzonitrile

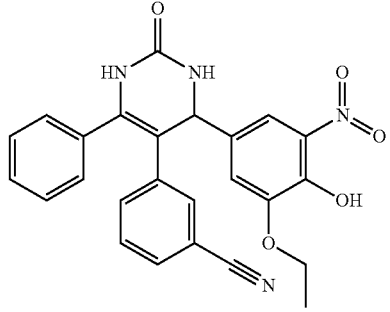 [SMILES: CCOc1cc(C2NC(=O)NC(c3ccccc3)=C2c2cccc(C#N)c2)cc([N+](=O)[O-])c1O]

To a solution of 3-(2-oxo-2-phenylethyl)benzonitrile (Intermediate 11) (80 mg, 0.36 mmol), 3-ethoxy-4-hydroxy-5-nitrobenzaldehyde (76 mg, 0.36 mmol), and urea (50 mg, 1.08 mmol) in 20 mL of ethanol was added 0.2 mL of concentrated HCl solution, and the mixture was stirred at reflux for 2 days. After the solvent was removed under reduced pressure, the residue was purified by thin layer chromatography (PE:EtOAc=1:2) to give Compound 29 (22 mg, yield 2.5%). ¹H NMR (CD₃OD 400 MHz): δ 7.45 (s, 1H), 7.27 (d, J=7.2 Hz, 1H), 7.21-7.18 (m, 5H), 7.12-7.05 (m, 3H), 6.98 (s, 1H), 5.20 (s, 1H), 3.97-3.94 (m, 2H), 1.30 (t, J=6.8 Hz, 3H); MS (ESI): m/z 457.2 [M+1]⁺.

Example 30

Compound 30, 5-(3,4-difluorophenyl)-4-(3-ethoxy-4-hydroxy-5-nitrophenyl)-6-phenyl-3,4-dihydropyrimidin-2(1H)-one

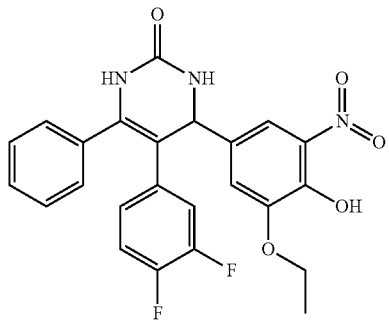 [SMILES: CCOc1cc(C2NC(=O)NC(c3ccccc3)=C2c2ccc(F)c(F)c2)cc([N+](=O)[O-])c1O]

To a solution of 2-(3,4-difluorophenyl)-1-phenylethanone (Intermediate 12) (150 mg, 0.65 mmol), 3-ethoxy-4-hydroxy-5-nitrobenzaldehyde (128.1 mg, 0.65 mmol), and urea (117 mg, 1.95 mmol) in 20 mL of ethanol was added 0.2 ml con. HCl. The mixture was refluxed for 2 days. After the solvent was removed under reduced pressure, the residue was purified by reverse-phase preparatory HPLC (26-53% acetonitrile+0.1% trifluoroacetic acid in water+0.1% trifluoroacetic acid, over 15 min.) to give Compound 30 (132 mg, yield 43.3%). ¹H NMR (DMSO-d₆ 400 MHz): δ 10.30 (s, 1H), 8.82 (s, 1H), 7.58 (s, 1H), 7.43 (s, 1H), 7.30-7.20 (m, 6H), 7.07 (m, 1H), 6.86 (m, 1H), 6.59 (s, 1H), 5.27 (s, 1H), 4.08 (m, 2H), 1.33 (t, J=6.8 Hz, 3H); MS (ESI): m/z 468.0 [M+1]⁺

Example 31

Compound 31, 6-(3,5-dichlorophenyl)-4-(3-ethoxy-4-hydroxy-5-nitrophenyl)-5-phenyl-3,4-dihydropyrimidin-2(1H)-one

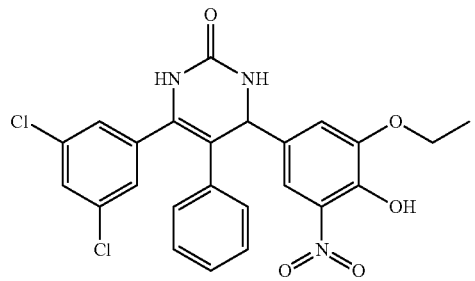 [SMILES: CCOc1cc(C2NC(=O)NC(c3cc(Cl)cc(Cl)c3)=C2c2ccccc2)cc([N+](=O)[O-])c1O]

To a solution of 1-(3,5-dichlorophenyl)-2-phenylethanone (Intermediate 13) (100 mg, 0.38 mmol), 3-ethoxy-4-hydroxy-5-nitrobenzaldehyde (74.6 mg, 0.38 mmol) and urea (68.0 mg, 1.13 mmol) in 20 mL of ethanol was added 0.2 mL of concentrated HCl solution, and the mixture was refluxed for 2 days. After the solvent was removed under reduced pressure, the residue was purified by reverse-phase preparatory HPLC (26-53% acetonitrile+0.1% trifluoroacetic acid in water+0.1% trifluoroacetic acid, over 15 min.) to give compound 31 (53 mg, yield 26.4%). ¹H NMR (DMSO-d₆ 400 MHz): δ 10.26 (s, 1H), 8.57 (s, 1H), 7.57 (s, 1H), 7.50 (s, 1H), 7.40 (s, 1H), 7.20 (s, 1H), 7.19 (s, 1H), 7.07-7.11 (m, 4H), 6.88 (d, J=6.8 Hz, 2H), 5.27 (d, J=2.0 Hz, 1H), 4.03 (m, 2H), 1.31 (t, J=7.2 Hz, 1H); MS (ESI): m/z 499.9 [M+1]⁺.

Example 32

Compound 32, 4-(3-ethoxy-4-hydroxy-5-nitrophenyl)-6-(3-fluorophenyl)-5-phenyl-3,4-dihydropyrimidin-2(1H)-one

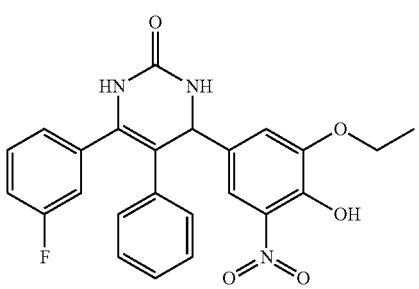

A mixture of 1-(3-fluorophenyl)-2-phenylethanone (100 mg, 0.47 mmol), 3-ethoxy-4-hydroxy-5-nitrobenzaldehyde (82 mg, 0.39 mmol), urea (70 mg, 1.17 mmol), and concentrated HCl solution (0.03 mL, 0.39 mmol) in EtOH (5 mL) was refluxed overnight. The mixture was evaporated in vacuo and purified by preparative HPLC to give Compound 32 (22.35 mg, yield 13%) as a yellow solid. ¹H NMR (DMSO-d₆ 400 MHz): δ 10.28 (s, 1H), 8.79 (s, 1H), 7.56 (s, 1H), 7.42 (s, 1H), 7.30-7.25 (m, 1H), 7.16 (s, 1H), 7.12-6.99 (m, 6H), 6.86 (d, J=7.6 Hz, 2H), 5.23 (d, J=2.4 Hz, 1H), 4.04 (q, J=7.2 Hz, 2H), 1.33 (t, J=7.2 Hz, 3H); MS (ESI): m/z 450.0 [M+1]⁺.

Example 33

Compound 33, 6-(4-bromophenyl)-4-(3-ethoxy-4-hydroxy-5-nitrophenyl)-5-phenyl-3,4-dihydropyrimidin-2(1H)-one

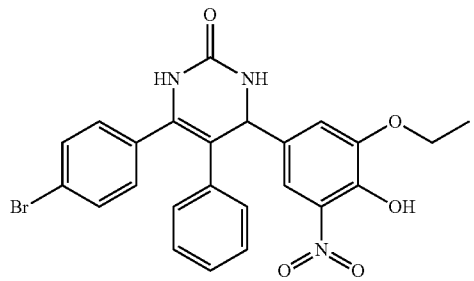

A mixture of 1-(4-bromophenyl)-2-phenylethanone (100 mg, 0.36 mmol), 3-ethoxy-4-hydroxy-5-nitrobenzaldehyde (64 mg, 0.30 mmol), urea (55 mg, 0.91 mmol), and concentrated HCl solution (0.03 mL, 0.36 mmol) in EtOH (5 mL) was refluxed overnight. The mixture was evaporated in vacuo, and purified by preparative HPLC to give Compound 33

(52.12 mg, yield 34%). ¹H NMR (DMSO-d₆ 400 MHz): δ 10.29 (s, 1H), 8.78 (s, 1H), 7.56 (s, 1H), 7.46-7.42 (m, 3H), 7.15-7.13 (m, 3H), 7.09-7.03 (m, 3H), 6.84 (d, J=6.8 Hz, 2H), 5.21 (d, J=2.0 Hz, 1H), 4.07-3.99 (m, 2H), 2.23 (s, 3H), 1.33 (t, J=6.8 Hz, 3H); MS (ESI): m/z 511.9 [M+1]⁺.

Example 34

Compound 34, 6-(biphenyl-4-yl)-4-(3-ethoxy-4-hydroxy-5-nitrophenyl)-5-phenyl-3,4-dihydropyrimidin-2(1H)-one

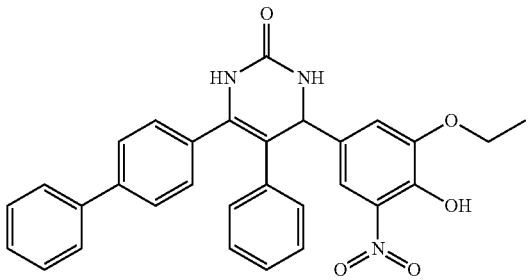 [SMILES: CCOc1cc(C2NC(=O)NC(c3ccc(-c4ccccc4)cc3)=C2c2ccccc2)cc([N+](=O)[O-])c1O]

A mixture of 1-(biphenyl-4-yl)-2-phenylethanone (Intermediate 14) (100 mg, 0.37 mmol), 3-ethoxy-4-hydroxy-5-nitrobenzaldehyde (65 mg, 0.31 mmol), urea (66 mg, 1.1 mmol), and concentrated HCl solution (0.03 mL, 0.37 mmol) in EtOH (5 mL) was refluxed overnight. The mixture was evaporated in vacuo, and purified by preparative HPLC to give Compound 34 (22.52 mg, yield 14%). ¹H NMR (DMSO-d₆ 300 MHz): δ 10.33 (s, 1H), 8.79 (s, 1H), 7.66 (d, J=8.4 Hz, 2H), 7.61-7.58 (m, 3H), 7.47-7.43 (m, 3H), 7.37 (d, J=6.9 Hz, 1H), 7.30 (d, J=8.4 Hz, 2H), 7.22 (s, 1H), 7.09-7.02 (m, 3H), 6.89 (d, J=7.8 Hz, 2H), 5.21 (d, J=2.7 Hz, 1H), 4.06 (q, J=3.6 Hz, 2H), 1.34 (t, J=6.9 Hz, 3H); MS (ESI): m/z 508.1 [M+1]⁺.

Example 35

Compound 35, 4-(3-ethoxy-4-hydroxy-5-nitrophenyl)-6-(4-fluorophenyl)-5-phenyl-3,4-dihydropyrimidin-2(1H)-one

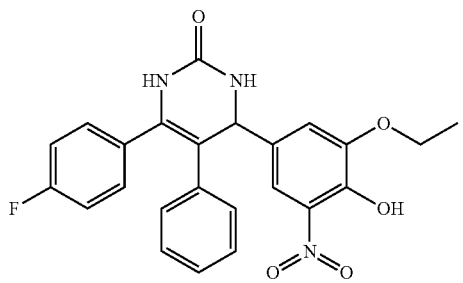 [SMILES: CCOc1cc(C2NC(=O)NC(c3ccc(F)cc3)=C2c2ccccc2)cc([N+](=O)[O-])c1O]

A mixture of 1-(4-fluorophenyl)-2-phenylethanone (200 mg, 0.93 mmol), 3-ethoxy-4-hydroxy-5-nitrobenzaldehyde (164 mg, 0.78 mmol), urea (140 mg, 2.3 mmol), and concentrated HCl solution (0.08 mL, 0.93 mmol) in EtOH (5 mL) was refluxed overnight. The mixture was evaporated in vacuo, and the residue was purified by preparative HPLC to give Compound 35 (120 mg, yield 29%). ¹H NMR (DMSO-d₆ 300 MHz): δ 10.28 (s, 1H), 8.76 (s, 1H), 7.54 (s, 1H), 7.42 (s, 1H), 7.25-7.21 (m, 2H), 7.16 (s, 1H), 7.11-6.97 (m, 5H), 6.81 (d, J=7.5 Hz, 2H), 5.19 (s, 1H), 4.08-3.99 (m, 2H), 1.32 (t, J=6.6 Hz, 3H); MS (ESI): m/z 450.0 [M+1]⁺.

Example 36

Compound 36, 6-(4-chlorophenyl)-4-(3-ethoxy-4-hydroxy-5-nitrophenyl)-5-phenyl-3,4-dihydropyrimidin-2(1H)-one

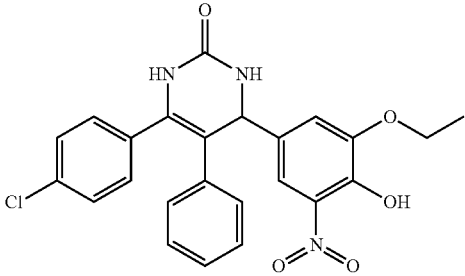

A mixture of 1-(4-chlorophenyl)-2-phenylethanone (350 mg, 1.52 mmol), 3-ethoxy-4-hydroxy-5-nitrobenzaldehyde (320 mg, 1.52 mmol), and urea (272 mg, 4.53 mmol) in anhydrous EtOH (15 mL) was added concentrated HCl solution (0.5 mL), and the reaction mixture was refluxed for overnight. TLC (EtOAc:MeOH=10:1) showed that about 30% of starting materials were consumed, and the reaction mixture was concentrated. The residue was purified by column chromatography (EtOAc:MeOH=40:1) and preparative HPLC to afford the product Compound 36 as a yellow solid (55.1 mg, yield: 7.8%). ¹H NMR (DMSO-d₆ 400 MHz): δ 10.30 (s, 1H), 8.79 (s, 1H), 7.55 (s, 1H), 7.42 (s, 1H), 7.30 (d, J=8.4 Hz, 2H), 7.20 (d, J=8.4 Hz, 2H), 7.18 (s, 1H), 7.00-7.10 (m, 3H), 6.82 (d, J=7.2 Hz, 2H), 5.20 (d, J=2.4 Hz, 1H), 4.00-4.10 (m, 2H), 1.33 (t, J=6.8 Hz, 3H); MS (ESI): m/z 466.0 [M+1]⁺.

Example 37

Compound 37, 6-(3-chlorophenyl)-4-(3-ethoxy-4-hydroxy-5-nitrophenyl)-5-phenyl-3,4-dihydropyrimidin-2(1H)-one

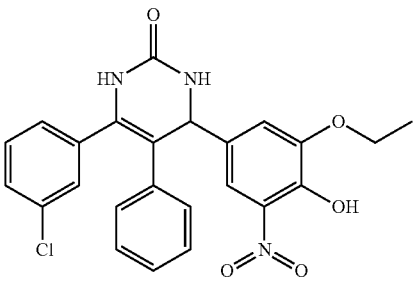 [SMILES: CCOc1cc(C2NC(=O)NC(c3cccc(Cl)c3)=C2c2ccccc2)cc([N+](=O)[O-])c1O]

A mixture of 1-(3-chlorophenyl)-2-phenylethanone (450 mg, 1.95 mmol), 3-ethoxy-4-hydroxy-5-nitrobenzaldehyde (411 mg, 1.95 mmol), and urea (350 mg, 5.83 mmol) in anhydrous EtOH (15 mL) was added concentrated HCl solution (0.5 mL), the reaction mixture was refluxed overnight. TLC (EtOAc:MeOH=10:1) showed that about 30% of starting materials were consumed, and the reaction mixture was concentrated. The residue was purified by column chromatography (EtOAc:MeOH=40:1) and preparative HPLC to afford Compound 37 as a yellow solid (78.1 mg, yield: 8.6%). $^1$H NMR (DMSO-$d_6$ 400 MHz): δ 10.30 (s, 1H), 8.81 (s, 1H), 7.56 (s, 1H), 7.42 (d, J=1.2 Hz, 1H), 7.30 (d, J=8.0 Hz, 1H), 7.20-7.25 (m, 2H), 7.02-7.7.13 (m, 5H), 6.85 (d, J=6.8 Hz, 2H), 5.25 (d, J=2.8 Hz, 1H), 4.00-4.10 (m, 2H), 1.33 (t, J=6.8 Hz, 3H); MS (ESI): m/z 466.0 [M+1]$^+$.

Example 38

Compound 38, 6-(3,4-dimethoxyphenyl)-4-(3-ethoxy-4-hydroxy-5-nitrophenyl)-5-phenyl-3,4-dihydropyrimidin-2(1H)-one

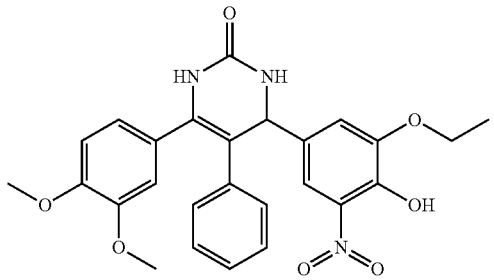 [SMILES: CCOc1cc(C2NC(=O)NC(c3ccc(OC)c(OC)c3)=C2c2ccccc2)cc([N+](=O)[O-])c1O]

A mixture of 1-(3,4-dimethoxyphenyl)-2-phenylethanone (180 mg, 0.7 mmol), 3-ethoxy-4-hydroxy-5-nitrobenzaldehyde (124 mg, 0.59 mmol), urea (105 mg, 1.8 mmol), and concentrated HCl solution (0.05 mL, 0.59 mmol) in EtOH (5 mL) was refluxed overnight. The mixture was evaporated in vacuo, and the residue was purified by preparative HPLC to give Compound 38 (100 mg, yield 35%) as a yellow solid. $^1$H NMR (CD$_3$OD 400 MHz): δ 7.63 (d, J=1.2 Hz, 1H), 7.19 (s, 1H), 7.13-7.06 (m, 3H), 6.93-6.85 (m, 4H), 6.73 (s, 1H), 5.34 (s, 1H), 4.11-4.02 (m, 2H), 3.80 (s, 3H), 3.57 (s, 3H), 1.41 (t, J=6.8 Hz, 3H); MS (ESI): m/z 492.0 [M+1]$^+$.

Example 39

Compound 39, 4-(3-ethoxy-4-hydroxy-5-nitrophenyl)-6-(3-fluoro-4-methoxyphenyl)-5-phenyl-3,4-dihydropyrimidin-2(1H)-one

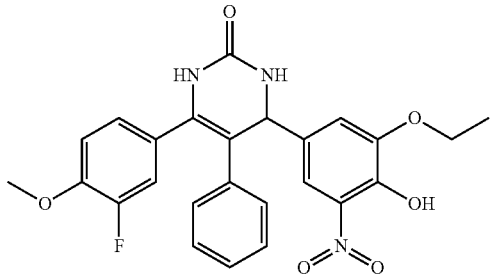 [SMILES: CCOc1cc(C2NC(=O)NC(c3ccc(OC)c(F)c3)=C2c2ccccc2)cc([N+](=O)[O-])c1O]

A mixture of 1-(3-fluoro-4-methoxyphenyl)-2-phenylethanone (100 mg, 0.41 mmol), 3-ethoxy-4-hydroxy-5-nitrobenzaldehyde (72 mg, 0.34 mmol), urea (61 mg, 1.02 mmol), and concentrated HCl solution (0.03 mL, 0.34 mmol) in EtOH (5 mL) was refluxed overnight. The mixture was evaporated in vacuo, and the residue was purified by preparative HPLC to give Compound 39 (78 mg, yield 48%). $^1$H NMR (DMSO-$d_6$ 400 MHz): δ 10.28 (s, 1H), 8.71 (s, 1H), 7.53 (s, 1H), 7.42 (s, 1H), 7.17 (s, 1H), 7.10-7.01 (m, 5H), 6.95 (d, J=9.2 Hz, 1H), 6.85 (d, J=6.8 Hz, 2H), 5.18 (s, 1H), 4.08-4.01 (m, 2H), 3.79 (s, 3H), 1.33 (t, J=7.2 Hz, 3H); MS (ESI): m/z 480.0 [M+1]$^+$.

Example 40

Compound 40, 4-(3-fluoro-5-hydroxy-4-methoxyphenyl)-5,6-diphenyl-3,4-dihydropyrimidin-2(1H)-one

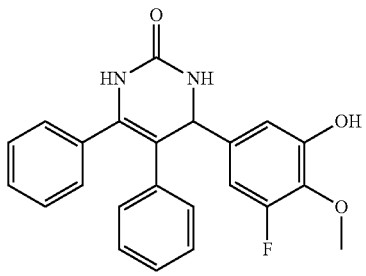 [SMILES: COc1c(O)cc(C2NC(=O)NC(c3ccccc3)=C2c2ccccc2)cc1F]

To a mixture of 3-fluoro-4-hydroxy-5-methoxybenzaldehyde (127 mg, 0.75 mmol), 1,2-diphenylethaone (176 mg, 0.9 mmol) and urea (135 mg, 2.25 mmol) in ethanol (10 mL) was added concentrated HCl (0.4 mL) and the reaction solution was heated to reflux for 3 days. The reaction solution was concentrated in vacuo and purified by silica gel column chromatography (DCM:MeOH=10:1) to afford Compound 40 as a white solid (21 mg, 7%). $^1$H NMR (DMSO-$d_6$ 500 MHz): δ 7.28 (br, 3H), 7.22 (br, 2H), 7.04 (m, 3H), 6.82 (d, 2H, J=5 Hz), 6.79-6.83 (m, 3H), 5.10 (s, 1H); MS (ESI): m/z 391.1 [M+1]$^+$.

Example 41

Compound 41, 4-(3-ethoxy-4-hydroxy-5-nitrophenyl)-1,3-dimethyl-5,6-diphenyl-3,4-dihydropyrimidin-2(1H)-one

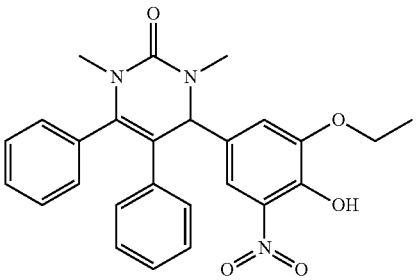 [SMILES: CCOc1cc(C2C(c3ccccc3)=C(c3ccccc3)N(C)C(=O)N2C)cc([N+](=O)[O-])c1O]

A mixture of 1,2-diphenylethanone (300 mg, 1.53 mmol), 3-ethoxy-4-hydroxy-5-nitrobenzaldehyde (324 mg, 1.53 mmol), and 1,3-dimethylurea (174 mg, 1.98 mmol) in DMF (5 mL) was added TMSCl (1.0 g, 9.12 mmol), and the reaction mixture was stirred at room temperature overnight under nitrogen. LCMS showed that about 30% of starting materials were consumed. H$_2$O (10 mL) was added to quench the reaction, and the aqueous layer was extracted with EtOAc (30 mL×3). The combined organic layer was washed with brine (20 mL), dried over Na$_2$SO$_4$, filtered, and concentrated. The residue was purified by column chromatography (PE: EtOAc=1:2) and preparative HPLC to afford Compound 41 as a yellow solid (82 mg, yield: 11.6%). $^1$H NMR (DMSO-d$_6$ 400 MHz): 610.40 (s, 1H), 7.50 (s, 1H), 7.30 (d, J=6.0 Hz, 3H), 7.25 (d, J=8.0 Hz, 3H), 7.00 (d, J=6.8 Hz, 3H), 6.75 (d, J=6.4 Hz, 2H), 5.11 (s, 1H), 4.00-4.17 (m, 2H), 2.82 (s, 3H), 2.75 (s, 3H), 1.33 (t, J=6.8 Hz, 3H); MS (ESI): m/z 460.1 [M+1]$^+$.

Example 42

Compound 42, 4-(4-(3-ethoxy-4-hydroxy-5-nitrophenyl)-2-oxo-6-phenyl-1,2,3,4-tetrahydropyrimidin-5-yl)benzonitrile

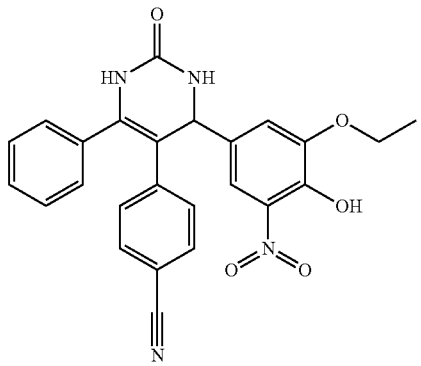 [SMILES: CCOc1cc(C2NC(=O)NC(c3ccccc3)=C2c2ccc(C#N)cc2)cc([N+](=O)[O-])c1O]

To a solution of 4-(2-oxo-2-phenylethyl)benzonitrile (Intermediate 15) (70 mg, 0.32 mmol), 3-ethoxy-4-hydroxy-5-nitrobenzaldehyde (68 mg, 0.32 mmol), and urea (44 mg, 0.96 mmol) in 20 mL of ethanol was added 0.2 mL of concentrated HCl solution, and the mixture was stirred at 130° C. for 2 days. After the solvent was removed under reduced pressure, the residue was purified by preparative HPLC (35-75% acetonitrile+0.1% trifluoroacetic acid in water, over 15 min.) to give the compound 42 (16 mg, yield 11%). $^1$H NMR (CD$_3$OD 400 MHz): δ 7.64 (s, 1H), 7.41 (d, J=7.6 Hz, 2H), 7.34-7.31 (m, 5H), 7.25 (s, 1H), 7.06 (d, J=8.4 Hz, 2H), 5.41 (s, 1H), 4.14-4.09 (m, 2H), 1.43 (t, J=7.2 Hz, 3H); MS (ESI): m/z 457.2 [M+1]$^+$.

Example 43

Compound 43, 6-(4-chloro-3-fluorophenyl)-4-(3-ethoxy-4-hydroxy-5-nitrophenyl)-5-phenyl-3,4-dihydropyrimidin-2(1H)-one

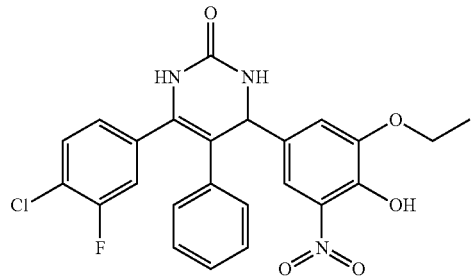 [SMILES: CCOc1cc(C2NC(=O)NC(c3ccc(Cl)c(F)c3)=C2c2ccccc2)cc([N+](=O)[O-])c1O]

To a solution of 1-(4-chloro-3-fluorophenyl)-2-phenylethanone (Intermediate 16) (100 mg, 0.40 mmol), 3-ethoxy-4-hydroxy-5-nitrobenzaldehyde (79.5 mg, 0.40 mmol), and urea (73.2 mg, 1.20 mmol) in 5 mL of ethanol was added 0.2 mL of concentrated HCl solution, and the mixture was refluxed for 2 days. After the solvent was removed under reduced pressure, the residue was purified by reverse-phase preparatory HPLC (26-53% acetonitrile+0.1% trifluoroacetic acid in water+0.1% trifluoroacetic acid, over 15 min.) to give Compound 43 (18 mg, yield 9.3%). $^1$H NMR (DMSO-d$_6$ 300 MHz) δ 10.29 (s, 1H), 8.83 (s, 1H), 7.57 (s, 1H), 7.44 (m, 2H), 7.28 (d, J=9.9 Hz, 1H), 7.13-6.86 (m, 4H), 5.26 (s, 1H), 4.04 (m, 2H), 1.32 (t, J=6.3 Hz, 3H); MS (ESI): m/z 483.9 [M+1]$^+$.

Example 44

Compound 44, 6-(3-chloro-4-fluorophenyl)-4-(3-ethoxy-4-hydroxy-5-nitrophenyl)-5-phenyl-3,4-dihydropyrimidin-2(1H)-one

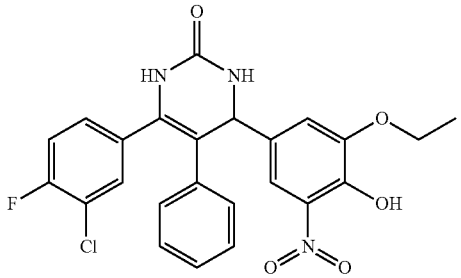

To a solution of 1-(3-chloro-4-fluorophenyl)-2-phenylethanone (Intermediate 17) (65 mg, 0.26 mmol), 3-ethoxy-4-hydroxy-5-nitrobenzaldehyde (51.6 mg, 0.26 mmol), and urea (47.6 mg, 0.78 mmol) in 5 mL of ethanol was added 0.2 mL of concentrated HCl solution, and the mixture was refluxed for 2 days. After the solvent was removed under reduced pressure, the residue was purified by reverse-phase preparatory HPLC (26-53% acetonitrile+0.1% trifluoroacetic acid in water+0.1% trifluoroacetic acid, over 15 min.) to give Compound 44 (22 mg, yield 17.4%). $^1$H NMR (DMSO-d$_6$ 300 MHz): δ 10.28 (s, 1H), 8.83 (s, 1H), 7.57 (s, 1H), 7.43 (m, 2H), 7.28 (t, J=9.0 Hz, 1H), 7.17-7.04 (m, 5H), 6.87 (d, J=6.3 Hz, 2H), 5.25 (d, J=2.4 Hz, 1H), 4.04 (m, 2H), 1.32 (t, J=6.9 Hz, 3H); MS (ESI): m/z 483.9[M+1]$^+$.

Example 45

Compound 45, 6-(3,4-difluorophenyl)-4-(3-ethoxy-4-hydroxy-5-nitrophenyl)-5-phenyl-3,4-dihydropyrimidin-2(1H)-one

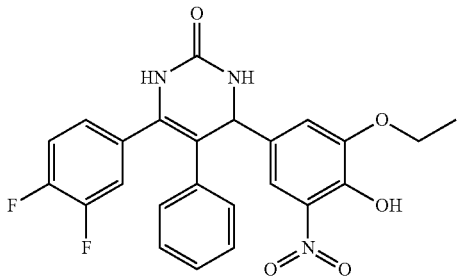

To a solution of 1-(3,4-difluorophenyl)-2-phenylethanone (120 mg, 0.52 mmol), 3-ethoxy-4-hydroxy-5-nitrobenzaldehyde (101.8 mg, 0.52 mmol), and urea (95.1 mg, 1.56 mmol) in 5 mL of ethanol was added 0.2 mL of concentrated HCl solution, and the mixture was refluxed for 2 days. After the solvent was removed under reduced pressure, the residue was purified by reverse-phase preparatory HPLC (26-53% acetonitrile+0.1% trifluoroacetic acid in water+0.1% trifluoroacetic acid, over 15 min.) to give Compound 45 (35 mg, yield 14.5%). $^1$H NMR (DMSO-$d_6$ 400 MHz TMS): δ 10.27 (s, 1H), 8.81 (s, 1H), 7.56 (s, 1H), 7.41 (s, 1H), 7.31 (m, 2H), 7.14 (s, 1H), 7.11-6.99 (m, 3H), 6.87 (m, 1H), 6.86 (d, J=7.2 Hz, 2H), 5.24 (d, J=2.0 Hz, 1H), 4.04 (m, 2H), 1.32 (t, J=7.2 Hz, 3H); MS (ESI): m/z 468.0[M+1]$^+$.

Example 46

Compound 46, 6-(3,5-difluorophenyl)-4-(3-ethoxy-4-hydroxy-5-nitrophenyl)-5-phenyl-3,4-dihydropyrimidin-2(1H)-one

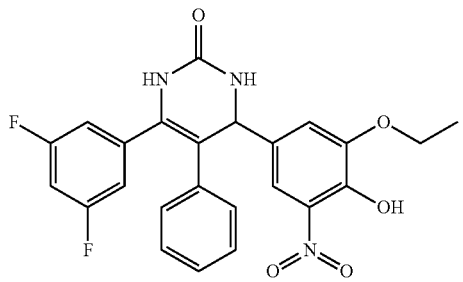

To a solution of 1-(3,5-difluorophenyl)-2-phenylethanone (Intermediate 18) (100 mg, 0.43 mmol), 3-ethoxy-4-hydroxy-5-nitrobenzaldehyde (84.9 mg, 0.43 mmol), and urea (78.6 mg, 1.29 mmol) in 5 mL of ethanol was added 0.2 mL of concentrated HCl, and the mixture was refluxed for 2 days. After the solvent was removed under reduced pressure, the residue was purified by reverse-phase preparatory HPLC (26-53% acetonitrile+0.1% trifluoroacetic acid in water+0.1% trifluoroacetic acid, over 15 min.) to give Compound 46 (40 mg, yield 19.9%). $^1$H NMR (DMSO-$d_6$ 400 MHz) δ 10.27 (s, 1H), 8.81 (s, 1H), 7.56 (s, 1H), 7.41 (s, 1H), 7.31 (m, 2H), 7.14 (s, 1H), 7.11-6.99 (m, 4H), 6.86 (d, J=7.2 Hz, 2H), 5.24 (s, 1H), 4.04 (m, 2H), 1.32 (t, J=7.2 Hz, 3H); MS (ESI): m/z 468.0 [M+1]$^+$.

Example 47

Compound 47, 6-(3,4-dichlorophenyl)-4-(3-ethoxy-4-hydroxy-5-nitrophenyl)-5-phenyl-3,4-dihydropyrimidin-2(1H)-one

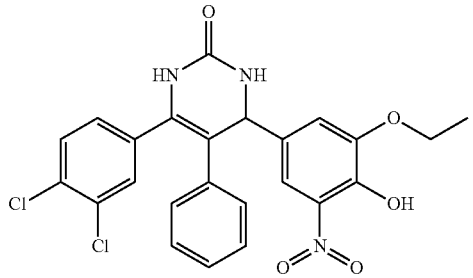

To a solution of 1-(3,4-dichlorophenyl)-2-phenylethanone (Intermediate 19) (100 mg, 0.38 mmol), 3-ethoxy-4-hydroxy-5-nitrobenzaldehyde (74.4 mg, 0.38 mmol), and urea (68.5 mg, 1.14 mmol) in 5 mL of ethanol was added 0.2 mL of concentrated HCl solution, and the mixture was refluxed for 2 days. After the solvent was removed under reduced pressure, the residue was purified by reverse-phase preparatory HPLC (26-53% acetonitrile+0.1% trifluoroacetic acid in water+0.1% trifluoroacetic acid, over 15 min.) to give Compound 47 (32 mg, yield 17.0%). $^1$H NMR (DMSO-$d_6$ 300 MHz) δ 10.28 (s, 1H), 8.85 (s, 1H), 7.58 (s, 1H), 7.48 (t, J=7.5 Hz, 2H), 7.41 (d, J=1.8 Hz, 1H), 7.13-7.05 (m, 5H), 6.88 (t, J=1.8 Hz, 2H), 5.25 (d, J=2.7 Hz, 1H), 4.02 (m, 2H), 1.32 (t, J=6.9 Hz, 3H); MS (ESI): m/z 499.9 [M+1]$^+$.

Example 48

Compound 48, 4-(3-ethoxy-4-hydroxy-5-nitrophenyl)-6-(4-hydroxyphenyl)-5-phenyl-3,4-dihydropyrimidin-2(1H)-one

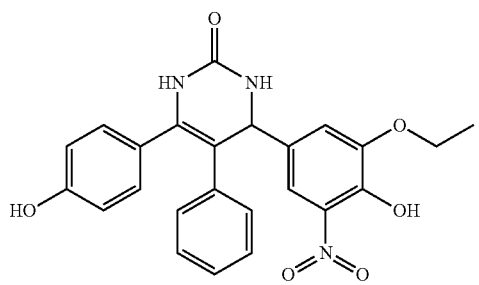 [SMILES: CCOc1cc(C2NC(=O)NC(c3ccc(O)cc3)=C2c2ccccc2)cc([N+](=O)[O-])c1O]

A mixture of 1-(4-(methoxymethoxy)phenyl)-2-phenylethanone (Intermediate 20) (100 mg, 0.39 mmol), 3-ethoxy-4-hydroxy-5-nitrobenzaldehyde (69 mg, 0.33 mmol), urea (59 mg, 0.98 mmol), and concentrated HCl solution (0.03 mL, 0.33 mmol) in EtOH (5 mL) was refluxed overnight. The mixture was evaporated in vacuo, and the residue was purified by preparative HPLC to give Compound 48 (65.12 mg, yield 45%). $^1$H NMR (CD$_3$OD 400 MHz): δ 7.62 (s, 1H), 7.20 (s, 1H), 7.10-7.05 (m, 5H), 6.90 (d, J=6.8 Hz, 2H), 6.66 (d, J=8.0 Hz, 2H), 5.31 (s, 1H), 4.11-4.04 (m, 2H), 1.41 (t, J=6.8 Hz, 3H); MS (ESI): m/z 448.0[M+1]$^+$.

Example 49

Compound 49, 6-(2,4-difluorophenyl)-4-(3-ethoxy-4-hydroxy-5-nitrophenyl)-5-phenyl-3,4-dihydropyrimidin-2(1H)-one

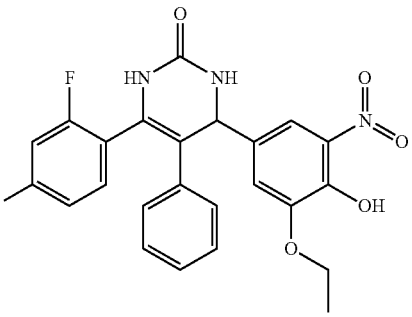

A mixture of 1-(2,4-difluorophenyl)-2-phenylethanone (Intermediate 21) (250 mg, 1.1 mmol), 3-ethoxy-4-hydroxy- 5-nitrobenzaldehyde (189 mg, 0.90 mmol), urea (162 mg, 2.69 mmol), and concentrated HCl solution (0.075 mL, 0.90 mmol) in EtOH (10 mL) was refluxed overnight. The mixture was evaporated in vacuo, and the residue was purified by preparative HPLC to give Compound 49 (30.03 mg, yield 7%). $^1$H NMR (DMSO-$d_6$ 400 MHz): δ 10.32 (s, 1H), 8.91 (s, 1H), 7.57 (s, 1H), 7.49 (s, 1H), 7.43-7.37 (m, 1H), 7.29 (s, 1H), 7.11-6.89 (m, 5H), 6.88 (d, J=7.2 Hz, 2H), 5.27 (s, 1H), 4.08 (q, J=7.2 Hz, 2H), 1.36 (t, J=7.2 Hz, 3H); MS (ESI): m/z 468.1 [M+1]$^+$.

Example 50

Compound 50, 4-(3-ethoxy-4-hydroxy-5-nitrophenyl)-6-(furan-3-yl)-5-phenyl-3,4-dihydropyrimidin-2(1H)-one

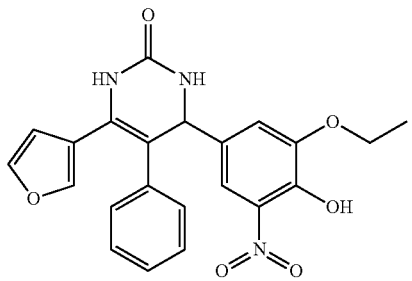

A mixture of 1-(furan-3-yl)-2-phenylethanone (Intermediate 22) (692 mg, 3.72 mmol), 3-ethoxy-4-hydroxy-5-nitrobenzaldehyde (942 mg, 4.46 mmol), and urea (669.6 mg, 11.16 mmol) in anhydrous EtOH (5 mL) was added concentrated HCl solution (0.2 mL), and the reaction mixture was refluxed (110° C.) for thirteen hours. TLC (eluting with EtOAc) showed that the most of the starting materials were consumed. The reaction mixture was concentrated, and purified by column chromatography and preparative HPLC to afford Compound 50 as a yellow solid (173 mg, yield: 11.0%). $^1$H NMR (DMSO-$d_6$ 400 MHz TMS): δ10.26 (s, 1H), 8.478 (s, 1H), 6.981-7.708 (m, 10H), 5.766 (s, 1H), 5.141 (d, J=2.4 Hz, 1H), 3.918-4.061 (m, 2H), 1.304 (t, J=6.8 Hz, 3H); MS (ESI): m/z 422.1[M+1]$^+$.

Example 51

Compound 51, 6-(2-chlorophenyl)-4-(3-ethoxy-4-hydroxy-5-nitrophenyl)-5-phenyl-3,4-dihydropyrimidin-2(1H)-one

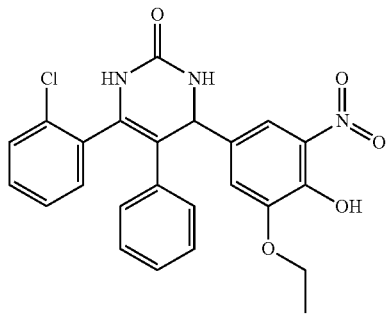 [SMILES: CCOc1cc(C2NC(=O)NC(c3ccccc3Cl)=C2c2ccccc2)cc([N+](=O)[O-])c1O]

To a solution of 1-(2-chlorophenyl)-2-phenylethanone (100 mg, 0.43 mmol), 3-ethoxy-4-hydroxy-5-nitrobenzaldehyde (91 mg, 0.43 mmol), and urea (60 mg, 1.29 mmol) in 10 mL of ethanol was added 0.2 mL of concentrated HCl solution. The mixture was stirred at 130° C. for 2 days, concentrated under reduced pressure, and purified by preparative HPLC (40-70% acetonitrile+0.1% trifluoroacetic acid in water, over 15 min.) to give Compound 51 (28.7 mg, yield 14.2%). $^1$H NMR (CD$_3$OD 400 MHz): δ 7.43 (s, 1H), 7.19-7.04 (m, 5H), 6.79 (d, J=6.0 Hz, 3H), 6.72 (s, 2H), 5.23 (s, 1H), 3.88-3.85 (m, 2H), 1.81 (t, J=6.8 Hz, 3H); MS (ESI): m/z 466.2 [M+1]$^+$.

Example 52

Compound 52, 3-(4-(3-ethoxy-4-hydroxy-5-nitrophenyl)-2-oxo-6-phenyl-1,2,3,4-tetrahydropyrimidin-5-yl)benzamide

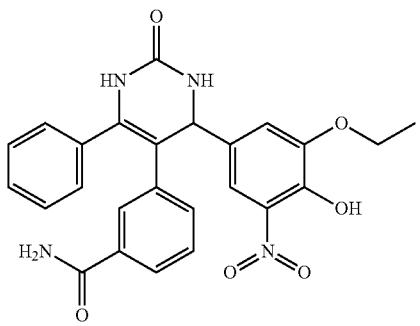 [SMILES: CCOc1cc(C2NC(=O)NC(c3ccccc3)=C2c2cccc(C(N)=O)c2)cc([N+](=O)[O-])c1O]

A mixture of 3-(4-(3-ethoxy-4-hydroxy-5-nitrophenyl)-2-oxo-6-phenyl-1,2,3,4-tetrahydropyrimidin-5-yl)benzonitrile (Compound 29) (40 mg, 0.088 mmol), H$_2$O$_2$ (0.5 mL), and K$_2$CO$_3$ (36 mg, 0.27 mmol) in DMSO (1 mL) was stirred at room temperature overnight. The mixture was quenched with aqueous saturated Na$_2$SO$_3$ solution, and the solution was extracted with a mixture of CH$_2$Cl$_2$/i-PrOH (3:1). The organic layer was concentrated in vacuo, and the mixture was purified by thin layer chromatography (ethyl acetate) to give compound 52 (20 mg, yield 47.6%). $^1$H NMR (CD$_3$OD 400 MHz): δ 7.64 (s, 1H), 7.56 (s, 2H), 7.28 (s, 5H), 7.20 (s, 1H), 7.12 (t, J=7.2 Hz, 1H), 6.97 (d, J=8.0 Hz, 1H), 5.43 (s, 1H), 4.11-4.03 (m, 2H), 1.40 (t, J=7.2 Hz, 3H); MS (ESI): m/z 475.3 [M+1]$^+$.

Example 53

Compound 53, 3-(6-(3-ethoxy-4-hydroxy-5-nitrophenyl)-2-oxo-5-phenyl-1,2,3,6-tetrahydropyrimidin-4-yl)benzonitrile

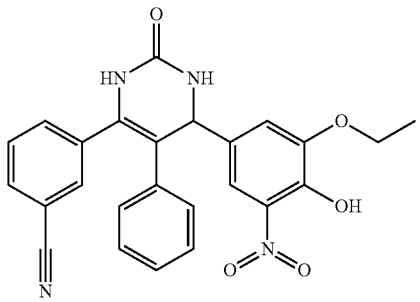 [SMILES: CCOc1cc(C2NC(=O)NC(c3cccc(C#N)c3)=C2c2ccccc2)cc([N+](=O)[O-])c1O]

To a solution of 3-(2-phenylacetyl)benzonitrile (Intermediate 23) (100 mg, 0.45 mmol), 3-ethoxy-4-hydroxy-5-nitrobenzaldehyde (89.1 mg, 0.45 mmol), and urea (82.3 mg, 1.35 mmol) in 5 mL of ethanol was added 0.2 mL of concentrated HCl, the mixture was refluxed for 2 days. After the solvent was removed under reduced pressure, the residue was purified by reverse-phase preparatory HPLC (26-53% acetonitrile+0.1% trifluoroacetic acid in water+0.1% trifluoroacetic acid, over 15 min.) to give Compound 53 (18.2 mg, yield 8.8%). $^1$H NMR (DMSO-$d_6$ 400 MHz) δ 10.27 (s, 1H), 8.86 (s, 1H), 7.71 (t, J=12.4 Hz, 2H), 7.57 (s, 1H), 7.44 (m, 3H), 7.14-7.06 (m, 4H), 6.85 (d, J=6.8 Hz, 2H), 5.28 (s, 1H), 4.06 (m, 2H), 1.32 (t, J=6.8 Hz, 3H); MS (ESI): m/z 456.9 [M+1]$^+$.

Example 54

Compound 54, 6-(4-(dimethylamino)phenyl)-4-(3-ethoxy-4-hydroxy-5-nitrophenyl)-5-phenyl-3,4-dihydropyrimidin-2(1H)-one

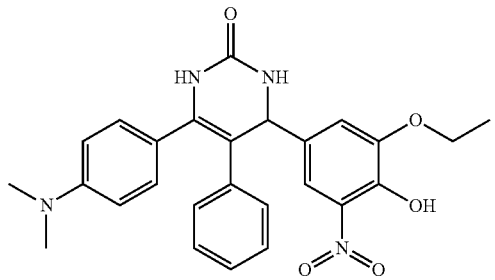 [SMILES: CCOc1cc(C2NC(=O)NC(c3ccc(N(C)C)cc3)=C2c2ccccc2)cc([N+](=O)[O-])c1O]

To a solution of 1-(4-(dimethylamino)phenyl)-2-phenylethanone (80 mg, 0.32 mmol), 3-ethoxy-4-hydroxy-5-nitrobenzaldehyde (63 mg, 0.32 mmol), and urea (60 mg, 0.96 mmol) in 5 mL of ethanol was added 0.2 mL of concentrated HCl solution, and the mixture was refluxed for 2 days. After the solvent was removed under reduced pressure, the residue was purified by reverse-phase preparatory HPLC (26-53% acetonitrile+0.1% trifluoroacetic acid in water+0.1% trifluoroacetic acid, over 15 min.) to give Compound 54 (27 mg, yield 16.3%). $^1$H NMR (DMSO-$d_6$ 400 MHz TMS): δ 10.29 (s, 1H), 8.51 (s, 1H), 7.47 (d, J=8.8 Hz, 2H), 7.23 (s, 1H), 7.07-6.97 (m, 5H), 6.83 (d, J=7.2 Hz, 2H), 6.58 (d, J=8.4 Hz, 2H), 5.07 (d, J=2.4 Hz, 1H), 4.05 (q, J=6.8 Hz, 2H), 2.88 (s, 6H), 1.34 (t, J=6.8 Hz, 3H); MS (ESI): m/z 475.0 [M+1]$^+$.

Example 55

Compound 55, 4-(3-ethoxy-4-hydroxy-5-nitrophenyl)-6-(2-fluorophenyl)-5-phenyl-3,4-dihydropyrimidin-2(1H)-one

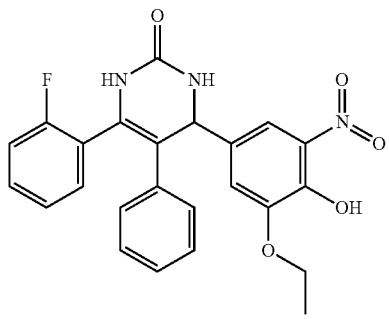

To a solution of 1-(2-fluorophenyl)-2-phenylethanone (Intermediate 24) (100 mg, 0.47 mmol), 3-ethoxy-4-hydroxy-5-nitrobenzaldehyde (92.0 mg, 0.47 mmol), and urea (85.4 mg, 1.40 mmol) in 5 mL of ethanol was added 0.2 mL of concentrated HCl solution, and the mixture was refluxed for 2 days. After the solvent was removed under reduced pressure, the residue was purified by reverse-phase preparatory HPLC (26-53% acetonitrile+0.1% trifluoroacetic acid in water+0.1% trifluoroacetic acid, over 15 min.) to give Compound 55 (83 mg, yield 39.7%). $^1$H NMR (DMSO-$d_6$ 400 MHz) δ 10.25 (s, 1H), 8.77 (s, 1H), 7.48 (s, 1H), 7.43 (s, 1H), 7.29 (d, J=5.2 Hz, 1H), 7.21-7.6.80 (m, 7H), 6.79 (d, J=6.8 Hz, 2H), 5.18 (s, 1H), 4.01 (m, 2H), 1.30 (t, J=6.8 Hz, 3H); MS (ESI): m/z 450.0 [M+1]$^+$.

Example 56

Compound 56, 4-(3-ethoxy-4-hydroxy-5-nitrophenyl)-6-(4-morpholinophenyl)-5-phenyl-3,4-dihydropyrimidin-2(1H)-one

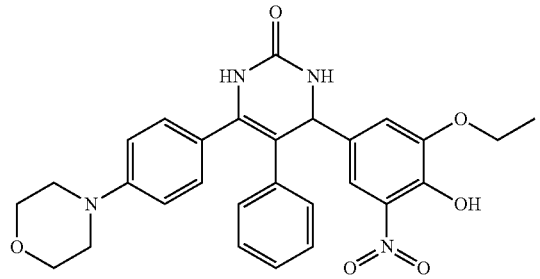 [SMILES: CCOc1cc(C2NC(=O)NC(c3ccc(N4CCOCC4)cc3)=C2c2ccccc2)cc([N+](=O)[O-])c1O]

A mixture of 1-(4-morpholinophenyl)-2-phenylethanone (Intermediate 25) (280 mg, 1.00 mmol), 3-ethoxy-4-hydroxy-5-nitrobenzaldehyde (175 mg, 0.83 mmol), urea (179 mg, 2.99 mmol), and concentrated HCl solution (0.07 mL, 0.83 mmol) in EtOH (5 mL) was refluxed for 48 h. The mixture was evaporated in vacuo, and the residue was purified by preparative HPLC to give Compound 56 (55.29 mg, yield 13%) as a solid. $^1$H NMR (CD$_3$OD 300 MHz): δ 7.62 (d, J=2.1 Hz, 1H), 7.20-7.15 (m, 3H), 7.10-7.04 (m, 3H), 6.92-6.85 (m, 4H), 5.30 (s, 1H), 4.12-4.02 (m, 2H), 3.81 (t, J=4.8 Hz, 4H), 3.15 (t, J=4.8 Hz, 4H), 1.41 (t, J=6.9 Hz, 3H); MS (ESI): m/z 517.0 [M+1]$^+$.

Example 57

Compound 57, 6-(4-aminophenyl)-4-(3-ethoxy-4-hydroxy-5-nitrophenyl)-5-phenyl-3,4-dihydropyrimidin-2(1H)-one

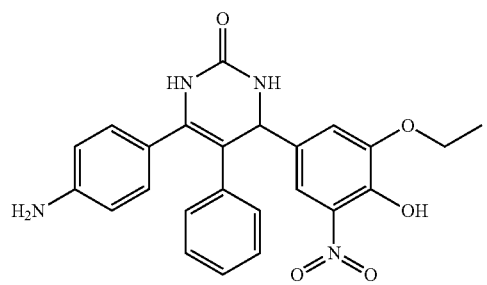 [SMILES: CCOc1cc(C2NC(=O)NC(c3ccc(N)cc3)=C2c2ccccc2)cc([N+](=O)[O-])c1O]

Step 1

A mixture of 6-(4-bromophenyl)-4-(3-ethoxy-4-hydroxy-5-nitrophenyl)-5-phenyl-3,4-dihydropyrimidin-2(1H)-one (Compound 33) (550 mg, 1.08 mmol), diphenylmethanimine (236 mg, 1.3 mmol), $Cs_2CO_3$ (702 mg, 2.16 mmol), $Pd_2(dba)_3$ (198 mg, 0.22 mmol), and xantphos (250 mg, 0.43 mmol) in dioxane (10 mL) was degassed and refluxed overnight under nitrogen. When LCMS indicated the starting material was consumed, the mixture was diluted with water, and extracted with EtOAc. The organic layer was concentrated, and purified by column to give 6-(4-(diphenylmethyleneamino)phenyl)-4-(3-ethoxy-4-hydroxy-5-nitrophenyl)-5-phenyl-3,4-dihydropyrimidin-2(1H)-one (230 mg, yield 35%) as a yellow solid.

Step 2

To a solution of 6-(4-(diphenylmethyleneamino)phenyl)-4-(3-ethoxy-4-hydroxy-5-nitrophenyl)-5-phenyl-3,4-dihydropyrimidin-2(1H)-one (230 mg, 0.38 mmol) in THF (2 mL) was added concentrated HCl solution (0.5 mL), and the mixture was stirred at room temperature for 2 h. The mixture was concentrated and purified by column to give Compound 57 (170 mg, yield 100%). $^1$H NMR (DMSO-$d_6$ 400 MHz): δ 10.31 (s, 1H), 8.54 (s, 1H), 7.50 (s, 1H), 7.45 (s, 1H), 7.22 (d, J=1.6 Hz, 1H), 7.07-6.97 (m, 5H), 6.83 (d, J=7.2 Hz, 2H), 6.59 (d, J=7.2 Hz, 2H), 5.09 (d, J=2.8 Hz, 1H), 4.06 (q, J=6.8 Hz, 2H), 1.34 (t, J=6.8 Hz, 3H); MS (ESI): m/z 447.0 [M+1]$^+$.

Example 58

Compound 58, 4-(3-ethoxy-4-hydroxy-5-nitrophenyl)-6-phenyl-5-(pyrazin-2-yl)-3,4-dihydropyrimidin-2(1H)-one

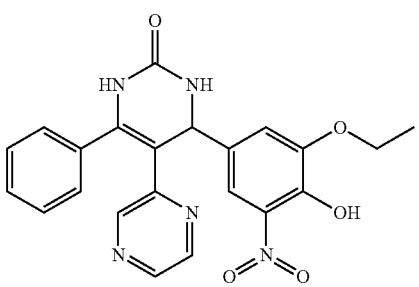 [SMILES: CCOc1cc(C2NC(=O)NC(c3ccccc3)=C2c2cnccn2)cc([N+](=O)[O-])c1O]

To a solution of 1-phenyl-2-(pyrazin-2-yl)ethanone (Intermediate 26) (150 mg, 0.76 mmol), 3-ethoxy-4-hydroxy-5-nitrobenzaldehyde (149 mg, 0.76 mmol), and urea (137 mg, 2.28 mmol) in 20 mL of ethanol was added 0.2 mL of concentrated HCl solution, the reaction mixture was stirred at reflux for 2 days. After the solvent was removed under reduced pressure, the residue was purified by reverse-phase preparatory HPLC (26-53% acetonitrile+0.1% trifluoroacetic acid in water+0.1% trifluoroacetic acid, over 15 min.) to give Compound 58 (72 mg, yield 21.9%). $^1$H NMR (DMSO-$d_6$ 300 MHz): δ10.27 (S, 1H), 9.22 (s, 1H), 8.43 (s, 1H), 8.15 (s, 1H), 7.84 (s, 1H), 7.65 (s, 1H), 7.44 (m, 4H), 7.32 (d, J=7.2 Hz, 3H), 5.45 (d, J=2.1 Hz, 1H), 4.10 (m, 2H), 1.35 (t, J=6.9 Hz, 3H); MS (ESI): m/z 434.0 [M+1]$^+$.

Example 59

Compound 59, 4-(3-ethoxy-4-hydroxy-5-nitrophenyl)-5-phenyl-6-(pyridin-2-yl)-3,4-dihydropyrimidin-2(1H)-one

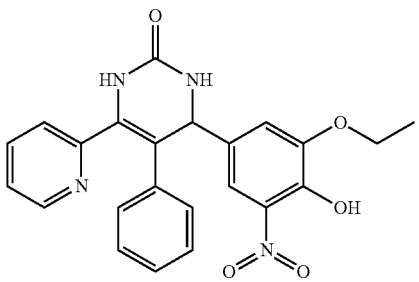 [SMILES: CCOc1cc(C2NC(=O)NC(c3ccccn3)=C2c2ccccc2)cc([N+](=O)[O-])c1O]

A mixture of 2-phenyl-1-(pyridin-2-yl)ethanone (Intermediate 27) (200 mg, 1.01 mmol), 3-ethoxy-4-hydroxy-5-nitrobenzaldehyde (214.1 mg, 1.01 mmol), urea (182.5 mg, 3.04 mmol), and concentrated hydrochloric acid solution (0.3 mL) in ethanol (1 mL) was refluxed for 60 h. After being cooled down to room temperature, the mixture was evaporated, and purified by preparative HPLC to give Compound 59 (132.5 mg, yield 30.2%). $^1$H NMR (DMSO-$d_6$ 400 MHz): δ10.26 (brs, 1H), 8.59 (d, J=4.4 Hz, 1H), 8.37 (s, 1H), 7.62-7.54 (m, 2H), 7.42 (s, 1H), 7.30-7.27 (m, 1H), 7.14 (d, J=6.4 Hz, 4H), 6.93-6.90 (m, 3H), 5.25 (s, 1H), 4.03-3.99 (m, 2H), 1.33-1.29 (m, 3H); MS (ESI): m/z 433.0 [M+H]$^+$.

Example 60

Compound 60, 5-(biphenyl-3-yl)-4-(3-ethoxy-4-hydroxy-5-nitrophenyl)-6-phenyl-3,4-dihydropyrimidin-2(1H)-one

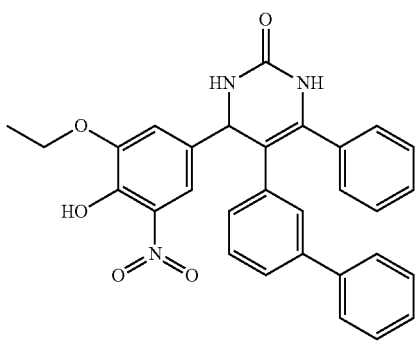 [SMILES: CCOc1cc(C2NC(=O)NC(c3ccccc3)=C2c2cccc(-c3ccccc3)c2)cc([N+](=O)[O-])c1O]

To a solution of 2-(biphenyl-3-yl)-1-phenylethanone (Intermediate 28) (120 mg, 0.44 mmol), 3-ethoxy-4-hydroxy-5-nitrobenzaldehyde (86.9 mg, 0.44 mmol), and urea (79.3 mg, 1.32 mmol) in 5 mL of ethanol was added 0.2 mL of concentrated HCl solution. The mixture was refluxed for 2 days. After the solvent was removed under reduced pressure, the residue was purified by reverse-phase preparatory HPLC (26-53% acetonitrile+0.1% trifluoroacetic acid in water+0.1% trifluoroacetic acid, over 15 min.) to give Compound 60 (25 mg, yield 11.2%). $^1$H NMR (DMSO-$d_6$ 400 MHz) δ 10.24 (s, 1H), 8.74 (s, 1H), 7.50 (s, 1H), 7.40 (s, 1H), 7.32-7.12 (m, 12H), 7.10 (t, J=8.0 Hz, 1H), 7.00 (m, 1H), 6.82 (d, J=6.8 Hz, 1H), 5.30 (d, J=2.8 Hz, 1H), 4.00 (m, 2H), 1.26 (t, J=6.8 Hz, 3H); MS (ESI): m/z 508.1 [M+1]⁺.

Example 61

Compound 61, 6-(benzo[d][1,3]dioxol-5-yl)-4-(3-ethoxy-4-hydroxy-5-nitrophenyl)-5-phenyl-3,4-dihydropyrimidin-2(1H)-one

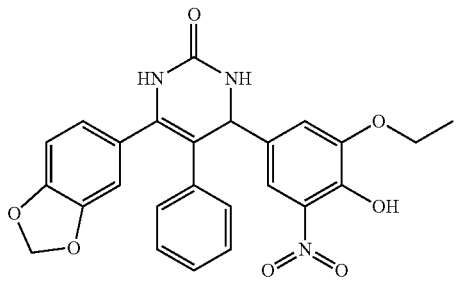 [SMILES: CCOc1cc(C2NC(=O)NC(c3ccc4c(c3)OCO4)=C2c2ccccc2)cc([N+](=O)[O-])c1O]

To a solution of 1-(benzo[d][1,3]dioxol-5-yl)-2-phenylethanone (Intermediate 29) (400 mg, 1.7 mmol), 3-ethoxy-4-hydroxy-5-nitrobenzaldehyde (352 mg, 1.7 mmol), and urea (230 mg, 5.0 mmol) in 10 mL of ethanol was added 0.2 mL of concentrated HCl solution, the mixture was stirred at 130° C. overnight. After the solvent was removed under reduced pressure, the residue was purified by preparative HPLC (35-65% acetonitrile+0.1% trifluoroacetic acid in water, over 15 min.) to give Compound 61 (92.5 mg, yield 11.7%). ¹H NMR (CD₃OD 400 MHz): δ 7.60 (s, 1H), 7.18 (s, 1H), 7.12-7.09 (m, 3H), 6.92 (d, J=7.2 Hz, 2H), 6.78 (d, J=8.0 Hz, 1H), 6.71 (m, 2H), 5.92 (s, 2H), 5.32 (s, 1H), 4.11-4.03 (m, 2H), 1.41 (t, J=7.2 Hz, 3H); MS (ESI): m/z 476.3 [M+1]⁺.

Example 62

Compound 62, 4-(3-ethoxy-4-hydroxy-5-nitrophenyl)-3-methyl-5,6-diphenyl-3,4-dihydropyrimidin-2 (1H)-one

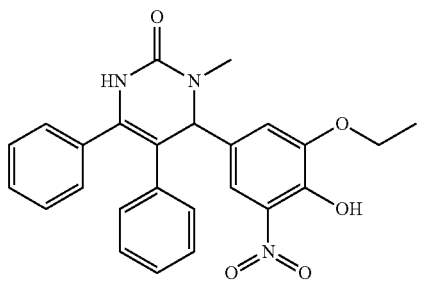 [SMILES: CCOc1cc(C2C(c3ccccc3)=C(c3ccccc3)NC(=O)N2C)cc([N+](=O)[O-])c1O]

Step 1

To a solution of 1,2-diphenylethanone (300 mg, 1.5 mmol) and 3-ethoxy-4-hydroxy-5-nitrobenzaldehyde (324 mg, 1.5 mmol) in anhydrous toluene (10 mL) was added piperidine (cat.), and the reaction mixture was refluxed overnight. TLC (PE:EtOAc=3:1) indicated that the starting materials were consumed. The solvent was removed under vacuum, and the residue was purified by column chromatography (PE: EtOAc=10:1) to afford the intermediate as a red solid (420 mg, yield: 70.6%). ¹H NMR (DMSO-d₆ 400 MHz): δ 10.50 (s, 1H), 7.90 (d, J=1.4 Hz, 3H), 7.80 (d, J=1.2 Hz, 2H), 7.58-7.61 (m, 2H), 7.25-7.7.50 (m, 21H), 7.20 (s, 1H), 7.05 (s, 1H), 6.75 (s, 1H), 3.80 (q, J=7.2 Hz, 3H), 3.62 (q, J=7.2 Hz, 2H), 1.17 (t, J=3.6 Hz, 7H), 1.12 (t, J=3.6 Hz, 3H); MS (ESI): m/z 390.1 [M+1]⁺.

Step 2

To a solution of the Intermediate prepared in Step 1 (480 mg, 1.2 mmol) and 1-methylurea (274 mg, 3.7 mmol) in anhydrous toluene (10 mL) was added NaH (99 mg, 4.8 mmol), then a few drops of MeOH were added to initiate the reaction, and the mixture was stirred at 60° C. overnight. TLC (EtOAc: MeOH=1:2) showed the starting materials were consumed. The reaction mixture was poured into ice-water, and acidified with 0.5 N HCl to pH=2. The aqueous layer was extracted with EtOAc (20 mL×3), the combined organic layer was washed with brine (20 mL), dried over Na₂SO₄, filtered, and concentrated. The residue was purified by column chromatography and preparative HPLC to afford Compound 62 as a yellow solid (55.2 mg, yield: 10.1%). ¹H NMR (DMSO-d₆ 400 MHz): δ 10.30 (s, 1H), 8.79 (s, 1H), 7.45 (s, 1H), 7.12-7.21 (m, 6H), 6.95-7.05 (m, 3H), 6.75 (d, J=6.4 Hz, 2H), 5.21 (s, 1H), 3.97-4.05 (m, 2H), 2.75 (s, 3H) 1.30 (t, J=7.2 Hz, 3H); MS (ESI): m/z 466.1 [M+1]⁺.

Example 63

Compound 63, 4-(6-(3-ethoxy-4-hydroxy-5-nitrophenyl)-2-oxo-5-phenyl-1,2,3,6-tetrahydropyrimidin-4-yl)benzonitrile

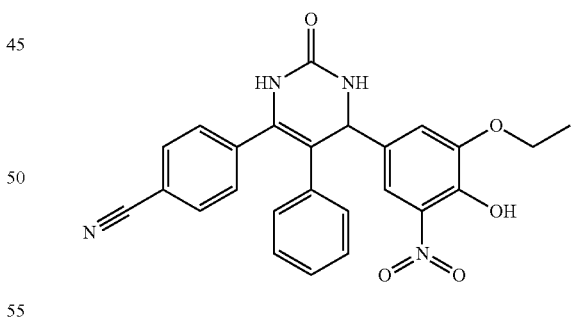

A mixture of 4-(2-phenylacetyl)benzonitrile (Intermediate 30) (50 mg, 0.23 mmol), 1,2-diphenylethanone (43 mg, 0.21 mmol), urea (41 mg, 0.68 mmol), and concentrated HCl solution (0.02 mL, 0.21 mmol) in EtOH (5 mL) was heated at reflux for 48 h. The mixture was evaporated in vacuo, and the residue was purified by preparative HPLC to give Compound 63 (22.27 mg, yield 40%). ¹H NMR (CD₃OD 400 MHz): δ 7.62-7.59 (m, 3H), 7.42 (d, J=8.0 Hz, 2H), 7.13-7.10 (m, 4H), 6.92-6.90 (m, 2H), 5.41 (s, 1H), 4.10-4.00 (m, 2H), 1.40 (t, J=7.2 Hz, 3H); MS (ESI): m/z 457.0 [M+1]⁺.

Example 64

Compound 64, 4-(3-ethoxy-5-fluoro-4-hydroxyphenyl)-5,6-diphenyl-3,4-dihydropyrimidin-2(1H)-one

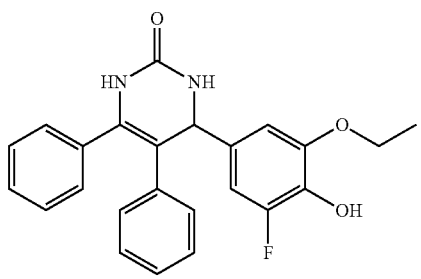 [SMILES: CCOc1cc(C2NC(=O)NC(c3ccccc3)=C2c2ccccc2)cc(F)c1O]

The mixture of 3-ethoxy-5-fluoro-4-hydroxybenzaldehyde (Intermediate 32) (160 mg, 0.87 mmol), 1,2-diphenylethanone (170 mg, 0.87 mmol), urea (157 mg, 2.61 mmol), and concentrated HCl solution (0.2 mL) in ethanol (20 mL) was degassed and refluxed for 3 days under $N_2$ protection. The solvent was removed under reduced pressure, and the residue was purified by preparative HPLC to give Compound 64 (30 mg, 10.6%). $^1$H NMR (DMSO-$d_6$ 300 MHz) δ 9.08 (s, br, 1H), 8.63 (s, 1H), 7.42 (s, 1H), 7.19-7.26 (m, 5H), 7.01-7.03 (m, 3H), 6.72-6.81 (m, 4H), 5.04 (d, J=2.7 Hz, 1H), 3.99 (q, $J_1$=6.9 Hz, $J_2$=9.0 Hz, 2H), 1.33 (t, J=6.9 Hz, 3H); MS (ESI): m/z 405.1 [M+1]$^+$.

Example 65

Compound 65, 4-(3-ethoxy-4-hydroxy-5-nitrophenyl)-5-phenyl-6-(pyridin-3-yl)-3,4-dihydropyrimidin-2(1H)-one

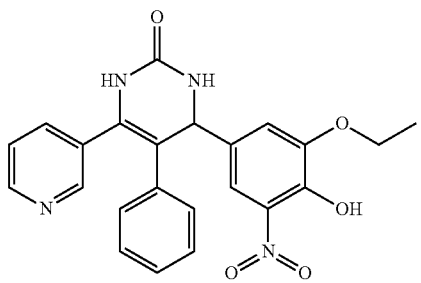 [SMILES: CCOc1cc(C2NC(=O)NC(c3cccnc3)=C2c2ccccc2)cc([N+](=O)[O-])c1O]

A mixture of 2-phenyl-1-(pyridin-3-yl)ethanone (Intermediate 31) (110 mg, 0.56 mmol), 3-ethoxy-4-hydroxy-5-nitrobenzaldehyde (107 mg, 0.51 mmol), urea (91 mg, 1.52 mmol), and concentrated HCl solution (0.04 mL, 0.56 mmol) in EtOH (5 mL) was refluxed overnight. The mixture was evaporated in vacuo and purified by preparative HPLC to give Compound 65 (46.21 mg, yield 21%). $^1$H NMR (DMSO-$d_6$ 400 MHz): δ 10.28 (s, 1H), 8.91 (s, 1H), 8.46 (d, J=5.2 Hz, 1H), 8.36 (s, 1H), 7.71 (d, J=7.2 Hz, 1H), 7.59 (s, 1H), 7.43 (s, 1H), 7.36 (t, J=5.2 Hz, 1H), 7.15 (s, 1H), 7.09-7.04 (m, 3H), 6.86 (d, J=6.8 Hz, 2H), 5.29 (d, J=2.0 Hz, 1H), 4.04 (q, J=6.8 Hz, 2H), 1.33 (t, J=6.8 Hz, 3H); MS (ESI): m/z 433.0 [M+1]$^+$.

Example 66

Compound 66, (R)-4-(3-ethoxy-4-hydroxy-5-nitrophenyl)-5-phenyl-6-(pyridin-3-yl)-3,4-dihydropyrimidin-2(1H)-one (Single Enantiomer of Compound 65)

The two enantiomers of Compound 65 were separated by chiral supercritical chromatography (SFC separation condition: Column: AS-20 UM, 300*300 mm, 20 UM; Mobile Phase: Supercritical Fluid CO2:MeOH=65:35, 80 ML/MIN; Detector Wavelength: 220 nm), the eluting solution for the first peak was collected and evaporated to give one enantiomer as Compound 66 (37 mg, yield 6%). $^1$H NMR (CD$_3$OD 400 MHz): δ 8.32 (d, J=4.4 Hz, 1H), 8.26 (s, 1H), 7.69 (d, J=8.0 Hz, 1H), 7.50 (s, 1H), 7.30-7.26 (m, 1H), 7.03-7.01 (m, 4H), 6.83-6.81 (m, 2H), 5.34 (s, 1H), 4.02-3.91 (m, 2H), 1.30 (t, J=6.8 Hz, 3H); MS (ESI): m/z 433.0 [M+1]$^+$.

Example 67

Compound 67, (S)-4-(3-ethoxy-4-hydroxy-5-nitrophenyl)-5-phenyl-6-(pyridin-3-yl)-3,4-dihydropyrimidin-2(1H)-one (Single Enantiomer of Compound 65)

The two enantiomers of Compound 65 were separated by chiral supercritical chromatography (SFC separation condition: Column: AS-20 UM, 300*300 mm, 20 UM; Mobile Phase: Supercritical Fluid CO2:MeOH=65:35, 80 ML/MIN; Detector Wavelength: 220 nm), the eluting solution for the second peak was collected and evaporated to give another enantiomer as Compound 67 (35 mg, yield 6%). $^1$H NMR (CD$_3$OD 400 MHz): δ 8.29 (d, J=4.4 Hz, 1H), 8.23 (s, 1H), 7.66 (d, J=8.4 Hz, 1H), 7.47 (s, 1H), 7.26-7.23 (m, 1H), 7.00-6.99 (m, 4H), 6.82-6.79 (m, 2H), 5.30 (s, 1H), 3.98-3.88 (m, 2H), 1.28 (t, J=6.8 Hz, 3H); MS (ESI): m/z 433.0 [M+1]$^+$.

Example 68

Compound 68, 4-(3-fluoro-4-hydroxy-5-methoxyphenyl)-5,6-diphenyl-3,4-dihydropyrimidin-2(1H)-one

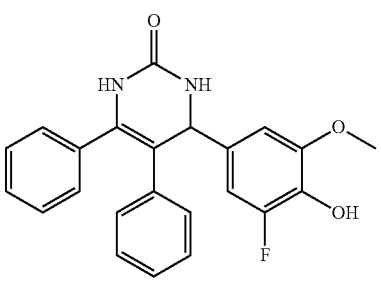 [SMILES: COc1cc(C2NC(=O)NC(c3ccccc3)=C2c2ccccc2)cc(F)c1O]

A mixture of 3-fluoro-4-hydroxy-5-methoxybenzaldehyde (50 mg, 0.294 mmol), 1,2-diphenylethanone (57.7 mg, 0.294 mmol), urea (52.9 mg, 0.882 mmol), and concentrated HCl solution (0.5 mL) in ethanol (2 mL) was refluxed at 80° C. for 52 h. The reaction mixture was evaporated under reduced pressure, and the residue was purified by preparative HPLC to give Compound 68 (32.1 mg, yield 28%). $^1$HNMR (DMSO-$d_6$ 400 MHZ): δ 9.25 (s, 1H), 8.70 (s, 1H), 7.49 (s, 1H), 7.32-7.26 (m, 5H), 7.11-7.05 (m, 3H), 6.88 (d, J=1.6 Hz, 2H), 6.86-6.79 (m, 2H), 5.11 (d, J=2.8 Hz, 1H), 3.79 (s, 3H); MS (ESI): m/z 391.0 [M+H]⁺.

Example 69

Compound 69, 3-ethoxy-2-hydroxy-5-(2-oxo-5,6-diphenyl-1,2,3,4-tetrahydropyrimidin-4-yl)benzonitrile

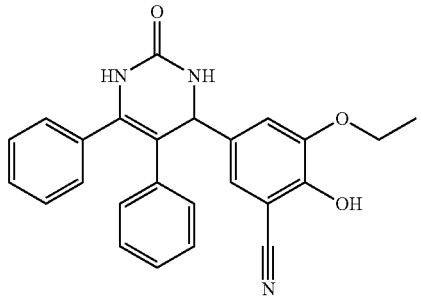 [SMILES: CCOc1cc(C2NC(=O)NC(c3ccccc3)=C2c2ccccc2)cc(C#N)c1O]

A mixture of 3-ethoxy-5-formyl-2-hydroxybenzonitrile (285 mg, 1.5 mmol), 1,2-diphenylethanone (320 mg, 1.6 mmol), and urea (270 mg, 4.5 mmol) in anhydrous EtOH (5 mL) was added concentrated HCl solution (0.5 mL). The reaction mixture was refluxed overnight. TLC (EtOAc:MeOH=10:1) showed 40% of the starting materials were consumed. The reaction mixture was concentrated, and purified by column chromatography (EtOAc:MeOH=40:1) and preparative HPLC to afford Compound 69 as a yellow solid (280 mg, yield: 45.7%). ¹H NMR (DMSO-d₆ 400 MHz TMS): δ 10.30 (s, 1H), 8.70 (d, J=1.2 Hz, 1H), 7.47 (s, 1H), 7.20-7.27 (m, 5H), 7.16 (d, J=1.6 Hz, 1H), 6.98-7.06 (m, 4H), 6.80-6.82 (m, 2H), 5.14 (d, J=2.4 Hz, 1H), 4.00-4.10 (m, 2H), 1.33 (t, J=7.2 Hz, 3H); MS (ESI): m/z 412.1 [M+1]⁺.

Example 70

Compound 70, 2-(4-(3-ethoxy-4-hydroxy-5-nitrophenyl)-2-oxo-6-phenyl-1,2,3,4-tetrahydropyrimidin-5-yl)benzonitrile

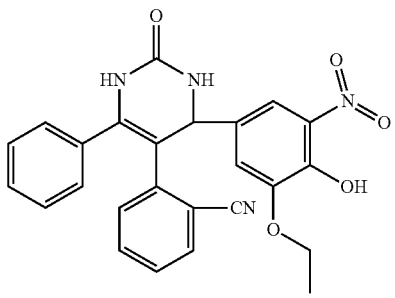 [SMILES: CCOc1cc(C2NC(=O)NC(c3ccccc3)=C2c2ccccc2C#N)cc([N+](=O)[O-])c1O]

A mixture of 2-(2-oxo-2-phenylethyl)benzonitrile (Intermediate 33) (100 mg, 0.45 mmol), 3-ethoxy-4-hydroxy-5-nitrobenzaldehyde (87 mg, 0.41 mmol), urea (81 mg, 1.36 mmol), and concentrated HCl solution (0.03 mL, 0.41 mmol) in EtOH (5 mL) was refluxed overnight. The mixture was concentrated, and purified by preparative HPLC to give Compound 70 (54.26 mg, yield 29%) as a yellow solid. ¹H NMR (DMSO-d₆ 300 MHz): δ 10.24 (s, 1H), 8.91 (s, 1H), 7.61 (s, 1H), 7.51-7.44 (m, 2H), 7.31 (s, 1H), 7.24-7.16 (m, 4H), 7.13-7.08 (m, 3H), 5.37 (s, 1H), 3.99-3.93 (m, 2H), 1.31 (t, J=6.8 Hz, 3H); MS (ESI): m/z 456.8 [M+1]⁺.

Example 71

Compound 71, 4-(3-ethoxy-4-hydroxy-5-nitrophenyl)-5-phenyl-6-(pyridin-4-yl)-3,4-dihydropyrimidin-2(1H)-one

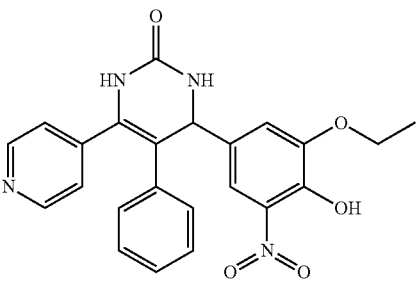 [SMILES: CCOc1cc(C2NC(=O)NC(c3ccncc3)=C2c2ccccc2)cc([N+](=O)[O-])c1O]

A mixture of 2-phenyl-1-(pyridin-4-yl)ethanone (Intermediate 35) (60 mg, 0.30 mmol), 3-ethoxy-4-hydroxy-5-nitrobenzaldehyde (58 mg, 0.28 mmol), urea (50 mg, 0.83 mmol), and concentrated HCl solution (0.02 mL, 0.28 mmol) in EtOH (5 mL) was refluxed overnight. The mixture was evaporated in vacuo and purified by preparative HPLC to give Compound 71 (55.17 mg, yield 46%). ¹H NMR (DMSO-d₆ 400 MHz): δ 10.29 (br, 1H), 8.92 (s, 1H), 8.53 (d, J=5.6 Hz, 2H), 7.61 (s, 1H), 7.41 (d, J=1.6 Hz, 1H), 7.35 (d, J=1.6 Hz, 2H), 7.12-7.09 (m, 4H), 6.89 (d, J=7.6 Hz, 2H), 5.31 (d, J=2.8 Hz, 1H), 4.03 (q, J=7.2 Hz, 2H), 1.32 (t, J=7.2 Hz, 3H); MS (ESI): m/z 433.0 [M+1]⁺.

Example 72

Compound 72, 7-ethoxy-5-(2-oxo-5,6-diphenyl-1,2,3,4-tetrahydropyrimidin-4-yl)benzo[d]oxazol-2(3H)-one

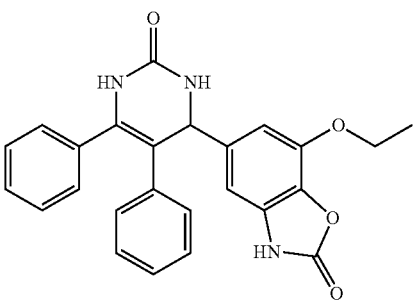 [SMILES: CCOc1cc(C2NC(=O)NC(c3ccccc3)=C2c2ccccc2)cc2[nH]c(=O)oc12]

Step 1

To a mixture of 4-(3-ethoxy-4-hydroxy-5-nitrophenyl)-5,6-diphenyl-3,4-dihydropyrimidin-2(1H)-one (Compound 1) (431 mg, 1.0 mmol) and NH₄Cl (268 mg, 5.0 mmol) in MeOH:THF:H₂O=2:1:1 (8 mL) was added iron power (280 mg, 5.0 mmol) and the reaction mixture was heated to reflux for 1.0 h. The reaction mixture was cooled to room temperature and filtered. The filtered mass was washed with methanol (5.0 mL). The filtrate was concentrated in vacuo to afford 4-(3-amino-5-ethoxy-4-hydroxyphenyl)-5,6-diphenyl-3,4-dihydropyrimidin-2(1H)-one as a white solid (386 mg, 96.3%), which was used directly for the next step.

Step 2

To a solution of CDI (243 mg, 1.50 mmol) in THF (3 mL) was added 4-(3-amino-5-ethoxy-4-hydroxyphenyl)-5,6-diphenyl-3,4-dihydropyrimidin-2(1H)-one (386 mg, 0.96 mmol) and the resultant mixture was heated to reflux for 1.0 h. The reaction mixture was added water (10 mL) and filtered. The filtered mass was washed with methanol (3 mL) and dried to afford Compound 72 as a yellow solid (110 mg, 30%). $^1$H NMR (DMSO-$d_6$ 500 MHz): δ 11.56 (s, 1H), 8.69 (s, 1H), 7.49 (s, 1H), 7.21 (s, 3H), 7.20 (s, 2H), 6.99-7.04 (m, 3H), 6.81 (d, J=6.0 Hz, 2H), 6.74 (d, J=6.0 Hz, 2H), 5.12 (s, 1H), 4.11 (q, J=6.8 Hz, 2H), 1.31 (t, J=7.0 Hz, 3H); MS (ESI): m/z 428.1 [M+1]$^+$.

Example 73

Compound 73, N-(4-(6-(3-ethoxy-4-hydroxy-5-nitrophenyl)-2-oxo-5-phenyl-1,2,3,6-tetrahydropyrimidin-4-yl)phenyl)acetamide

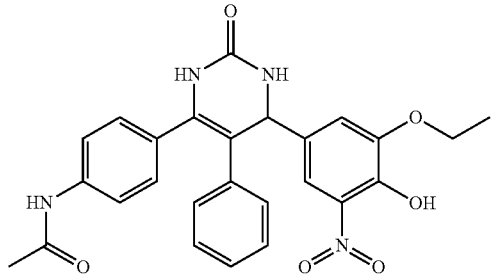 [SMILES: CCOc1cc(C2NC(=O)NC(c3ccc(NC(C)=O)cc3)=C2c2ccccc2)cc([N+](=O)[O-])c1O]

To a solution of compound 6-(4-aminophenyl)-4-(3-ethoxy-4-hydroxy-5-nitrophenyl)-5-phenyl-3,4-dihydropyrimidin-2(1H)-one (Compound 84) (100 mg, 0.22 mmol) in DCM (2 mL) was added Ac$_2$O (27 mg, 0.27 mmol) at room temperature, and the mixture was stirred at room temperature for 4 hours. The mixture was evaporated in vacuo and purified by column to give the Compound 73 (32.07 mg, yield 34%). $^1$H NMR (DMSO-$d_6$ 300 MHz): δ 10.28 (brs, 1H), 9.95 (s, 1H), 8.66 (s, 1H), 7.52 (s, 1H), 7.45-7.42 (m, 3H), 7.19 (d, J=1.8 Hz, 1H), 7.13-6.97 (m, 5H), 6.83 (d, J=6.6 Hz, 2H), 5.17 (d, J=2.7 Hz, 1H), 4.10-4.01 (m, 2H), 2.02 (s, 3H), 1.33 (t, J=6.9 Hz, 3H); MS (ESI): m/z 489.1 [M+1]$^+$.

Example 74

Compound 74, 4-(3-ethoxy-4-hydroxy-5-nitrophenyl)-6-phenyl-5-(pyridin-4-yl)-3,4-dihydropyrimidin-2(1H)-one

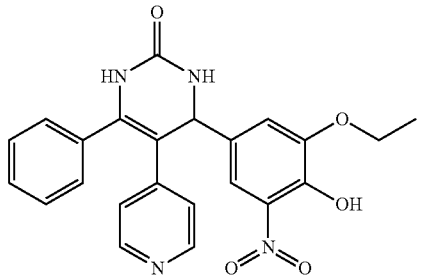

A mixture of 1-phenyl-2-(pyridin-4-yl)ethanone (Intermediate 36) (100 mg, 0.507 mmol), 3-ethoxy-4-hydroxy-5-nitrobenzaldehyde (107 mg, 0.507 mmol), urea (91.3 mg, 4.587 mmol), and concentrated hydrochloric acid (0.3 mL) in ethanol (1 mL) was refluxed at 79° C. for 80 h. After being cooled down to room temperature, the mixture was evaporated, and purified by preparative HPLC to give Compound 74 (80.1 mg, yield 38.3%). $^1$H NMR (DMSO-$d_6$ 400 MHz): δ 10.41 (s, 1H), 9.57 (s, 1H), 8.34 (d, J=6.4 Hz, 2H), 8.02 (s, 1H), 7.50-7.42 (m, 4H), 7.39 (d, J=7.2 Hz, 2H), 7.34 (d, J=1.6 Hz, 1H), 7.06 (d, J=6.4 Hz, 2H), 5.39 (d, J=3.2 Hz, 1H), 4.15-4.10 (m, 2H), 1.38-1.35 (m, 3H); MS (ESI): m/z 433.0 [M+H]$^+$.

Example 75

Compound 75, N-(3-ethoxy-2-hydroxy-5-(2-oxo-5,6-diphenyl-1,2,3,4-tetrahydropyrimidin-4-yl)phenyl)methanesulfonamide

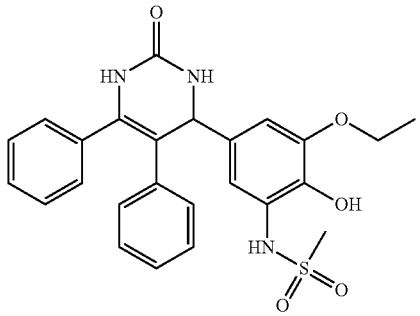 [SMILES: CCOc1cc(C2NC(=O)NC(c3ccccc3)=C2c2ccccc2)cc(NS(C)(=O)=O)c1O]

4-(3-ethoxy-4-hydroxy-5-nitrophenyl)-5,6-diphenyl-3,4-dihydropyrimidin-2(1H)-one (Compound 1) (400 mg, 0.93 mmol) was dissolved in an EtOH:H$_2$O:THF (8 mL, 2:1:1) mixture. To this was added Zn dust (124 mg, 1.89 mmol) and NH$_4$Cl (104 mg, 1.94 mmol) and stirred at room temperature for 18 hours. After removing a 1 mL aliquot of the reaction mixture, the remaining solution was filtered through a celite pad followed by a solvent swap to DCM/THF (2 mL/2 mL). Et$_3$N (0.1 mL, 0.72 mmol) was added and the solution was stirred for 15 minutes. Mesyl chloride (40 µL, 0.24 mmol) was added and the solution stirred at room temperature for 18 hours. Additional Et$_3$N (0.1 mL, 0.72 mmol) and mesyl chloride (30 µL, 0.18 mmol) was then added and stirred for an additional 6 hours. The crude mixture was concentrated in vacuo and purified by silica-gel column chromatography (0-5% MeOH in EtOAc) to afford 25 mg of Compound 75 as a faint yellow solid. $^1$H NMR (CD$_3$OD 300 MHz): δ 7.25 (m, 5H), 7.16 (d, 1H), 7.03 (d, 1H), 7.01 (d, 2H), 6.89 (m, 2H), 6.84 (d, 1H), 5.19 (s, 1H), 4.62 (s, 1H), 4.10 (q, 2H), 2.87 (s, 3H), 1.40 (t, 3H); MS (ESI): m/z 480.23 [M+1]$^+$.

Example 76

Compound 76, N-(2-hydroxy-3-methoxy-5-(2-oxo-5,6-diphenyl-1,2,3,4-tetrahydropyrimidin-4-yl)phenyl)methanesulfonamide

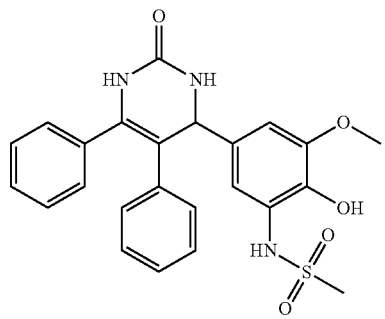 [SMILES: COc1cc(C2NC(=O)NC(c3ccccc3)=C2c2ccccc2)cc(NS(C)(=O)=O)c1O]

4-(4-Hydroxy-3-methoxy-5-nitrophenyl)-5,6-diphenyl-3,4-dihydropyrimidin-2(1H)-one (Compound 9) (100 mg, 0.24 mmol) was dissolved in an EtOH:H₂O:THF (4 mL, 2:1:1) mixture. To this was added Zn dust (26 mg, 0.40 mmol) and NH₄Cl (26 mg, 0.48 mmol) and stirred at room temperature for 1 day, followed by stirring at 50° C. for 1 day. The solution was filtered through a celite pad followed by a solvent swap to DCM (5 mL). Excess Et₃N (0.1 ml, 0.72 mmol) was added and stirred for 15 minutes, followed by excess addition of mesyl chloride (50 µL, 0.3 mmol) and stirring over night. The crude mixture was directly purified by silica-gel column chromatography (0 to 5% MeOH in EtOAc) to yield 10 mg of Compound 76 as a faint yellow solid. ¹H NMR (CD₃OD 300 MHz): δ 7.27 (m, 5H), 7.06 (m, 1H), 7.04 (d, 2H), 6.91 (m, 2H), 6.61 (d, 1H), 6.38 (d, 1H), 5.51 (s, 1H), 5.14 (s, 1H), 3.77 (s, 3H)); MS (ESI): m/z 466.17 [M+1]⁺.

Example 77

Compound 77, 3-ethoxy-2-hydroxy-5-(2-oxo-5,6-diphenyl-1,2,3,4-tetrahydropyrimidin-4-yl)benzoic acid

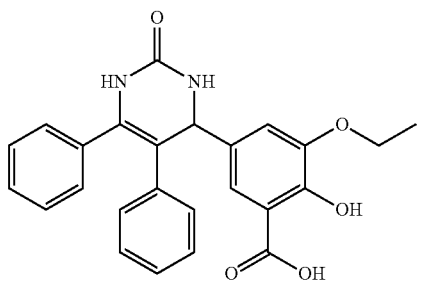 [SMILES: CCOc1cc(C2NC(=O)NC(c3ccccc3)=C2c2ccccc2)cc(C(=O)O)c1O]

To a mixture of 3-ethoxy-5-formyl-2-hydroxybenzoic acid (Intermediate 37) (130 mg, 0.60 mmol), 1,2-diphenylethanone (150 mg, 0.76), and urea (80 mg, 1.3 mmol) in anhydrous EtOH (5 mL) was added concentrated HCl solution (0.2 mL), the reaction mixture was refluxed overnight. TLC (EtOAc:MeOH=10:1) showed about 50% of the starting materials were consumed. The reaction mixture was concentrated, and purified by column chromatograph (EtOAc:MeOH=40:1) and preparative HPLC to afford Compound 77 as a yellow solid (15 mg, yield: 5.6%). ¹H NMR (DMSO-d₆ 400 MHz): δ 11.37 (s, 1H), 8.66 (s, 1H), 7.47 (s, 1H), 7.43 (d, J=2.0 Hz, 1H), 7.25-7.27 (m, 3H), 7.21-7.25 (m, 2H), 7.14 (d, J=2.0 Hz, 1H), 6.97-7.05 (m, 3H), 6.81 (d, J=2.4 Hz, 2H), 5.10 (d, J=2.8 Hz, 1H), 3.97-4.02 (m, 2H), 1.31 (t, J=6.8 Hz, 3H); MS (ESI): m/z 431.1 [M+1]⁺.

Example 78

Compound 78, 4-(3-ethoxy-4-hydroxy-5-nitrophenyl)-5-phenyl-6-(thiophen-2-yl)-3,4-dihydropyrimidin-2(1H)-one

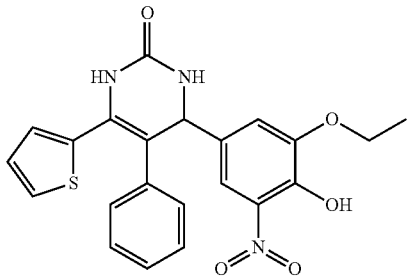

A mixture of 2-phenyl-1-(thiophen-2-yl)ethanone (Intermediate 38) (100 mg, 0.49 mmol), 3-ethoxy-4-hydroxy-5-nitrobenzaldehyde (95 mg, 0.45 mmol), urea (81 mg, 1.35 mmol), and concentrated HCl solution (0.04 mL, 0.45 mmol) in EtOH (5 mL) was refluxed overnight. The mixture was diluted with water, and extracted with EtOAc. The organic layer was separated, and the aqueous layer was extracted with EtOAc. The combined organic layer was dried over Na₂SO₄, evaporated in vacuo, and purified by preparative HPLC to give Compound 78 (45 mg, yield 23%). ¹H NMR (DMSO-d₆ 300 MHz): δ 10.22 (s, 1H), 8.61 (s, 1H), 7.47 (s, 1H), 7.34-7.29 (m, 2H), 7.15-7.13 (m, 1H), 7.09-7.06 (m, 3H), 6.99 (s, 1H), 6.87-6.83 (m, 3H), 5.02 (d, J=2.4 Hz, 1H), 3.92 (q, J=7.2 Hz, 2H), 1.22 (t, J=7.2 Hz, 3H); MS (ESI): m/z 438.0[M+1]⁺.

Example 79

Compound 79, 4-(3-ethoxy-4-hydroxy-5-nitrophenyl)-5-phenyl-6-(thiophen-3-yl)-3,4-dihydropyrimidin-2(1H)-one

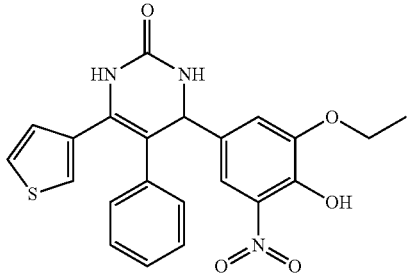

A mixture of 2-phenyl-1-(thiophen-3-yl)ethanone (Intermediate 39) (100 mg, 0.49 mmol), 3-ethoxy-4-hydroxy-5-nitrobenzaldehyde (95 mg, 0.45 mmol), urea (81 mg, 1.35 mmol), and concentrated HCl solution (0.04 mL, 0.45 mmol) in EtOH (5 mL) was refluxed overnight. The mixture was diluted with water, and extracted with EtOAc. The organic layer was separated, and the aqueous layer was extracted with EtOAc. The combined organic layer was dried over Na₂SO₄, evaporated in vacuo, and purified by preparative HPLC to give Compound 79 (45 mg, yield 23%). ¹H NMR (DMSO-d₆ 300 MHz): δ 10.19 (s, 1H), 8.50 (s, 1H), 7.43-7.40 (m, 2H), 7.30-7.24 (m, 2H), 7.04-7.00 (m, 4H), 6.83-6.80 (m, 2H), 6.52 (s, J=5.1 Hz, 1H), 5.07 (d, J=2.4 Hz, 1H), 3.97-3.88 (m, 2H), 1.22 (t, J=6.9 Hz, 3H); MS (ESI): m/z 438.0 [M+1]⁺.

Example 80

Compound 80, 4-(3-ethoxy-4-hydroxy-5-nitrophenyl)-6-(1-methyl-1H-imidazol-4-yl)-5-phenyl-3,4-dihydropyrimidin-2(1H)-one

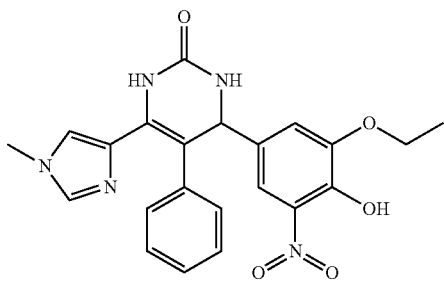 [SMILES: CCOc1cc(C2NC(=O)NC(c3cn(C)cn3)=C2c2ccccc2)cc([N+](=O)[O-])c1O]

A mixture of 1-(1-methyl-1H-imidazol-4-yl)-2-phenylethanone (Intermediate 40) (130 mg, 0.65 mmol), compound 3-ethoxy-4-hydroxy-5-nitrobenzaldehyde (165 mg, 0.78 mmol), and urea (117 mg, 1.95 mmol) in anhydrous EtOH (5 mL) was added concentrated HCl solution (0.2 mL), the reaction mixture was refluxed for 16 hours. The reaction mixture was concentrated under reduced pressure, and purified by column chromatograph and preparative HPLC to afford Compound 80 as a yellow solid (87 mg, yield: 30.8%). $^1$H NMR (DMSO-$d_6$ 400 MHz): δ 10.31 (s, 1H), 8.62 (m, 2H), 7.68 (s, 1H), 7.37 (d, J=2.0 Hz, 1H), 7.19-7.22 (m, 3H), 7.06 (m, 2H), 6.97-7.00 (m, 2H), 5.25 (d, J=2.4 Hz, 1H), 3.95-4.07 (m, 2H), 3.67 (s, 3H), 1.29-1.33 (t, J=6.8 Hz, 3H); MS (ESI): m/z 436.1 [M+1]$^+$.

Example 81

Compound 81, 4-(3-ethoxy-4-hydroxy-5-nitrophenyl)-6-(naphthalen-1-yl)-5-phenyl-3,4-dihydropyrimidin-2(1H)-one

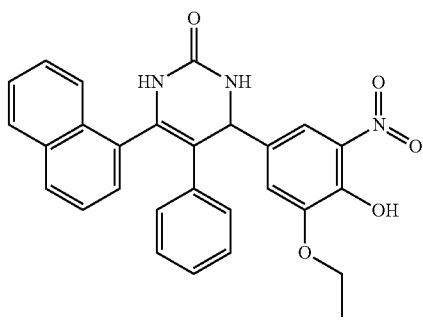 [SMILES: CCOc1cc(C2NC(=O)NC(c3cccc4ccccc34)=C2c2ccccc2)cc([N+](=O)[O-])c1O]

To a mixture of 1-(naphthalen-1-yl)-2-phenylethanone (Intermediate 41) (250 mg, 1.02 mmol), 3-ethoxy-4-hydroxy-5-nitrobenzaldehyde (257.3 mg, 1.22 mmol), and urea (182.9 mg, 3.05 mmol) in anhydrous EtOH (5 mL) was added concentrated HCl solution (0.2 mL), and the reaction mixture was refluxed for 14 hours. The reaction mixture was concentrated under reduced pressure, and purified by column chromatography and preparative HPLC to afford Compound 81 as a yellow solid (89 mg, yield: 18.1%). $^1$H NMR (DMSO-$d_6$ 400 MHz): δ 10.30 (s, 1H), 8.84 (s, 1H), 6.49-7.89 (m, 8H), 6.87-7.23 (m, 7H), 5.26 (d, J=2.8 Hz, 1H), 4.02-4.11 (m, 2H), 1.32-1.36 (t, J=6.8 Hz, 3H); MS (ESI): m/z 482.1 [M+1]$^+$.

Example 82

Compound 82, 3-ethoxy-2-hydroxy-5-(2-oxo-5,6-diphenyl-1,2,3,4-tetrahydropyrimidin-4-yl)benzamide

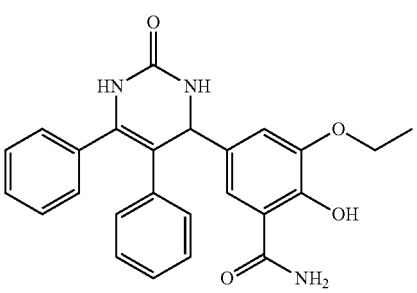 [SMILES: CCOc1cc(C2NC(=O)NC(c3ccccc3)=C2c2ccccc2)cc(C(N)=O)c1O]

A mixture of Compound 77 (described previously) (280 mg, 0.65 mmol), NH$_4$Cl (41 mg, 0.78 mmol), EDCI (149 mg, 0.78 mmol), HOBT (105 mg, 0.78 mmol), and NMM (0.29 mL, 2.6 mmol) in DMF (5 mL) was stirred at room temperature for two hours. LCMS showed most of the starting material was consumed. 100 mL of a mixture of EtOAc and MeOH (v/v=10:1) was added to dilute the mixture. The organic layer was washed with brine (20 mL×2), dried over Na$_2$SO$_4$, filtered, concentrated, and purified by preparative HPLC to afford Compound 82 as a yellow solid (46 mg, yield: 16.4%). $^1$H NMR (DMSO-$d_6$ 400 MHz): δ 12.94 (s, 1H), 8.58 (s, 1H), 8.30 (s, 1H), 7.86 (s, 1H), 7.37 (s, 1H), 7.33 (s, 1H), 7.20-7.25 (m, 5H), 7.11 (s, 1H), 6.97-7.02 (m, 3H), 6.80 (d, J=6.8 Hz, 2H), 5.10 (d, J=2.4 Hz, 1H), 4.00 (q, J=7.2 Hz, 2H), 1.32 (t, J=6.8 Hz, 3H); MS (ESI): m/z 430.1 [M+1]$^+$.

Example 83

Compound 83, methyl 4-(6-(3-ethoxy-4-hydroxy-5-nitrophenyl)-2-oxo-5-phenyl-1,2,3,6-tetrahydropyrimidin-4-yl)phenylcarbamate

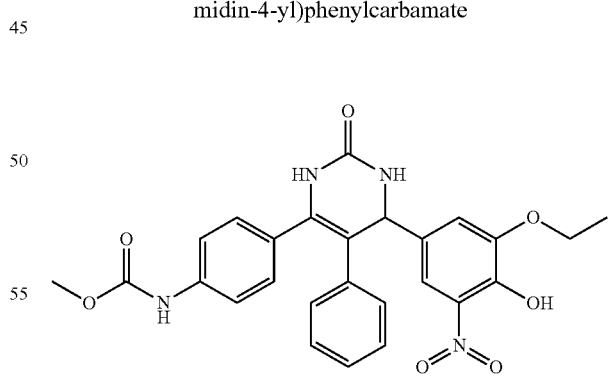

Step 1

To a solution of 6-(4-aminophenyl)-4-(3-ethoxy-4-hydroxy-5-nitrophenyl)-5-phenyl-3,4-dihydropyrimidin-2 (1H)-one (Compound 57) (100 mg, 0.224 mmol), and triethylamine (29.5 mg, 0.291 mmol) in anhydrous dichloromethane (5 mL) was added methyl chloroformate (23.2 mg, 0.246 mmol) at 0° C. The mixture was stirred at 0° C. for 5 h. The reaction mixture was poured into water (10 mL), and the mixture was extracted with dichloromethane (20 mL×2). The organic layers were washed with brine (20 mL), dried over anhydrous sodium sulfate, and purified by preparative HPLC to give methyl 4-(6-(3-ethoxy-4-(methoxycarbonyloxy)-5-nitrophenyl)-2-oxo-5-phenyl-1,2,3,6-tetrahydropyrimidin-4-yl)phenylcarbamate (60 mg, yield 47.6%)

Step 2

To a mixture of the intermediate from Step 1 (60 mg, 0.107 mmol) in ethanol (2 mL) was added sodium hydroxide aqueous solution (2 mL, 1.25 mol/L) at 0° C., and the mixture was stirred at 28° C. for 4 h. The reaction mixture was adjusted to pH=5 with diluted hydrochloric acid. The mixture was poured into water (20 mL), and extracted with ethyl acetate (30 mL). The organic layer was washed with brine (50 mL), dried over anhydrous sodium sulfate, evaporated, and purified by preparative HPLC to give Compound 83 (24.1 mg, yield 44.6%). $^1$H NMR (DMSO-$d_6$ 400 MHz): δ 10.28 (s, 1H), 9.70 (s, 1H), 8.64 (s, 1H), 7.51 (s, 1H), 7.44 (s, 1H), 7.32 (d, J=8.8 Hz, 2H), 7.19 (s, 1H), 7.11 (d, J=8.4 Hz, 2H), 7.07-7.00 (m, 3H), 6.84 (d, J=7.2 Hz, 2H), 5.16 (d, J=2.8 Hz, 1H), 4.06-4.01 (m, 2H), 3.65 (s, 3H), 1.35-1.31 (m, 3H); MS (ESI): m/z 505.0 [M+H]$^+$.

Example 84

Compound 84, 4-(3-ethoxy-4-hydroxy-5-nitrophenyl)-6-phenyl-5-(pyridin-3-yl)-3,4-dihydropyrimidin-2(1H)-one

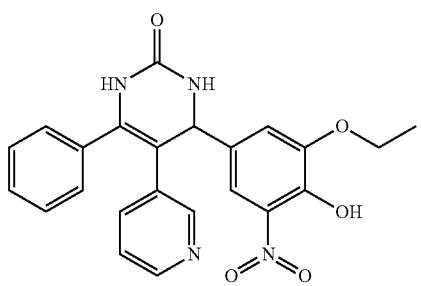

A mixture of 1-phenyl-2-(pyridin-3-yl)ethanone (Intermediate 42) (200 mg, 1.01 mmol), 3-ethoxy-4-hydroxy-5-nitrobenzaldehyde (213.3 mg, 1.01 mmol), urea (181.8 mg, 3.03 mmol), and concentrated hydrochloric acid solution (0.5 mL) in ethanol (2 mL) was refluxed at 78° C. for 70 h. After being cooled down to room temperature, the reaction mixture was evaporated, and the residue was purified by preparative HPLC to give Compound 84 (191.1 mg, yield 43.7%). $^1$H NMR (DMSO-$d_6$ 400 MHz): δ 10.34 (s, 1H), 9.06 (s, 1H), 8.35-8.33 (m, 1H), 8.10 (d, J=2.0 Hz, 1H), 7.72 (s, 1H), 7.59 (d, J=8.0 Hz, 1H), 7.45-7.39 (m, 2H), 7.33-7.23 (m, 6H), 5.39 (d, J=2.8 Hz, 1H), 4.11-4.06 (m, 2H), 1.36-1.33 (m, 3H); MS (ESI): m/z 433.0 [M+H]$^+$.

Example 85

Compound 85, 4-(3-ethoxy-4-hydroxy-5-nitrophenyl)-6-(naphthalen-2-yl)-5-phenyl-3,4-dihydropyrimidin-2(1H)-one

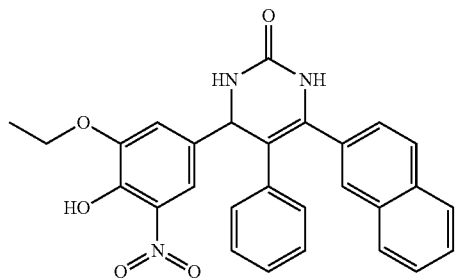 [SMILES: CCOc1cc(C2NC(=O)NC(c3ccc4ccccc4c3)=C2c2ccccc2)cc([N+](=O)[O-])c1O]

A mixture of 1-(naphthalen-2-yl)-2-phenylethanone (Intermediate 43) (260 mg, 1.06 mmol), -ethoxy-4-hydroxy-5-nitrobenzaldehyde (267.6 mg, 1.27 mmol), and urea (190.2 mg, 3.17 mmol) in anhydrous EtOH (5 mL) was added concentrated HCl solution (0.2 mL), and the reaction mixture was refluxed for 14 hours. The reaction mixture was concentrated under reduce pressure, and the residue was purified by column chromatography (EtOAc:MeOH=50:1) and preparative HPLC to afford Compound 85 as a yellow solid (64 mg, yield: 12.6%). $^1$H NMR (DMSO-$d_6$ 400 MHz): δ 10.12 (d, J=12.0 Hz, 1H), 8.65 (d, J=16.0 Hz, 1H), 7.67-7.81 (m, 3H), 7.30-7.46 (m, 5H), 6.99-7.18 (m, 2H), 6.58-6.73 (m, 5H), 5.14-5.35 (m, 1H), 3.90-3.96 (m, 2H), 1.16-1.22 (m, 3H); MS (ESI): m/z 482.1 [M+1]$^+$.

Example 86

Compound 86, 2-hydroxy-5-(2-oxo-5,6-diphenyl-1,2,3,4-tetrahydropyrimidin-4-yl)benzoic acid

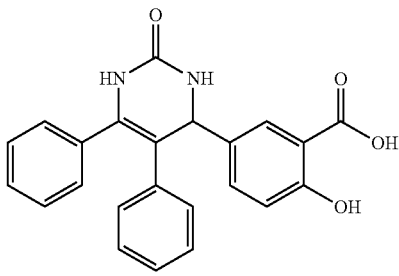 [SMILES: O=C1NC(c2ccccc2)=C(c2ccccc2)C(c2ccc(O)c(C(=O)O)c2)N1]

To a mixture of 1,2-diphenylethanone (200 mg, 1.03 mmol), 5-formyl-2-hydroxybenzoic acid (203 mg, 1.22 mmol), and urea (184 mg, 3.06 mmol) in anhydrous EtOH was added concentrated HCl solution (105 mg, 1.03 mmol). The reaction was refluxed for three days. The reaction mixture was concentrated, and purified by column chromatography and preparative HPLC to give Compound 86 as an off-white solid (40 mg, yield 10.2%). $^1$H NMR (DMSO-$d_6$ 400 MHz): δ 11.20 (s, 1H), 8.63 (s, 1H), 7.78 (d, J=2.4 Hz, 1H), 7.42-7.50 (m, 2H), 7.13-7.28 (m, 5H), 6.90-7.00 (m, 4H), 6.75 (d, J=6.4 Hz, 2H), 5.10 (d, J=2.4 Hz, 1H); MS (ESI): m/z 387.1 [M+1]⁺.

Example 87

Compound 87, 4-(4-hydroxy-3-methoxyphenyl)-5,6-diphenyl-3,4-dihydropyrimidin-2(1H)-one

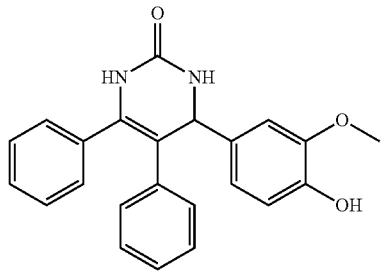 [SMILES: COc1cc(C2NC(=O)NC(c3ccccc3)=C2c2ccccc2)ccc1O]

To a solution of 1,2-diphenylethanone (392 mg, 2.0 mmol), 4-hydroxy-3-methoxybenzaldehyde (274 mg, 1.8 mmol) and urea (324 mg, 5.4 mmol) in EtOH (40 mL) was added concentrated HCl (0.17 mL). The mixture was stirred at 85° C. for 3 days. The volatiles were removed under reduced pressure and the residue was diluted with water (50 mL), extracted with ethyl acetate (100 mL×2), washed with saturated aqueous NaHCO₃ (50 mL×2), dried over Na₂SO₄, concentrated (standard aqueous/EtOAc workup) and purified by silica gel column chromatography (PE:EA=1:1) to afford Compound 87 as an off-white power (100 mg, 15%). ¹H NMR (DMSO-d₆ 500 MHz): δ 8.94 (s, 1H), 8.58 (s, 1H), 7.36 (s, 1H), 7.53 (s, 1H), 7.40 (s, 3H), 7.34 (s, 3H), 7.10 (d, J=5.2 Hz, 1H), 7.20-7.25 (m, 5H), 6.99 (t, J=18 Hz, 3H), 6.90 (s, 1H), 6.80 (t, J=7.0 Hz, 3H), 6.74 (d, J=8.0 Hz, 1H), 4.99 (d, J=2.5 Hz, 1H); MS (ESI): m/z 373.0 [M+1]⁺.

Example 88

Compound 88, 5-(4-(dimethylamino)phenyl)-4-(3-ethoxy-4-hydroxy-5-nitrophenyl)-6-phenyl-3,4-dihydropyrimidin-2(1H)-one

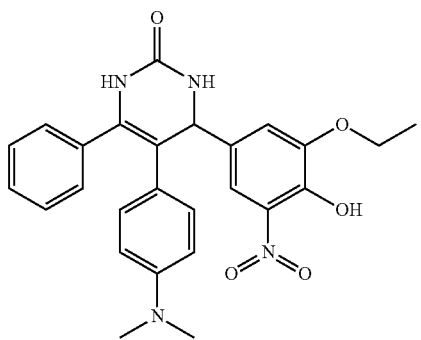 [SMILES: CCOc1cc(C2NC(=O)NC(c3ccccc3)=C2c2ccc(N(C)C)cc2)cc([N+](=O)[O-])c1O]

To a solution of 2-(4-(dimethylamino)phenyl)-1-phenylethanone (Intermediate 44) (235 mg, 1 mmol), 3-ethoxy-4-hydroxy-5-nitrobenzaldehyde (212 mg, 1 mmol), and urea (138 mg, 3 mmol) in 10 mL of ethanol was added 0.2 mL of concentrated HCl solution, and the mixture was stirred at 130° C. for 2 days. After the solvent was removed under reduced pressure, the residue was purified by preparative HPLC (40-80% acetonitrile+0.1% trifluoroacetic acid in water, over 15 min.) to give the Compound 88 (65 mg, yield 13.9%). ¹H NMR (CD₃OD 400 MHz): δ 7.43 (s, 1H), 7.25-7.19 (m, 8H), 7.02 (d, J=8.4 Hz, 2H), 5.30 (s, 1H), 4.06-4.00 (m, 2H), 3.06 (s, 6H), 1.33 (t, J=6.8 Hz, 3H); MS (ESI): m/z 475.3 [M+1]⁺.

Example 89

Compound 89, 4-(8-nitro-2,3-dihydrobenzo[b][1,4]dioxin-6-yl)-5,6-diphenyl-3,4-dihydropyrimidin-2(1H)-one

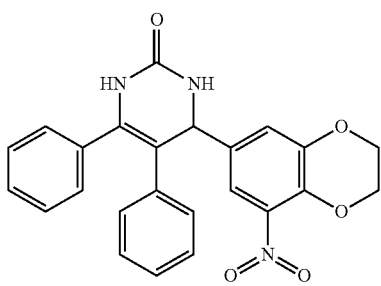 [SMILES: O=C1NC(c2ccccc2)=C(c2ccccc2)C(c2cc3c(c([N+](=O)[O-])c2)OCCO3)N1]

A mixture of 8-nitro-2,3-dihydrobenzo[b][1,4]dioxine-6-carbaldehyde (Intermediate 45) (110 mg, 0.529 mmol), 1,2-diphenylethanone (103.8 mg, 0.529 mmol), urea (95.2 mg, 1.587 mmol), and concentrated hydrochloric acid (0.1 mL) in ethanol (10 mL) was refluxed at 77° C. for 63 h. Volatiles were removed, and purified by preparative HPLC to give Compound 89 (12.1 mg, yield 5.5%). ¹H NMR (CD₃OD 400 MHZ): δ 7.32 (s, 1H), 7.14 (s, 5H), 7.06 (s, 1H), 6.95-6.94 (m, 3H), 6.78-6.76 (m, 2H), 5.20 (s, 1H), 4.26-4.24 (m, 4H); MS (ESI): m/z 430.0 [M+H]⁺.

Example 90

Compound 90, 4-(2-oxo-5,6-diphenyl-1,2,3,4-tetrahydropyrimidin-4-yl)benzoic acid

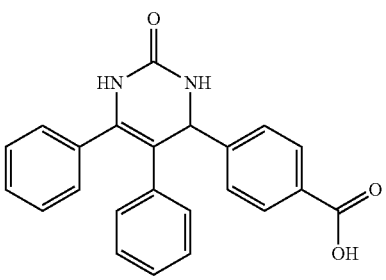

To a solution of 1,2-diphenylethanone (392 mg, 2.0 mmol), 4-formylbenzoic acid (274 mg, 1.8 mmol) and urea (324 mg, 5.4 mmol) in EtOH (40 mL) was added concentrated HCl (0.17 mL). The mixture was stirred at 85° C. for 3 days. The volatiles were removed under reduced pressure and standard aqueous/EtOAc workup procedure was followed. Purification by inverse-phase column to afford Compound 90 as a tan powder (11 mg, 2%). ¹H NMR (MeOH-d₄ 500 MHz TMS): δ

7.99 (d, J=7.0 Hz, 2H), 7.47 (d, J=7.0 Hz, 2H), 7.25 (s, 5H), 7.03 (s, 3H), 6.85 (s, 2H), 5.40 (s, 1H); MS (ESI): m/z 371.0 [M+1]$^+$.

Example 91

Compound 91, 4-(3-(isoxazol-4-yl)phenyl)-5,6-diphenyl-3,4-dihydropyrimidin-2(1H)-one

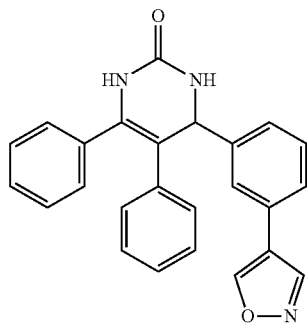 [SMILES: O=C1NC(c2ccccc2)=C(c2ccccc2)C(c2cccc(-c3cnoc3)c2)N1]

To a solution of 1,2-diphenylethanone (46 mg, 0.233 mmol), 3-(isoxazol-4-yl)benzaldehyde (Intermediate 46) (36 mg, 0.209 mmol) and urea (48 mg, 0.627 mmol) in EtOH (10 mL) was added concentrated HCl (0.4 mL). The mixture was stirred at 85° C. for 14 h. The volatiles were removed under reduced pressure and the residue was purified by silica gel column chromatography (PE:EA=1:1) to afford Compound 91 as an off-white power (18 mg, 22.2%). $^1$H NMR (MeOH-d$_4$ 500 MHz): δ 8.99 (s, 1H), 8.74 (s, 1H), 7.50-7.53 (m, 2H), 7.39-7.50 (m, 2H), 7.23-7.25 (m, 5H), 7.00-7.02 (m, 2H), 6.84-6.87 (m, 2H), 5.35 (s, 1H); MS (ESI): m/z 394.1 [M+1]$^+$.

Example 92

Compound 92, 1,1'-(2-hydroxy-5-(2-oxo-5,6-diphenyl-1,2,3,4-tetrahydropyrimidin-4-yl)-1,3-phenylene)diethanone

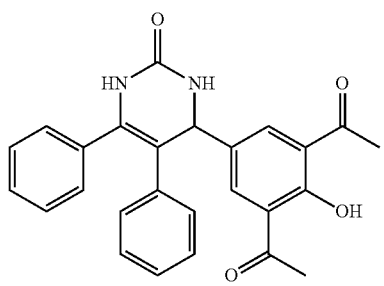 [SMILES: CC(=O)c1cc(C2NC(=O)NC(c3ccccc3)=C2c2ccccc2)cc(C(C)=O)c1O]

Step 1: Synthesis of 4-(4-methoxyphenyl)-5,6-diphenyl-3,4-dihydropyrimidin-2(1H)-one A mixture of 1,2-diphenylethanone (1 g, 5.1 mmol), urea (1.22 g, 20.38 mmol), 4-methoxybenzaldehyde (0.76 g, 1.1 mmol) and conc. HCl (0.4 mL) in EtOH (100 mL) was heated at 85° C. for 108 h. The volatiles were removed under reduced pressure and the residue was purified by column chromatography to afford 4-(4-methoxyphenyl)-5,6-diphenyl-3,4-dihydropyrimidin-2(1H)-one as a yellow solid (400 mg, 22%)

Step 2: Synthesis of 1,1'-(2-hydroxy-5-(2-oxo-5,6-diphenyl-1,2,3,4-tetrahydropyrimidin-4-yl)-1,3-phenylene)diethanone Acetyl chloride (76 mg, 0.97 mmol) was added dropwise to the solution of 4-(4-methoxyphenyl)-5,6-diphenyl-3,4-dihydropyrimidin-2(1H)-one (300 mg, 0.84 mmol) in dry DCM (6 mL) at 0° C. Aluminum trichloride (393 mg, 1.15 mmol) was then added. The mixture was stirred at room temperature overnight. The mixture was poured into 1N HCl solution (15 mL) with ice-bath and extracted with DCM (15 mL×3), the combined organic layers were washed with water and brine, dried over Na$_2$SO$_4$, filtered and concentrated in vacuo. The residue was purified twice by Prep-TLC (PE:EA=2:3) to afford Compound 92 (21 mg, 5.8%). MS (ESI): m/z 427.1 [M+1]$^+$.

Example 93

Compound 93, 3-(2-oxo-5,6-diphenyl-1,2,3,4-tetrahydropyrimidin-4-yl)benzoic acid

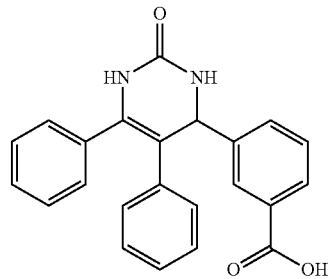 [SMILES: O=C1NC(c2ccccc2)=C(c2ccccc2)C(c2cccc(C(=O)O)c2)N1]

To a solution of 1,2-diphenylethanone (784 mg, 4.0 mmol), 3-formylbenzoic acid (500 mg, 3.33 mmol) and urea (600 mg, 10.0 mmol) in EtOH (40 mL) was added concentrated HCl (1.6 mL). The mixture was stirred at 85° C. for 3 days. The volatiles were removed under reduced pressure and standard aqueous/EtOAc workup procedure was followed. Purification by column chromatography (100% EA) gave Compound 93 as an off-white powder (186 mg, 15%). $^1$H NMR (DMSO-d$_6$ 500 MHz): δ 8.70 (s, 1H), 7.99 (s, 1H), 7.83 (d, J=7.5 Hz, 1H), 7.57 (s, 2H), 7.50 (t, J=14.5 Hz, 1H), 7.21-7.25 (m, 5H), 6.79-7.02 (m, 3H), 6.78 (d, J=7.0 Hz, 2H), 5.24 (d, J=2.0 Hz, 1H); MS (ESI): m/z 371.1 [M+1]$^+$.

Example 94

Compound 94, 2-hydroxy-3-(2-oxo-5,6-diphenyl-1,2,3,4-tetrahydropyrimidin-4-yl)benzonitrile

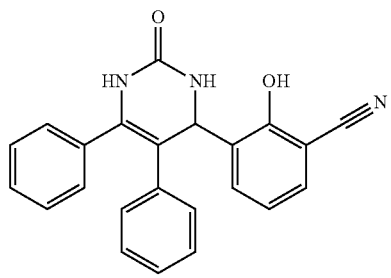 [SMILES: N#Cc1cccc(C2NC(=O)NC(c3ccccc3)=C2c2ccccc2)c1O]

To a solution of 1,2-diphenylethanone (1.6 g, 8.16 mmol), and 3-formyl-2-hydroxybenzonitrile (Intermediate 47b) (1.0 g, 6.80 mmol) in AcOH (5 mL) was added urea (1.2 g, 20.4 mmol). The mixture was stirred at 120° C. under microwave for 3 h. The volatiles were removed under reduced pressure and standard aqueous workup procedure was followed. The crude was recrystallized by EA (10 mL) to afford Compound 94 as a white power (436 mg, 26%). $^1$H NMR (DMSO-d$_6$ 500 MHz): δ 8.10 (s, 1H), 7.79 (d, J=2.5 Hz, 1H), 7.75 (d, J=2.0 Hz, 1H), 7.58 (d, J=7.5 Hz, 3H), 7.30-7.36 (m, 3H), 7.18 (s, 1H), 7.02 (d, J=6.0 Hz, 3H), 6.78 (d, J=6.0 Hz, 2H), 4.44 (d, J=2.0 Hz, 1H), 4.14 (s, 1H); MS (ESI): m/z 368.1 [M+1]$^+$.

Example 95

Compound 95, 4-(4-hydroxy-3-nitrophenyl)-5,6-diphenyl-3,4-dihydropyrimidin-2(1H)-one

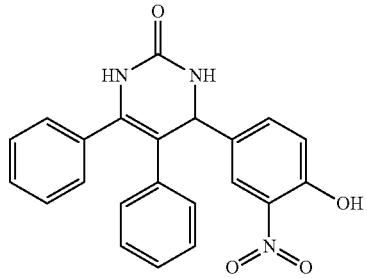 [SMILES: O=C1NC(c2ccccc2)=C(c2ccccc2)C(c2ccc(O)c([N+](=O)[O-])c2)N1]

To a solution of 1,2-diphenylethanone (704 mg, 3.59 mmol), 4-hydroxy-3-nitrobenzaldehyde (500 mg, 2.99 mmol) and urea (538 mg, 8.97 mmol) in EtOH (40 mL) was added concentrated HCl (1.6 mL). The mixture was stirred at 85° C. for 3 days. The volatiles were removed under reduced pressure and standard aqueous workup procedure was followed. Purification by silica gel column chromatography (PE:EA=1:1) gave Compound 95 as an off-white power (102 mg, 9%). $^1$H NMR (DMSO-d$_6$ 500 MHz TMS): δ 10.09 (s, 1H), 8.69 (s, 1H), 7.82 (d, J=2.0 Hz, 1H), 7.52-7.57 (m, 2H), 7.21-7.26 (m, 5H), 7.13 (d, J=10.5 Hz, 1H), 7.01 (t, J=27.5 Hz, 3H), 7.81 (d, J=8.5 Hz, 2H), 5.26 (d, J=3.5 Hz, 1H); MS (ESI): m/z 388.1 [M+1]$^+$ Example 96

Compound 96, 2-hydroxy-5-(2-oxo-5,6-diphenyl-1,2,3,4-tetrahydropyrimidin-4-yl)benzonitrile

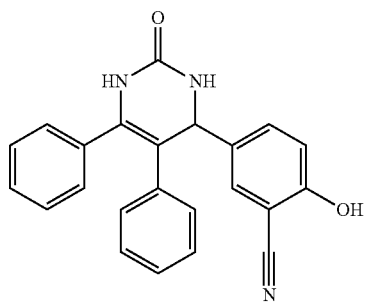 [SMILES: N#Cc1cc(C2NC(=O)NC(c3ccccc3)=C2c2ccccc2)ccc1O]

To a solution of 1,2-diphenylethanone (720 mg, 3.67 mmol), 5-formyl-2-hydroxybenzonitrile (Intermediate 47a) (450 mg, 3.06 mmol) and urea (551 mg, 9.18 mmol) in EtOH (23 mL) was added concentrated HCl (0.9 mL). The mixture was stirred at 90° C. for 40 h. Followed standard aqueous workup procedure and recrystallized from EA (6 mL), then further purified by prep-HPLC to afford Compound 96 as a white power (36 mg, 3%). $^1$H NMR (MeOH-d$_4$ 500 MHz): δ 7.50 (t, J=7.5 Hz, 1H), 7.42 (d, J=2.0 Hz, 1H), 7.25 (s, 5H), 7.05 (t, J=2.5 Hz, 3H), 6.93 (d, J=8.5 Hz, 1H), 6.85 (t, J=4.0 Hz, 2H), 5.30 (s, 1H); MS (ESI): m/z 368.1 [M+1]$^+$.

Example 97

Compound 97, 2-ethoxy-4-(2-oxo-5,6-diphenyl-1,2,3,4-tetrahydropyrimidin-4-yl)benzoic acid

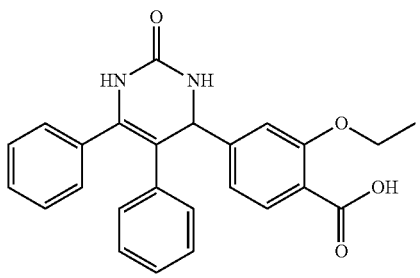 [SMILES: CCOc1cc(C2NC(=O)NC(c3ccccc3)=C2c2ccccc2)ccc1C(=O)O]

To a solution of 1,2-diphenylethanone (53 mg, 0.270 mmol), ethyl 2-ethoxy-4-formylbenzoate (Intermediate 48) (50 mg, 0.225 mmol) and urea (41 mg, 0.675 mmol) in EtOH (2.5 mL) was added concentrated HCl (0.1 mL). The mixture was stirred at 90° C. for 16 h. The volatiles were removed under reduced pressure to afford crude ethyl 2-ethoxy-4-(2-oxo-5,6-diphenyl-1,2,3,4-tetrahydropyrimidin-4-yl)benzoate, which was dissolved in THF/H$_2$O/MeOH (v/v/v=1/1/1, 0.6 mL) followed by addition of lithium hydroxide monohydrate (14 mg, 0.338 mmol). The solution was stirred at room temperature overnight. Most of THF and MeOH were evaporated under reduced pressure and the resulting aqueous solution was acidified with 10% hydrochloric acid to pH=6.0. The resulting precipitate was purified by prep-HPLC to afford Compound 97 as a white powder (11 mg, 12%). $^1$H NMR (MeOH-d$_4$ 500 MHz): δ 7.68 (d, J=8.0 Hz, 1H), 7.14 (s, 5H), 6.94-6.98 (m, 4H), 6.89 (s, 1H), 6.76 (t, J=3.5 Hz, 2H), 5.26 (s, 1H), 3.90-4.00 (m, 2H), 1.27 (t, J=7.0 Hz, 3H); MS (ESI): m/z 415.1 [M+1]$^+$.

Example 98

Compound 98, 3-(2-oxo-5,6-diphenyl-1,2,3,4-tetrahydropyrimidin-4-yl)benzamide

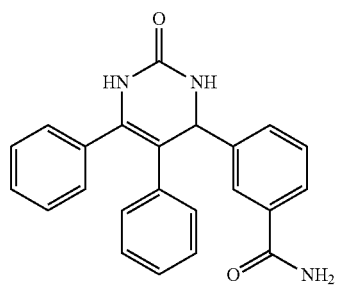 [SMILES: NC(=O)c1cccc(C2NC(=O)NC(c3ccccc3)=C2c2ccccc2)c1]

Prepared as a side product during the preparation of Compound 99. Isolated under same conditions as described for synthesis of Compound 99, a white solid (6.7%). ¹H NMR (MeOH-d₄ 500 MHz): δ 7.90 (s, 1H), 7.78 (d, J=7.5 Hz, 1H), 7.59 (d, J=7.0 Hz, 1H), 7.46 (t, J=3.0 Hz, 1H), 7.25-7.27 (m, 5H), 7.01 (s, 3H), 6.85 (s, 2H), 5.41 (s, 1H); MS (ESI): m/z 370.1 [M+1]⁺.

Example 99

Compound 99, N-hydroxy-3-(2-oxo-5,6-diphenyl-1,2,3,4-tetrahydropyrimidin-4-yl)benzimidamide

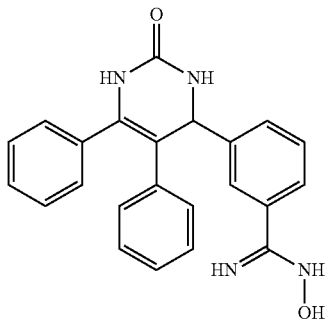 [SMILES: N=C(NO)c1cccc(C2NC(=O)NC(c3ccccc3)=C2c2ccccc2)c1]

Step 1: Synthesis of 3-(2-oxo-5,6-diphenyl-1,2,3,4-tetrahydropyrimidin-4-yl)benzonitrile To a mixture of 3-formylbenzonitrile (1.31 g, 10.0 mmol, 1.0 eq), 1,2-diphenylethaone (2.35 g, 12.0 mmol, 1.2 eq) and urea (1.8 g, 30.0 mmol, 3.10 eq) in ethanol (100 mL) was added concentrated HCl (4 mL) and the reaction solution was heated to reflux for 3 days. The reaction solution was concentrated in vacuo and purified by silica gel column chromatography (DCM:MeOH=20:1) to afford 3-(2-oxo-5,6-diphenyl-1,2,3,4-tetrahydropyrimidin-4-yl)benzonitrile as a white solid (700 mg, 21%).

Step 2: Synthesis of N-hydroxy-3-(2-oxo-5,6-diphenyl-1,2,3,4-tetrahydropyrimidin-4-yl)benzimidamide A mixture of 3-(2-oxo-5,6-diphenyl-1,2,3,4-tetrahydropyrimidin-4-yl)benzonitrile (700 mg, 2 mmol, 1 eq), NH₂OH—HCl (144 mg, 2.2 mmol, 1.1 eq) and Na₂CO₃ (414 mg, 4.0 mmol, 2.0 eq) in methanol (5.0 mL) was heated to reflux overnight. The mixture was cooled to room temperature and filtered. The filtered mass was washed with methanol (5.0 mL) and purified by prep-HPLC to afford Compound 99 as a yellow solid (150 mg, 19.5%) and Compound 98 as a white solid (6.7%). Data for Compound 99: ¹H NMR (MeOH-d₄ 500 MHz TMS): δ 7.69-7.72 (m, 2H), 7.58-7.61 (m, 2H), 7.26 (br, 5H), 7.04 (br, 2H), 6.88 (br, 2H), 5.51 (s 1H); MS (ESI): m/z 385.1.1 [M+1]⁺.

Example 100

Compound 100, 4-(3-bromo-5-ethoxy-4-hydroxyphenyl)-5,6-diphenyl-3,4-dihydropyrimidin-2(1H)-one

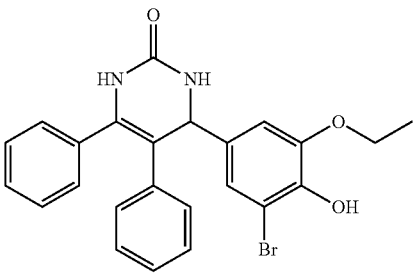

To a solution of 1,2-diphenylethanone (4.80 g, 25 mmol), 3-bromo-5-ethoxy-4-hydroxybenzaldehyde (5.00 g, 20 mmol) and urea (3.68 g, 61 mmol) in EtOH (250 mL) was added conc. HCl (10 mL). The mixture was heated at reflux for 112 h. Followed standard aqueous workup procedure and purified by silica gel column chromatography (PE:EA=1:3) to afford Compound 100 as a white solid (1.06 g, 11%). ¹H NMR (MeOH-d₄ 500 MHz TMS): δ 7.24 (s, 5H), 7.09 (s, 1H), 7.04 (s, 3H), 6.85 (s, 3H), 5.17 (s, 1H), 4.03 (m, 2H), 1.37 (t, J=7.5 Hz, 3H); MS (ESI): m/z 465.0 [M+1]⁺.

Example 101

Compound 101, N-(4-(6-(3-ethoxy-4-hydroxy-5-nitrophenyl)-2-oxo-5-phenyl-1,2,3,6-tetrahydropyrimidin-4-yl)phenyl)methanesulfonamide

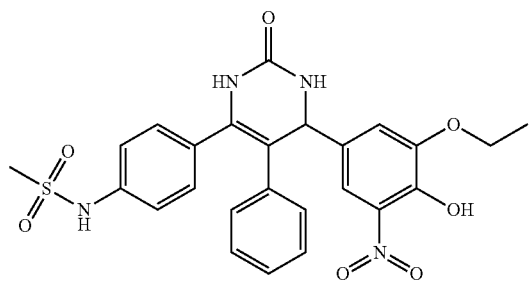 [SMILES: CCOc1cc(C2NC(=O)NC(c3ccc(NS(C)(=O)=O)cc3)=C2c2ccccc2)cc([N+](=O)[O-])c1O]

Step 1: Synthesis of 2-ethoxy-4-(6-(4-(methylsulfonamido)phenyl)-2-oxo-5-phenyl-1,2,3,4-tetrahydropyrimidin-4-yl)-6-nitrophenyl methanesulfonate To a solution of 6-(4-aminophenyl)-4-(3-ethoxy-4-hydroxy-5-nitrophenyl)-5-phenyl-3,4-dihydropyrimidin-2 (1H)-one (Compound 57) (100 mg, 0.224 mmol) and triethylamine (29.5 mg, 0.291 mmol) in anhydrous dichloromethane (3 mL) was added MsCl (28 mg, 0.246 mmol) at 0° C., and the mixture was stirred at 0° C. for 5 h. The reaction mixture was poured into water (10 mL), and extracted with dichloromethane (20 mL). The organic layers were washed with brine (20 mL), dried over anhydrous sodium sulfate, and purified by preparative HPLC to give 2-ethoxy-4-(6-(4-(methylsulfonamido)phenyl)-2-oxo-5-phenyl-1,2,3,4-tetrahydropyrimidin-4-yl)-6-nitrophenyl methanesulfonate (60 mg, yield 44.3%).

Step 2: Synthesis of Compound 101

To a mixture of 2-ethoxy-4-(6-(4-(methylsulfonamido)phenyl)-2-oxo-5-phenyl-1,2,3,4-tetrahydropyrimidin-4-yl)-6-nitrophenyl methanesulfonate (60 mg, 0.10 mmol) in ethanol (2 mL) was added sodium hydroxide aqueous solution (2 mL, 1.25 mol/L) at 0° C. The mixture was heated at 80° C. for 5 h, cooled down to room temperature, adjusted to pH=5 with diluted hydrochloric acid, poured into water (20 mL), and extracted with ethyl acetate (30 mL). The organic layer was washed with brine (5 mL), dried over anhydrous sodium sulfate, and evaporated. The residue was purified by preparative HPLC to give Compound 101 (36.0 mg, yield 68.9%). HNMR (DMSO-$d_6$ 300 MHz): δ 10.34 (s, 1H), 9.91 (s, 1H), 8.73 (s, 1H), 7.59 (s, 1H), 7.49 (s, 1H), 7.23 (d, J=9.0 Hz, 3H), 7.12-7.06 (m, 5H), 6.90 (d, J=6.9 Hz, 2H), 5.24 (d, J=2.7 Hz, 1H), 4.12-4.08 (m, 2H), 3.04 (s, 3H), 1.42-1.37 (m, 3H); MS (ESI): m/z 525.0 [M+H]$^+$.

Example 102

Compound 102, 4-(4-hydroxy-3-isopropoxy-5-nitrophenyl)-5,6-diphenyl-3,4-dihydropyrimidin-2(1H)-one The mixture of 4-hydroxy-3-isopropoxy-5-nitrobenzaldehyde (Intermediate 49) (116 mg, 0.516 mmol), 1,2-diphenylethanone (121 mg, 0.618 mmol), urea (93 mg, 1.55 mmol) and concentrated hydrochloric acid (0.1 mL) in anhydrous ethanol (5 mL) was stirred with reflux (110° C.) under $N_2$ protection overnight. The reaction mixture was concentrated and the residue was purified by silica gel column chromatography, followed by preparative HPLC to give compound 102 (36.3 mg, yield 15.8%) as a solid. $^1$H NMR (DMSO-$d_6$ 400 MHz): δ 10.14 (s, 1H), 8.72 (s, 1H), 6.82-7.55 (m, 13H), 5.21 (d, J=2.8 Hz, 1H), 4.47-4.53 (m, 1H), 1.28 (d, J=6.0 Hz, 3H), 1.25 (d, J=6.0 Hz, 3H); MS (ESI): m/z 446.1 [M+1]$^+$.

Example 103

Compound 103, 4-(3-ethoxy-4-hydroxy-5-(methylsulfonyl)phenyl)-5,6-diphenyl-3,4-dihydropyrimidin-2(1H)-one Step 1: Synthesis of 4-(3-ethoxy-4-hydroxy-5-(methylthio)phenyl)-5,6-diphenyl-3,4-dihydropyrimidin-2(1H)-one To a solution of 3-ethoxy-4-hydroxy-5-(methylthio)benzaldehyde (Intermediate 50) (300 mg, 1.42 mmol), 1,2-diphenylethanone (330 mg, 1.68 mmol) and urea (170 mg, 2.80 mmol) in ethanol (5 mL) was added conc. HCl (0.3 mL) and the reaction mixture was refluxed under $N_2$ atmosphere overnight. The resulting mixture was cooled and purified by silica gel column to give desired product (200 mg, yield 33%).

Step 2: Synthesis of Compound 103

To the solution of 4-(3-ethoxy-4-hydroxy-5-(methylthio)phenyl)-5,6-diphenyl-3,4-dihydropyrimidin-2(1H)-one (200 mg, 0.46 mmol) in DCM (10 mL) was added m-CPBA (112 mg, 0.55 mmol) at 0° C., the mixture was stirred over 2 hours at 0° C. The reaction solution was washed with $Na_2SO_3$ solution, and brine, then concentrated under reduced pressure. The residue was purified by prep-HPLC (0.1% TFA as additive) to give Compound 103 (24.5 mg, yield 11%) and Compound 104 (40 mg, yield 19%). Data for Compound 103: $^1$H NMR (400 MHz, DMSO-$d_6$): δ 10.18 (s, 1H), 8.70 (s, 1H), 7.51 (s, 1H), 7.43 (s, 1H), 7.27-7.21 (m, 6H), 7.03-6.99 (m, 3H), 6.80 (d, J=6.8 Hz, 2H), 5.13 (d, J=2.8 Hz, 1H), 4.10-4.00 (m, 2H), 3.23 (s, 3H), 1.34 (t, J=6.8 Hz, 3H) MS (ESI): m/z 465.3 [M+1]$^+$.

Example 104

Compound 104, 4-(3-ethoxy-4-hydroxy-5-(methylsulfinyl)phenyl)-5,6-diphenyl-3,4-dihydropyrimidin-2(1H)-one See procedure described for Compound 103 in Example 103. Data for Compound 104: $^1$H NMR (300 MHz, DMSO-d$_6$): δ 9.66 (s, 1H), 8.65 (s, 1H), 7.450-7.40 (m, 1H), 7.29-7.10 (m, 6H), 7.10-6.99 (m, 4H), 6.82-6.77 (m, 2H), 5.14 (s, 1H), 4.10-3.98 (m, 2H), 2.65 (d, J=7.2 Hz, 3H), 1.33 (t, J=7.2 Hz, 3H) MS (ESI): m/z 449.2 [M+1]$^+$

Example 105

Compound 105, 3-ethoxy-2-hydroxy-5-(2-oxo-6-phenyl-5-(thiophen-3-yl)-1,2,3,4-tetrahydropyrimidin-4-yl)benzonitrile

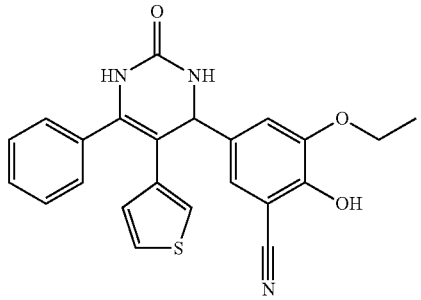

To a solution of 3-ethoxy-5-formyl-2-hydroxybenzonitrile (Intermediate 51) (70 mg, 0.37 mmol), 1-phenyl-2-(thiophen-3-yl)ethanone (Intermediate 2) (50 mg, 0.28 mmol) and urea (71 mg, 1.1 mmol) in 3 mL of ethanol was added 0.2 mL of concentrated HCl. Refluxed for 2 days. Solvent removed and resulting residue was purified by prep-HPLC (0.1% TFA as additive) to give Compound 105 (18 mg, yield 12%). $^1$H NMR (DMSO-d$_6$ 300 MHz): δ 10.33 (s, 1H), 8.70 (s, 1H), 7.51 (s, 1H), 7.37-7.10 (m, 8H), 6.84 (s, 1H), 6.22 (d, J=4.8 Hz, 1H), 5.16 (d, J=2.4 Hz, 1H), 4.07 (q, J=6.9 Hz, 2H), 1.35 (t, J=6.9 Hz, 3H). MS (ESI): m/z 418.0 [M+1]$^+$.

Example 106

Compound 106, 4-(3-ethoxy-4-hydroxy-5-nitrophenyl)-5-phenyl-6-(1H-pyrrol-3-yl)-3,4-dihydropyrimidin-2(1H)-one

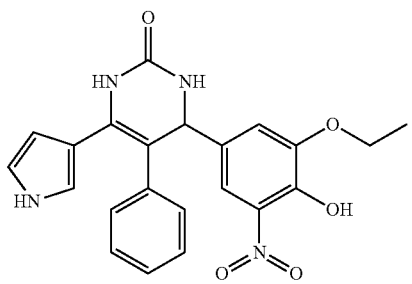 [SMILES: CCOc1cc(C2NC(=O)NC(c3cc[nH]c3)=C2c2ccccc2)cc([N+](=O)[O-])c1O]

A mixture of Compound 107 (100 mg, 0.18 mmol) and NaOH aqueous solution (2 mL, 4M) in methanol (5 mL) was stirred at room temperature for 1 hour. The mixture was diluted with water, extracted with EtOAc, dried over Na$_2$SO$_4$, concentrated in vacuo, and purified by column chromatography (PE:EtOAc=1:3) to afford the Compound 106 (50 mg, yield 66.7%). $^1$H NMR (CD$_3$OD 300 MHz): δ 7.42 (d, J=1.8 Hz, 1H), 7.06-7.01 (m, 4H), 6.90-6.88 (m, 2H), 6.49-6.46 (m, 2H), 5.70 (d, J=1.8 Hz, 1H), 5.06 (s, 1H), 3.95-3.90 (m, 2H), 1.28 (t, J=6.9 Hz, 3H); MS (ESI): m/z 421.2 [M+1]$^+$.

Example 107

Compound 107, 4-(3-ethoxy-4-hydroxy-5-nitrophenyl)-5-phenyl-6-(1-(phenylsulfonyl)-1H-pyrrol-3-yl)-3,4-dihydropyrimidin-2(1H)-one

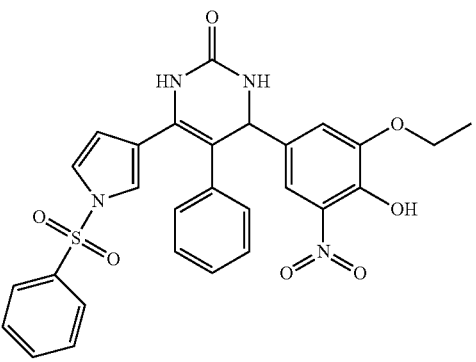 [SMILES: CCOc1cc(C2NC(=O)NC(c3ccn(S(=O)(=O)c4ccccc4)c3)=C2c2ccccc2)cc([N+](=O)[O-])c1O]

To a solution of 2-phenyl-1-(1-(phenylsulfonyl)-1H-pyrrol-3-yl)ethanone (Intermediate 52) (200 mg, 0.6 mmol), 3-ethoxy-4-hydroxy-5-nitrobenzaldehyde (130 mg, 0.6 mmol), and urea (108 mg, 1.8 mmol) in 10 mL of ethanol was added 0.2 mL of concentrated HCl solution. The mixture refluxed overnight, concentrated in vacuo, and purified by TLC (PE:EtOAc=1:2) to afford the Compound 107 (95 mg, yield 27.6%). $^1$H NMR (DMSO-d$_6$ 400 MHz): δ10.25 (s, 1H), 8.53 (s, 1H), 7.86 (d, J=7.6 Hz, 2H), 7.77 (t, J=7.6 Hz, 1H), 7.65 (t, J=8.0 Hz, 2H), 7.49 (s, 1H), 7.36 (s, 1H), 7.31 (d, J=2.0 Hz, 1H), 7.17-7.14 (m, 3H), 7.12 (t, J=2.8 Hz, 1H), 7.00 (d, J=2.0 Hz, 1H), 6.91-6.89 (m, 2H), 5.70 (m, 1H), 5.10 (d, J=2.4 Hz, 1H), 4.05-3.90 (m, 2H), 1.29 (t, J=7.2 Hz, 3H); MS (ESI): m/z 561.3 [M+1]$^+$.

Example 108

Compound 108, 4-(3-ethoxy-4-hydroxy-5-nitrophenyl)-6-(4-fluorophenyl)-5-(3-methoxyphenyl)-3,4-dihydropyrimidin-2(1H)-one A mixture of 1-(4-fluorophenyl)-2-(3-methoxyphenyl)ethanone (Intermediate 53) (200 mg, 0.82 mmol), 3-ethoxy-4-hydroxy-5-nitrobenzaldehyde (157 mg, 0.74 mmol), urea (134 mg, 2.23 mmol), concentrated HCl (0.06 mL, 0.74 mmol) in EtOH (5 mL) was refluxed overnight. Followed standard aqueous/EtOAc workup procedure, then purified by preparative HPLC to give Compound 108 (70 mg, yield 20%). $^1$H NMR (DMSO-d$_6$ 300 MHz): δ 10.29 (s, 1H), 8.77 (s, 1H), 7.55 (s, 1H), 7.45 (s, 1H), 7.27-7.24 (m, 2H), 7.20 (s, 1H), 7.15-7.09 (m, 2H), 6.99-6.94 (m, 1H), 6.59 (d, J=7.2 Hz, 1H), 6.39 (d, J=6.3 Hz, 2H), 5.22 (s, 1H), 4.07-4.05 (m, 2H), 3.49 (s, 3H), 1.33 (t, J=6.6 Hz, 3H); MS (ESI): m/z 479.9 [M+1]$^+$.

Example 109

Compound 109, 4-(3-ethoxy-4-hydroxy-5-nitrophenyl)-6-(4-fluorophenyl)-5-(thiophen-3-yl)-3,4-dihydropyrimidin-2(1H)-one

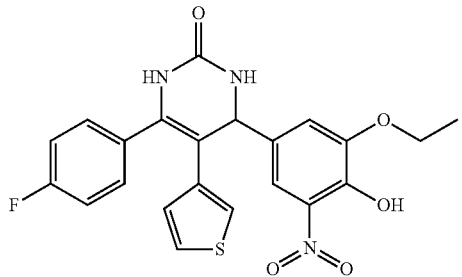 [SMILES: CCOc1cc(C2NC(=O)NC(c3ccc(F)cc3)=C2c2ccsc2)cc([N+](=O)[O-])c1O]

A mixture of 1-(4-fluorophenyl)-2-(thiophen-3-yl)ethanone (Intermediate 54) (100 mg, 0.45 mmol), 3-ethoxy-4-hydroxy-5-nitrobenzaldehyde (87 mg, 0.41 mmol), urea (74 mg, 1.24 mmol), concentrated HCl (0.04 mL, 0.41 mmol) in EtOH (5 mL) was refluxed overnight. Followed standard aqueous/EtOAc workup procedure, then purified by preparative HPLC to give Compound 109 (50 mg, yield 27%). $^1$H NMR (DMSO-d$_6$ 400 MHz): δ 10.30 (s, 1H), 8.77 (s, 1H), 7.58 (s, 1H), 7.49 (s, 1H), 7.34-7.30 (m, 2H), 7.27 (s, 1H), 7.23-7.18 (m, 3H), 6.88 (s, 1H), 6.27 (d, J=5.2 Hz, 1H), 5.21 (d, J=2.8 Hz, 1H), 4.13-4.06 (m, 2H), 1.36 (t, J=6.8 Hz, 3H); MS (ESI): m/z 456.0 [M+1]$^+$.

Example 110

Compound 110, 2-hydroxy-3-nitro-5-(2-oxo-5,6-diphenyl-1,2,3,4-tetrahydropyrimidin-4-yl)benzoic acid

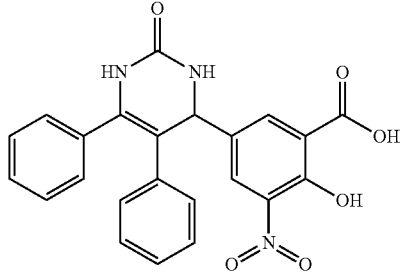 [SMILES: O=C1NC(c2ccccc2)=C(c2ccccc2)C(c2cc(C(=O)O)c(O)c([N+](=O)[O-])c2)N1]

A mixture of 5-formyl-2-hydroxy-3-nitrobenzoic acid (Intermediate 55) (200 mg, 0.95 mmol), 1,2-diphenylethanone (185.8 mg, 0.95 mmol), urea (170.5 mg, 2.84 mmol), concentrated hydrochloric acid solution (0.3 mL) in ethanol (2 mL) was refluxed at 78° C. for 33 h. The reaction mixture was evaporated in vacuo, and purified by preparative HPLC to give Compound 110 (75.7 mg, yield 18.5%). $^1$H NMR (DMSO-D$_6$, 400 MHZ): δ 8.78 (s, 1H), 8.15 (d, J=2.0 Hz, 1H), 8.09 (d, J=2.4 Hz, 1H), 7.60 (s, 1H), 7.26-7.19 (m, 5H), 7.04-6.99 (m, 3H), 6.81 (d, J=6.4 Hz, 2H), 5.27 (d, J=2.8 Hz, 1H); MS (ESI): m/z 432.1 [M+H]$^+$.

Example 111

Compound 111, 4-(3-ethoxy-4-hydroxy-5-nitrophenyl)-6-(furan-2-yl)-5-phenyl-3,4-dihydropyrimidin-2 (1H)-one

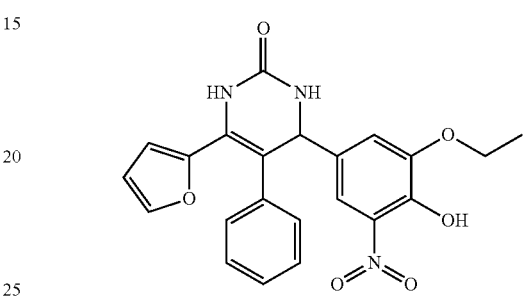

A mixture of 1-(furan-2-yl)-2-phenylethanone (commercially available) (420 mg, 2.26 mmol), 3-ethoxy-4-hydroxy-5-nitrobenzaldehyde (433 mg, 2.05 mmol), urea (369 mg, 6.15 mmol), concentrated HCl (0.2 mL, 2.05 mmol) in EtOH (5 mL) was refluxed overnight. Followed standard aqueous/EtOAc workup procedure, then purified by preparative HPLC to give Compound 111 (83 mg, yield 9%). $^1$H NMR (DMSO-d$_6$ 400 MHz): δ 10.32 (s, 1H), 8.63 (s, 1H), 7.60 (s, 1H), 7.53 (s, 1H), 7.37 (d, J=1.6 Hz, 1H), 7.21-7.18 (m, 3H), 7.10 (d, J=1.2 Hz, 1H), 6.93-6.91 (m, 2H), 6.43 (d, J=3.2 Hz, 1H), 6.29 (d, J=3.2 Hz, 1H), 5.12 (d, J=2.8 Hz, 1H), 4.06-3.96 (m, 2H), 1.32 (t, J=6.8 Hz, 3H); MS (ESI): m/z 422.0 [M+1]$^+$.

Example 112

Compound 112, 2-ethoxy-4-(2-imino-5,6-diphenyl-1,2,3,4-tetrahydropyrimidin-4-yl)-6-nitrophenol

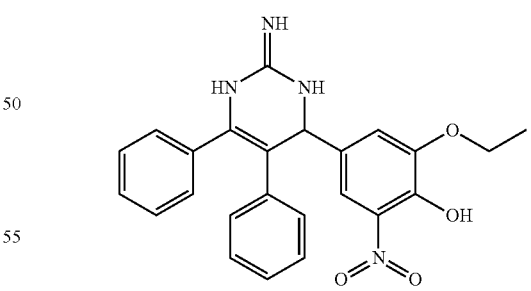

A mixture of 1,2-diphenylethanone (500 mg, 2.55 mmol), 3-ethoxy-4-hydroxy-5-nitrobenzaldehyde (538.5 mg, 2.55 mmol), guanidine hydrochloride (731 mg, 7.65 mmol), diisopropylamine (1.1 mL) in ethanol (5 mL) was refluxed at 80° C. for 60 h. The mixture was evaporated under reduced pressure and the residue was treated with a mixture of saturated aqueous sodium bisulfite solution (50 mL), dichloromethane (100 mL) and isopropanol (30 mL), and the resulting mixture was stirred at room temperature for 30 min. The organic layer was separated and the aqueous layer was extracted with a mixture of dichloromethane and isopropanol (3:1, 50 mL×2). The combined organic layer was dried over anhydrous sodium sulfate and purified by preparative HPLC. The product containing fractions were treated with HCl/MeOH (2 mL, 2 N) and concentrated in vacuo to give Compound 112 as an HCl salt (280 mg, yield 25.45%). $^1$H NMR (DMSO-$d_6$ 400 MHZ): δ 10.48 (s, 1H), 10.27 (s, 1H), 9.35 (s, 1H), 7.59 (s, 2H), 7.53 (s, 1H), 7.52-7.31 (m, 5H), 7.26 (d, J=2.0 Hz, 1H), 7.12-7.10 (m, 3H), 6.92-6.90 (m, 2H), 5.57 (d, J=3.2 Hz, 1H), 4.1-4.06 (q, J=7.2 Hz, 2H), 1.36-1.32 (t, J=7.2 Hz, 3H); MS (ESI): m/z 431.0 [M+H]$^+$.

Example 113

Compound 113, 4-(3-ethoxy-4-hydroxy-5-nitrophenyl)-5-phenyl-6-(4-(trifluoromethyl)phenyl)-3,4-dihydropyrimidin-2(1H)-one

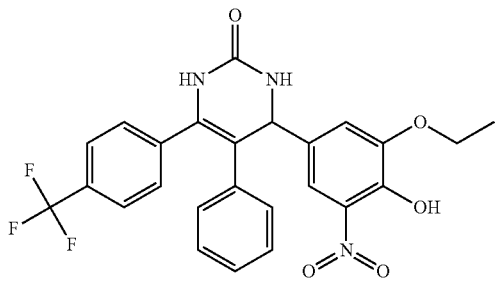 [SMILES: CCOc1cc(C2NC(=O)NC(c3ccc(C(F)(F)F)cc3)=C2c2ccccc2)cc([N+](=O)[O-])c1O]

A mixture of 2-phenyl-1-(4-(trifluoromethyl)phenyl)ethanone (commercially available) (200 mg, 0.76 mmol), 3-ethoxy-4-hydroxy-5-nitrobenzaldehyde (145 mg, 0.69 mmol), urea (124 mg, 2.06 mmol), conc. HCl (0.06 mL, 0.69 mmol) in EtOH (5 mL) was refluxed overnight. Followed a standard aqueous/EtOAc workup, then purified by preparative HPLC to give Compound 113 (135.34 mg, yield 39%). $^1$H NMR (DMSO-$d_6$ 400 MHz): δ 8.83 (d, J=1.6 Hz, 1H), 7.60-7.56 (m, 3H), 7.40-7.39 (m, 3H), 7.13 (s, 1H), 7.06-7.00 (m, 3H), 6.83-6.80 (m, 2H), 5.23 (d, J=2.4 Hz, 1H), 4.06-3.97 (m, 2H), 1.30 (t, J=7.2 Hz, 3H); MS (ESI): m/z 500.0 [M+1]$^+$.

Example 114

Compound 114, 4-(3-ethoxy-4-hydroxy-5-nitrophenyl)-5-phenyl-6-o-tolyl-3,4-dihydropyrimidin-2(1H)-one

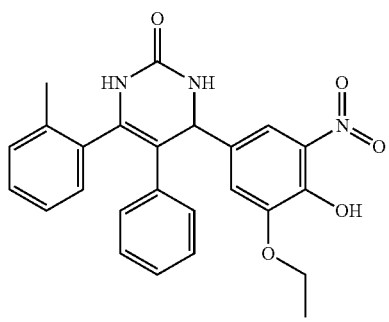 [SMILES: CCOc1cc(C2NC(=O)NC(c3ccccc3C)=C2c2ccccc2)cc([N+](=O)[O-])c1O]

A mixture of 2-phenyl-1-o-tolylethanone (commercially available) (200 mg, 0.95 mmol), 3-ethoxy-4-hydroxy-5-nitrobenzaldehyde (183 mg, 0.86 mmol), urea (156 mg, 2.59 mmol), concentrated HCl (0.07 mL, 0.86 mmol) in EtOH (5 mL) was refluxed overnight. Followed standard aqueous/EtOAc workup, then purified by preparative HPLC to give Compound 114 (31.75 mg, yield 8%). $^1$H NMR (DMSO-$d_6$ 400 MHz): δ 10.33 (br, 1H), 8.59 (s, 1H), 7.51-7.44 (m, 2H), 7.23-7.13 (m, 4H), 6.96-6.89 (m, 4H), 6.80-6.77 (m, 2H), 5.36-5.21 (m, 1H), 4.08-3.99 (m, 2H), 2.36 (s, 1.6H), 2.13 (s, 1.3H), 1.34-1.28 (m, 3H); MS (ESI): m/z 446.0 [M+1]$^+$.

Example 115

Compound 115, 4-(3-ethoxy-4-hydroxy-5-nitrophenyl)-5-(3-fluorophenyl)-6-phenyl-3,4-dihydropyrimidin-2(1H)-one

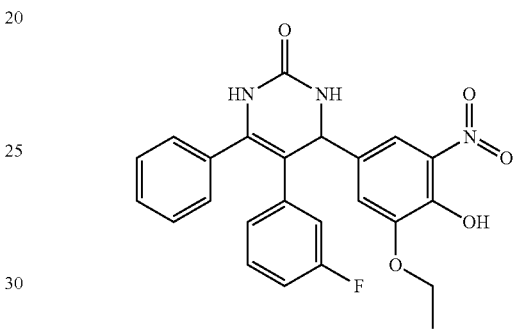

A mixture of 2-(3-fluorophenyl)-1-phenylethanone (commercially available) (200 mg, 0.93 mmol), 3-ethoxy-4-hydroxy-5-nitrobenzaldehyde (197 mg, 0.93 mmol), urea (168 mg, 2.8 mmol), conc. hydrochloric acid (0.5 mL) in ethanol (3 mL) was refluxed for 61 hours. After cooling to room temperature, the mixture was evaporated and purified by silica gel column chromatography (petroleum ether/ethyl acetate=3:1) to give Compound 115 (85.8 mg, yield 20%). HNMR (DMSO-$d_6$ 400 MHZ): δ 10.31 (brs, 1H), 8.82 (s, 1H), 7.59 (s, 1H), 7.45 (d, J=1.2 Hz, 1H), 7.31-7.22 (m, 6H), 7.10-7.00 (m, 1H), 6.84-6.80 (m, 1H), 6.64-6.56 (m, 2H), 5.26 (d, J=2.4 Hz, 1H), 4.15-4.00 (m, 2H), 1.36 (t, J=6.8 Hz, 3H). MS (ESI): m/z 450.0 [M+H]$^+$.

Example 116

Compound 116, 4-(3-ethoxy-4-hydroxy-5-nitrophenyl)-6-(pyridin-3-yl)-5-(thiophen-3-yl)-3,4-dihydropyrimidin-2(1H)-one

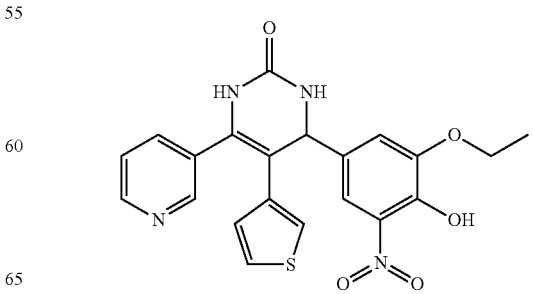

A mixture of 1-(pyridin-3-yl)-2-(thiophen-3-yl)ethanone (Intermediate 56) (100 mg, 0.492 mmol), 3-ethoxy-4-hydroxy-5-nitrobenzaldehyde (94 mg, 0.45 mmol), urea (81 mg, 1.34 mmol), concentrated HCl (0.04 mL, 0.45 mmol) in EtOH (5 mL) was refluxed overnight. Then the mixture was evaporated in vacuo and the residue was purified by preparative HPLC to give Compound 116 (65 mg, yield 33%). $^1$H NMR (DMSO-$d_6$ 400 MHz): δ 10.30 (s, 1H), 8.92 (s, 1H), 8.56-8.54 (m, 1H), 8.46-8.44 (m, 1H), 7.77 (d, J=8.0 Hz, 1H), 7.63 (s, 1H), 7.48-7.43 (m, 2H), 7.25-7.22 (m, 2H), 6.94 (s, 1H), 6.35 (d, J=5.2 Hz, 1H), 5.27 (d, J=2.8 Hz, 1H), 4.12-4.04 (m, 2H), 1.35 (t, J=6.8 Hz, 3H); MS (ESI): 438.9 m/z [M+1]$^+$.

Example 117

Compound 117, (Z)-2-ethoxy-4-(2-(methylimino)-5,6-diphenyl-1,2,3,4-tetrahydropyrimidin-4-yl)-6-nitrophenol

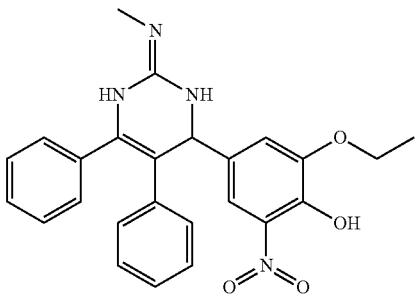 [SMILES: CCOc1cc(C2N/C(=N/C)NC(c3ccccc3)=C2c2ccccc2)cc([N+](=O)[O-])c1O]

A mixture of crude 4-(3-ethoxy-4-hydroxy-5-nitrophenyl)-5,6-diphenyl-3,4-dihydropyrimidine-2(1H)-thione (Compound 8) (392 mg, 0.877 mmol), m-CPBA (887 mg of 85% purity, 4.38 mmol) and aqueous methylamine solution (3 mL) in ethanol (20 mL) was stirred at 0° C. for 2 h, then at room temperature overnight. Na$_2$SO$_3$ (2 g) was added and then dilute hydrochloride acid was added drop wise to adjust the pH to about 6. The above mixture was extracted with ethyl acetate (40 mL×3), dried over Na$_2$SO$_4$, filtered, concentrated and purified by silica gel column chromatography, followed by preparative HPLC twice to afford Compound 117 (26 mg, yield: 6.7%). $^1$H NMR (DMSO-$d_6$ 400 MHz): δ 8.73 (s, 1H), 7.83 (d, J=7.2 Hz, 1H), 7.53 (s, 1H), 7.48 (s, 2H), 7.33 (s, 4H), 7.10-7.11 (m, 3H), 7.01 (s, 1H), 6.89-6.91 (m, 3H), 5.22 (s, 1H), 3.93 (d, J=6.8 Hz, 1H), 2.78 (s, 3H), 1.24-1.27 (t, J=4.8 Hz, 3H); MS (ESI): m/z 445.2[M+1]$^+$.

Example 118

Compound 118, 4-(3-ethoxy-4-hydroxy-5-nitrophenyl)-6-(1-methyl-1H-pyrazol-4-yl)-5-(thiophen-3-yl)-3,4-dihydropyrimidin-2(1H)-one

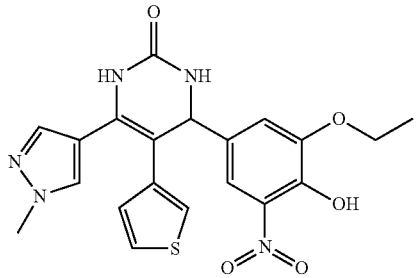 [SMILES: CCOc1cc(C2NC(=O)NC(c3cnn(C)c3)=C2c2ccsc2)cc([N+](=O)[O-])c1O]

To a solution of 1-(1-methyl-1H-pyrazol-4-yl)-2-(thiophen-3-yl)ethanone (Intermediate 57) (160 mg, 0.78 mmol), 3-ethoxy-4-hydroxy-5-nitrobenzaldehyde (164 mg, 0.78 mmol) and urea (110 mg, 2.4 mmol) in 15 mL of ethanol was added 0.2 mL of conc. HCl, and the mixture was stirred at reflux overnight. The mixture was cooled to room temperature and filtered. The solid was washed with ethanol and dried in vacuo to give Compound 118 as an HCl salt (49 mg, yield 14.3%). $^1$H NMR (DMSO-$d_6$ 400 MHz): δ 10.26 (s, 1H), 8.45 (s, 1H), 7.61 (s, 1H), 7.48 (s, 1H), 7.38 (d, J=4.8 Hz, 1H), 7.38 (s, 1H), 7.09 (d, J=1.6 Hz, 1H), 7.04 (s, 2H), 6.62 (d, J=5.2 Hz, 1H), 5.07 (d, J=2.4 Hz, 1H), 4.05-4.05 (m, 2H), 3.75 (s, 3H), 1.33 (t, J=6.8 Hz, 3H); MS (ESI): m/z 442.2 [M+1]$^+$.

Example 119

Compound 119, 4-(3-ethoxy-4-hydroxy-5-nitrophenyl)-6-(1-methyl-1H-pyrazol-3-yl)-5-(thiophen-3-yl)-3,4-dihydropyrimidin-2(1H)-one

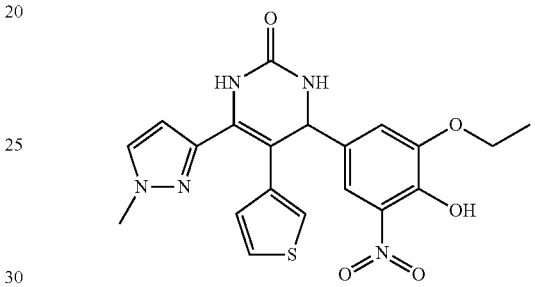

A mixture of 1-(1-methyl-1H-pyrazol-3-yl)-2-(thiophen-3-yl)ethanone (Intermediate 58) (750 mg, 3.6 mmol), 4-hydroxy-3-methoxy-5-nitrobenzaldehyde (782 mg, 3.7 mmol), urea (666 mg, 11.1 mmol) and conc. HCl (0.2 mL) in EtOH (10 mL) was refluxed overnight. The mixture was concentrated under reduced pressure to dryness and purified by prep-HPLC (0.1% TFA as additive) to give Compound 119 (1.3 g, yield 81%). $^1$H NMR and MS (ESI) characterization included for the individual enantiomers, see Compound 149 and Compound 150.

Example 120

Compound 120, 4-(3-chloro-4-hydroxy-5-nitrophenyl)-5,6-diphenyl-3,4-dihydropyrimidin-2(1H)-one

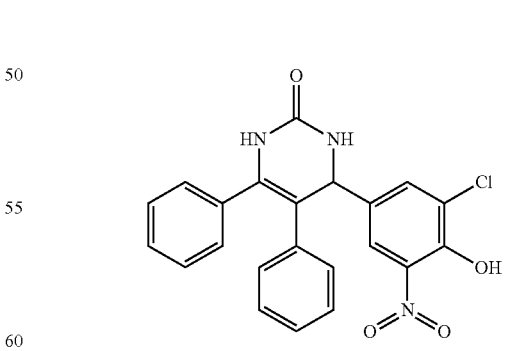

A mixture of 3-chloro-4-hydroxy-5-nitrobenzaldehyde (Intermediate 59) (150 mg, 0.74 mmol), 1,2-diphenylethanone (146.0 mg, 0.74 mmol), urea (133.9 mg, 2.23 mmol), concentrated hydrochloric acid (0.5 mL) in ethanol (3 mL) was refluxed at 78° C. for 45 h. After cooling, the mixture was evaporated and the residue was purified by preparative HPLC to give Compound 120 (129.1 mg, yield 41.4%). HNMR (DMSO-$d_6$ 400 MHz): δ 11.09 (s, 1H), 8.79 (s, 1H), 7.87 (d, J=2.0 Hz, 1H), 7.71 (d, J=2.0 Hz, 1H), 7.59 (s, 1H), 7.27-7.21 (m, 5H), 7.05-7.00 (m, 3H), 6.83-6.81 (m, 2H), 5.28 (d, J=2.8 Hz, 1H); MS (ESI): m/z 422.0 [M+H]$^+$.

Example 121

Compound 121, 6-(3-chloro-5-fluorophenyl)-4-(3-ethoxy-4-hydroxy-5-nitrophenyl)-5-phenyl-3,4-dihydropyrimidin-2(1H)-one

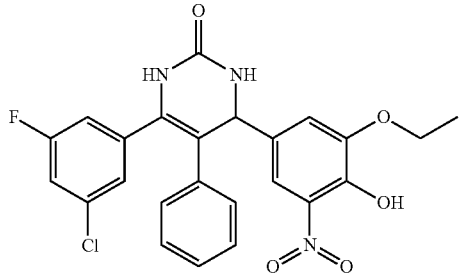 [SMILES: CCOc1cc(C2NC(=O)NC(c3cc(F)cc(Cl)c3)=C2c2ccccc2)cc([N+](=O)[O-])c1O]

A mixture of 1-(3-chloro-5-fluorophenyl)-2-phenylethanone (Intermediate 60) (150 mg, 0.60 mmol), 3-ethoxy-4-hydroxy-5-nitrobenzaldehyde (116 mg, 0.55 mmol), urea (99 mg, 1.65 mmol), concentrated HCl (0.05 mL, 0.55 mmol) in EtOH (5 mL) was refluxed overnight. Followed standard aqueous/EtOAc workup and purified by preparative HPLC to give Compound 121 (155 mg, yield 58%). $^1$H NMR (DMSO-$d_6$ 400 MHz): δ 10.27 (brs, 1H), 8.85 (s, 1H), 7.58 (s, 1H), 7.40 (d, J=1.6 Hz, 1H), 7.34 (d, J=8.8 Hz, 1H), 7.25 (s, 1H), 7.12 (d, J=6.4 Hz, 2H), 7.08 (d, J=7.6 Hz, 2H), 7.01 (d, J=7.2 Hz, 1H), 6.88 (d, J=7.2 Hz, 2H), 5.27 (d, J=2.4 Hz, 1H), 4.09-3.99 (m, 2H), 1.32 (t, J=7.2 Hz, 3H); MS (ESI): m/z 484.1 [M+1]$^+$.

Example 122

Compound 122, 2-hydroxy-3-nitro-5-(2-oxo-5,6-diphenyl-1,2,3,4-tetrahydropyrimidin-4-yl)benzonitrile

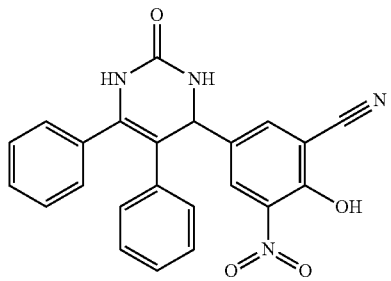 [SMILES: N#Cc1cc(C2NC(=O)NC(c3ccccc3)=C2c2ccccc2)cc([N+](=O)[O-])c1O]

A mixture of 5-formyl-2-hydroxy-3-nitrobenzonitrile (Intermediate 61) (150 mg, 0.78 mmol), 1,2-diphenylethanone (153 mg, 0.78 mmol), urea (141 mg, 2.34 mmol), conc. hydrochloric acid (0.5 mL) in ethanol (3 mL) was refluxed for 37 hours. The mixture was evaporated and purified by prep.-HPLC (0.1% TFA as additive) to give Compound 122 (51 mg, yield 16%). HNMR (DMSO-$d_6$, 400 MHz): δ 8.77 (s, 1H), 8.16 (d, J=2.0 Hz, 1H), 7.92 (d, J=2.4 Hz, 1H), 7.56 (d, J=2.0 Hz, 1H), 7.25-7.21 (m, 5H), 7.01-6.98 (m, 3H), 6.82-6.79 (m, 2H), 5.31 (d, J=2.8 Hz, 1H), MS (ESI): m/z 413.0 [M+H]$^+$.

Example 123

Compound 123, 2-hydroxy-5-(2-oxo-5,6-diphenyl-1,2,3,4-tetrahydropyrimidin-4-yl)benzenesulfonic acid

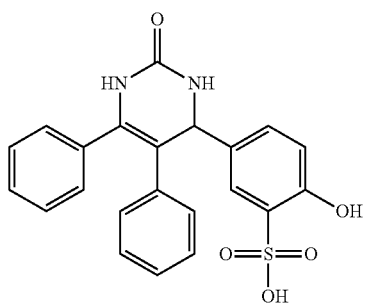 [SMILES: O=C1NC(c2ccccc2)=C(c2ccccc2)C(c2ccc(O)c(S(=O)(=O)O)c2)N1]

Step 1: Synthesis of 4-(4-hydroxyphenyl)-5,6-diphenyl-3,4-dihydropyrimidin-2(1H)-one Followed the procedure described in Example 86, starting from 4-hydroxybenzaldehyde, 1,2-diphenylethanone and urea, and acetic acid was used instead of HCl.

Step 2: Synthesis of 2-hydroxy-5-(2-oxo-5,6-diphenyl-1,2,3,4-tetrahydropyrimidin-4-yl)benzenesulfonic acid To a solution of 4-(4-hydroxyphenyl)-5,6-diphenyl-3,4-dihydropyrimidin-2(1H)-one (68 mg, 0.2 mmol) in CHCl$_3$ (1 mL) was added ClSO$_3$H (35 mg, 0.3 mmol). The mixture was heated to 50° C. overnight. The residue was purified by prep-HPLC to give Compound 123 as a white power (6 mg, 7%). $^1$H NMR (MeOH-$d_4$ 500 MHz): δ 7.75 (d, J=7.5 Hz, 1H), 7.38 (d, J=7 Hz, 1H), 7.30 (m, 2H), 7.24 (t, J=1, 5 Hz, 3H), 7.01 (t, J=3.5, 5 Hz, 3H), 6.87 (m, 3H), 5.23 (s, 1H); MS (ESI): m/z 423.0 [M+1]$^+$.

Example 124

Compound 124, (R)-3-ethoxy-2-hydroxy-5-(2-oxo-6-(pyridin-3-yl)-5-(thiophen-3-yl)-1,2,3,4-tetrahydropyrimidin-4-yl)benzoic acid

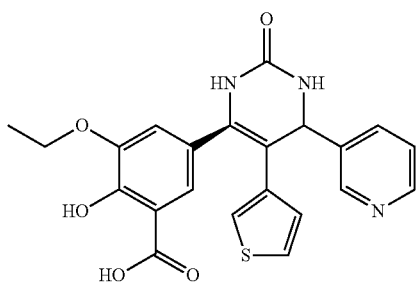

Single enantiomer of Compound 126 (see Example 126 for synthesis). The two enantiomers were separated by chiral supercritical chromatography (SFC separation condition: Column: AS-20 UM, 300*300 mm, 20 UM; Mobile Phase: Supercritical Fluid CO2:MeOH=70:30, 80 ML/MIN; Detector Wavelength: 220 nm), the eluting solution for the first peak was collected and evaporated to give one enantiomer as Compound 124 (29.29 mg, yield 4%). $^1$H NMR (DMSO-$d_6$ 400 MHz): δ 11.38 (br, 1H), 8.90 (s, 1H), 8.59 (d, J=6.0 Hz, 1H), 8.49 (s, 1H), 7.85 (d, J=8.0 Hz, 1H), 7.58-7.52 (m, 2H), 7.44 (d, J=2.0 Hz, 1H), 7.26-7.24 (m, 1H), 7.16 (d, J=2.0 Hz, 1H), 6.90-6.89 (m, 1H), 6.35 (dd, J=0.8 Hz, J=4.8 Hz, 1H), 5.19 (d, J=2.0 Hz, 1H), 4.05-3.96 (m, 2H), 1.33 (t, J=6.8 Hz, 3H); MS (ESI): =m/z 438.0 [M+1]$^+$; [α]$^{20}_D$=0.403 (c=8.9 mg/mL, MeOH).

Example 125

Compound 125, (S)-3-ethoxy-2-hydroxy-5-(2-oxo-6-(pyridin-3-yl)-5-(thiophen-3-yl)-1,2,3,4-tetrahydropyrimidin-4-yl)benzoic acid

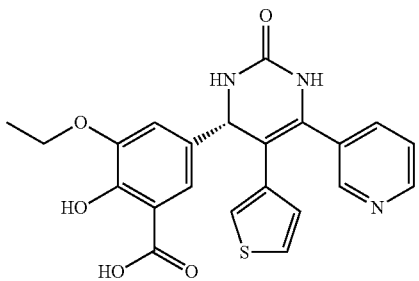 [SMILES: CCOc1cc([C@@H]2NC(=O)NC(c3cccnc3)=C2c2ccsc2)cc(C(=O)O)c1O]

Single enantiomer of Compound 126 (see Example 126 for synthesis). The two enantiomers were separated by chiral supercritical chromatography (see Example 124 for conditions). The eluting solution for the second peak was collected and evaporated to give another enantiomer as Compound 125 (13.09 mg, yield 2%). $^1$H NMR (DMSO-$d_6$ 400 MHz): δ 11.35 (br, 1H), 8.87 (d, J=1.6 Hz, 1H), 8.56 (dd, J=1.6 Hz, J=5.2 Hz, 1H), 8.45 (d, J=1.6 Hz, 1H), 7.80 (d, J=8.0 Hz, 1H), 7.56 (s, 1H), 7.51-7.48 (m, 1H), 7.42 (d, J=2.0 Hz, 1H), 7.24-7.22 (m, 1H), 7.15 (d, J=2.0 Hz, 1H), 6.87 (dd, J=1.2 Hz, J=3.2 Hz, 1H), 6.33 (dd, J=1.2 Hz, J=4.8 Hz, 1H), 5.16 (d, J=2.8 Hz, 1H), 4.03-3.95 (m, 2H), 1.31 (t, J=6.8 Hz, 3H); m/z 438.0 [M+1]$^+$; [α]$^{20}_D$=-0.398 (c=11.3 mg/mL, MeOH).

Example 126

Compound 126, 3-ethoxy-2-hydroxy-5-(2-oxo-6-(pyridin-3-yl)-5-(thiophen-3-yl)-1,2,3,4-tetrahydropyrimidin-4-yl)benzoic acid

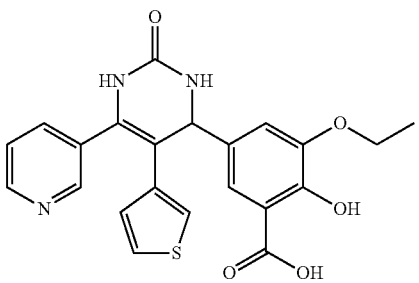 [SMILES: CCOc1cc(C2NC(=O)NC(c3cccnc3)=C2c2ccsc2)cc(C(=O)O)c1O]

A mixture of 1-(pyridin-3-yl)-2-(thiophen-3-yl)ethanone (Intermediate 56) (372 mg, 1.83 mmol), 3-ethoxy-5-formyl-2-hydroxybenzoic acid (Intermediate 62) (350 mg, 1.67 mmol), urea (300 mg, 5.00 mmol) and HCl (12 M, 0.14 mL, 1.67 mmol) in EtOH (10 mL) was refluxed overnight. The mixture was concentrated in vacuo and purified by preparative HPLC to give Compound 126 (240 mg, yield 33%) as a yellow solid. $^1$H NMR (DMSO-$d_6$ 400 MHz): δ 11.35 (br, 1H), 8.87 (d, J=1.6 Hz, 1H), 8.56 (dd, J=1.6 Hz, J=5.2 Hz, 1H), 8.45 (d, J=1.6 Hz, 1H), 7.80 (d, J=8.0 Hz, 1H), 7.56 (s, 1H), 7.51-7.48 (m, 1H), 7.42 (d, J=2.0 Hz, 1H), 7.24-7.22 (m, 1H), 7.15 (d, J=2.0 Hz, 1H), 6.87 (dd, J=1.2 Hz, J=3.2 Hz, 1H), 6.33 (dd, J=1.2 Hz, J=4.8 Hz, 1H), 5.16 (d, J=2.4 Hz, 1H), 4.03-3.95 (m, 2H), 1.31 (t, J=6.8 Hz, 3H); MS (ESI): m/z 438.0 [M+1]$^+$;

Example 127

Compound 127, 4-(3-fluoro-4-hydroxy-5-nitrophenyl)-5,6-diphenyl-3,4-dihydropyrimidin-2(1H)-one

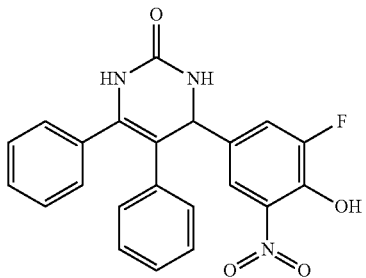 [SMILES: O=C1NC(c2ccccc2)=C(c2ccccc2)C(c2cc(F)c(O)c([N+](=O)[O-])c2)N1]

A mixture of 3-fluoro-4-hydroxy-5-nitrobenzaldehyde (Intermediate 63) (150 mg, 0.81 mmol), 1,2-diphenylethanone (159 mg, 0.81 mmol), urea (145 mg, 2.43 mmol), concentrated hydrochloric acid (0.5 mL) in ethanol (2 mL) was refluxed at 86° C. for 46 hours. After cooling, the mixture was evaporated and the crude product was purified by preparative HPLC to give Compound 127 (136.1 mg, yield 41.4%). HNMR (DMSO-$d_6$ 400 MHz): δ 11.25 (s, 1H), 8.77 (s, 1H), 7.70 (s, 1H), 7.59 (s, 1H), 7.52-7.49 (m, 1H), 7.27-7.22 (m, 5H), 7.06-6.98 (m, 3H), 6.83 (d, J=6.4 Hz, 2H), 5.27 (d, J=2.4 Hz, 1H); MS (ESI): m/z 406.0 [M+H]$^+$.

Example 128

Compound 128, 3-ethoxy-2-hydroxy-5-(2-oxo-6-(pyridin-3-yl)-5-(thiophen-3-yl)-1,2,3,4-tetrahydropyrimidin-4-yl)benzonitrile

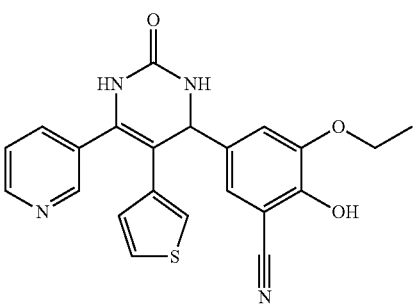 [SMILES: CCOc1cc(C2NC(=O)NC(c3cccnc3)=C2c2ccsc2)cc(C#N)c1O]

To a solution of 1-(pyridin-3-yl)-2-(thiophen-3-yl)ethanone (Intermediate 56) (100 mg, 0.50 mmol), 3-ethoxy-5-formyl-2-hydroxy-benzonitrile (Intermediate 51) (95.6 mg, 0.50 mmol) and urea (150 mg, 2.50 mmol) in 3 mL of ethanol was added 0.2 mL of concentrated HCl, and the mixture was refluxed for 2 days. After the solvent was removed under reduced pressure, the residue was purified by reverse-phase preparatory HPLC (26-53% acetonitrile+0.1% trifluoroacetic acid in water+0.1% trifluoroacetic acid, over 15 min.) to give compound 128 (110 mg, yield 53.5%). $^1$H NMR (DMSO-$d_6$ 400 MHz) δ 8.99 (s, 1H), 8.74 (s, 2H), 8.16 (d, J=8.0 Hz, 1H), 7.77 (m, 1H), 7.63 (s, 1H), 7.28 (m, 2H), 7.17 (m, 3H), 6.98 (d, J=2.4 Hz, 1H), 6.46 (d, J=4.8 Hz, 1H), 5.27 (d, J=6.4 Hz, 1H), 4.07 (m, 2H); 1.34 (t, J=7.2 Hz, 3H); MS (ESI): m/z 419.2 [M+1]$^+$.

Example 129

Compound 129, 4-(3-ethoxy-4-hydroxy-5-nitrophenyl)-6-(3-hydroxyphenyl)-5-phenyl-3,4-dihydropyrimidin-2(1H)-one

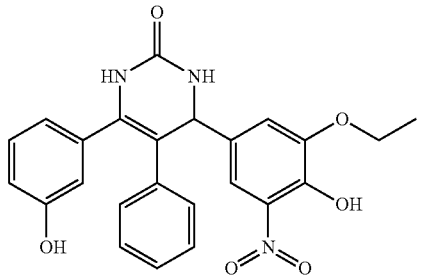 [SMILES: CCOc1cc(C2NC(=O)NC(c3cccc(O)c3)=C2c2ccccc2)cc([N+](=O)[O-])c1O]

A mixture of 1-(3-hydroxyphenyl)-2-phenylethanone (Intermediate 64) (154 mg, 0.726 mmol), 3-ethoxy-4-hydroxy-5-nitrobenzaldehyde (153.3 mg, 0.726 mmol), urea (130.7 mg, 2.178 mmol), concentrated hydrochloric acid (0.5 mL) in ethanol (2 mL) was refluxed at 79° C. for 50 h. Removed solvent and purified by preparative HPLC to give Compound 129 (110 mg, yield 33.9%). HNMR (DMSO-$d_6$ 400 MHz): δ 10.29 (s, 1H), 9.41 (s, 1H), 8.62 (d, J=1.6 Hz, 1H), 7.50 (s, 1H), 7.43 (d, J=2.0 Hz, 1H), 7.19 (d, J=2.0 Hz, 1H), 7.05-6.97 (m, 4H), 6.83-6.80 (m, 2H), 6.65-6.58 (m, 3H), 5.12 (d, J=2.8 Hz, 1H), 4.05-4.02 (m, 2H), 1.34-1.30 (m, 3H); MS (ESI): m/z 448.0 [M+H]$^+$.

Example 130

Compound 130, 4-(4-hydroxy-3-nitro-5-propoxyphenyl)-5,6-diphenyl-3,4-dihydropyrimidin-2(1H)-one

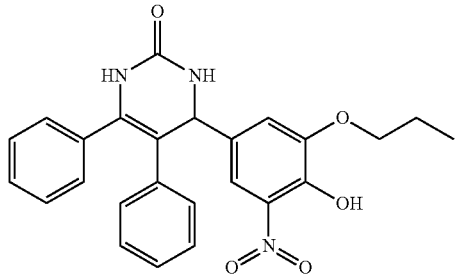 [SMILES: CCCOc1cc(C2NC(=O)NC(c3ccccc3)=C2c2ccccc2)cc([N+](=O)[O-])c1O]

The mixture of 4-hydroxy-3-nitro-5-propoxybenzaldehyde (Intermediate 65) (126 mg, 0.56 mmol), 1,2-diphenylethanone (131 mg, 0.672 mmol), urea (100 mg, 1.68 mmol) and concentrated hydrochloric acid (0.1 mL) in ethanol (5 mL) was stirred at reflux (110° C.) under N$_2$ overnight. The reaction was concentrated and purified by silica gel column chromatography, followed by preparative HPLC to give Compound 130 (27 mg, yield 10.8%) as a solid. $^1$H NMR (DMSO-$d_6$ 400 MHz): δ 10.27 (s, 1H), 8.72 (d, J=1.6 Hz, 1H), 7.54 (s, 1H), 7.45 (d, J=2.0 Hz, 1H), 7.18-7.27 (m, 6H), 7.00-7.06 (m, 3H), 6.82-6.84 (m, 2H), 5.197 (d, J=2.8 Hz, 1H), 3.90-3.97 (m, 2H), 1.71-1.76 (m, 2H), 0.970 (t, J=7.6 Hz, 3H); MS (ESI): m/z 446.3 [M+1]$^+$.

Example 131

Compound 131, 4-(3-ethoxy-4-hydroxy-5-nitrophenyl)-6-(pyrazin-2-yl)-5-(thiophen-3-yl)-3,4-dihydropyrimidin-2(1H)-one

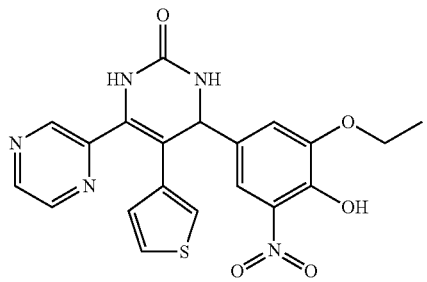 [SMILES: CCOc1cc(C2NC(=O)NC(c3cnccn3)=C2c2ccsc2)cc([N+](=O)[O-])c1O]

To a solution of 1-(pyrazin-2-yl)-2-(thiophen-3-yl)ethanone (Intermediate 66) (30 mg, 0.15 mmol), 3-ethoxy-4-hydroxy-5-nitrobenzaldehyde (31 mg, 0.15 mmol) and urea (27 mg, 0.45 mmol) in 2 mL of ethanol was added 0.2 mL of conc. HCl, and was stirred at reflux overnight. The mixture was cooled and then purified by preparative HPLC (30-60% acetonitrile+0.15% trifluoroacetic acid in water, over 15 min.), the desired eluting solution was treated with HCl/MeOH (2 mL, 2M) and concentrated in vacuo to give Compound 131 as HCl salt (8.3 mg, yield 12.3%). $^1$H NMR (CD$_3$OD 400 MHz): δ 8.69 (dd, J=1.6 Hz, 2.4 Hz, 1H), 8.48 (d, J=3.6 Hz, 1H), 8.17 (d, J=1.6 Hz, 1H), 7.60 (d, J=2.0 Hz, 1H), 7.37 (dd, J=3.2 Hz, 5.2 Hz, 1H), 7.18 (d, J=2.0 Hz, 1H), 7.02 (dd, J=1.2 Hz, 2.8 Hz, 1H), 6.66 (dd, J=1.2 Hz, 5.2 Hz, 1H), 5.42 (s, 1H), 4.11-4.06 (m, 2H), 1.42 (t, J=7.2 Hz, 3H); MS (ESI): m/z 440.2 [M+1]$^+$.

Example 132

Compound 132, 4-(3-ethoxy-4-hydroxy-5-nitrophenyl)-5-phenyl-6-(quinolin-6-yl)-3,4-dihydropyrimidin-2(1H)-one

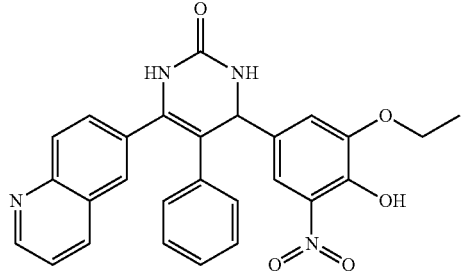 [SMILES: CCOc1cc(C2NC(=O)NC(c3ccc4ncccc4c3)=C2c2ccccc2)cc([N+](=O)[O-])c1O]

To a solution of 2-phenyl-1-(quinolin-6-yl)ethanone (Intermediate 67) (100 mg, 0.4 mmol), 3-ethoxy-4-hydroxy-5-nitrobenzaldehyde (85 mg, 0.4 mmol) and urea (72 mg, 1.2 mmol) in 2 mL of ethanol was added 0.5 mL of conc. HCl and was stirred at reflux overnight. The mixture was cooled to room temperature and purified by preparative HPLC (20-50% acetonitrile+0.15% trifluoroacetic acid in water, over 15 min.), followed by column chromatography (PE:EtOAc=2:1~EtOAc:MeOH=10:1) to give Compound 132 (18 mg, yield 11.8%). $^1$H NMR (CD$_3$OD 400 MHz): δ 8.84 (d, J=3.2 Hz, 1H), 8.30 (d, J=8.8 Hz, 1H), 7.94 (s, 1H), 7.86 (d, J=8.8 Hz, 1H), 7.66 (s, 1H), 7.59-7.52 (m, 2H), 7.19 (s, 1H), 7.06 (m, 3H), 6.95-6.94 (m, 2H), 5.45 (s, 1H), 4.13-4.05 (m, 2H), 1.41 (t, J=6.8 Hz, 3H); MS (ESI): m/z 483.3 [M+1]⁺.

Example 133

Compound 133, 4-(3-ethoxy-4-hydroxy-5-nitrophenyl)-6-(isoquinolin-6-yl)-5-phenyl-3,4-dihydropyrimidin-2(1H)-one

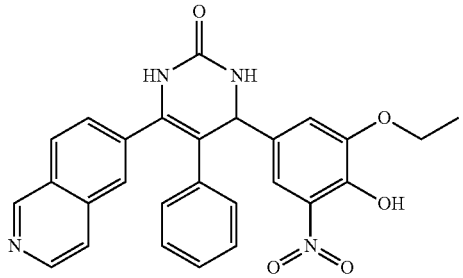 [SMILES: CCOc1cc(C2NC(=O)NC(c3ccc4cnccc4c3)=C2c2ccccc2)cc([N+](=O)[O-])c1O]

To a solution of 1-(isoquinolin-6-yl)-2-phenylethanone (Intermediate 68) (100 mg, 0.4 mmol), 3-ethoxy-4-hydroxy-5-nitrobenzaldehyde (85 mg, 0.4 mmol) and urea (72 mg, 1.2 mmol) in 2 mL of ethanol was added 0.5 mL of conc. HCl and the mixture was refluxed overnight. The reaction was evaporated and purified by preparative HPLC (20-50% acetonitrile+0.15% trifluoroacetic acid in water, over 15 min.), followed by column chromatography (PE:EtOAc=3:1~EtOAc: MeOH=10:1) to give Compound 133 (67 mg, yield 34.3%). ¹H NMR (CD₃OD 400 MHz): δ 9.18 (s, 1H), 8.42 (d, J=5.6 Hz, 1H), 7.95 (d, J=8.8 Hz, 1H), 7.94 (s, 1H), 7.76 (d, J=6.0 Hz, 1H), 7.65 (d, J=2.0 Hz, 1H), 7.48 (dd, J=2.0 Hz, 8.8 Hz, 1H), 7.17 (d, J=1.6 Hz, 1H), 7.07-7.06 (m, 3H), 6.95-6.93 (m, 2H), 5.45 (s, 1H), 4.13-4.02 (m, 2H), 1.41 (t, J=6.8 Hz, 3H); MS (ESI): m/z 483.3 [M+1]⁺.

Example 134

Compound 134, 4-(3-ethoxy-4-hydroxy-5-nitrophenyl)-5-(3-methoxyphenyl)-6-(pyridin-3-yl)-3,4-dihydropyrimidin-2(1H)-one

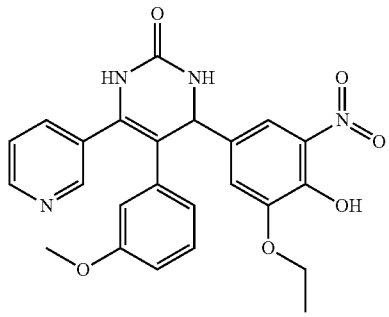 [SMILES: CCOc1cc(C2NC(=O)NC(c3cccnc3)=C2c2cccc(OC)c2)cc([N+](=O)[O-])c1O]

To a solution of 2-(3-methoxyphenyl)-1-(pyridin-3-yl) ethanone (Intermediate 69) (60 mg, 0.26 mmol), 3-ethoxy-4-hydroxy-5-nitro-benzaldehyde (55.8 mg, 0.26 mmol) and urea (46.8 mg, 0.78 mmol) in 3 mL of ethanol was added 0.2 mL of concentrated HCl. The mixture was refluxed for 2 days. After the solvent was removed, the residue was purified by reverse-phase preparatory HPLC (26-53% acetonitrile+0.1% trifluoroacetic acid in water+0.1% trifluoroacetic acid, over 15 min.) to give Compound 134 (30 mg, yield 24.6%). ¹H NMR (CD₃OD 400 MHz): δ 8.75 (s, 1H), 8.55 (d, J=8.0 Hz, 1H), 8.01 (dd, J₁=6.0 Hz, J₂=8.4 Hz, 1H), 7.60 (d, J=2.0 Hz, 1H), 7.08 (m, 2H), 6.75 (dd, J₁=2.4 Hz, J₂=8.4 Hz, 1H), 6.55 (s, 1H), 6.49 (d, J=3.6 Hz, 1H), 5.53 (s, 1H), 4.02 (m, 2H), 3.64 (s, 3H); 1.39 (t, J=6.8 Hz, 3H); MS (ESI): m/z 463.1 [M+1]⁺.

Example 135

Compound 135, 3-ethoxy-2-hydroxy-5-(5-(3-methoxyphenyl)-2-oxo-6-(pyridin-3-yl)-1,2,3,4-tetrahydropyrimidin-4-yl)benzoic acid

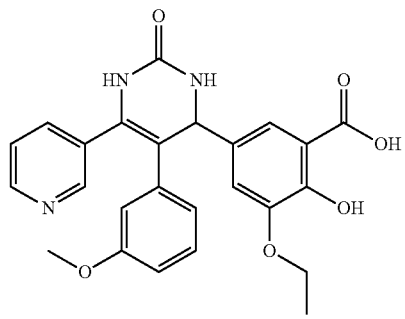 [SMILES: CCOc1cc(C2NC(=O)NC(c3cccnc3)=C2c2cccc(OC)c2)cc(C(=O)O)c1O]

To a solution of 2-(3-methoxyphenyl)-1-(pyridin-3-yl) ethanone (Intermediate 69) (70 mg, 0.31 mmol), 3-ethoxy-5-formyl-2-hydroxy-benzoic acid (Intermediate 62) (65 mg, 0.31 mmol) and urea (60 mg, 1.0 mmol) in 3 mL of ethanol was added 0.2 mL of concentrated HCl, then the mixture was refluxed for 2 days. The solvent was removed and the residue was purified by reverse-phase preparatory HPLC (26-53% acetonitrile+0.1% trifluoroacetic acid in water+0.1% trifluoroacetic acid, over 15 min.) to give Compound 135 (25 mg, yield 16.9%). ¹H NMR (CD₃OD 400 MHz): δ 8.73 (d, J=6.8 Hz, 1H), 8.72 (s, 1H), 8.52 (d, J=8.4 Hz, 1H), 7.50 (d, J=2.0 Hz, 1H), 7.08 (t, J=8.0 Hz, 1H), 7.01 (d, J=2.4 Hz, 1H), 7.17 (m, 3H), 6.98 (d, J=2.4 Hz, 1H), 6.74 (dd, J₁=2.4 Hz, J₂=8.4 Hz, 1H), 6.50 (dd, J₁=2.4 Hz, J₂=12.0 Hz, 2H), 5.41 (s, 1H); 4.00 (m, 2H), 3.63 (s, 3H), 1.36 (t, J=6.8 Hz, 3H); MS (ESI): m/z 462.1 [M+1]⁺.

Example 136

Compound 136, 4-(3-ethoxy-4-hydroxy-5-nitrophenyl)-6-(pyridin-4-yl)-5-(thiophen-3-yl)-3,4-dihydropyrimidin-2(1H)-one

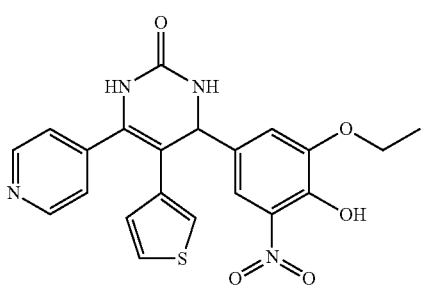 [SMILES: CCOc1cc(C2NC(=O)NC(c3ccncc3)=C2c2ccsc2)cc([N+](=O)[O-])c1O]

A mixture of 1-(pyridin-4-yl)-2-(thiophen-3-yl)ethanone (Intermediate 70) (180 mg, 0.89 mmol), 3-ethoxy-4-hydroxy-5-nitrobenzaldehyde (188 mg, 0.89 mmol), urea (160 mg, 2.70 mmol), conc. hydrochloric acid (0.5 mL) in ethanol (3 mL) was refluxed for 45 hours. The mixture was concentrated and purified by prep-HPLC (0.1% TFA as additive). To the residue was added HCl/MeOH (2 mL, 2 N) and concentrated to give Compound 136 as HCl salt (24.3 mg, yield 6%). HNMR (DMSO-$d_6$ 400 MHZ): δ 10.31 (brs, 1H), 9.03 (s, 1H), 8.72 (d, J=6.4 Hz, 2H), 7.71 (s, 1H), 7.61 (d, J=6.0 Hz, 2H), 7.45 (d, J=2.0 Hz, 1H), 7.30 (dd, J=4.8, 2.8 Hz, 1H), 7.17 (d, J=1.6 Hz, 1H), 7.02 (dd, J=2.8, 1.2 Hz, 1H), 6.50 (dd, J=5.2, 1.2 Hz, 1H), 5.32 (d, J=2.4 Hz, 1H), 4.05 (q, J=6.8 Hz, 2H), 1.34 (t, J=6.8 Hz, 3H). MS (ESI): m/z 438.9 [M+H]$^+$.

Example 137

Compound 137, 4-(4-hydroxy-3-(2-hydroxyethoxy)-5-nitrophenyl)-5,6-diphenyl-3,4-dihydropyrimidin-2(1H)-one

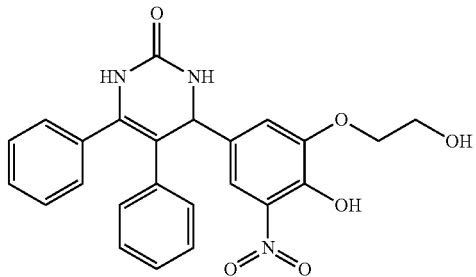 [SMILES: O=C1NC(c2ccccc2)=C(c2ccccc2)C(c2cc(OCCO)c(O)c([N+](=O)[O-])c2)N1]

To the solution of 4-hydroxy-3-(2-hydroxyethoxy)-5-nitrobenzaldehyde (Intermediate 71) (60 mg, 0.27 mmol), 1,2-diphenyl-ethanone (53 mg, 0.27 mmol) and urea (48.6 mg, 0.81 mmol) in 4 mL of ethanol was added 0.2 mL of concentrated HCl, and the mixture was stirred at reflux for 2 days. The mixture was concentrated and purified by reverse-phase preparatory HPLC (26-53% acetonitrile+0.1% trifluoroacetic acid in water+0.1% trifluoroacetic acid, over 15 min.) to give Compound 137 (28 mg, yield 23.7%). $^1$H NMR (DMSO-$d_6$ 400 MHz): δ 10.23 (s, 1H), 8.75 (s, 1H), 7.55 (s, 1H), 7.46 (s, 1H), 7.26 (m, 6H), 7.02 (m, 3H), 6.83 (d, J=7.2 Hz, 2H), 5.19 (d, J=2.4 Hz, 1H), 3.99 (m, 2H), 3.75 (m, 2H); MS (ESI): m/z 448.1 [M+1]$^+$.

Example 138

Compound 138, 2-hydroxy-4-(2-oxo-5,6-diphenyl-1,2,3,4-tetrahydropyrimidin-4-yl)benzoic acid

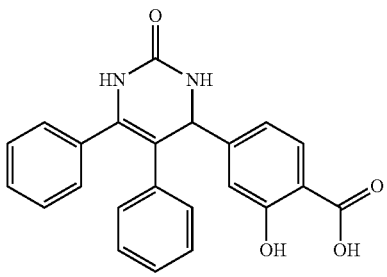

A mixture of methyl 4-formyl-2-hydroxybenzoate (Intermediate 84) (125 mg, 0.69 mmol), 1,2-diphenylethanone (136.2 mg, 0.69 mmol), urea (124.8 mg, 2.08 mmol), concentrated hydrochloric acid (1.0 mL) in ethanol (5 mL) was heated at 90° C. for 40 hours. Followed standard aqueous/EtOAc workup procedure to give crude ethyl 2-hydroxy-4-(2-oxo-5,6-diphenyl-1,2,3,4-tetrahydropyrimidin-4-yl)benzoate (200 mg, yield 69.5%). To a solution of this crude material (200 mg, 0.483 mmol) in water (5 mL) and ethanol (5 mL) was added sodium hydroxide (38.64 mg, 0.966 mmol) at 0° C. The mixture was stirred at 30° C. for 4 hours, then partitioned between ethyl acetate (70 mL) and water (50 mL). The organic layer was discarded and the aqueous layer was adjusted to pH=3 by hydrochloric acid (2M). Followed a standard aqueous/EtOAc workup. The residue was purified by preparative HPLC to give Compound 138 (31.3 mg, yield 16.8%). HNMR (DMSO-$d_6$ 400 MHz): δ 11.27 (s, 1H), 8.71 (s, 1H), 7.77 (d, J=8.0 Hz, 1H), 7.26 (s, 1H), 7.25-7.19 (m, 5H), 7.03-6.99 (m, 3H), 6.93 (d, J=8.0 Hz, 1H), 6.87 (s, 1H), 6.81 (d, J=6.4 Hz, 2H), 5.16 (d, J=2.8 Hz, 1H); MS (ESI): m/z 387.0 [M+H]$^+$.

Example 139

Compound 139, 4-(3-ethoxy-4-hydroxy-5-nitrophenyl)-6-(1-methyl-1H-pyrazol-5-yl)-5-(thiophen-3-yl)-3,4-dihydropyrimidin-2(1H)-one

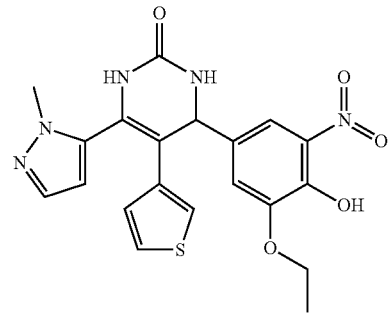 [SMILES: CCOc1cc(C2NC(=O)NC(c3ccnn3C)=C2c2ccsc2)cc([N+](=O)[O-])c1O]

To a mixture of 1-(1-methyl-1H-pyrazol-5-yl)-2-(thiophen-3-yl)ethanone (Intermediate 72) (90 mg, 0.32 mmol), 3-ethoxy-4-hydroxy-5-nitrobenzaldehyde (110 mg, 0.52 mmol) and urea (52 mg, 0.87 mmol) in EtOH (4 mL) was added concentrated HCl (0.1 mL). The reaction was refluxed overnight. Purified by column chromatography and preparative HPLC to give Compound 139 as a yellow solid (32 mg, yield: 16.7%). $^1$HNMR (DMSO-$d_6$ 400 MHz): δ 10.44 (s, 1H), 8.91 (s, 1H), 7.75 (s, 1H), 7.57 (d, J=1.6 Hz, 1H), 7.53 (d, J=2.0 Hz, 1H), 7.34-7.36 (m, 2H), 7.06-7.07 (m, 1H), 6.39 (d, J=2.0 Hz, 1H), 6.21 (d, J=4.8 Hz, 1H), 5.42 (d, J=2.4 Hz, 3H), 4.14 (q, J=7.2 Hz, 2H), 3.62 (s, 3H), 1.42 (t, J=7.2 Hz, 3H); MS (ESI): m/z 442.0 [M+1]$^+$.

Example 140

Compound 140, 2-nitro-4-(2-oxo-5,6-diphenyl-1,2,3,4-tetrahydropyrimidin-4-yl)benzoic acid

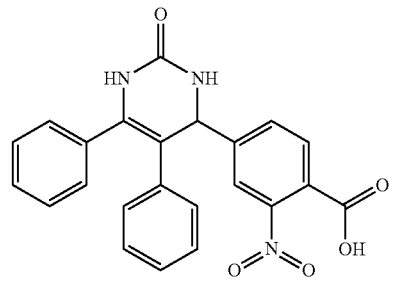 [SMILES: O=C1NC(c2ccccc2)=C(c2ccccc2)C(c2ccc(C(=O)O)c([N+](=O)[O-])c2)N1]

A mixture of 4-formyl-2-nitrobenzoic acid (Intermediate 73) (120 mg, 0.615 mmol), 1,2-diphenylethanone (120 mg, 0.615 mmol), urea (110 mg, 1.845 mmol), hydrochloric acid (0.5 mL) in ethanol (2 mL) was heated at 92° C. for 41 hours. A standard aqueous/EtOAc workup was followed to give crude ethyl 2-nitro-4-(2-oxo-5,6-diphenyl-1,2,3,4-tetrahydropyrimidin-4-yl)benzoate (170 mg, yield 62.3%). This was taken up in water (3 mL) and ethanol (3 mL) and sodium hydroxide (30.6 mg, 0.766 mmol) was added at 0° C., and the mixture was stirred at 28° C. for 5 hours. The reaction mixture was partitioned between water (30 mL) and ethyl acetate (70 mL). The organic layer was discarded and the aqueous layer was adjusted to pH=3 with hydrochloric acid (2 mol/L). Then the resulting mixture was extracted with ethyl acetate (30 mL×3). The organic layers were washed with brine (50 mL), dried over sodium sulfate and evaporated. Purified by preparative HPLC to give Compound 140 (37.1 mg, yield 23.3%). HNMR (DMSO-$d_6$ 300 MHz): δ 11.38 (s, 1H), 8.82 (s, 1H), 7.84 (d, J=7.8 Hz, 2H), 7.75-7.69 (m, 2H), 7.24 (m, 5H), 7.04-7.01 (m, 3H), 6.83 (d, J=7.8 Hz, 2H), 5.45 (d, J=2.7 Hz, 1H); MS (ESI): m/z 416.0 [M+H]$^+$.

Example 141

Compound 141, 4-(3-ethoxy-4-hydroxy-5-nitrophenyl)-5-(3-ethylphenyl)-6-phenyl-3,4-dihydropyrimidin-2(1H)-one

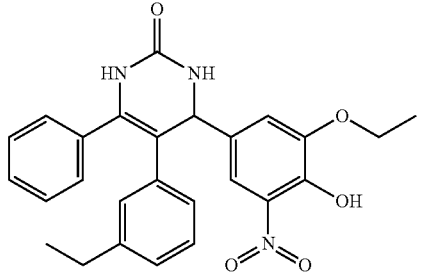

A mixture of 2-(3-ethylphenyl)-1-phenylethanone (Intermediate 74) (90 mg, 0.40 mmol), 3-ethoxy-4-hydroxy-5-nitrobenzaldehyde (84.5 mg, 0.40 mmol), urea (72 mg, 1.2 mmol), conc. HCl (0.2 mL) in ethanol (1 mL) was stirred at 115° C. for 6 h. Solvent was removed in vacuo and purification by prep-HPLC (0.1% TFA as additive) gave Compound 141 (46.3 mg, yield 25%). $^1$H NMR (DMSO 400 MHz): δ 10.29 (brs, 1H), 8.71 (s, 1H), 7.54 (s, 1H), 7.46 (s, 1H), 7.28-7.20 (m, 5H), 6.97-6.91 (m, 1H), 7.43 (d, J=7.6 Hz, 1H), 6.71-6.61 (m, 2H), 5.22 (d, J=2.8 Hz, 1H), 4.04 (q, J=6.8 Hz, 2H), 2.29 (q, J=7.6 Hz, 2H) 1.33 (t, J=6.8 Hz, 3H), 0.85 (t, J=7.6 Hz, 3H), MS (ESI): m/z 460.3 [M+H]$^+$.

Example 142

Compound 142, 3-ethoxy-2-hydroxy-5-(6-(1-methyl-1H-pyrazol-4-yl)-2-oxo-5-(thiophen-3-yl)-1,2,3,4-tetrahydropyrimidin-4-yl)benzoic acid

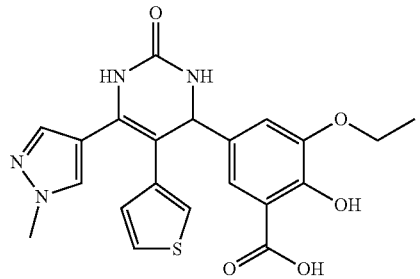 [SMILES: CCOc1cc(C2NC(=O)NC(c3cnn(C)c3)=C2c2ccsc2)cc(C(=O)O)c1O]

A mixture of 1-(1-methyl-1H-pyrazol-4-yl)-2-(thiophen-3-yl)ethanone (Intermediate 57) (250 mg, 1.2 mmol), 3-ethoxy-5-formyl-2-hydroxybenzoic acid (Intermediate 62) (237 mg, 1.2 mmol), urea (217.8 mg, 3.6 mmol) and conc. HCl (0.2 mL) in EtOH (10 mL) was refluxed overnight. The mixture was concentrated under reduced pressure to dryness and purified by prep-HPLC (0.1% TFA as additive) to give Compound 142 (120 mg, yield 23%). $^1$H NMR (DMSO-$d_6$ 400 MHz): δ 8.39 (s, 1H), 7.60 (s, 1H), 7.40-7.34 (m, 3H), 7.00-6.96 (m, 3H), 6.59 (dd, J=0.8 Hz, 4.8 Hz, 1H), 4.96 (d, J=2.8 Hz, 1H), 3.99-3.90 (m, 2H), 3.74 (s, 3H), 1.31 (t, J=6.8 Hz, 3H); MS (ESI): m/z 441.0 [M+1]$^+$;

Example 143

Compound 143, (S)-4-(3-ethoxy-4-hydroxy-5-nitrophenyl)-6-(pyridin-3-yl)-5-(thiophen-3-yl)-3,4-dihydropyrimidin-2(1H)-one

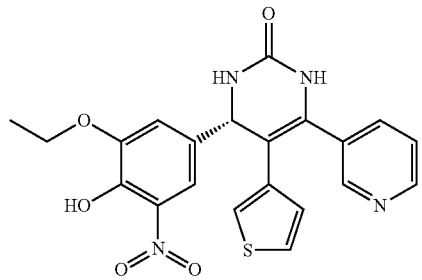

The two enantiomers of Compound 116 (see Example 116) were separated by chiral SFC separation (OD 250 mm*20 mm, 10 um) eluting with supercritical $CO_2$:MeOH=60:40 to give the front fraction as Compound 143 (188.5 mg, yield 21%). $^1$H NMR (DMSO 400 MHz): δ 10.30 (s, 1H), 8.91 (s, 1H), 8.52-8.50 (m, 1H), 8.40 (d, J=1.6 Hz, 1H), 7.70 (d, J=8.0 Hz, 1H), 7.62 (s, 1H), 7.48 (d, J=1.6 Hz, 1H), 7.42-7.38 (m, 1H), 7.25-7.15 (m, 2H), 6.91 (d, J=1.6 Hz, 1H), 6.31 (m, 1H), 5.22 (d, J=2.4 Hz, 1H), 4.10-4.00 (m, 2H), 1.33 (t, J=6.8 Hz, 3H); MS (ESI): m/z 438.9 [M$^+$+H].

Example 144

Compound 144, (R)-4-(3-ethoxy-4-hydroxy-5-nitrophenyl)-6-(pyridin-3-yl)-5-(thiophen-3-yl)-3,4-dihydropyrimidin-2(1H)-one

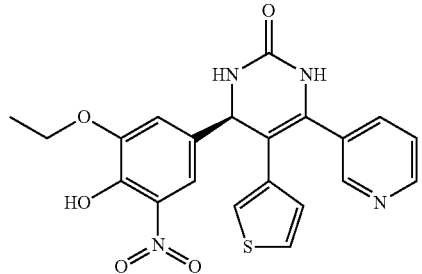 [SMILES: CCOc1cc([C@H]2NC(=O)NC(c3cccnc3)=C2c2ccsc2)cc([N+](=O)[O-])c1O]

The two enantiomers of Compound 116 (see Example 116) were separated by chiral SFC separation (OD 250 mm*20 mm, 10 um) eluting with supercritical $CO_2$:MeOH=60:40 to give the back fraction as Compound 144 (197.6 mg, yield 22%). $^1$H NMR (MeOD 400 MHz): δ 8.40-8.36 (m, 1H), 8.31 (s, 1H), 7.71 (d, J=8.0 Hz, 1H), 7.52 (d, J=2.0 Hz, 1H), 7.34-7.29 (m, 1H), 7.07-7.02 (m, 2H), 6.71 (d, J=2.0 Hz, 1H), 6.39 (dd, J=1.2 Hz, 1.2 Hz, 1H), 5.21 (s, 1H), 4.02-3.93 (m, 2H), 1.31 (t, J=6.8 Hz, 3H); MS (ESI): m/z 438.9 [M⁺+H].

Example 145

Compound 145, 2-chloro-4-(2-oxo-5,6-diphenyl-1,2,3,4-tetrahydropyrimidin-4-yl)benzoic acid

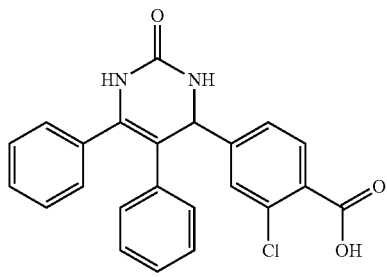 [SMILES: O=C1NC(c2ccccc2)=C(c2ccccc2)C(c2ccc(C(=O)O)c(Cl)c2)N1]

To a mixture of methyl 2-chloro-4-formylbenzoate (Intermediate 75) (210 mg, 1.1 mmol), 1,2-diphenylethanone (208 mg, 1.1 mmol), urea (191 mg, 3.2 mmol) and conc. HCl (0.5 mL) in ethanol (2 mL) was refluxed at 95° C. for 30 hours. A standard aqueous/EtOAc workup procedure was followed to give crude ethyl 2-chloro-4-(2-oxo-5,6-diphenyl-1,2,3,4-tetrahydropyrimidin-4-yl)benzoate (360 mg). This was taken up in water (2.5 mL) and ethanol (2.5 mL) and sodium hydroxide (67 mg, 1.7 mmol) was added at 30° C. The resulting mixture was stirred at 40° C. for 6 hours. HCl (2 N) was added until pH=3. A standard aqueous/EtOAc workup procedure was followed and crude was purified by prep-HPLC (0.1% TFA as additive) to give Compound 145 (57.3 mg, yield 17%). ¹H NMR (DMSO 400 MHz): δ 13.37 (brs, 1H), 8.76 (s, 1H), 7.78 (d, J=7.6 Hz, 1H), 7.63 (s, 1H), 7.43-7.36 (m, 2H), 7.26-7.19 (m, 5H), 7.05-6.98 (m, 3H), 6.81 (d, J=6.4 Hz, 2H), 5.28 (d, J=2.4 Hz, 1H), MS (ESI): m/z 404.9 [M+H]⁺.

Example 146

Compound 146, (S)-3-ethoxy-2-hydroxy-5-(6-(1-methyl-1H-pyrazol-4-yl)-2-oxo-5-(thiophen-3-yl)-1,2,3,4-tetrahydropyrimidin-4-yl)benzoic acid

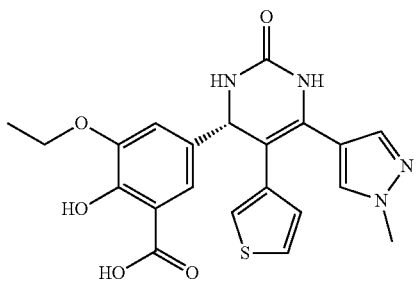 [SMILES: CCOc1cc([C@@H]2NC(=O)NC(c3cnn(C)c3)=C2c2ccsc2)cc(C(=O)O)c1O]

The two enantiomers of Compound 142 (see Example 142) were separated by chiral supercritical chromatography (SFC separation condition: Column: AS-SUM, 300*300 mm, 20 UM; Mobile Phase: 35% MeOH+DIEA, 40 ML/MIN; Detector Wavelength: 220 nm), the eluting solution for the first peak was collected and evaporated under reduced pressure to give one enantiomer as Compound 146 (30 mg, yield 25%). ¹H NMR (MeOH-d4, 300 MHz): δ 7.44 (d, J=2.0 Hz, 2H), 7.24-7.21 (m, 1H), 7.10 (s, 1H), 7.04 (s, 1H), 6.85 (s, 1H), 6.59 (d, J=5.1 Hz, 1H), 5.07 (s, 1H), 3.99-3.96 (m, 2H), 3.78 (s, 3H), 1.35 (t, J=6.9 Hz, 1H); MS (ESI): m/z 440.9 [M+1]⁺; [α]²⁰_D=0.118 (c=2.79 mg/mL, MeOH).

Example 147

Compound 147, (R)-3-ethoxy-2-hydroxy-5-(6-(1-methyl-1H-pyrazol-4-yl)-2-oxo-5-(thiophen-3-yl)-1,2,3,4-tetrahydropyrimidin-4-yl)benzoic acid

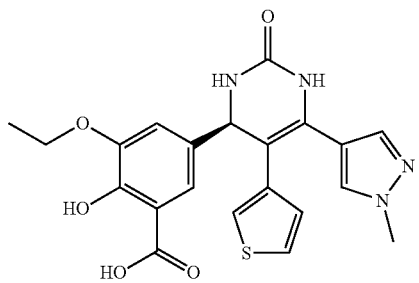 [SMILES: CCOc1cc([C@H]2NC(=O)NC(c3cnn(C)c3)=C2c2ccsc2)cc(C(=O)O)c1O]

The two enantiomers of Compound 142 (see Example 142) were separated by chiral supercritical chromatography (see Example 146 for conditions) and the eluting solution for the second peak was collected and evaporated under reduced pressure to give Compound 147 (27 mg, yield 23%). ¹H NMR (MeOD, 300 MHz TMS): δ 7.44 (s, 1H), 7.23 (s, 1H), 7.10 (s, 1H), 7.03 (s, 1H), 6.84 (s, 1H), 6.58 (d, J=3.9 Hz, 1H), 5.06 (s, 1H), 4.00 (t, J=3.0 Hz, 1H), 3.78 (s, 3H), 1.35 (t, J=7.2 Hz, 1H). MS (ESI): m/z 441.0 [M+1]⁺; [α]²⁰_D=−0.094 (c=3.65 mg/mL, MeOH).

Example 148

Compound 148, (S)-4-(3-ethoxy-4-hydroxy-5-nitrophenyl)-6-(1-methyl-1H-pyrazol-3-yl)-5-(thiophen-3-yl)-3,4-dihydropyrimidin-2(1H)-one

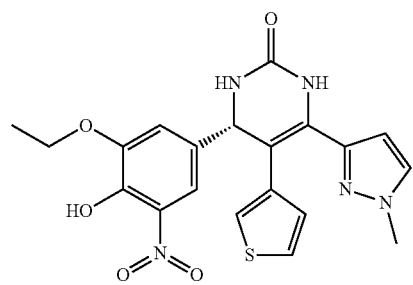 [SMILES: CCOc1cc([C@@H]2NC(=O)NC(c3ccn(C)n3)=C2c2ccsc2)cc([N+](=O)[O-])c1O]

The two enantiomers of Compound 119 (see Example 119) were separated by chiral supercritical chromatography (SFC separation condition: Column: AS-SUM, 300*300 mm, 20 UM; Mobile Phase: 35% MeOH+DIEA, 40 ML/MIN; Detector Wavelength: 220 nm); the eluting solution for the first peak was collected and evaporated under reduced pressure to give one enantiomer as Compound 148 (630 mg, yield 48%). ¹H NMR (DMSO-d6, 400 MHz): δ 10.29 (s, 1H), 7.71 (s, 1H), 7.64-7.60 (m, 2H), 7.41-7.38 (m, 2H), 7.11 (s, 2H), 6.64 (d, J=4.0 Hz, 1H), 5.52 (d, J=2.4 Hz, 1H), 5.14 (d, J=2.4 Hz, 1H), 4.07-3.99 (m, 2H); 3.84 (s, 3H), 1.33 (t, J=6.8 Hz, 3H); MS (ESI): m/z 442.1 [M+1]$^+$; [α]$^{20}_D$=0.160 (c=5.12 mg/mL, MeOH);

Example 149

Compound 149, (R)-4-(3-ethoxy-4-hydroxy-5-nitro-phenyl)-6-(1-methyl-1H-pyrazol-3-yl)-5-(thiophen-3-yl)-3,4-dihydropyrimidin-2(1H)-one

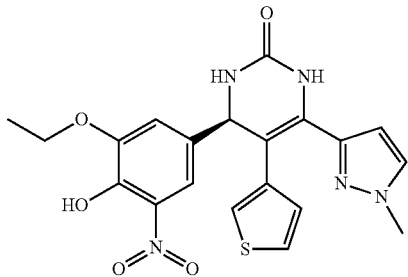 [SMILES: CCOc1cc([C@H]2NC(=O)NC(c3ccn(C)n3)=C2c2ccsc2)cc([N+](=O)[O-])c1O]

The two enantiomers of Compound 119 (see Example 119) were separated by chiral supercritical chromatography (see Example 148 for conditions); the eluting solution for the second peak was collected and evaporated under reduced pressure to give another enantiomer as Compound 149 (640 mg, yield 49%). $^1$H NMR (DMSO-d6, 400 MHz): δ 10.28 (s, 1H), 7.70 (s, 1H), 7.62-7.59 (m, 2H), 7.41-7.37 (m, 2H), 7.11-7.09 (m, 2H), 6.64 (dd, J=1.2 Hz, 5.2 Hz, 1H), 5.52 (d, J=2.4 Hz, 1H), 5.13 (d, J=2.8 Hz, 1H), 4.07-3.98 (m, 2H); 3.83 (s, 3H), 1.33 (t, J=6.8 Hz, 3H), MS (ESI): m/z 442.0 [M+1]$^+$; [α]$^{20}_D$=–0.159 (c=52.75 mg/mL, MeOH).

Example 150

Compound 150, 4-ethoxy-6-(2-oxo-5,6-diphenyl-1,2,3,4-tetrahydropyrimidin-4-yl)benzo[d]oxazol-2(3H)-one

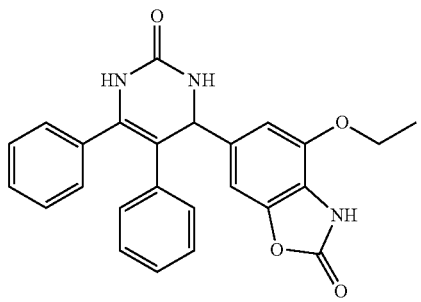 [SMILES: CCOc1cc(C2NC(=O)NC(c3ccccc3)=C2c2ccccc2)cc2oc(=O)[nH]c12]

To a solution of 4-ethoxy-2-oxo-2,3-dihydrobenzo[d]oxazole-6-carbaldehyde (Intermediate 76) (70 mg, 0.34 mmol), 1,2-diphenylethanone (70 mg, 0.36 mmol) and urea (82 mg, 1.4 mmol) in 5 mL of ethanol was added 0.2 ml con. HCl under N$_2$. The reaction mixture was refluxed overnight. The reaction mixture was purified by prep-HPLC (0.1% TFA as additive) and solvent removed to give Compound 150 as white solid (32 mg, yield 22%). $^1$H NMR (CD$_3$OD 400 MHz): 7.27 (m, 5H), 7.06-7.04 (m, 3H), 6.92-6.87 (m, 3H), 6.82 (s, 1H), 5.33 (s, 1H), 4.14-4.08 (m, 2H), 1.41 (t, J=6.8 Hz, 3H). MS (ESI): m/z 428.2 [M+1]$^+$.

Example 151

Compound 151, 3-fluoro-2-hydroxy-5-(2-oxo-5,6-diphenyl-1,2,3,4-tetrahydropyrimidin-4-yl)benzoic acid

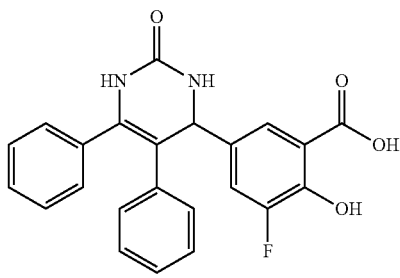 [SMILES: O=C1NC(c2ccccc2)=C(c2ccccc2)C(c2cc(F)c(O)c(C(=O)O)c2)N1]

Step 1: Synthesis of 4-(3-bromo-5-fluoro-4-hydroxyphenyl)-5,6-diphenyl-3,4-dihydropyrimidin-2(1H)-one To a mixture of 3-bromo-5-fluoro-4-hydroxybenzaldehyde (Intermediate 77) (600 mg, 2.7 mmol), 1,2-diphenylethanone (538 mg, 2.7 mmol), urea (493 mg, 8.2 mmol) and conc HCl (1 mL) in ethanol (4 mL) was heated at 95° C. for 50 hours. The mixture was evaporated under reduced pressure and was purified by silica gel column chromatography (petroleum ether/ethyl acetate=2:1) to give product (400 mg, yield 33%) as yellow solid. $^1$H NMR (DMSO 300 MHz): δ10.41 (brs, 1H), 8.66 (s, 1H), 7.45 (s, 1H), 7.24-6.95 (m, 10H), 6.75 (d, J=7.8 Hz, 2H), 5.07 (s, 1H).

Step 2: Synthesis of methyl 3-fluoro-2-hydroxy-5-(2-oxo-5,6-diphenyl-1,2,3,4-tetrahydropyrimidin-4-yl)benzoate To a mixture of the above from Step 1 (200 mg, 0.50 mmol) in methanol (10 mL) was added Pd(dppf)Cl$_2$ (80 mg) at 27° C. under carbon monoxide atmosphere (40 psi) for 25 hours. After being cooled, the mixture was filtered and the filtrate was evaporated under reduced pressure to give product (200 mg, yield 100%).

Step 3: Synthesis of 3-fluoro-2-hydroxy-5-(2-oxo-5,6-diphenyl-1,2,3,4-tetrahydropyrimidin-4-yl)benzoic acid To a mixture of the above from Step 2 (200 mg, 0.50 mmol) in water (3.0 mL) and ethanol (3.0 mL) was added lithium hydroxide (34.5 mg, 1.4 mmol) at 30° C. The resulting mixture was stirred at 40° C. for 14 hours. The reaction mixture was acidified with 2N of HCl to pH=3. Followed a standard aqueous/EtOAc workup procedure and then purified by prep-HPLC (0.1% TFA as additive) to give Compound 151 (37.1 mg, yield 19%). $^1$H NMR (DMSO 300 MHz): δ8.69 (s, 1H), 7.61 (s, 1H), 7.49 (s, 1H), 7.36 (d, J=11.7 Hz, 1H), 7.22-7.16

(m, 5H), 7.01-6.95 (m, 3H), 6.78-6.72 (m, 2H), 5.12 (s 1H), MS (ESI): m/z 405.0 [M+H]+.

Example 152

Compound 152, 2-fluoro-4-(2-oxo-5,6-diphenyl-1,2,3,4-tetrahydropyrimidin-4-yl)benzoic acid

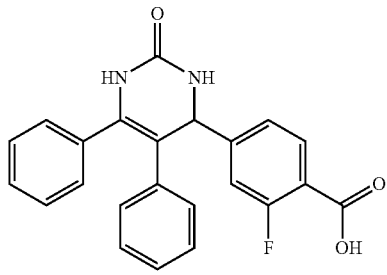 [SMILES: O=C1NC(c2ccccc2)=C(c2ccccc2)C(c2ccc(C(=O)O)c(F)c2)N1]

Step 1: Synthesis of 4-(4-bromo-3-fluorophenyl)-5,6-diphenyl-3,4-dihydropyrimidin-2(1H)-one To a mixture of 4-bromo-3-fluorobenzaldehyde (100 mg, 0.5 mmol), 1,2-diphenylethanone (118 mg, 0.6 mmol) and urea (90 mg, 1.5 mmol) in ethanol (3 mL) was added conc. HCL (0.1 mL). The mixture was refluxed under N$_2$ atmosphere for 6 hrs. Solvent was removed; purified by silica gel column chromatography (PE:EtOAc=10:1 to PE:EtOAc=1:1) to give product (130 mg, yield 62%). $^1$H NMR (DMSO-d$_6$ 400 MHz): δ 8.74 (s, 1H), 7.74-7.68 (m, 1H), 7.54 (s, 1H), 7.26-7.15 (m, 7H), 7.03-6.95 (m, 3H), 6.81-6.79 (m, 2H), 5.24 (d, J=2.8 Hz, 1H).

Step 2: Synthesis of methyl 2-fluoro-4-(2-oxo-5,6-diphenyl-1,2,3,4-tetrahydropyrimidin-4-yl)benzoate To a solution of the above compound from Step 1 (100 mg, 0.24 mmol) and triethylamine (0.2 mL) in methanol (20 mL) was added dppf (65 mg, 0.12 mmol) and Pd(OAc)$_2$ (53 mg, 0.24 mmol). The reaction was stirred under CO atmosphere (35 psi) at 75° C. overnight. The reaction mixture was filtered, the filtrate was concentrated, and then purified by silica gel column chromatography (PE:EtOAc=10:1 to PE:EtOAc=1:1) to give product (90 mg, 95%).

Step 3: Synthesis of 2-fluoro-4-(2-oxo-5,6-diphenyl-1,2,3,4-tetrahydropyrimidin-4-yl)benzoic acid Followed procedure described in Step 3 of Example 151, where reaction was run at 10~15° C. for 1 hr. Purified by silica gel column chromatography (PE:EtOAc=20:1 to PE:EtOAc=5:1) and prep-HPLC (0.1% TFA as additive) to give compound 152 (20 mg, yield 23%). $^1$H NMR (DMSO-d$_6$ 400 MHz): δ 13.13 (s, 1H), 8.66 (s, 1H), 7.79-7.75 (m, 1H), 7.54 (s, 1H), 7.20-7.05 (m, 7H), 6.96-6.90 (m, 3H), 6.73-6.71 (m, 2H), 5.20 (d, J=2.8 Hz, 1H). MS (ESI): m/z 431.9[M+1]+.

Example 153

Compound 153, 2-ethoxy-6-nitro-4-(2-oxo-5,6-diphenyl-1,2,3,4-tetrahydropyrimidin-4-yl)benzoic acid

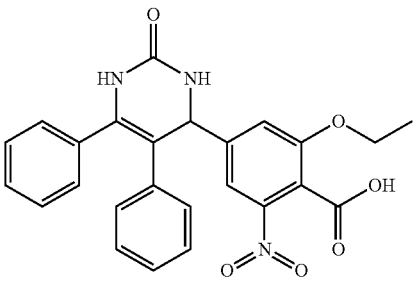 [SMILES: CCOc1cc(C2NC(=O)NC(c3ccccc3)=C2c2ccccc2)cc([N+](=O)[O-])c1C(=O)O]

To a mixture of methyl 2-ethoxy-4-formyl-6-nitrobenzoate (Intermediate 78) (100 mg, 0.4 mmol), 1,2-diphenylethanone (116 mg, 0.6 mmol) and urea (72 mg, 1.2 mmol) in ethanol (3 mL) was added conc. HCl (0.1 mL). Refluxed under N$_2$ atmosphere overnight. Concentrated under reduced pressure, then purified by silica gel column chromatography (PE:EtOAc=10:1 to PE:EtOAc=1:1) to give methyl 2-ethoxy-6-nitro-4-(2-oxo-5,6-diphenyl-1,2,3,4-tetrahydropyrimidin-4-yl)benzoate (110 mg, yield 58%). This was taken up in ethanol (5 mL) and aq. NaOH (0.5 M, 2 mL, 1 mmol) was added. The mixture was stirred under N$_2$ atmosphere at 60° C. for 5 hrs. The reaction mixture was acidified with conc. HCl (3 mL), and then extracted with a solution (DCM:i-propanol=10:1, 30 mL×2). The combined organic layers were dried over anhydrous Na$_2$SO$_4$, filtered and concentrated under reduced pressure. The residue was purified by prep-HPLC (0.1% TFA as additive) to give Compound 153 (58 mg, yield 55%). $^1$H NMR (DMSO-d$_6$ 400 MHz): δ 13.60 (s, 1H), 8.83 (s, 1H), 7.74 (s, 1H), 7.69 (s, 1H), 7.39 (s, 1H), 7.28-7.21 (m, 5H), 7.07-7.00 (m, 3H), 6.85 (d, J=6.8 Hz, 2H), 5.42 (d, J=2.4 Hz, 1H), 4.12-4.00 (m, 2H), 1.26 (t, J=7.0 Hz, 3H). MS (ESI): m/z 460.1[M+1]+.

Example 154

Compound 154, 4-(4-hydroxy-3-nitro-5-(trifluoromethyl)phenyl)-5,6-diphenyl-3,4-dihydropyrimidin-2(1H)-one

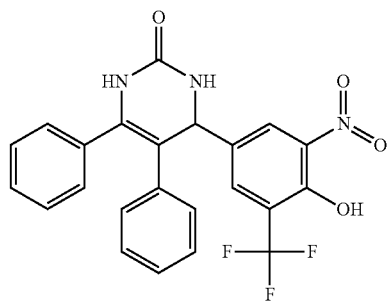 [SMILES: O=C1NC(c2ccccc2)=C(c2ccccc2)C(c2cc([N+](=O)[O-])c(O)c(C(F)(F)F)c2)N1]

To a mixture of 4-hydroxy-3-nitro-5-(trifluoromethyl)benzaldehyde (Intermediate 79) (100 mg, 0.40 mmol), 1,2-diphenylethanone (83 mg, 0.40 mmol), urea (77 mg, 1.30 mmol)

and conc. HCl (0.05 mL) in ethanol (1 mL) was heated at 90° C. for 37 hours. Solvent was removed under reduced pressure and the residue was purified by prep-HPLC (0.1% TFA as additive) to give Compound 154 (31.2 mg, yield 30%) as yellow solid. $^1$H NMR (DMSO 300 MHz): δ 8.81 (s, 1H), 8.17 (s, 1H), 7.87 (s, 1H), 7.62 (s, 1H), 7.25-7.17 (m, 5H), 7.03-6.96 (m, 3H), 6.78 (d, J=7.2 Hz, 2H), 5.34 (s, 1H), MS (ESI): m/z 456.0 [M+H]$^+$.

Example 155

Compound 155, 4-(4-hydroxy-3-(2-methoxyethoxy)-5-nitrophenyl)-5,6-diphenyl-3,4-dihydropyrimidin-2(1H)-one

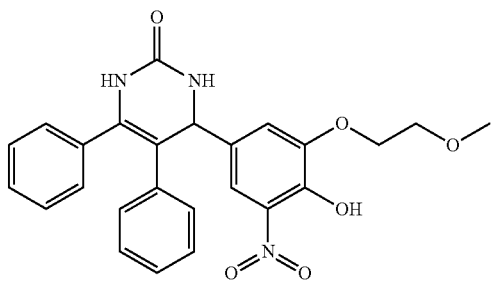 [SMILES: COCCOc1cc(C2NC(=O)NC(c3ccccc3)=C2c2ccccc2)cc([N+](=O)[O-])c1O]

To a solution of 4-hydroxy-3-(2-methoxyethoxy)-5-nitrobenzaldehyde (Intermediate 80) (200 mg, 0.83 mmol), 1,2-diphenylethanone (196 mg, 1.0 mmol) and urea (150 mg, 2.5 mmol) in ethanol (3 mL) was added conc.HCl (0.2 mL), then the resulting mixture was refluxed for 2 days. The mixture was concentrated under reduced pressure and purified by prep-HPLC (0.1% TFA as additive) to give Compound 155 (162 mg, yield 42%) as yellow solid. $^1$H NMR (MeOD 400 MHz) δ 7.62 (d, J=1.6 Hz, 1H), 7.27-7.24 (m, 6H), 7.07-7.03 (m, 3H), 6.91-6.86 (m, 2H), 5.37 (s, 1H), 4.17-4.10 (m, 2H), 3.76 (t, J=4.4 Hz, 2H), 3.43 (s, 3H). MS (ESI): m/z 462.1 [M+1]$^+$.

Example 156

Compound 156, 4-(4-hydroxy-3-nitro-5-propylphenyl)-5,6-diphenyl-3,4-dihydropyrimidin-2(1H)-one

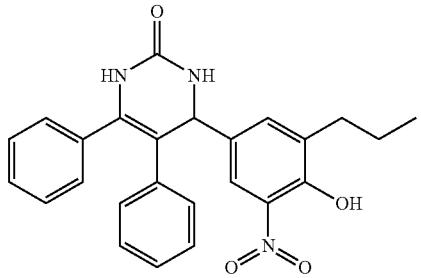

To a solution of 4-(tert-butyldimethylsilyloxy)-3-nitro-5-propylbenzaldehyde (Intermediate 81) (100 mg, 0.31 mmol), 1,2-diphenylethanone (78 mg, 0.40 mmol) and urea (60 mg, 1.0 mmol) in ethanol (5 mL) was added conc. HCl (0.2 mL) and the reaction mixture was refluxed under N$_2$ atmosphere overnight. Reaction was cooled and then purified by prep-HPLC (0.1% TFA as additive). The solution was concentrated under reduced pressure to give Compound 156 as a yellow solid (21 mg, yield 16%). $^1$H NMR (CD$_3$OD 400 MHz): δ 7.95 (d, J=2.0 Hz, 1H), 7.52 (s, 1H), 7.26 (m, 5H), 7.06-7.03 (m, 3H), 6.89-6.86 (m, 2H), 5.39 (s, 1H), 2.70 (t, J=7.6 Hz, 2H), 1.66-1.59 (m, 2H), 0.93 (t, J=7.2 Hz, 3H). MS (ESI): m/z 430.2 [M+1]$^+$.

Example 157

Compound 157, 4-(2-oxo-5,6-diphenyl-1,2,3,4-tetrahydropyrimidin-4-yl)-2-(trifluoromethyl)benzoic acid

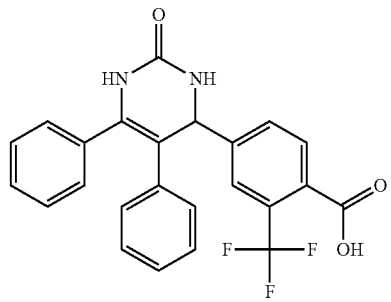 [SMILES: O=C1NC(c2ccccc2)=C(c2ccccc2)C(c2ccc(C(=O)O)c(C(F)(F)F)c2)N1]

To a solution of methyl 4-formyl-2-(trifluoromethyl)benzoate (Intermediate 82) (180 mg, 0.80 mmol), 1,2-diphenylethanone (222 mg, 0.80 mmol) and urea (145 mg, 2.4 mmol) in ethanol (3 mL) was added conc. HCl (0.2 mL), then the resulting mixture was refluxed for 2 days. The mixture was concentrated in vacuo to give methyl 4-(2-oxo-5,6-diphenyl-1,2,3,4-tetrahydropyrimidin-4-yl)-2-(trifluoromethyl)benzoate, which was used crude. This was taken up in MeOH (3 mL) and 2 N aq. NaOH (3 mL) was added; then the resulting mixture was stirred at 40° C. for 3 hours. The mixture was acidified with aqueous HCl till pH=5 and then followed a standard aqueous/EtOAc workup. Purified by prep-HPLC (0.1% TFA as additive) to give Compound 157 (34 mg, two steps yield 10%) as white solid. $^1$H NMR (MeOD 400 MHz) δ 7.82 (d, J=8.0 Hz, 1H), 7.72-7.67 (m, 2H), 7.36-7.20 (m, 5H), 7.10-7.05 (m, 3H), 6.88-6.85 (m, 2H), 5.30 (s, 1H). MS (ESI): m/z 439.2 [M+1]$^+$.

Example 158

Compound 158, 2-fluoro-6-hydroxy-4-(2-oxo-5,6-diphenyl-1,2,3,4-tetrahydropyrimidin-4-yl)benzoic acid

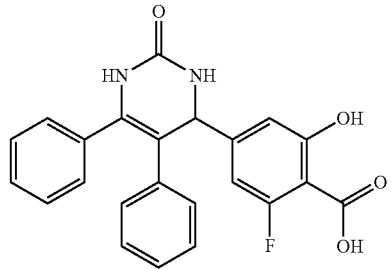

To a solution of methyl 2-fluoro-4-formyl-6-hydroxybenzoate (Intermediate 83) (150 mg, 0.76 mmol), 1,2-diphenylethanone (150 mg, 0.76 mmol) and urea (144 mg, 2.4 mmol) in ethanol (5 mL) was added conc. HCl (0.2 mL) and the reaction mixture was refluxed under N$_2$ overnight. Removed solvent in vacuo and the residue (320 mg) was used without further purification. A mixture of this intermediate compound (320 mg) and aqueous NaOH (2 M, 10 mL) in MeOH (10 mL) was stirred at 40° C. for 3 hours. The resulting mixture was cooled and acidified with aqueous HCl (2 M, 12 mL) and a standard aqueous/EtOAc workup was followed. Purification by prep-HPLC (0.1% TFA as additive) gave Compound 158 as a yellow solid (41 mg, two step yield 13%). $^1$H NMR (CD$_3$OD 400 MHz): δ 7.30-7.20 (m, 5H), 7.10-7.05 (m, 3H), 6.91-6.88 (m, 2H), 6.75 (s, 1H), 6.65 (d, J=11.6 Hz, 1H), 5.29 (s, 1H). MS (ESI): m/z 405.0 [M+1]$^+$.

Example 159

Compound 159, 2-hydroxy-4-(6-(1-methyl-1H-pyrazol-4-yl)-2-oxo-5-(thiophen-3-yl)-1,2,3,4-tetrahydropyrimidin-4-yl)benzoic acid

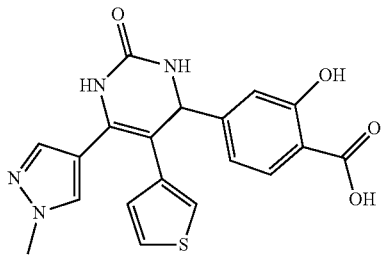 [SMILES: Cn1cc(C2=C(c3ccsc3)C(c3ccc(C(=O)O)c(O)c3)NC(=O)N2)cn1]

A mixture of 1-(1-methyl-1H-pyrazol-4-yl)-2-(thiophen-3-yl) ethanone (Intermediate 57) (200 mg, 0.97 mmol), methyl 4-formyl-2-hydroxybenzoate (Intermediate 84) (175 mg, 0.97 mmol), urea (180 mg, 3.0 mmol) and conc. HCl (0.2 mL) in EtOH (5 mL) was refluxed under N$_2$ overnight. Solvent was removed in vacuo and the residue was taken up in a mixture of MeOH (10 mL) and aq. NaOH (2 M, 10 mL) and was stirred at 40° C. under N$_2$ atmosphere for 5 hours. The resulting mixture was cooled to room temperature, and then acidified with aq. HCl (2 M, 12 mL) to pH=5. Followed a standard aqueous/EtOAc workup and purified by prep-HPLC (0.1% TFA as additive) to give Compound 159 (140 mg, two steps yield 36%). $^1$H NMR (DMSO-d6, 400 MHz): δ 11.09 (brs, 1H), 8.29 (s, 1H), 7.59 (d, J=8.4 Hz, 1H), 7.45 (s, 1H), 7.37 (s, 1H), 7.22-7.20 (m, 1H), 6.88-6.83 (m, 2H), 6.72-6.69 (m, 1H), 6.66 (s, 1H); 6.43 (d, J=4.8 Hz, 1H), 4.87 (s, 1H), 3.59 (s, 3H); MS (ESI): m/z 397.3 [M+1]$^+$.

Example 160

Compound 160, 2-hydroxy-4-(2-oxo-5-phenyl-6-(pyridin-3-yl)-1,2,3,4-tetrahydropyrimidin-4-yl)benzoic acid

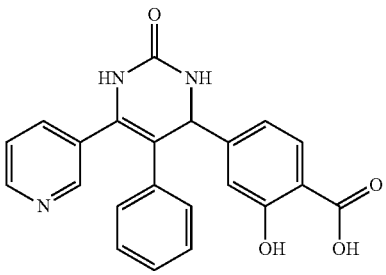 [SMILES: O=C1NC(c2cccnc2)=C(c2ccccc2)C(c2ccc(C(=O)O)c(O)c2)N1]

A mixture of 2-phenyl-1-(pyridin-3-yl)ethanone (Intermediate 31) (220 mg, 1.1 mmol), methyl 4-formyl-2-hydroxybenzoate (Intermediate 84) (200 mg, 1.1 mmol), urea (198 mg, 3.3 mmol) and conc. HCl (0.2 mL) in EtOH (5 mL) was refluxed overnight. Solvent was removed in vacuo and the residue was taken up in a mixture of MeOH (10 mL) and aq. NaOH (2 M, 10 mL) and was stirred at 40° C. for 5 hours. The resulting mixture was cooled to room temperature, and then acidified with aq. HCl (2 M, 12 mL) to pH=5. Followed a standard aqueous/EtOAc workup and purified by prep-HPLC (0.1% TFA as additive) to give Compound 160 (50 mg, two steps yield 12%). $^1$H NMR (DMSO-d6, 400 MHz): δ 8.94 (s, 1H), 8.48 (d, J=3.6 Hz, 1H), 8.40 (s, 1H), 7.76 (m, 2H), 7.65 (s, 1H), 7.42-7.38 (m, 1H), 7.06-7.00 (m, 3H), 6.93 (d, J=8.0 Hz, 1H), 6.90-6.84 (m, 3H), 5.25 (s, 1H). MS (ESI): m/z 388.2 [M+1]$^+$.

Example 161

Compound 161, 2-ethoxy-6-hydroxy-4-(2-oxo-5,6-diphenyl-1,2,3,4-tetrahydropyrimidin-4-yl)benzoic acid

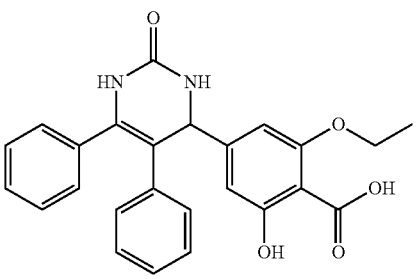 [SMILES: CCOc1cc(C2NC(=O)NC(c3ccccc3)=C2c2ccccc2)cc(O)c1C(=O)O]

A mixture of methyl 2-ethoxy-4-formyl-6-hydroxybenzoate (Intermediate 85) (150 mg, 0.67 mmol), 1,2-diphenylethanone (137 mg, 0.70 mmol), urea (120 mg, 2.0 mmol) and conc. HCl (0.5 mL) in EtOH (5 mL) was refluxed under N$_2$ overnight. The mixture was concentrated under reduced pressure. The residue was taken up in MeOH (10 mL) and aq. NaOH (2 M, 10 mL) and was stirred at 40° C. under N$_2$ for 5 hours. The resulting mixture was cooled to room temperature, and then acidified with aqueous HCl (2 M, 12 mL), followed by a standard aqueous/EtOAc workup and purification by prep-HPLC (0.1% TFA as additive) to give Compound 161 (38 mg, 2-step yield 13%). $^1$H NMR (CD$_3$OD 400 MHz): δ 7.25-7.20 (m, 5H), 7.08-7.00 (m, 3H), 6.89-6.84 (m, 2H), 6.62 (d, J=1.6 Hz, 1H), 6.47 (d, J=1.6 Hz, 1H), 5.24 (s, 1H), 4.17-4.04 (m, 2H), 1.37 (t, J=7.2 Hz, 3H). MS (ESI): m/z 431.5 [M+1]$^+$.

Example 162

Compound 162, 4-(4-(2H-tetrazol-5-yl)phenyl)-5-phenyl-6-(pyridin-3-yl)-3,4-dihydropyrimidin-2 (1H)-one

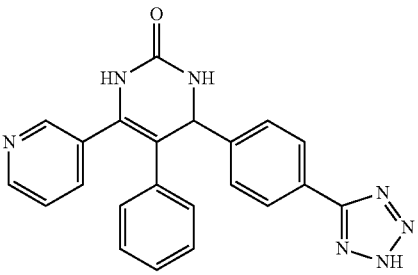 [SMILES: O=C1NC(c2cccnc2)=C(c2ccccc2)C(c2ccc(-c3nn[nH]n3)cc2)N1]

A mixture of 4-(2H-tetrazol-5-yl)benzaldehyde (106 mg), 2-phenyl-1-(pyridin-3-yl)ethanone (Intermediate 31) (100 mg, 0.51 mmol), urea (120 mg, 2.0 mmol) and conc. HCl (0.2 mL) in EtOH (5 mL) was refluxed under N$_2$ overnight. The mixture was concentrated under reduced pressure and purified by prep-HPLC (0.1% TFA as additive) to give Compound 162 (50 mg, 2-step yield 25%). ¹H NMR (DMSO-d₆ 400 MHz): δ 8.97 (s, 1H), 8.52 (d, J=4.4 Hz, 1H), 8.89 (s, 1H), 8.05-7.97 (m, 2H), 7.85 (d, J=8.0 Hz, 1H), 7.69 (s, 1H), 7.57 (d, J=8.0 Hz, 2H), 7.49-7.44 (m, 1H), 7.07-7.00 (m, 3H), 6.89-6.85 (m, 2H), 5.38 (s, 1H). MS (ESI): m/z 396.4 [M+1]⁺

Example 163

Compound 163, 2-chloro-6-hydroxy-4-(2-oxo-5,6-diphenyl-1,2,3,4-tetrahydropyrimidin-4-yl)benzoic acid

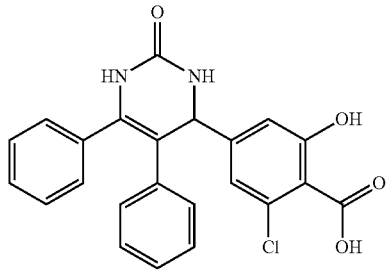 [SMILES: O=C1NC(c2ccccc2)=C(c2ccccc2)C(c2cc(O)c(C(=O)O)c(Cl)c2)N1]

To a solution of methyl 2-chloro-4-formyl-6-hydroxybenzoate (Intermediate 86) (150 mg, 0.70 mmol), 1,2-diphenylethanone (165 mg, 0.84 mmol) and urea (126 mg, 2.1 mmol) in ethanol (5 mL) was added conc. HCl (0.2 mL) and mixture was refluxed under N₂ overnight. The mixture was concentrated under reduced pressure. The residue was taken up in aqueous NaOH (2 M, 5 mL) and MeOH (5 mL) and was stirred at 50° C. under N₂ atmosphere for 6 hours. The resulting mixture was cooled to room temperature and acidified with aqueous HCl (2 M, 6 mL), followed by a standard aqueous/EtOAc workup and purification by prep-HPLC (0.1% TFA as additive) to give Compound 163 (75 mg, 2-step yield 26%). ¹H NMR (CD₃OD 400 MHz): δ 7.30-7.25 (m, 5H), 7.15-7.05 (m, 3H), 6.95-6.87 (m, 4H), 5.26 (s, 1H). MS (ESI): m/z 421.4 [M+1]⁺.

Example 164

Compound 164, 4-(4-(2H-tetrazol-5-yl)phenyl)-5,6-diphenyl-3,4-dihydropyrimidin-2(1H)-one

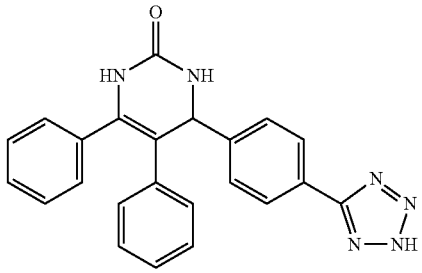 [SMILES: O=C1NC(c2ccccc2)=C(c2ccccc2)C(c2ccc(-c3nn[nH]n3)cc2)N1]

A mixture of 1,2-diphenylethanone (150 mg, 0.76 mmol), 4-(2H-tetrazol-5-yl)benzaldehyde (400 mg), urea (230 mg, 3.8 mmol) and conc. HCl (0.5 mL) in EtOH (5 mL) was refluxed under N₂ overnight. Solvent was removed in vacuo and purified by prep-HPLC (0.1% TFA as additive) to give Compound 164 (45 mg, yield 15%) as off-white solid. ¹H NMR DMSO-d₆ 400 MHz): δ 8.75-8.68 (m, 1H), 8.00 (d, J=8.0 Hz, 2H), 7.65-7.60 (m, 1H), 7.55 (d, J=8.0 Hz, 2H), 7.28-7.16 (m, 5H), 7.06-6.96 (m, 3H), 6.84-6.78 (m, 2H), 5.28 (s, 1H). MS (ESI): m/z 395.5 [M+1]⁺.

Example 165

Compound 165, 2-hydroxy-6-methoxy-4-(2-oxo-5,6-diphenyl-1,2,3,4-tetrahydropyrimidin-4-yl)benzoic acid

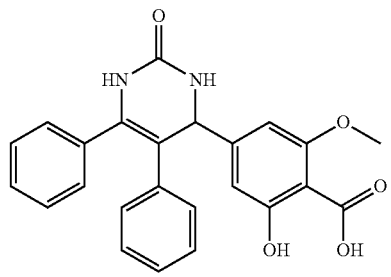 [SMILES: COc1cc(C2NC(=O)NC(c3ccccc3)=C2c2ccccc2)cc(O)c1C(=O)O]

A mixture of methyl 4-formyl-2-hydroxy-6-methoxybenzoate (Intermediate 87) (150 mg, 0.76 mmol), 1,2-diphenylethanone (160 mg, 0.76 mmol), urea (150 mg, 2.5 mmol) and conc. HCl (0.5 mL) in EtOH (5 mL) was refluxed under N₂ overnight. The mixture was concentrated in vacuo. The residue was taken up in MeOH (10 mL) and aq. NaOH (2 M, 10 mL) and was stirred at 50° C. under N₂ for 5 hours. The resulting mixture was cooled, and then acidified with aqueous HCl (2 M, 12 mL) to pH=3 followed by a standard aqueous/EtOAc workup and purification by prep-HPLC (0.1% TFA as additive) to give Compound 165 (31 mg, 2-step yield 10%). ¹H NMR (CD₃OD 400 MHz): δ 7.30-7.20 (m, 5H), 7.12-7.06 (m, 3H), 6.94-6.88 (m, 2H), 6.67 (d, J=1.6 Hz, 1H), 6.50 (d, J=1.6 Hz, 1H), 5.29 (s, 1H), 3.85 (s, 3H). MS (ESI): m/z 417.4 [M+1]⁺.

Example 166

Compound 166, 4-(4-(2H-tetrazol-5-yl)phenyl)-6-(pyridin-3-yl)-5-(thiophen-3-yl)-3,4-dihydropyrimidin-2(1H)-one

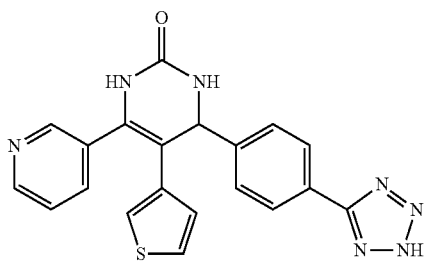 [SMILES: O=C1NC(c2cccnc2)=C(c2ccsc2)C(c2ccc(-c3nn[nH]n3)cc2)N1]

A mixture of 1-(pyridin-3-yl)-2-(thiophen-3-yl)ethanone (Intermediate 56) (80 mg, 0.39 mmol), 4-(2H-tetrazol-5-yl)benzaldehyde (300 mg), urea (120 mg, 2.0 mmol) and conc. HCl (0.5 mL) in EtOH (5 mL) was refluxed under N₂ overnight. The mixture was concentrated under reduced pressure and purified by prep-HPLC (0.1% TFA as additive) to give Compound 166 (56 mg, yield 35%) as yellow solid. ¹H NMR (CD$_3$OD 400 MHz): δ 8.71-8.61 (m, 2H), 8.30 (d, J=8.0 Hz, 1H), 8.04 (d, J=8.0 Hz, 2H), 7.85-7.78 (m, 1H), 7.65 (d, J=8.0 Hz, 2H), 7.22 (dd, J=2.8 Hz, J=4.8 Hz, 1H), 6.89 (dd, J=1.6 Hz, J=3.2 Hz, 1H), 6.56 (dd, J=1.2 Hz, J=5.2 Hz, 1H), 5.50 (s, 1H). MS (ESI): m/z 402.3 [M+1]$^+$.

Example 167

Compound 167, 2-hydroxy-4-(6-(1-methyl-1H-pyrazol-4-yl)-2-oxo-5-phenyl-1,2,3,4-tetrahydropyrimidin-4-yl)benzoic acid

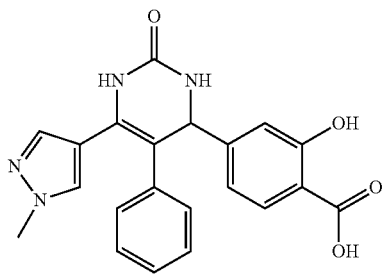 [SMILES: Cn1cc(C2=C(c3ccccc3)C(c3ccc(C(=O)O)c(O)c3)NC(=O)N2)cn1]

A mixture of 1-(1-methyl-1H-pyrazol-4-yl)-2-phenylethanone (Intermediate 88) (150 mg, 0.75 mmol), methyl 4-formyl-2-hydroxybenzoate (Intermediate 84) (135 mg, 0.75 mmol), urea (138 mg, 2.3 mmol) and conc. HCl (0.5 mL) in EtOH (5 mL) was refluxed under N$_2$ atmosphere overnight. The mixture was concentrated under reduced pressure. The residue was taken up in MeOH (10 mL) and aq. NaOH (2 M, 10 mL) and was stirred at 60° C. under N$_2$ overnight. The mixture was cooled, and then acidified with aqueous HCl (2 M, 12 mL) to pH=3 followed by a standard aqueous/EtOAc workup and purification by prep-HPLC (0.1% TFA as additive) to give Compound 167 (58 mg, 2-step yield 20%) as off-white solid. $^1$H NMR (CD$_3$OD 400 MHz): δ 7.81 (d, J=8.0 Hz, 1H), 7.38 (s, 1H), 7.25-7.20 (m, 3H), 6.88-6.78 (m, 3H), 6.84 (d, J=8.0 Hz, 1H), 6.82 (s, 1H), 5.17 (s, 1H), 3.77 (s, 3H). MS (ESI): m/z 390.7 [M+1]$^+$.

Example 168

Compound 168, (R)-2-hydroxy-4-(6-(1-methyl-1H-pyrazol-4-yl)-2-oxo-5-(thiophen-3-yl)-1,2,3,4-tetrahydropyrimidin-4-yl)benzoic acid

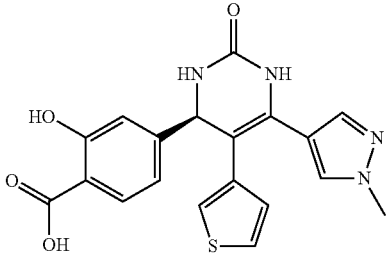 [SMILES: Cn1cc(C2=C(c3ccsc3)[C@@H](c3ccc(C(=O)O)c(O)c3)NC(=O)N2)cn1]

The two enantiomers of Compound 159 (see Example 159) were separated by chiral supercritical chromatography (SFC separation condition: Column: AS-SUM, 300*300 mm, 20 UM; Mobile Phase: 35% MeOH+DIEA, 40 ML/MIN; Detector Wavelength: 220 nm), the eluting solution for the first peak was collected and evaporated in vacuo to give one enantiomer as Compound 168 (40 mg, yield 40%) as yellow solid. $^1$H NMR (DMSO-d6, 400 MHz): δ 8.49 (s, 1H), 7.78 (d, J=8.0 Hz, 1H), 7.66 (s, 1H), 7.56 (s, 1H), 7.43-7.40 (m, 1H), 7.11 (s, 1H), 7.05 (d, J=1.6 Hz, 1H), 6.87 (d, J=8.0 Hz, 1H), 6.84 (s, 1H), 6.64 (d, J=4.8 Hz, 1H); 5.09-5.00 (m, 1H), 3.83 (s, 3H). MS (ESI): m/z 396.9 [M+1]$^+$;

Example 169

Compound 169, (S)-2-hydroxy-4-(6-(1-methyl-1H-pyrazol-4-yl)-2-oxo-5-(thiophen-3-yl)-1,2,3,4-tetrahydropyrimidin-4-yl)benzoic acid

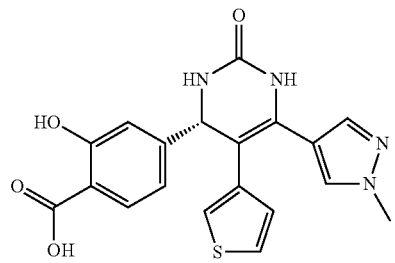 [SMILES: Cn1cc(C2=C(c3ccsc3)[C@H](c3ccc(C(=O)O)c(O)c3)NC(=O)N2)cn1]

The two enantiomers of Compound 159 (see Example 159) were separated by chiral supercritical chromatography (see example 168 for column conditions). The eluting solution for the second peak was collected and evaporated under reduced pressure to give another enantiomer as Compound 169 (43 mg, yield 43%) as yellow solid. $^1$H NMR (DMSO-d6, 400 MHz): δ 8.50 (s, 1H), 7.78 (d, J=8.0 Hz, 1H), 7.66 (s, 1H), 7.57 (s, 1H), 7.44-7.41 (m, 1H), 7.09 (s, 1H), 7.05 (d, J=2.0 Hz, 1H), 6.87 (d, J=8.0 Hz, 1H), 6.84 (s, 1H), 6.64 (d, J=5.2 Hz, 1H); 5.08-5.00 (m, 1H), 3.81 (s, 3H). MS (ESI): m/z 396.9 [M+1]$^+$.

Example 170

Compound 170, 4-(3-(2-(dimethylamino)ethoxy)-4-hydroxy-5-nitrophenyl)-5,6-diphenyl-3,4-dihydropyrimidin-2(1H)-one

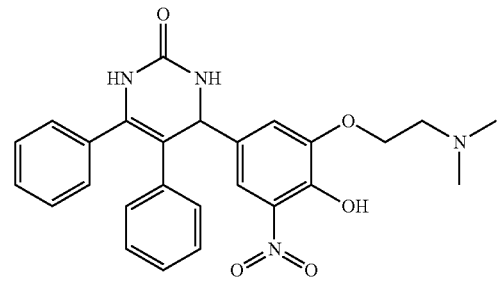 [SMILES: CN(C)CCOc1cc(C2NC(=O)NC(c3ccccc3)=C2c2ccccc2)cc([N+](=O)[O-])c1O]

To a solution of 3-(2-(dimethylamino)ethoxy)-4-hydroxy-5-nitrobenzaldehyde (Intermediate 89) (100 mg, 0.39 mmol), 1,2-diphenyl-ethanone (77 mg, 0.39 mmol) and urea (70 mg, 1.2 mmol) in ethanol (3 mL) was added conc.HCl (0.2 mL); the resulting mixture was refluxed overnight. The mixture was concentrated and purified by prep-HPLC (0.1% TFA as additive) to give Compound 170 (45 mg, yield 22%) as yellow solid. $^1$H NMR (MeOD 400 MHz) δ 7.81 (d, J=2.0 Hz, 1H), 7.39 (d, J=2.0 Hz, 1H), 7.38-7.25 (m, 5H), 7.16-7.04 (m, 3H), 6.98-6.88 (m, 2H), 5.47 (s, 1H), 4.46-4.35 (m, 2H), 3.71-3.62 (m, 2H), 3.08 (s, 6H). MS (ESI): m/z 475.1 [M+1]$^+$.

Example 171

Compound 171, 4-(3-ethoxy-4-hydroxy-5-nitrophenyl)-5-phenyl-6-(tetrahydrofuran-2-yl)-3,4-dihydropyrimidin-2(1H)-one

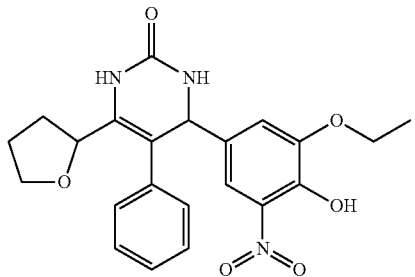 [SMILES: CCOc1cc(C2NC(=O)NC(C3CCCO3)=C2c2ccccc2)cc([N+](=O)[O-])c1O]

A mixture of 2-phenyl-1-(tetrahydrofuran-2-yl)ethanone (Intermediate 90) (522 mg, 2.75 mmol), 3-ethoxy-4-hydroxy-5-nitrobenzaldehyde (695 mg, 3.3 mmol), and urea (495 mg, 8.25 mmol) in anhydrous EtOH (4 mL) was added concentrated HCl solution (0.2 mL), the reaction mixture was refluxed for 14 hours. The reaction mixture was concentrated, and purified by column chromatography and preparative HPLC to give product, contaminated with an impurity (21 mg). This was further purified by preparative TLC and preparative HPLC to give Compound 171 (14 mg). $^1$H NMR (DMSO-d$_6$ 400 MHz): δ 10.170 (s, 1H), 8.318 (s, 1H), 7.629 (d, J=2.4 Hz, 1H), 7.276-7.344 (m, 5H), 7.066-7.163 (m, 2H), 5.384 (s, 1H), 4.245 (d, J=4.0 Hz, 1H), 3.844-4.025 (m, 4H), 1.964-2.220 (m, 4H), 1.227-1.262 (t, J=3.0 Hz, 3H); MS (ESI): m/z 426.1 [M+1]$^+$.

Example 172

Compound 172, 6-cyclopentyl-4-(3-ethoxy-4-hydroxy-5-nitrophenyl)-5-phenyl-3,4-dihydropyrimidin-2(1H)-one

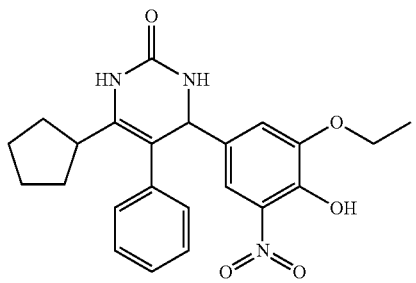 [SMILES: CCOc1cc(C2NC(=O)NC(C3CCCC3)=C2c2ccccc2)cc([N+](=O)[O-])c1O]

A mixture of 1-cyclopentyl-2-phenylethanone (Intermediate 91) (1.6 mmol, 300 mg), 3-ethoxy-4-hydroxy-5-nitrobenzaldehyde (1.91 mmol, 404 mg), and urea (4.8 mmol, 288 mg) in anhydrous ethanol (5 mL) was added concentrated HCl (0.2 mL), the above mixture was refluxed for 13 hours. The reaction mixture was concentrated and the residue was purified by column chromatography, followed by preparative HPLC to afford the product Compound 172 as yellow solid (20 mg, yield: 2.96%). $^1$H NMR (DMSO 400 MHz): δ 10.23 (s, 1H), 8.25 (s, 1H), 6.98-7.33 (m, 8H), 5.00 (d, J=2.4 Hz, 1H), 3.94-4.04 (m, 2H), 2.65-2.69 (t, J=9.2 Hz, 1H), 1.24-1.79 (m, 11H); MS (ESI): m/z 424.1 [M+1]$^+$.

Example 173

Compound 173, 4-(3-ethoxy-4-hydroxy-5-nitrophenyl)-5-phenyl-6-(tetrahydrofuran-3-yl)-3,4-dihydropyrimidin-2(1H)-one

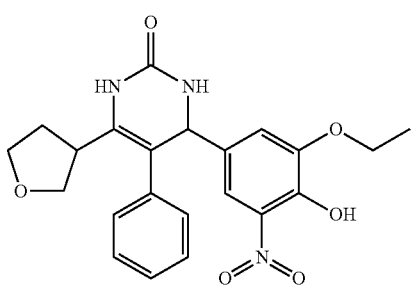 [SMILES: CCOc1cc(C2NC(=O)NC(C3CCOC3)=C2c2ccccc2)cc([N+](=O)[O-])c1O]

To a solution of 2-phenyl-1-(tetrahydrofuran-3-yl)ethanone (Intermediate 92) (60 mg, 0.32 mmol), 3-ethoxy-4-hydroxy-5-nitrobenzaldehyde (67.5 mg, 0.32 mmol) and urea (57.4 mg, 0.96 mmol) in 20 mL of ethanol was added 0.2 mL of conc. HCl, and the mixture was refluxed for 2 days. The solvent was removed under reduced pressure, and the residue was purified by reverse-phase preparatory HPLC (26-53% acetonitrile+0.1% trifluoroacetic acid in water+0.1% trifluoroacetic acid, over 15 min.) to give Compound 173 (26 mg, yield 20.0%). $^1$H NMR (DMSO-d$_6$ 400 MHz): δ 10.25 (s, 1H), 8.05 (m, 1H), 7.42 (d, J=7.2 Hz, 1H), 7.28 (m, 4H), 7.08 (d, J=7.2 Hz, 2H), 6.95 (d, J=18.8, 1H), 5.08 (m, 1H), 3.98 (m, 3H), 3.62 (m, 3H), 3.01 (m, 1H), 2.13 (m, 2H), 1.31 (m, 3H); MS (ESI): m/z 426.2 [M+1]$^+$.

Example 174

Compound 174, 6-cyclohexyl-4-(3-ethoxy-4-hydroxy-5-nitrophenyl)-5-(thiophen-3-yl)-3,4-dihydropyrimidin-2(1H)-one

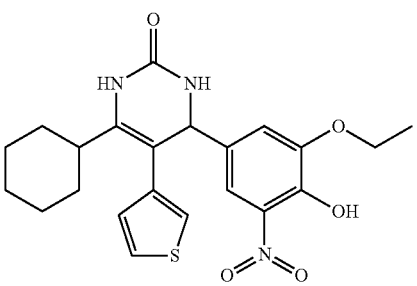 [SMILES: CCOc1cc(C2NC(=O)NC(C3CCCCC3)=C2c2ccsc2)cc([N+](=O)[O-])c1O]

A mixture of 1-cyclohexyl-2-(thiophen-3-yl)ethanone (Intermediate 95) (176 mg, 0.56 mmol), 3-ethoxy-4-hydroxy-5-nitrobenzaldehyde (140 mg, 0.67 mmol), urea (100 mg, 1.68 mmol) and concentrated HCl solution (0.1 mL) in absolute ethanol (5 mL) was reflux under N$_2$ overnight. Solvent was removed, and residue was purified by column chromatography and prep-HPLC to give Compound 174 (23 mg, yield: 9%) as a yellow solid. $^1$H NMR (DMSO-d$_6$ 400 MHz): δ 10.25 (brs, 1H), 8.26 (s, 1H), 7.45 (dd, J=4.8, 2.0 Hz, 1H), 7.35-7.25 (m, 2H), 7.09 (d, J=1.6 Hz, 1H), 7.06 (d, J=1.6 Hz, 1H), 6.85 (d, J=4.0 Hz, 1H), 4.98 (d, J=2.4 Hz, 1H), 4.10-3.90 (m, 2H), 1.90-1.40 (m, 7H), 1.35 (t, J=7.2 Hz, 3H), 1.20-1.00 (m, 3H). MS (ESI): m/z 444.2 [M+1]$^+$.

Example 175

Compound 175, 4-(3-ethoxy-4-hydroxy-5-nitrophenyl)-5-phenyl-6-((S)-tetrahydrofuran-2-yl)-3,4-dihydropyrimidin-2(1H)-one

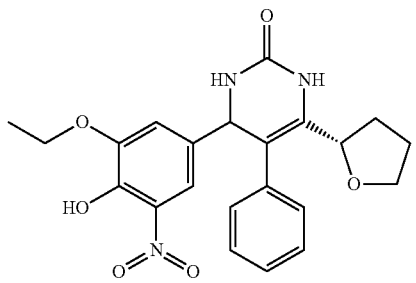 [SMILES: CCOc1cc(C2NC(=O)NC([C@@H]3CCCO3)=C2c2ccccc2)cc([N+](=O)[O-])c1O]

To a mixture of (S)-2-phenyl-1-(tetrahydrofuran-2-yl) ethanone (Intermediate 93) (150 mg, 0.8 mmol), 3-ethoxy-4-hydroxy-5-nitro-benzaldehyde (200 mg, 0.9 mmol), and urea (142 mg, 2.4 mmol) in absolute ethanol (3 mL) was added conc. HCl (one drop). The mixture was refluxed under N$_2$ for 3 hrs. The reaction mixture was concentrated in vacuo, and was purified by silica gel column chromatography (PE:EtOAc=10:1 to PE:EtOAc=1:2) and prep-HPLC (0.1% TFA as additive) to give Compound 175 (30 mg, yield 9%). $^1$H NMR (DMSO 400 MHz): δ 10.28-10.16 (m, 1H), 7.65-7.45 (m, 0.5H), 7.40-7.17 (m, 4.5H), 7.10-7.03 (m, 1.5H), 6.98-6.95 (m, 0.5H), 5.38-5.36 (s, 0.5H), 5.16-5.08 (m, 0.5H), 4.30-4.20 (m, 0.5H), 4.10-3.85 (m, 3H), 3.62-3.53 (m, 0.5H), 2.21-1.65 (m, 3.5H), 1.31-1.19 (m, 3H); MS (ESI): m/z 426.1 [M+1]$^+$.

Example 176

Compound 176, 4-(3-ethoxy-4-hydroxy-5-nitrophenyl)-5-phenyl-6-((R)-tetrahydrofuran-2-yl)-3,4-dihydropyrimidin-2(1H)-one

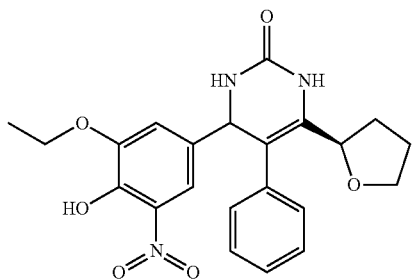 [SMILES: CCOc1cc(C2NC(=O)NC([C@H]3CCCO3)=C2c2ccccc2)cc([N+](=O)[O-])c1O]

To a mixture of (R)-2-phenyl-1-(tetrahydrofuran-2-yl) ethanone (Intermediate 94) (200 mg, 1.0 mmol), 3-ethoxy-4-hydroxy-5-nitrobenzaldehyde (266 mg, 1.3 mmol), and urea (189 mg, 3.2 mmol) in absolute ethanol (3 mL) was added conc. HCl (one drop). The mixture was refluxed under N$_2$ for 3.5 hrs. The reaction mixture was concentrated under reduced pressure and purified by silica gel column chromatography (PE:EtOAc=10:1 to PE:EtOAc=1:2) and prep-HPLC (0.1% TFA as additive) to give Compound 176 (21 mg, yield 5%). $^1$H NMR (DMSO 400 MHz): δ 10.18 (s, 1H), 8.34 (s, 1H), 7.64 (s, 1H), 7.34-7.27 (m, 5H), 7.16-7.10 (m, 1H), 7.07-7.04 (m, 1H), 5.38 (s, 1H), 4.26-4.21 (m, 1H), 4.03-3.92 (m, 3H), 3.92-3.87 (m, 1H), 2.22-2.18 (m, 1H), 2.17-2.04 (m, 2H), 2.00-1.95 (m, 1H), 1.32-1.22 (m, 3H); MS (ESI): m/z 426.0 [M+1]$^+$.

Example 177

Compound 177, 5-cyclohexyl-4-(3-ethoxy-4-hydroxy-5-nitrophenyl)-6-phenyl-3,4-dihydropyrimidin-2(1H)-one

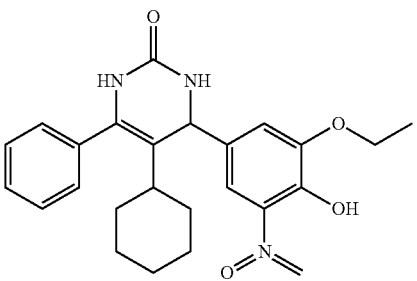 [SMILES: C=[N+]([O-])c1cc(C2NC(=O)NC(c3ccccc3)=C2C2CCCCC2)cc(OCC)c1O]

A mixture of urea (150 mg, 2.5 mmol), 3-ethoxy-4-hydroxy-5-nitrobenzaldehyde (104 mg, 0.49 mmol), CuCl (99 mg, 1.0 mmol), BF$_3$-Et$_2$O (142 mg, 1.0 mmol) and AcOH (0.2 mL) in anhydrous THF (10 mL) was stirred under refluxing under N$_2$ atmosphere for 0.5 hour. Then 2-cyclohexyl-1-phenylethanone (Intermediate 96) (100 mg, 0.49 mmol) in anhydrous THF (0.5 mL) was added and the reaction mixture was refluxed overnight. Followed a standard aqueous/EtOAc workup and purified by prep-HPLC (0.1% TFA as additive) to give Compound 177 (20 mg, yield 9%). $^1$H NMR (CD$_3$OD 400 MHz): δ 7.74 (d, J=2.0 Hz, 1H), 7.53-7.38 (m, 6H), 7.39 (d, J=2.0 Hz, 1H), 4.99 (s, 1H), 4.21 (q, J=7.2 Hz, 1H), 2.35-2.28 (m, 1H), 1.69 (m, 1H), 1.64 (m, 1H), 1.55-1.47 (m, 7H), 1.05-0.92 (m, 3H), 0.85-0.79 (m, 1H). MS (ESI): m/z 438.3 [M+1]$^+$.

Example 178

Synthesis of Intermediates

Intermediate 1: Synthesis of 1-phenyl-2-(thiophen-2-yl)ethanone

Step 1: Synthesis of 2-(thiophen-2-yl)acetyl chloride

To a solution of 2-(thiophen-2-yl)acetic acid (2 g, 14 mmol) in DCM (50 mL) was added dropwise SOCl$_2$ (0.5 mL), the mixture was heated at 50° C. overnight. The reaction mixture was concentrated under reduced pressure to give compound 2-(thiophen-2-yl)acetyl chloride, which was used directly in the next step without further purification.

Step 2: Synthesis of 1-phenyl-2-(thiophen-2-yl)ethanone (Intermediate 1)

To the solution of 2-(thiophen-2-yl)acetyl chloride (from above step) in benzene (100 mL) was added AlCl$_3$ (3.88 g, 29.4 mmol) for 5 batches, after the completion of the addition, the mixture was heated to reflux for 1 hour. The reaction mixture was poured into ice-water and extracted with EtOAc (200 mL×3). The combined organic layer was washed with brine, dried over sodium sulfate, and concentrated under reduced pressure to the crude product, which was purified by column chromatography (EtOAc:Petroleum=20:1) to give Intermediate 1 (600 mg, yield 21.2%).

Intermediate 2: Synthesis of
1-phenyl-2-(thiophen-3-yl)ethanone

Step 1: Synthesis of
N-methoxy-N-methyl-2-(thiophen-3-yl)acetamide

A mixture of 2-(thiophen-3-yl)acetic acid (2.0 g, 14.1 mmol), O,N-dimethylhydroxylamine (1.68 g, 16.9 mmol), EDCI (2.95 g, 15.5 mmol), HOBT (2.15 g, 15.5 mmol), and TEA (3.7 mL, 31 mmol) in anhydrous DCM (50 mL) was stirred at room temperature under nitrogen for two hours. The reaction mixture was diluted with $CH_2Cl_2$, and the organic layer was washed with aqueous HCl solution (0.5 mol/$L^1$, 30 mL×2), saturated $NaHCO_3$ (30 mL×2) and brine (30 mL), dried over $Na_2SO_4$, filtered, and concentrated to give the crude N-methoxy-N-methyl-2-(thiophen-3-yl)acetamide (2.0 g, yield 76.6%).

Step 2: Synthesis of
1-phenyl-2-(thiophen-3-yl)ethanone (Intermediate 2)

To the solution of bromo-benzene (1.0 g, 6.36 mmol) in anhydrous THF (30 mL) was added n-BuLi (5.9 mmol, 2.4 mL) at −78° C. under nitrogen, and the mixture was stirred at −78° C. for further 20 min., a solution of N-methoxy-N-methyl-2-(thiophen-3-yl)acetamide (1 g, 5.4 mmol) in anhydrous THF (10 mL) was added. The resulting mixture was stirred at −78° C. under nitrogen for about 30 min., poured into $NH_4Cl$ aqueous solution, and extracted with EtOAc. The organic layers were washed with brine, dried over sodium sulfate, concentrated, and purified by column chromatograph (PE:EtOAc=20:1) to afford Intermediate 2 as a colorless oil (600 mg, yield 55.0%).

Intermediate 3: Synthesis of
1-phenyl-2-(thiazol-2-yl)ethanone

To a solution of 2-methylthiazole (500 mg, 5.1 mmol) in anhydrous THF (10 mL) at −78° C. under nitrogen was added dropwise n-BuLi (2.5 mol/L, 2.0 mL), after being stirred at this temperature for 1 hour, a solution of ethyl benzoate (1.1 g, 7.3 mmol) in anhydrous THF (5 mL) was added, and the reaction mixture was stirred at room temperature overnight. When TLC (PE:EtOAc=7:1) indicated that the starting materials were consumed, water was added to quench the reaction, and the aqueous layer extracted with EtOAc (10 mL×3). The combined organic layer was washed with brine (10 mL), dried over $Na_2SO_4$, filtered, concentrated, and purified by column chromatography (PE:EtOAc=15:1) to afford Intermediate 3 as a yellow oil (170 mg, yield: 17.0%).

Intermediate 4: Synthesis of
1-phenyl-2-m-tolylethanone

Step 1

A mixture of 2-m-tolylacetic acid (1 g, 6.7 mmol), N,O-dimethylhydroxylamine hydrochloride (654 mg, 6.7 mmol), 1-(3-dimethylaminopropyl)-3-ethylcarbodiimide hydrochloride (1.28 g, 6.7 mmol), hydroxybenzotriazole (910 mg, 6.7 mmol) and triethylamine (3.38 g, 33.5 mmol) in dichloromethane (30 mL) was stirred at room temperature overnight. When TLC indicated that 2-m-tolylacetic acid was consumed, the reaction mixture was diluted with water (30 mL), and extracted with EtOAc (30 mL×3). The combined organic layer was dried over $Na_2SO_4$, concentrated in vacuo, and purified by column chromatography (PE:EtOAc=10:1) to afford N-methoxy-N-methyl-2-m-tolylacetamide (900 mg, yield 70%).

Step 2

Under $N_2$, to a mixture of N-methoxy-N-methyl-2-m-tolylacetamide (500 mg, 2.6 mmol) in anhydrous THF was added phenylmagnesium bromide (6.5 mL, 6.5 mmol) at −78° C., and the mixture was stirred for 3 hours. When TLC indicated that the starting material was consumed, the reaction mixture was diluted with EtOAc, washed with water and brine, concentrated, and purified by column chromatography (PE:EtOAc=30:1) to give Intermediate 4 (460 mg, yield 84.6%).

Intermediate 5: Synthesis of
2-(biphenyl-4-yl)-1-phenylethanone

Step 1

A mixture of 2-(biphenyl-4-yl)acetic acid (1 g, 4.7 mmol), N,O-dimethylhydroxylamine hydrochloride (458 mg, 4.7 mmol), 1-(3-dimethylaminopropyl)-3-ethylcarbodiimide hydrochloride (900 g, 4.7 mmol), hydroxybenzotriazole (635 mg, 4.7 mmol), and triethylamine (1.42 g, 14.1 mmol) in dichloromethane (30 mL) was stirred at room temperature overnight. When TLC indicated that 2-(biphenyl-4-yl)acetic acid was consumed, the reaction mixture was diluted with water (30 mL), and extracted with EtOAc (30 mL×3). The combined organic layer was dried over $Na_2SO_4$, concentrated in vacuo, and purified by column chromatography (PE:EtOAc=8:1) to afford 2-(biphenyl-4-yl)-N-methoxy-N-methylacetamide (1.0 g, yield 83%).

Step 2

Under $N_2$, to a mixture of 2-(biphenyl-4-yl)-N-methoxy-N-methylacetamide (500 mg, 1.96 mmol) in anhydrous THF was added phenylmagnesium bromide (5 mL, 5 mmol) at −78° C., and the mixture was stirred for 3 hours. When TLC indicated that the starting material was consumed, the reaction mixture was diluted with EtOAc, washed with water and brine, concentrated, and purified by column chromatography (PE:EtOAc=20:1) to give Intermediate 5 (430 mg, yield 80.7%).

Intermediate 6: Synthesis of
2-(3,4-dichlorophenyl)-1-phenylethanone

Step 1

A mixture of 2-(3,4-dichlorophenyl)acetic acid (1 g, 4.9 mmol), N,O-dimethylhydroxylamine hydrochloride (480 mg, 4.9 mmol), 1-(3-dimethylaminopropyl)-3-ethylcarbodiimide hydrochloride (940 mg, 4.9 mmol), hydroxybenzotriazole (660 mg, 4.9 mmol), and triethylamine (2.5 g, 25 mmol) in dichloromethane (30 mL) was stirred at room temperature overnight. The reaction mixture was diluted with water (30 mL), and extracted with EtOAc (30 mL×3). The combined organic layers were dried over Na$_2$SO$_4$, concentrated in vacuo, and purified by column chromatography (PE:EtOAc=10:1) to afford 2-(3,4-dichlorophenyl)-N-methoxy-N-methylacetamide (880 mg, yield 72.7%).

Step 2

Under N$_2$, to a mixture of 2-(3,4-dichlorophenyl)-N-methoxy-N-methylacetamide (440 mg, 1.8 mmol) in anhydrous THF was added phenylmagnesium bromide (4.4 mL, 4.4 mmol) at −78° C., and the mixture was stirred for 3 hours. When TLC indicated that the starting material was consumed, the reaction mixture was diluted with EtOAc, washed with water and brine, concentrated, and purified by column chromatography (PE:EtOAc=20:1) to give Intermediate 6 (400 mg, yield 85%).

Intermediate 7: Synthesis of
2-(3,4-dimethoxyphenyl)-1-phenylethanone

Step 1

A mixture of 2-(3,4-dimethoxyphenyl)acetic acid (1 g, 5.1 mmol), N,O-dimethylhydroxylamine hydrochloride (480 mg, 5.1 mmol), 1-(3-dimethylaminopropyl)-3-ethylcarbodiimide hydrochloride (978 mg, 5.1 mmol), hydroxybenzotriazole (690 mg, 5.1 mmol) and triethylamine (2.57 g, 25.5 mmol) in dichloromethane (30 mL) was stirred at room temperature overnight. The reaction mixture was diluted with water (30 mL), and extracted with EtOAc (30 mL×3). The combined organic layer was dried over Na$_2$SO$_4$, concentrated in vacuo, and purified by column chromatography (PE:EtOAc=8:1) to afford 2-(3,4-dimethoxyphenyl)-N-methoxy-N-methylacetamide (370 mg, yield 30.3%).

Step 2

Under N$_2$, to a mixture of 2-(3,4-dimethoxyphenyl)-N-methoxy-N-methylacetamide (200 mg, 0.84 mmol) in anhydrous THF was added phenylmagnesium bromide (2.1 mL, 2.1 mmol) at −78° C., and the mixture was stirred for 2 hours. When TLC indicated that the start material was consumed, the reaction mixture was diluted with EtOAc, washed with water and brine, concentrated, and purified by column chromatography (PE:EtOAc=20:1) to give Intermediate 7 (130 mg, yield 61%).

Intermediate 8: Synthesis of
2-(4-bromophenyl)-1-phenylethanone

Prepared by the same two step synthesis described in the synthesis of Intermediate 7, starting from 2-(4-bromophenyl) acetic acid.

Intermediate 9: Synthesis of
1-phenyl-2-o-tolylethanone

Step 1

Followed procedure described in Step 1 of Intermediate 7, starting from 2-o-tolylacetic acid, where crude material was purified by column chromatography (PE:EtOAc=10:1) to afford N-methoxy-N-methyl-2-o-tolylacetamide (810 mg, yield 67.5%) as an oil.

Step 2

Followed procedure described in Step 2 of Intermediate 7, where the crude was purified by column chromatography (PE:EtOAc=30:1) to give Intermediate 9 (200 mg, yield 45.9%) as an oil.

Intermediate 10: Synthesis of
2-(2-chlorophenyl)-1-phenylethanone

Step 1

A mixture of 2-(2-chlorophenyl)acetic acid (1.0 g, 5.9 mmol), O,N-dimethyl-hydroxylamine (0.631 g, 6.3 mmol), EDCI (1.2 g, 6.3 mmol), HOBT (0.874 g, 6.3 mmol), and NMM (2.6 mL, 23.6 mmol) in anhydrous CH$_2$Cl$_2$ (20 mL) was stirred at room temperature for two hours under nitrogen. The reaction mixture was diluted with a mixture of CH$_2$Cl$_2$ and MeOH (v/v=10:1, 100 mL). The organic layer was washed with aqueous HCl (0.5 mol/L, 30 mL×2), saturated NaHCO$_3$ (30 mL×2) and brine (30 mL), dried over Na$_2$SO$_4$, filtered, and concentrated to give crude 2-(2-chlorophenyl)-N-methoxy-N-methylacetamide (0.7 g, yield: 56.0%).

Step 2

To a solution of 2-(2-chlorophenyl)-N-methoxy-N-methylacetamide (0.51 g, 2.4 mmol) in anhydrous THF (10 mL) cooled to −78° C., a solution of phenylmagnesium bromide (1 mol/L, 3.5 mL) in THF was added. The reaction mixture was stirred at this temperature for five hours. TLC (PE:EtOAc=10:1) indicated that 50% of the starting materials were consumed. H$_2$O (10 mL) was added to quench the reaction, and the aqueous layer extracted with EtOAc (10 mL×3). The combined organic layer was washed with brine (10 mL), dried over Na$_2$SO$_4$, filtered, concentrated, and purified by column chromatography (PE:EtOAc=50:1) to afford Intermediate 10 as a colorless oil (80 mg, yield: 14.8%).

Intermediate 11: Synthesis of
3-(2-oxo-2-phenylethyl)benzonitrile

Step 1

Followed procedure described in Step 1 of Intermediate 7, starting from 2-(3-cyanophenyl)acetic acid, to afford 2-(3-cyanophenyl)-N-methoxy-N-methylacetamide (340 mg, yield 53.6%).

Step 2

Followed the procedure described in Step 2 of Intermediate 7, where the mixture was stirred for 1 hour at −78° C. and at room temperature for 1 hour. Workup and purification followed step 2 of intermediate 7, to give Intermediate 11 (80 mg, yield 21.7%).

Intermediate 12: Synthesis of
2-(3,4-difluorophenyl)-1-phenylethanone

Step 1

Followed the procedure described in Step 1 of Intermediate 7, starting from 2-(3,4-difluorophenyl)acetic acid, and purified by column chromatography (PE:EtOAc=10:1) to afford 2-(3,4-difluorophenyl)-N-methoxy-N-methylacetamide (840 mg, yield 70.1%) as an oil.

Step 2

Followed the procedure described in Step 2 of Intermediate 7, where the mixture was stirred for 3 hours. Purification was achieved by column chromatography (PE:EtOAc=30:1) to give Intermediate 12 (250 mg, yield 28.9%) as an oil.

Intermediate 13: Synthesis of 1-(3,5-dichlorophenyl)-2-phenylethanone

To a solution of 1-bromo-3,5-dichlorobenzene (1 g, 4.4 mmol) in anhydrous THF (10 mL) was added n-BuLi (339 mg, 5.3 mmol) at −78° C. After being stirred for 30 minutes, a solution of N-methoxy-N-methyl-2-phenyl-acetamide (prepared following step 1 of Intermediate 4) (790 mg, 4.4 mmol) in THF (5 mL) was added, and the mixture was stirred for 3 hours. When TLC indicated that starting material was consumed, the reaction mixture was diluted with water (50 mL), and extracted with EtOAc (20 mL×3). The combined organic layer was dried over $Na_2SO_4$, concentrated in vacuum, and purified by column chromatography (PE:EtOAc=50:1) to afford 1-(3,5-dichlorophenyl)-2-phenylethanone (213 mg, yield 19.4%).

Intermediate 14: Synthesis of 1-(biphenyl-4-yl)-2-phenylethanone

To a solution of 4-bromobiphenyl (683 mg, 2.9 mmol) in anhydrous THF (5 mL) was added n-BuLi (1.2 mL, 2.9 mmol) dropwise at −78° C. After being stirred at the temperature for 0.5 h, a solution of N-methoxy-N-methyl-2-phenyl-acetamide (prepared following step 1 of Intermediate 4) (500 mg, 2.8 mmol) in anhydrous THF (5 mL) was added via a syringe, and the mixture was stirred at −78° C. for 2 h. The reaction was quenched with saturated $NH_4Cl$ aqueous solution, and extracted with EtOAc. The organic layer was dried over $Na_2SO_4$, concentrated in vacuo, and purified by column chromatography (PE:EtOAc=20:1) to give 1-(biphenyl-4-yl)-2-phenylethanone (180 mg, yield 24%).

Intermediate 15: Synthesis of 4-(2-oxo-2-phenylethyl)benzonitrile

Step 1

Followed the procedure described in Step 1 of Intermediate 5 starting from 2-(4-cyanophenyl)acetic acid to give the desired 2-(4-cyanophenyl)-N-methoxy-N-methylacetamide (0.4 g, yield 63%).

Step 2

Followed the procedure described in Step 2 of Intermediate 5, where the mixture was stirred for 1 hour at −78° C. and then at room temperature for 1 hour. Workup and purification followed step 2 of intermediate 5, to give the desired compound, Intermediate 15, (70 mg, yield 16%).

Intermediate 16: Synthesis of 1-(4-chloro-3-fluorophenyl)-2-phenylethanone

Prepared following the procedure described in Intermediate 13, starting from 4-bromo-1-chloro-2-fluorobenzene, where the crude product was purified by column chromatography (PE:EtOAc=100:1) to afford Intermediate 16 (200 mg, yield 18.2%).

Intermediate 17: Synthesis of 1-(3-chloro-4-fluorophenyl)-2-phenylethanone

Prepared following the procedure described in Intermediate 13, starting from 4-bromo-2-chloro-1-fluorobenzene, where the crude product was purified by column chromatography (PE:EtOAc=100:1) to afford Intermediate 17 (110 mg, yield 20.0%).

Intermediate 18: Synthesis of 1-(3,5-difluorophenyl)-2-phenylethanone

Prepared following the procedure described in Intermediate 13, starting from 1-bromo-3,5-difluorobenzene, where the crude product was purified by column chromatography (PE:EtOAc=100:1) to afford Intermediate 18 (100 mg, yield 10.3%).

Intermediate 19: Synthesis of 1-(3,4-dichlorophenyl)-2-phenylethanone

Prepared following the procedure described in Intermediate 13, starting from 4-bromo-1,2-dichlorobenzene, where the crude product was purified by column chromatography (PE:EtOAc=100:1) to afford Intermediate 19 (230 mg, yield 42.4%).

Intermediate 20: Synthesis of 1-(4-(methoxymethoxy)phenyl)-2-phenylethanone

Step 1

To a solution of 4-bromophenol (1.0 g, 5.8 mmol) in anhydrous THF (10 mL) was added NaH (60%, 254 mg, 6.4 mmol) at 0° C. After being stirred at the temperature for 0.5 h, MOM-Cl (698 mg, 8.7 mmol) was added to the mixture. The mixture was stirred at 0° C. for 0.5 h, warmed to room temperature for 2 h, quenched with water, and extracted with EtOAc. The organic layer was dried over $Na_2SO_4$, concentrated in vacuo, and purified by column chromatography (PE:EtOAc=50:1) to give 1-bromo-4-(methoxymethoxy)benzene (1 g, yield 80%).

Step 2

Prepared following the procedure described in Intermediate 13, where the crude product was purified by column chromatography (PE:EtOAc=100:1) to afford Intermediate 20 (280 mg, yield 39%).

Intermediate 21: Synthesis of 1-(2,4-difluorophenyl)-2-phenylethanone

Prepared following the procedure described in Intermediate 14, starting from 1-bromo-2,4-difluorobenzene, where the crude product was purified by column chromatography (PE:EtOAc=50:1) to afford Intermediate 21 (250 mg, yield 19%).

Intermediate 22: Synthesis of 1-(furan-3-yl)-2-phenylethanone

Step 1

Followed step 1 of Intermediate 10, starting from furan-3-carboxylic acid to prepare the desired N-methoxy-N-methyl-furan-3-carboxamide (913 mg, yield: 65.9%).

Step 2

A solution of N-methoxy-N-methylfuran-3-carboxamide (913 mg, 5.89 mmol) in anhydrous THF (10 mL) was cooled to −78° C. under nitrogen, and a solution of benzylmagnesium chloride in THF (2 mol/L, 3.53 mL) was added through a syringe. The reaction mixture was stirred at this temperature for 5 hours. TLC (PE:EtOAc=5:1) indicated reaction was nearly complete, saturated NH$_4$Cl solution (20 mL) was added to quench the reaction, and the aqueous layer was extracted with EtOAc (80 mL). The organic layer was washed with brine (30 mL), dried over Na$_2$SO$_4$, filtered, and concentrated to afford 1-(furan-3-yl)-2-phenylethanone as a yellow oil (696 mg, yield: 63.2%).

Intermediate 23: Synthesis of 3-(2-phenylacetyl)benzonitrile

Step 1

Followed the procedure described in Intermediate 12, starting from 1,3-dibromobenzene, where the crude product was purified by column chromatography (PE:EtOAc=100:1) to give the desired 1-(3-bromophenyl)-2-phenylethanone (520 mg, yield 47.7%).

Step 2

The mixture of 1-(3-bromophenyl)-2-phenylethanone (200 mg, 0.73 mmol), zinc cyanide (128 mg, 1.09 mmol), and tetrakis(triphenylphosphine)palladium (84.3 mg, 0.073 mmol) in N,N-dimethylrormamide (4 mL) was degassed, and heated at 80° C. under N$_2$ for 20 hours. The mixture was poured into water, and extracted with EtOAc. The combined organic layer was dried over Na$_2$SO$_4$, concentrated in vacuo, and purified by column chromatography (PE:EtOAc=50:1) to afford 3-(2-phenylacetyl)benzonitrile (130 mg, yield 80.7%).

Intermediate 24: Synthesis of 1-(2-fluorophenyl)-2-phenylethanone

Prepared from 1-bromo-2-fluorobenzene following the procedure described in Intermediate 13, where the crude product was purified by column chromatography (PE:EtOAc=100:1) to afford Intermediate 24 (300 mg, yield 33.5%).

Intermediate 25: Synthesis of 1-(4-morpholinophenyl)-2-phenylethanone

Prepared from 4-(4-bromophenyl)morpholine following the procedure described in Intermediate 14, where the crude product was purified by column chromatography (PE:EtOAc=5:1) to afford Intermediate 25 (280 mg, yield 36%).

Intermediate 26: Synthesis of 1-phenyl-2-(pyrazin-2-yl)ethanone

To a mixture of diisopropyl-amine (1.29 g, 12.7 mmol) in anhydrous THF (10 mL) was added n-BuLi (2.5 M/L in hexane, 4.7 mL, 11.7 mmol) at −78° C., after being stirred for 30 minutes, a solution of 2-methylpyrazine (1 g, 10.6 mmol) in THF (5 mL) was added, and the mixture was stirred at −78° C. for 30 minutes, a solution of methyl benzoate (1.4 g, 10.6 mmol) in THF (5 mL) was added, and the mixture was stirred at this temperature for 3 hours. When TLC indicated that the starting material was consumed, the reaction mixture was diluted with EtOAc, and the mixture was washed with water and brine, and concentrated. The residue was purified by column chromatography (PE:EtOAc=30:1) to give Intermediate 26 (700 mg, yield 33.3%).

Intermediate 27: Synthesis of 2-phenyl-1-(pyridin-2-yl)ethanone

A solution of ethyl picolinate (1.0 g, 6.62 mmol) in anhydrous tetrahydrofuran (15 mL) was added benzylmagnesium chloride (3.64 mL, 7.28 mmol) at −78° C. The mixture was stirred at −78° C. for 5 h, and poured into saturated aqueous ammonium chloride solution (70 mL), and extracted with ethyl acetate (50 mL×2). The organic layer was washed with brine (80 mL), and dried over anhydrous sodium sulfate. The solvent was removed, and the residue was purified by silica gel column chromatography (petroleum ether/ethyl acetate=10:1) to give Intermediate 27 (700 mg, yield 53.6%).

Intermediate 28: Synthesis of 2-(biphenyl-3-yl)-1-phenylethanone

Step 1

Followed the procedure described in Step 1 of Intermediate 7, starting from 2-(3-bromophenyl)acetic acid, and purified by column chromatography (PE:EtOAc=30:1) to afford 2-(3-bromophenyl)-N-methoxy-N-methylacetamide (2.1 g, yield 58.3%).

Step 2

The mixture of 2-(3-bromophenyl)-N-methoxy-N-methylacetamide (2.0 g, 7.7 mmol), phenylboronic acid (1.42 g, 11.6 mmol), 1-1'-bis(diphenylphosphino)derrocene palladium dichloride (500 mg, 0.77 mmol), and saturated aqueous sodium carbonate solution (1 mL) in N,N-dimethylformamide (20 mL) was heated at 80° C. under N$_2$ overnight. The mixture was poured into water, extracted with EA, dried over Na$_2$SO$_4$, concentrated in vacuo, and purified by column chromatography (PE:EtOAc=30:1-10:1) to afford 2-(biphenyl-3-yl)-N-methoxy-N-methylacetamide (1.8 g, yield 94.7%).

Step 3

Followed the procedure described in Step 2 of Intermediate 7, where the mixture was stirred for 3 hours at −78° C. After workup, the crude was purified by column chromatography (PE:EtOAc=30:1) to afford 2-(biphenyl-3-yl)-1-phenylethanone (120 mg, yield 18.8%).

Intermediate 29: Synthesis of 1-(benzo[d][1,3]dioxol-5-yl)-2-phenylethanone

Prepared from 4-bromobenzo[d][1,3]dioxole following the procedure described in Intermediate 13, where the crude product was purified by column chromatography (PE:EtOAc=20:1) to give Intermediate 29 (400 mg, yield 50.4%).

Intermediate 30: Synthesis of 4-(2-phenylacetyl)benzonitrile

Prepared from 4-bromobenzonitrile following the procedure described in Intermediate 14, (70 mg, yield 11%).

Intermediate 31: Synthesis of 2-phenyl-1-(pyridin-3-yl)ethanone

Step 1

Followed the procedure described in Step 1 of Intermediate 7, starting from nicotinic acid where reaction was stirred at room temperature for 4 h. The crude was purified by column chromatography (PE:EtOAc=2:1) to afford N-methoxy-N-methylnicotinamide (1.4 g, yield 52%).

Step 2

Followed the procedure described in Step 2 of Intermediate 7 with N-methoxy-N-methylnicotinamide and benzylmagnesium chloride, where the mixture was stirred for 3 hours. Purification was achieved by column chromatography (PE:EtOAc=5:1) to give Intermediate 31 (110 mg, yield 19%).

Intermediate 32: Synthesis of 3-ethoxy-5-fluoro-4-hydroxybenzaldehyde

Step 1

To the solution of 3-fluoro-4-hydroxy-5-methoxybenzaldehyde (800 mg, 4.7 mmol) in DCM (50 mL) was added $AlCl_3$ (680 mg, 5.1 mmol) portionwise, and at 0° C., pyridine (950 mg, 9.4 mmol) was added, and the resulting mixture was refluxed overnight. The reaction mixture was quenched with HCl ice-water solution, and extracted with EtOAc (50 mL×3). The combined organic layers were washed with brine, dried over $Na_2SO_4$, and concentrated under reduced pressure to give the 3-fluoro-4,5-dihydroxybenzaldehyde as a pale solid (600 mg, yield 81%), which was used directly in the next step without further purification.

Step 2

To the solution of 3-fluoro-4,5-dihydroxybenzaldehyde (200 mg, 1.28 mmol) in DMF (50 mL) was added iodo-ethane (240 mg, 1.53 mmol) and $K_2CO_3$ (210 mg, 1.53 mmol) at 0° C., and the mixture was stirred at room temperature overnight. The reaction mixture was poured into ice-water solution, and extracted with EtOAc. The combined organic layers were washed with brine, dried with $Na_2SO_4$, concentrated under reduced pressure, and purified by column chromatography to give 3,4-diethoxy-5-fluorobenzaldehyde (100 mg, 36.8% yield).

Step 3

To the solution of 3,4-diethoxy-5-fluorobenzaldehyde (300 mg, 1.4 mmol) in DCM (50 mL) was added $AlCl_3$ (207 mg, 1.55 mmol), and at 0° C., pyridine (230 mg, 2.8 mmol) was added, and the resulting mixture was refluxed overnight. The reaction mixture was cooled to room temperature, poured into ice water solution, and extracted with EtOAc. The organic layer was washed with brine, dried over $Na_2SO_4$, concentrated under reduced pressure, and purified by column chromatography on silica gel to give 3-ethoxy-5-fluoro-4-hydroxybenzaldehyde (160 mg).

Intermediate 33: Synthesis of 2-(2-oxo-2-phenylethyl)benzonitrile

A suspension of NaH (1.4 g, 60% oil dispersion, 34 mmol) in dry dimethoxyethane (10 mL) was heated at reflux, a solution of 2-methylbenzonitrile (1 g, 8.5 mmol) in 5 mL of dimethoxyathane and a solution of ethyl benzoate (1.3 g, 8.5 mmol) in 10 mL of dimethoxyathane were added. The resulting suspension was heated at reflux for 20 hours. The reaction mixture was cooled, and water was added cautiously. The aqueous phase was extracted with EtOAc. The combined organic layers were dried over $Na_2SO_4$, filtered, concentrated, and purified by column chromatography to give Intermediate 33 (380 mg, yield 20%) as a yellow solid.

Intermediate 34: Synthesis of 3-ethoxy-5-formyl-2-hydroxybenzoic acid

Step 1

A solution of 3-bromo-5-ethoxy-4-hydroxybenzaldehyde (1.0 g, 4.1 mmol) in DMF (10 mL) was cooled at 0° C., NaH (180 mg, 4.5 mmol) was added, and the mixture was stirred for 15 minutes. MOM-Cl (360 mg, 4.5 mmol) was added, and the mixture was warmed to room temperature in two hours. TLC (PE:EtOAc=5:1) indicated that the starting material was consumed. Ice water was added to quench the reaction, and aqueous layer was extracted with EtOAc (30 mL×3). The combined organic layer was washed with brine (20 mL), dried over $Na_2SO_4$, filtered, concentrated, and purified by column chromatograph to give 3-bromo-5-ethoxy-4-(methoxymethoxy)benzaldehyde (0.7 g, yield: 59.3%).

Step 2

A mixture of 3-bromo-5-ethoxy-4-(methoxymethoxy)benzaldehyde (600 mg, 2.1 mmol) and CuCN (280 mg, 3.1 mmol) in DMF (10 mL) was heated at 180° C. for 4 hours. TLC (PE:EtOAc=1:1) indicated that the most of the starting material was consumed. The solvent was removed in vacuo, and the residue was purified by column chromatograph to afford 3-ethoxy-5-formyl-2-hydroxybenzonitrile (200 mg, yield: 50.0%).

Step 3

A solution of 3-ethoxy-5-formyl-2-hydroxybenzonitrile (230 mg, 1.2 mmol) in a mixture of EtOH (5 mL) and 2N aqueous NaOH (5 mL) was refluxed for two days. The reaction mixture was acidified to pH=1 with 1N HCl. The aqueous layer was extracted with a mixture of EtOAc and MeOH (v/v=10:1, 30 mL×3), and the combined organic layer was washed with brine, dried over $Na_2SO_4$, filtered, concentrated, and purified by column chromatography to give Intermediate 34 (130 mg, yield: 51.6%).

Intermediate 35: Synthesis of 2-phenyl-1-(pyridin-4-yl)ethanone

Step 1

Followed procedure described in Step 1 of Intermediate 7, starting from isonicotinic acid, where the reaction was stirred at room temperature for 4 hours. The crude material was purified by column chromatography (PE:EtOAc=2:1) to afford N-methoxy-N-methylisonicotinamide (1.5 g, yield 56%).

Step 2

To a solution of N-methoxy-N-methylisonicotinamide (500 mg, 3.0 mmol) in anhydrous THF (10 mL) was added benzylmagnesium chloride (2 M in THF, 1.8 mL, 3.6 mmol) drop wise at −78° C. After being stirred at the temperature for 2 h, the reaction was quenched with NH$_4$Cl aqueous solution, and extracted with EtOAc. The organic layer was dried over Na$_2$SO$_4$, concentrated in vacuo, and purified by column chromatography (PE:EtOAc=5:1) to give Intermediate 35 (60 mg, yield 10%).

Intermediate 36: Synthesis of 1-phenyl-2-(pyridin-4-yl)ethanone

Prepared following the procedure described in the synthesis of Intermediate 26, with purification by column chromatography (petroleum ether/ethyl acetate=6:1) to give Intermediate 36 (420 mg, yield 42.6%).

Intermediate 37: Synthesis of 3-ethoxy-5-formyl-2-hydroxybenzoic acid

Step 1

A solution of 3-bromo-5-ethoxy-4-hydroxybenzaldehyde (1.0 g, 4.1 mmol) in DMF (10 mL) was cooled at 0° C., NaH (180 mg, 4.5 mmol) was added, and the mixture was stirred for 15 minutes. MOM-Cl (360 mg, 4.5 mmol) was added, and the mixture was warmed to room temperature in two hours. TLC (PE:EtOAc=5:1) indicated that the starting material was consumed. Ice water was added to quench the reaction, and aqueous layer was extracted with EtOAc (30 mL×3). The combined organic layer was washed with brine (20 mL), dried over Na$_2$SO$_4$, filtered, concentrated, and purified by column chromatography to give 3-bromo-5-ethoxy-4-(methoxymethoxy)benzaldehyde (0.7 g, yield: 59.3%).

Step 2

A mixture of 3-bromo-5-ethoxy-4-(methoxymethoxy) benzaldehyde (600 mg, 2.1 mmol) and CuCN (280 mg, 3.1 mmol) in DMF (10 mL) was heated at 180° C. for 4 hours. TLC (PE:EtOAc=1:1) indicated that the most of the starting material was consumed. The solvent was removed in vacuo, and the residue was purified by column chromatography to afford the 3-ethoxy-5-formyl-2-hydroxybenzonitrile (200 mg, yield: 50.0%).

Step 3

A solution of 3-ethoxy-5-formyl-2-hydroxybenzonitrile (230 mg, 1.2 mmol) in a mixture of EtOH (5 mL) and 2 N aqueous NaOH (5 mL) was refluxed for two days. The reaction mixture was acidified to pH=1 with 1 N HCl. The aqueous layer was extracted with a mixture of EtOAc and MeOH (v/v=10:1, 30 mL×3), and the combined organic layer was washed with brine, dried over Na$_2$SO$_4$, filtered, concentrated, and purified by column chromatograph to give Intermediate 37 (130 mg, yield: 51.6%).

Intermediate 38: Synthesis of 2-phenyl-1-(thiophen-2-yl)ethanone

Step 1

A mixture of thiophene-2-carboxylic acid (2 g, 15.6 mmol), N,O-dimethylhydroxylamine hydrochloride (1.5 g, 15.6 mmol), EDCI (3.1 g, 15.6 mmol), HOBT (2.4 g, 15.6 mmol), Et$_3$N (6.5 mL, 46.8 mmol) in DCM (30 mL) was stirred at room temperature for 4 hours. The mixture was concentrated in vacuo and purified by column to give N-methoxy-N-methylthiophene-2-carboxamide (1.8 g, yield 67%) as an oil.

Step 2

The N-methoxy-N-methylthiophene-2-carboxamide (600 mg, 3.5 mol) was converted to Intermediate 38 following the procedure described in Step 2 of Intermediate 35 to give Intermediate 38 (350 mg, 49%) as a white solid Intermediate 39: Synthesis of 2-phenyl-1-(thiophen-3-yl)ethanone Step 1

Followed the procedure described in Step 1 of Intermediate 38 starting from thiophene-3-carboxylic acid to give the desired N-methoxy-N-methylthiophene-3-carboxamide (1.7 g, yield 64%) as an oil.

Step 2

The N-methoxy-N-methylthiophene-3-carboxamide (600 mg, 3.5 mol) was converted to Intermediate 39 following the procedure described in Step 2 of Intermediate 35 to give the desired (1.7 g, yield 64%) as an oil.

Intermediate 40: Synthesis of 1-(1-methyl-1H-imidazol-4-yl)-2-phenylethanone

Step 1

Followed step 1 of Intermediate 10, starting from 1-methyl-1H-imidazole-4-carboxylic acid to prepare the desired N-methoxy-N,1-dimethyl-1H-imidazole-4-carboxamide (0.52 g, yield 38.0%).

Step 2

Followed step 2 of Intermediate 35 to afford Intermediate 40 as a brown oil (130 mg, yield: 21.7%).

Intermediate 41: Synthesis of 1-(naphthalen-1-yl)-2-phenylethanone

Step 1

Followed step 1 of Intermediate 10, starting from 1-naphthoic acid to prepare the desired N-methoxy-N-methyl-1-naphthamide (1.08 g, yield: 86.2%).

Step 2

Followed step 2 of Intermediate 35 to afford Intermediate 41 (354 mg, yield: 28.9%) as a solid.

Intermediate 42: Synthesis of 1-phenyl-2-(pyridin-3-yl)ethanone

Prepared following the procedure described in the synthesis of Intermediate 26, with purification by column chromatography (petroleum ether/ethyl acetate=15:1) to give Intermediate 42 (470 mg, yield 15.9%).

Intermediate 43: Synthesis of 1-(naphthalen-2-yl)-2-phenylethanone

Step 1

Followed step 1 of Intermediate 10, starting from 2-naphthoic acid to prepare the desired N-methoxy-N-methyl-2-naphthamide (1.04 g, yield: 83%).

Step 2

Followed step 2 of Intermediate 35 to afford Intermediate 43 (270 mg, yield: 22.9%) as a solid.

Intermediate 44: Synthesis of 2-(4-(dimethylamino)phenyl)-1-phenylethanone

Step 1: Synthesis of 2-(4-(dimethylamino)phenyl)-N-methoxy-N-methylacetamide

Followed the procedure described in Step 1 of Intermediate 7 starting from 2-(4-(dimethylamino)phenyl)acetic acid to give the desired 2-(4-(dimethylamino)phenyl)-N-methoxy-N-methylacetamide (yield 72.6%).

Step 2: Synthesis of 2-(4-(dimethylamino)phenyl)-1-phenylethanone

Followed the procedure described in Step 2 of Intermediate 7, where the mixture was stirred for 1 hour at −78° C. and at room temperature for 1 hour. Workup according to step 2 of intermediate 7, followed by prep HPLC to give Intermediate 44 (yield 72.5%).

Intermediate 45: Synthesis of 8-nitro-2,3-dihydrobenzo[b][1,4]dioxine-6-carbaldehyde Step 1: Synthesis of 3,4-dihydroxy-5-nitrobenzaldehyde To a solution of 4-hydroxy-3-methoxy-5-nitrobenzaldehyde (3 g, 15.2 mmol) in acetic acid (3.1 mL) was added 40% hydrobromic acid (9.24 mL). The mixture was heated at 90° C. for 17 h. Reaction mixture was cooled and poured into ice water (100 mL), followed by a standard aqueous/EtOAc workup and purified by column chromatography on silica gel (petroleum ether/ethyl acetate=5:1) to give 3,4-dihydroxy-5-nitrobenzaldehyde (1.1 g, yield 39.5%).

Step 2: Synthesis of 8-nitro-2,3-dihydrobenzo[b][1,4]dioxine-6-carbaldehyde

To a mixture of potassium fluoride dihydrate (2.573 g, 27.3 mmol), and 3,4-dihydroxy-5-nitrobenzaldehyde (500 mg, 2.73 mmol) in N,N-dimethylformamide (20 mL) was added 1,2-dibromoethane (3.8 mL, 43.7 mmol), and the mixture was heated at 130° C. for 17 h. The reaction mixture was quenched with water followed by a standard aqueous/EtOAc workup and purified by column chromatography on silica gel (petroleum ether/ethyl acetate=15:1) to give Intermediate 45 (350 mg, yield 62.1%).

Intermediate 46: Synthesis of 3-(isoxazol-4-yl)benzaldehyde

Step 1: Synthesis of 4-iodoisoxazole

To a solution of NIS (23.0 g, 100 mmol) in TFA (200 mL) was added isoxazole (6.9 g, 100 mmol) in one portion at room temperature and the resultant mixture was stirred for 18 h. The mixture was partitioned between PE (200 mL) and water (1000 mL). The organic phase was separated and washed with saturated sodium bisulfate, dried with anhydrous $Na_2SO_4$, filtered and concentrated to give a yellow solid (1.2 g, 7%).

Step 2: Synthesis of 3-(isoxazol-4-yl)benzaldehyde

To a mixture of 4-iodoisoxazole (1 g, 5.13 mmol), 3-formylphenylboric acid (923 mg, 6.15 mmol) and sodium carbonate in DME/$H_2$O/Toluene/EtOH (15 mL, 3/1/10/6, V/V) was added Pd(PPh$_3$)$_4$ (200 mg). The mixture was purged with $N_2$ for 30 min and heated to 80° C. for 3 h. The reaction mixture was cooled followed by a standard aqueous/EtOAc workup and purified by prep-TLC (EA:PE=1:5) to give Intermediate 46 (12 mg, 1.5%).

Intermediate 47a and 47b: Synthesis of 5-formyl-2-hydroxybenzonitrile (Intermediate 47a) and 3-formyl-2-hydroxybenzonitrile (Intermediate 47b)

To a solution of 2-hydroxybenzonitrile (4.70 g, 41.6 mmol) in acetic acid (40 mL) was added hexamethylenetetraamine (8.7 g, 62.4 mmol) and the mixture was heated to 120° C. for 2 h. The mixture was cooled to room temperature, followed by a standard aqueous/EtOAc workup and purified by silica gel column chromatography (PE:EA=1:1) to afford 5-formyl-2-hydroxybenzonitrile (Intermediate 47a) as a white powder (540 mg, 9%) and 3-formyl-2-hydroxybenzonitrile (Intermediate 47b) as a white powder (1.17 g, 19%).

Intermediate 48: Synthesis of ethyl 2-ethoxy-4-formylbenzoate

Step 1: Synthesis of ethyl 2-ethoxy-4-methylbenzoate

To a mixture of 2-hydroxy-4-methylbenzoic acid (5.0 g, 32.9 mmol), $K_2CO_3$ (18.9 g, 136.6 mmol) and acetone (50 mL) was added ethyl iodide (41.0 g, 263.2 mmol). The mixture was stirred at room temperature for 3 days. After filtration, the organic layer was concentrated to afford ethyl 2-ethoxy-4-methylbenzoate as colorless oil (5.7 g, 85%), which was used directly for next step.

Step 2: Synthesis of ethyl 4-(bromomethyl)-2-ethoxybenzoate

To a solution of ethyl 2-ethoxy-4-methylbenzoate (100 mg, 0.481 mmol) in 2 mL of trifluoromethyl toluene was added NBS (94 mg, 0.529 mmol) and AIBN (10 mg) in portions. The mixture was heated to reflux and stirred for 24 h. The reaction mixture was concentrated, diluted with 10 mL of EA, washed with 5 mL of 4 N NaOH, 5 mL of brine, dried over anhydrous $Na_2SO_4$ and concentrated under reduced pressure to afford ethyl 4-(bromomethyl)-2-ethoxybenzoate as brown oil (42 mg, 30%), which was used for the next step directly.

Step 2: Synthesis of ethyl 2-ethoxy-4-formylbenzoate

To a solution of ethyl 4-(bromomethyl)-2-ethoxybenzoate (42 mg, 0.146 mmol) in 20 mL of $CHCl_3$ was added hexamethylenetetramine (21 mg, 0.146 mmol). The mixture was heated at 70° C. for 16 h. Filtration afforded 72 mg of a light yellow solid. The solid was added to 2 mL of $AcOH/H_2O$ (v/v=1/1) and the resultant mixture was heated at 90° C. for 16 h. The reaction mixture was cooled, followed by a standard aqueous/EtOAc workup to afford ethyl 2-ethoxy-4-formylbenzoate (Intermediate 48) as a brown oil (32 mg, 86%), MS (ESI): m/z 223.1 [M+1]$^+$.

Intermediate 49:
4-hydroxy-3-isopropoxy-5-nitrobenzaldehyde

To a mixture of 3,4-dihydroxy-5-nitrobenzaldehyde (1.0 g, 5.46 mmol) in dry DMF (10 mL) was added $Cs_2CO_3$ (3563 mg, 10.93 mmol), NaI (819 mg, 5.46 mmol) and 2-bromopropane (1009 mg, 8.20 mmol) and the mixture was stirred at 60° C. overnight. The mixture was cooled to room temperature and added 1N HCl till pH=7, followed by a standard aqueous/EtOAc workup. The residue was purified by silica gel column chromatography (DCM:THF=20:1) to give Intermediate 49 as a yellow solid (230 mg, 18.7%). $^1H$ NMR (DMSO-$d_6$ 500 MHz TMS): δ 9.86 (s, 1H), 8.08 (s, 1H), 7.65 (s, 1H), 4.79 (m, 1H), 1.28 (d, J=6.5 Hz, 6H).

Intermediate 50:
3-ethoxy-4-hydroxy-5-(methylthio)benzaldehyde

To the solution of 3-bromo-5-ethoxy-4-hydroxybenzaldehyde (1.00 g, 4.08 mmol) in pyridine (10 mL) was added Cu powder (0.52 g, 8.1 mmol) and methyl disulfide (0.77 g, 8.2 mmol), the mixture was then heated at 90° C. overnight. The reaction mixture was filtered, and the solvent was removed under reduced pressure, the residue was poured into water, and 6 N HCl (5 mL) was added, then the mixture was extracted with DCM (50 mL×3), the combined organic layers were washed with brine, dried over $Na_2SO_4$ and concentrated. The residue was purified by silica gel column (PE: EA=5:1) to give Intermediate 50 (600 mg, yield 69%).

Intermediate 51:
3-ethoxy-5-formyl-2-hydroxybenzonitrile

A mixture of 3-bromo-5-ethoxy-4-hydroxybenzaldehyde (200 mg, 0.82 mmol) and copper (I) cyanide in DMF (5 mL) was refluxed overnight. The reaction mixture was diluted with water (20 mL), extracted with EtOAc, dried over $Na_2SO_4$, and concentrated under reduced pressure. Purified by column chromatography on silica gel to afford Intermediate 51 (70 mg, yield 45%).

Intermediate 52: 2-phenyl-1-(1-(phenylsulfonyl)-1H-pyrrol-3-yl)ethanone

Step 1: Synthesis of 1-(phenylsulfonyl)-1H-pyrrole

To a solution of 1H-pyrrole (5 g, 74.5 mmol) in DMF (50 mL) was added NaH (4.5 g, 110 mmol) portionwise at 0° C., and the mixture was stirred at this temperature for 1 hour. Benzenesulfonyl chloride (19.4 g, 110 mmol) was added, and the mixture was stirred at room temperature overnight, followed by a standard aqueous/EtOAc workup and purified by column chromatography (PE:EtOAc=100:1).

Step 2: Synthesis of 2-phenyl-1-(1-(phenylsulfonyl)-1H-pyrrol-3-yl)ethanone

Under $N_2$, a mixture of phenyl-acetyl chloride (1.5 g, 9.7 mmol) in 1,2-dichloro-ethane (20 mL) was added $AlCl_3$ (2.24 g, 16.8 mmol) and then stirred at room temperature for 15 minutes. 1-(phenylsulfonyl)-1H-pyrrole (1.74 g, 8.4 mmol) was added. The mixture was stirred at room temperature overnight, followed by a standard aqueous/EtOAc workup. Purified by column chromatography to afford the Intermediate 52 (1.4 g, yield 51.8%).

Intermediate 53:
1-(4-fluorophenyl)-2-(3-methoxyphenyl)ethanone

Step 1

Followed the procedure described in Step 1 of Intermediate 7, starting from 2-(3-methoxyphenyl)acetic acid with a minor deviation where reaction was stirred at room temperature for 4 h. Isolated yield of N-methoxy-2-(3-methoxyphenyl)-N-methylacetamide was 1.5 g, yield 60% as an oil.

Step 2

Followed the procedure described in Synthesis of Intermediate 14 using N-methoxy-2-(3-methoxyphenyl)-N-methylacetamide and 1-bromo-4-fluorobenzene to give desired Intermediate 53 (260 mg, 37% yield).

Intermediate 54:
1-(4-fluorophenyl)-2-(thiophen-3-yl)ethanone

Followed the procedure described in synthesis of Intermediate 14 using N-methoxy-N-methyl-2-(thiophen-3-yl)acetamide (prepared in Step 1 of Intermediate 2) and 1-bromo-4-fluorobenzene to give Intermediate 54, (260 mg, 45%).

Intermediate 55: 5-formyl-2-hydroxy-3-nitrobenzoic acid

A solution of 5-formyl-2-hydroxybenzoic acid (2 g, 12.04 mmol) in concentrated sulfuric acid (5 mL) was added a mixture of concentrated nitric acid (1 mL) and concentrated sulfuric acid (1 mL) at 0° C. The resulting suspension was stirred at 0° C. for 3 h, and poured into ice water (30 mL). The solid was collected by filtration, washed with water (30 mL), and dried in vacuo to give Intermediate 55 (2.2 g, yield 86.6%).

Intermediate 56: 1-(pyridin-3-yl)-2-(thiophen-3-yl)ethanone

Step 1: Synthesis of nicotinoyl chloride

To a solution of nicotinic acid (2 g, 16.2 mmol) in anhydrous THF (30 mL) was added $SOCl_2$ (2.4 mL, 32.5 mmol). After stirring at 80° C. for 2 hours, the mixture was concentrated in vacuo.

Step 2: Synthesis of ethyl 3-oxo-3-(pyridin-3-yl)-2-(thiophen-3-yl)propanoate

To a solution of ethyl 2-(thiophen-3-yl)acetate (2.3 g, 16.2 mmol) in anhydrous THF (20 mL) was added LiHMDS (19.4 mL, 19.44 mmol) at −78° C. After stirring at that temperature for 0.5 h, a solution of nicotinoyl chloride (2.8 g, 16.2 mmol) in anhydrous THF (10 mL) was added into the reaction mixture and stirred at −78° C. for 4 hours. The mixture was quenched with $NH_4Cl$ solution, extracted with EtOAc. The organic layer was concentrated in vacuo and purified by column on silica gel (1.7 g, yield 38%).

Step 3: Synthesis of 1-(pyridin-3-yl)-2-(thiophen-3-yl)ethanone

To a solution of ethyl 3-oxo-3-(pyridin-3-yl)-2-(thiophen-3-yl)propanoate (2 g, 7.26 mmol) in DMSO (20 mL) was added catalytic amount of brine (0.2 mL). The reaction mixture was heated at 160° C. for 2 h. The reaction mixture was cooled to room temperature, diluted with water, and extracted with EtOAc. The organic layer was concentrated in vacuo and purified by column chromatography to afford Intermediate 56 (1 g, yield 68%).

Intermediate 57: 1-(1-methyl-1H-pyrazol-4-yl)-2-(thiophen-3-yl)ethanone

Followed same three step procedure described in Intermediate 56.

Step 1: Synthesis of 1-methyl-1H-pyrazole-4-carbonyl chloride

Started with 1-methyl-1H-pyrazole-4-carboxylic acid, and used toluene instead of THF.

Step 2: Synthesis of ethyl 3-(1-methyl-1H-pyrazol-4-yl)-3-oxo-2-(thiophen-3-yl)propanoate Used crude from step 1 and ethyl 2-(thiophen-3-yl)acetate. After stirring at −78° C., the reaction was warmed to room temperature and stirred overnight.

Step 3: Synthesis of 1-(1-methyl-1H-pyrazol-4-yl)-2-(thiophen-3-yl)ethanone

Reaction mix stirred at 180° C. for 2 hours. Purified by column chromatography (PE:EtOAc=10:1) to give Intermediate 57 (160 mg, yield 61.8%).

Intermediate 58: 1-(1-methyl-1H-pyrazol-3-yl)-2-(thiophen-3-yl)ethanone

Followed same three step procedure described in Intermediate 56.

Step 1: Synthesis of 1-methyl-1H-pyrazole-3-carbonyl chloride

Started with 1-methyl-1H-pyrazole-3-carboxylic acid, and used toluene instead of THF.

Step 2: Synthesis of ethyl 3-(1-methyl-1H-pyrazol-3-yl)-3-oxo-2-(thiophen-3-yl)propanoate Used crude from step 1 and ethyl 2-(thiophen-3-yl)acetate. Purified by silica gel column chromatography (PE:EtOAc=10:1) (1.8 g, 2-step yield 82%).

Step 3: Synthesis of 1-(1-methyl-1H-pyrazol-3-yl)-2-(thiophen-3-yl)ethanone

Purified by column chromatography (PE:EtOAc=8:1) to give Intermediate 58 (960 mg, yield 74%).

Intermediate 59: 3-chloro-4-hydroxy-5-nitrobenzaldehyde

To a solution of 3-chloro-4-hydroxybenzaldehyde (400 mg, 2.55 mmol) in acetic acid (5 mL) was added concentrated nitric acid (0.1 mL) and at 0° C., the resulting suspension was stirred at 25° C. for 6 h. The mixture was poured into ice water; the solid was collected by filtration, washed with water (30 mL) and dried in vacuo to give Intermediate 59 (300 mg, 58.4%).

Intermediate 60: 1-(3-chloro-5-fluorophenyl)-2-phenylethanone

Step 1: Synthesis of 3-chloro-5-fluoro-N-methoxy-N-methylbenzamide

Followed the procedure described in Step 1 of Intermediate 7, starting from 3-chloro-5-fluorobenzoic acid.

Step 2: Synthesis of 1-(3-chloro-5-fluorophenyl)-2-phenylethanone

Followed the procedure described in Step 2 of Intermediate 22 using 3-chloro-5-fluoro-N-methoxy-N-methylbenzamide and benzylmagnesium chloride, with a purification by column chromatography to give desired Intermediate 60 (850 mg, 75%)

Intermediate 61: 5-formyl-2-hydroxy-3-nitrobenzonitrile

Step 1: Synthesis of 5-formyl-2-hydroxybenzonitrile

To a mixture of 3-bromo-4-hydroxybenzaldehyde (1.00 g, 4.97 mmol) in DMF (10 mL) was added cuprous cyanide (660 mg, 7.46 mmol). The mixture was heated at 180° C. for 8 hours. The solution was filtered off and purified by chromatography on silica gel (PE/EtOAc=8:1) (210 mg, 29%).

Step 2: Synthesis of 5-formyl-2-hydroxy-3-nitrobenzonitrile

To a solution of 5-formyl-2-hydroxybenzonitrile (200 mg, 1.36 mmol) in acetic acid (4 mL) was added slowly concentrated nitric acid (0.8 mL) at 0° C. The resulting mixture was stirred for 5 hours. Then the mixture was poured into ice-water (40 mL) and ethyl acetate (100 mL). Organic was washed with brine (80 mL), dried over sodium sulfate and evaporated in vacuo, followed by column chromatography (petroleum ether/ethyl acetate=3:1) to give Intermediate 61 (250 mg, yield 96%).

Intermediate 62: 3-ethoxy-5-formyl-2-hydroxybenzoic acid

A mixture of 3-ethoxy-5-formyl-2-hydroxybenzonitrile (Intermediate 51) (500 mg, 2.6 mmol) in NaOH aqueous solution (8 M, 10 mL) and EtOH (10 mL) was refluxed for 2 days. The mixture was acidified with HCl solution to pH=4-5 and extracted with EtOAc. The organic layer was dried over Na$_2$SO$_4$ and concentrated to give Intermediate 62 (450 mg, yield 82%).

Intermediate 63:
3-fluoro-4-hydroxy-5-nitrobenzaldehyde

Followed procedure described for Intermediate 59, starting with 3-fluoro-4-hydroxybenzaldehyde. Desired product isolated in 53% yield.

Intermediate 64:
1-(3-hydroxyphenyl)-2-phenylethanone

Step 1: Synthesis of
3-hydroxy-N-methoxy-N-methylbenzamide

Followed the procedure described in Step 1 of Intermediate 7, starting from 3-hydroxybenzoic acid, where reaction was run for 6 h at 30° C. instead of room temperature overnight.

Step 2: Synthesis of
1-(3-chloro-5-fluorophenyl)-2-phenylethanone

Followed the procedure described in Step 2 of Intermediate 22, with a purification by column chromatography (petroleum ether/ethyl acetate=10:1) to give Intermediate 64 (260 mg, yield 55.4%).

Intermediate 65:
4-hydroxy-3-nitro-5-propoxybenzaldehyde

Step 1: Synthesis of
3,4-dihydroxy-5-nitrobenzaldehyde

To a solution of 4-hydroxy-3-methoxy-5-nitrobenzaldehyde (2.0 g, 10.15 mmol) in anhydrous CH$_2$Cl$_2$ (10 mL) was added boron tribromide (4 mL) at 0° C. Reaction was warmed to room temperature and stirred for 2 hour under N$_2$. Followed a standard aqueous/EtOAc workup. The residue was purified by silica gel column chromatography (1.2 mg, yield: 64.6%).

Step 2: Synthesis of
3-nitro-4,5-dipropoxybenzaldehyde

To a solution of 3,4-dihydroxy-5-nitrobenzaldehyde (400 mg, 2.185 mmol) in DMF (5 mL) was added K$_2$CO$_3$ (603 mg, 4.37 mmol) and 1-bromopropane (0.5 mL, excess), and the reaction was stirred at 80° C. overnight. Ethyl acetate (100 mL) was added and was washed with 2N aqueous HCl solution (20 mL×1), brine (20 mL×3), dried over Na$_2$SO$_4$, filtered, concentrated. The residue was purified by column chromatography (192 mg, yield: 32.91%).

Step 3: Synthesis of
4-hydroxy-3-nitro-5-propoxybenzaldehyde

To a solution of 3-nitro-4,5-dipropoxybenzaldehyde (153 mg, 0.573 mmol) in anhydrous CH$_2$Cl$_2$ (5 mL) was added anhydrous AlCl$_3$ (151 mg, 1.15 mmol) at 0° C., after the addition, the reaction mixture was stirred at 50° C. for 1 hour. The reaction was quenched by water (20 mL), and the mixture was acidified with 2N aqueous HCl solution (20 mL), followed by a standard aqueous/EtOAc workup. Purification by column chromatography gave Intermediate 65 (126 mg, yield: 97.7%).

Intermediate 66: 1-(pyrazin-2-yl)-2-(thiophen-3-yl)ethanone

Followed same three step procedure described in Intermediate 56.

Step 1: Synthesis of pyrazine-2-carbonyl chloride

Started with 1 pyrazine-2-carboxylic acid, and used toluene instead of THF.

Step 2: Synthesis of ethyl 3-oxo-3-(pyrazin-2-yl)-2-(thiophen-3-yl)propanoate

Used crude from step 1 and ethyl 2-(thiophen-3-yl)acetate.

Step 3: Synthesis of 1-(pyrazin-2-yl)-2-(thiophen-3-yl)ethanone

Reaction was run at 180° C. for 6 hours. Purified by column chromatography (PE:EtOAc=8:1) to give Intermediate 66 (30 mg, yield 6.1%).

Intermediate 67: 2-phenyl-1-(quinolin-6-yl)ethanone

Followed same three step procedure described in Intermediate 56.

Step 1: Synthesis of quinoline-6-carbonyl chloride

Started with quinoline-6-carboxylic acid, and used toluene instead of THF.

Step 2: Synthesis of ethyl
3-oxo-2-phenyl-3-(quinolin-6-yl)propanoate

Used crude from step 1 and ethyl 2-phenylacetate.

Step 3: Synthesis of
2-phenyl-1-(quinolin-6-yl)ethanone

Reaction run at 180° C. for 6 hours. Purified by column chromatography (PE:EtOAc=5:1) to give Intermediate 67 (100 mg, 35.2%).

Intermediate 68:
1-(isoquinolin-6-yl)-2-phenylethanone

Step 1: Synthesis of isoquinoline-6-carbonitrile

Under N$_2$, a mixture of 6-bromoisoquinoline (400 mg, 1.9 mmol), Zn(CN)$_2$ (446 mg, 3.8 mmol) and Pd(PPh$_3$)$_4$ (40 mg) in DMF (20 mL) was stirred at 100° C. for 1 hour. Cooled the mixture to room temperature and dissolved in water. Followed standard aqueous/EtOAc workup and purified by column chromatography (PE:EtOAc=10:1).

Step 2: Synthesis of isoquinoline-6-carboxylic acid

A mixture of isoquinoline-6-carbonitrile (250 mg, 1.6 mmol) and aqueous KOH (5 mL, 2M) was stirred at 150° C. for 4 hours. The mixture was concentrated in vacuo and used in the next step directly.

Step 3, 4, and 5

Followed same three step procedure described in Intermediate 67 to give Intermediate 68, 1-(isoquinolin-6-yl)-2-phenylethanone.

Intermediate 69: 2-(3-methoxyphenyl)-1-(pyridin-3-yl)ethanone

Followed the three step procedure described in Intermediate 56.

Step 1: Synthesis of nicotinoyl chloride

See step 1, Intermediate 56.

Step 2: Synthesis of methyl 2-(3-methoxyphenyl)-3-oxo-3-(pyridin-3-yl)propanoate Used crude from step 1 and methyl 2-(3-methoxyphenyl) acetate.

Step 3: Synthesis of 2-(3-methoxyphenyl)-1-(pyridin-3-yl)ethanone

Reaction run at 180° C. for 1 hours. Used crude after workup.

Intermediate 70: 1-(pyridin-4-yl)-2-(thiophen-3-yl)ethanone

Followed the three step procedure described in Intermediate 56.

Step 1: Synthesis of isonicotinoyl chloride

Started with isonicotinic acid, and used toluene instead of THF.

Step 2: Synthesis of ethyl 3-oxo-3-(pyridin-4-yl)-2-(thiophen-3-yl)propanoate Used crude from step 1 and ethyl 2-(thiophen-3-yl)acetate.

Step 3: Synthesis of 1-(pyridin-4-yl)-2-(thiophen-3-yl)ethanone

Reaction run at 150° C. for 3 hours. Purified by silica gel column chromatography (petroleum ether/ethyl acetate=10:1) to give Intermediate 70 (900 mg, yield 100%).

Intermediate 71: 4-hydroxy-3-(2-hydroxyethoxy)-5-nitrobenzaldehyde

Step 1: Synthesis of 3-(2-hydroxyethoxy)-4-methoxybenzaldehyde

Followed procedure described in Intermediate 65, step 2 starting from 3-hydroxy-4-methoxybenzaldehyde and 2-bromoethanol, using crude material for next step.

Step 2: Synthesis of 4-hydroxy-3-(2-hydroxyethoxy)benzaldehyde

Followed procedure described in Intermediate 65, step 3 where reaction was refluxed for 2 days.

Step 3: Synthesis of 4-hydroxy-3-(2-hydroxyethoxy)-5-nitrobenzaldehyde

Followed procedure described for Intermediate 61, starting from the 4-hydroxy-3-(2-hydroxyethoxy)benzaldehyde to give desired product, Intermediate 71.

Intermediate 72: 1-(1-methyl-1H-pyrazol-5-yl)-2-(thiophen-3-yl)ethanone

Step 1: Synthesis of ethyl 3-(1-methyl-1H-pyrazol-5-yl)-3-oxo-2-(thiophen-3-yl)propanoate To a solution of 1-methyl-1H-pyrazole-5-carboxylic acid (300 mg, 2.4 mmol) in DMF (7 mL) was added CDI (372 mg, 2.6 mmol), and the reaction mixture was heated to 50° C. for two hours. Then the mixture was cooled to −5° C., a solution of ethyl 2-(thiophen-3-yl)acetate (444 mg, 2.6 mmol) in DMF (1 mL) was added to the mixture and NaH (330 mg, 8.2 mmol) was added in portions. The mixture was stirred at 0° C. for 10 minutes, then warmed to room temperature and stirred for 1 hour. Ice water was added, followed by a standard aqueous/EtOAc workup. Crude was purified by column chromatography (PE:EtOAc=5:1) (150 mg, yield: 22.7%).

Step 2: Synthesis of 1-(1-methyl-1H-pyrazol-5-yl)-2-(thiophen-3-yl)ethanone Followed Step 3 of Intermediate 56 starting with the above from Step 1, with purification by column chromatography (PE:EtOAc=10:1) to give Intermediate 72 (90 mg, yield: 81.1%).

Intermediate 73: 4-formyl-2-nitrobenzoic acid

Step 1: Synthesis of 4-formyl-2-nitrobenzonitrile

A mixture of 4-bromo-3-nitrobenzaldehyde (1 g, 4.35 mmol) in dimethylformamide (10 mL) was added cuprous cyanide (584.8 mg, 6.53 mmol). The resultant solution was stirred at 160° C. for 5 hours. After cooling, a standard aqueous/EtOAc workup was followed. Purified by silica gel column chromatography to give product (430 mg, yield 56.1%).

Step 2: Synthesis of 4-formyl-2-nitrobenzoic acid

A mixture of 4-formyl-2-nitrobenzonitrile (150 mg, 0.85 mmol) in conc. sulfuric acid (2 mL) and water (4 mL) was heated at 100° C. for 13 hours. Followed standard aqueous/EtOAc workup to give Intermediate 73.

Intermediate 74: 2-(3-ethylphenyl)-1-phenylethanone

Step 1: Synthesis of ethyl 2-(3-vinylphenyl)acetate

To a mixture of ethyl 2-(3-bromophenyl)acetate (1.5 g, 6.1 mmol) in anhydrous DMF (15 mL) was added tributyl(vinyl)stannane (2.1 mL, 7.4 mmol) and tetrakis(triphenylphosphine) palladium (400 mg, 0.5 mmol) under nitrogen atmosphere. The resulting mixture was stirred at 110° C. for 8 hours. Followed a standard aqueous/EtOAc workup. Purified by silica gel column chromatography (petroleum: ether/ethyl acetate=15:1) (640 mg, yield 54%).

Step 2: Synthesis of ethyl 2-(3-ethylphenyl)acetate

To a solution of ethyl 2-(3-vinylphenyl)acetate (640 mg, 3.6 mmol) in ethanol (10 mL) was added 10% of Pd/C (100 mg) and stirred at 30° C. under hydrogen atmosphere (15 psi) for 7 hours. Then the solution was filtered and the solvent was removed in vacuo (500 mg, yield 77%).

Step 3: Synthesis of 2-(3-ethylphenyl)acetic acid

To a mixture of the preceding compound (400 mg, 2.1 mmol) in ethanol (2 mL) was added sodium hydroxide (166 mg, 4.1 mmol) and water (2 mL). The resulting mixture was stirred at 26° C. for 6 hours. The reaction mixture was acidified with 2N of HCl to pH=5. Followed a standard aqueous/EtOAc workup procedure to give crude product (400.0 mg).

Step 4: Synthesis of 2-(3-ethylphenyl)-N-methoxy-N-methylacetamide

Followed Step 1 of Intermediate 7, where reaction was run for 7 h at 30° C.

Step 5: Synthesis of 2-(3-ethylphenyl)-1-phenylethanone

Followed Step 2 of Intermediate 10, to give Intermediate 74 (80 mg, yield: 14.8%).

Intermediate 75: methyl 2-chloro-4-formylbenzoate

Step 1: Synthesis of 3-chloro-4-(methoxycarbonyl)benzoic acid

To a mixture of 3-amino-4-(methoxycarbonyl)benzoic acid (781 mg, 4.0 mmol) suspended in acetic acid (10 mL) and conc. HCl (10 mL) was added aq. $NaNO_2$ (276 mg, 4.0 mmol, 5 mL) at 0° C. The resulting mixture was stirred for 30 minutes. CuCl (400 mg, 8.0 mmol) in 10 mL of conc. HCl. was added to the mixture at 0° C. The resulting mixture was stirred at 30° C. for 6 hours. Followed a standard aqueous/EtOAc workup procedure (800 mg, yield 93%).

Step 2: Synthesis of methyl 2-chloro-4-(hydroxymethyl)benzoate

To a solution of 3-chloro-4-(methoxycarbonyl)benzoic acid (400 mg, 1.9 mmol) in anhydrous THF (15 mL) was added Borane methyl sulfide complex (10 M, 0.56 mL, 5.6 mmol). The resulting solution was heated at 76° C. for 6 hours. After being cooled, the mixture was slowly poured into water (40 mL) at −10° C., then followed a standard aqueous/EtOAc workup procedure to give crude product (350 mg, yield 94%).

Step 3: Synthesis of methyl 2-chloro-4-formylbenzoate

A mixture of methyl 2-chloro-4-(hydroxymethyl)benzoate (350 mg, 1.7 mmol) in and manganese oxide (756 mg, 30.9 mmol) in dichloromethane (10 mL) was stirred at 27° C. for 6 hours. The mixture was filtered and evaporated in vacuo to give Intermediate 75 (210 mg, 61%).

Intermediate 76: 4-ethoxy-2-oxo-2,3-dihydrobenzo[d]oxazole-6-carbaldehyde

Step 1: Synthesis of ethyl 4-bromo-3,5-diethoxybenzoate

A mixture of 4-bromo-3,5-dihydroxybenzoic acid (2.0 g, 8.6 mmol), EtI (6.7 g, 43.0 mmol) and $K_2CO_3$ (5.9 g, 43.0 mmol) in DMF (20 mL) was stirred at 50° C. overnight. Followed standard aqueous/EtOAc workup (2.5 g, yield 93%).

Step 2: Synthesis of ethyl 4-cyano-3,5-diethoxybenzoate

Followed Step 1 of Intermediate 68 where reaction was stirred overnight instead of 1 hour, and crude was purified by column chromatography (PE:EtOAc=15:1) (1.0 g, yield 60%).

Step 3: Synthesis of 2,6-diethoxyterephthalic acid

A mixture of ethyl 4-cyano-3,5-diethoxybenzoate (1.0 g, 3.8 mmol) and KOH (5.0 g, 89.3 mmol) in water (30 mL) was stirred at 130° C. overnight. The mixture was acidified with aqueous HCl (2M) until pH=5. Solvent removed in vacuo and used for next step directly without further purification.

Step 4: Synthesis of diethyl 2,6-diethoxyterephthalate

Followed Step 1 of Intermediate 76 where crude was purified by column chromatography on silica gel (PE:EtOAc=10:1) to give 600 mg, yield 50%.

Step 5: Synthesis of ethyl 4-ethoxy-2-oxo-2,3-dihydrobenzo[d]oxazole-6-carboxylate A mixture of diethyl 2,6-diethoxyterephthalate (300 mg, 0.97 mmol) and $NH_2OH$ HCl salt (47 mg, 6.8 mmol) in PPA (1 mL) was stirred at 70° C. under $N_2$ atmosphere overnight. A standard aqueous/EtOAc workup procedure was followed. The residue was purified by column chromatography on silica gel (PE:EtOAc=10:1) to give 80 mg of product, yield 33%.

Step 6: Synthesis of 4-ethoxy-6-(hydroxymethyl)benzo[d]oxazol-2(3H)-one

To a solution of above from step 5 (140 mg, 0.56 mmol) in DCM (10 mL) and THF (5 mL) was added DIBAL-H (1 M, 2 mL, 2.0 mmol) at −78° C. under $N_2$ atmosphere and the reaction mixture was stirred at the same temperature for 2 hours. A standard aqueous/EtOAc workup procedure was followed, and material was used crude.

Step 7: Synthesis of 4-ethoxy-2-oxo-2,3-dihydrobenzo[d]oxazole-6-carbaldehyde

A mixture of above from step 6 (137 mg) and $MnO_2$ (500 mg) in DCM (20 mL) was stirred at 50° C. overnight. The mixture was filtered and the filtrate was concentrated under reduced pressure and purified by column chromatography on silica gel (PE:EtOAc=8:1) to give 80 mg, yield 59%.

Intermediate 77: Synthesis of 3-bromo-5-fluoro-4-hydroxybenzaldehyde

To a mixture of 3-fluoro-4-hydroxybenzaldehyde (700 mg, 5.0 mmol) in acetic acid (5 mL) and dichloromethane (5 mL) was added bromine (0.5 mL, 9.8 mmol) at 0° C. The resulting mixture was stirred at 20° C. for 7 hours and then it was poured into water (50 mL), filtrated, the filtered cake was dried to give Intermediate 77 (700 mg, yield 64%).

Intermediate 78: Synthesis of methyl 2-ethoxy-4-formyl-6-nitrobenzoate

Step 1: Synthesis of 2-ethoxy-4-formyl-6-nitrophenyl trifluoromethanesulfonate To a solution of 3-ethoxy-4-hydroxy-5-nitrobenzaldehyde (5.0 g, 23.7 mmol) and triethylamine (11.9 g, 118.5 mmol) in anhydrous DCM (70 mL) was added trifluoromethanesulfonic anhydride (10.0 g, 35.6 mmol) dropwise at 0° C. The mixture was stirred under $N_2$ atmosphere for 1 hr. The reaction was quenched with water (100 mL), followed by a standard aqueous/EtOAc workup. The residue was purified by silica gel column chromatography (PE:EtOAc=50:1 to PE:EtOAc=5:1) (6.2 g, yield 76%).

Step 2: Synthesis of 3-ethoxy-4-iodo-5-nitrobenzaldehyde

To a solution of 2-ethoxy-4-formyl-6-nitrophenyl trifluoromethanesulfonate (4.7 g, 13.7 mmol) in DMSO (10 mL) was added sodium iodide (6.2 g, 41.1 mmol). The mixture was stirred under $N_2$ atmosphere at 3-10° C. overnight. EtOAc/aqueous workup. Purified by silica gel column chromatography (PE:EtOAc=50:1 to PE:EtOAc=10:1) (4.0 g, yield 91%).

Step 3: Synthesis of methyl 2-ethoxy-4-formyl-6-nitrobenzoate

To a solution of the above (4.0 g, 12.5 mmol) in DMF (30 mL) was added Pd(OAc)$_2$ (40 mg, 0.2 mmol), dppf (50 mg, 0.09 mmol), triethylamine (3.8 g, 37.4 mmol) and methanol (20 mL, excess). The mixture was stirred under CO atmosphere (30 psi) at 75° C. overnight. The reaction mixture was filtered and concentrated under reduced pressure. Purified by silica gel column chromatography (PE:EtOAc=20:1 to PE:EtOAc=5:1) to give Intermediate 78 (1.5 g, yield 48%).

Intermediate 79: Synthesis of 4-hydroxy-3-nitro-5-(trifluoromethyl)benzaldehyde To a mixture of 4-hydroxy-3-(trifluoromethyl)benzaldehyde (200 mg, 1.05 mmol) suspended in conc. sulfuric acid (2 mL) was added conc. nitric acid (0.1 mL) slowly at 0° C. for 5 min. The mixture was poured into ice water (30 mL), isolated by filtration, dried to give Intermediate 78 (210 mg, yield 85%) as yellow solid.

Intermediate 80: 4-hydroxy-3-(2-methoxyethoxy)-5-nitrobenzaldehyde

Step 1: Synthesis of 4-methoxy-3-(2-methoxyethoxy)benzaldehyde

Followed the procedure described in Step 2 of Intermediate 65 starting from 3-hydroxy-4-methoxybenzaldehyde, isolated 2.4 g, yield 89%.

Step 2: Synthesis of 4-hydroxy-3-(2-methoxyethoxy)benzaldehyde

Followed the procedure described in Step 3 of Intermediate 65, where the reaction was refluxed for 2 days. Isolated 900 mg, yield 97% after column chromatography (PE:EtOAc=10:1).

Step 3: Synthesis of 4-hydroxy-3-(2-methoxyethoxy)-5-nitrobenzaldehyde

Followed the procedure described in Step 2 of Intermediate 61, where crude was taken on without purification. Product (450 mg, 92%) was isolated as a yellow solid.

Intermediate 81: 4-(tert-butyldimethylsilyloxy)-3-nitro-5-propylbenzaldehyde

Step 1: Synthesis of ethyl 4-(allyloxy)benzoate

To a mixture of ethyl 4-hydroxybenzoate (10.0 g, 60.0 mmol) in acetone (100 mL) was added $K_2CO_3$ (33.0 g, 239.1 mmol) at 10° C.; stirred for 0.5 hour. Then 3-bromo-propene (8.0 g, 66.0 mmol) was added dropwise and the reaction mixture was stirred at 10° C. for 5 hours. The resulting mixture was filtered and the filtrate was concentrated under reduced pressure to give product (12.0 g, 96%).

Step 2: Synthesis of ethyl 3-allyl-4-hydroxybenzoate

A mixture of the above crude (10.0 g, 48.5 mmol) in Ph$_2$O (50 mL) was stirred at 200° C. for 5 hours. Cooled reaction and purified by column chromatography on silica gel (PE:EtOAc=50:1) to give product (6.7 g, yield 67%).

Step 3: Synthesis of ethyl 4-hydroxy-3-propylbenzoate

Followed Step 2 of Intermediate 74, gave 5.5 g, yield 81% of product.

Step 4: Synthesis of ethyl 4-hydroxy-3-nitro-5-propylbenzoate

Followed the procedure described in Step 2 of Intermediate 61, where reaction was complete in 10 min. and crude was taken on without purification. Product (1.3 g, yield 97%) was isolated as a yellow oil.

Step 5: Synthesis of ethyl 4-(tert-butyldimethylsilyloxy)-3-nitro-5-propylbenzoate A mixture of ethyl 4-hydroxy-3-nitro-5-propylbenzoate (1.5 g, 5.9 mmol), TBSCl (1.3 g, 8.9 mmol) and imidazole (800 mg, 11.8 mmol) in DMF (20 mL) was stirred at 30° C. overnight. A standard aqueous/EtOAc workup was followed by a purification by column chromatography (PE:EtOAc=15:1) to give product as a yellow oil (1.9 g, yield 86%).

Step 6: Synthesis of (4-(tert-butyldimethylsilyloxy)-3-nitro-5-propylphenyl)methanol Followed Step 6 of Intermediate 76 to give crude product as a yellow oil (200 mg, yield 75%).

Step 7: Synthesis of 4-(tert-butyldimethylsilyloxy)-3-nitro-5-propylbenzaldehyde Followed Step 7 of Intermediate 76 where reaction was stirred at 30° C. overnight. Product was isolated after workup and was taken on crude as a yellow oil (100 mg, yield 50%).

Intermediate 82: methyl 4-formyl-2-(trifluoromethyl)benzoate

Step 1: Synthesis of 4-formyl-2-(trifluoromethyl)phenyl trifluoromethanesulfonate To a mixture of 4-hydroxy-3-(trifluoromethyl)benzaldehyde (500 mg, 2.7 mmol), TEA (805 mg, 8.0 mmol) in anhydrous DCM (10 mL) was added $Tf_2O$ (820 mg, 2.9 mmol) drop wise at 0° C., and stirred at the same temperature for 30 mins. Followed a standard aqueous/EtOAc workup and purified by column chromatography (PE:EtOAc=10:1) to give product (560 mg, 66% yield).

Step 2: Synthesis of methyl 4-formyl-2-(trifluoromethyl)benzoate

To a mixture of the compound from step 1 (500 mg, 1.6 mmol) in MeOH (20 mL) and DMF (5 mL) was added $Pd(OAc)_2$ (10 mg, 0.05 mmol), dppf (10 mg, 0.02 mmol) and TEA (2 drops) under argon atmosphere. The suspension was degassed under vacuum and purged with carbon monoxide for several times. Then the mixture was stirred at 70° C. under carbon monoxide atmosphere (40 psi) for 12 hours. The mixture was filtered through a pad of Celite and the filter cake was washed with EtOAc. The solvent was removed in vacuo. Purified crude by column chromatography (PE:EtOAc=10:1) to give Intermediate 82 (180 mg, yield 38%).

Intermediate 83: methyl 2-fluoro-4-formyl-6-hydroxybenzoate

Step 1: Synthesis of 2-fluoro-4-formyl-6-methoxyphenyl trifluoromethanesulfonate Followed the procedure described in Intermediate 82, Step 1 to give product, 61% yield.

Step 2: Synthesis of methyl 2-fluoro-4-formyl-6-methoxybenzoate

A mixture of the compound from above (step 1) (1.1 g, 3.6 mmol), $Pd(OAc)_2$ (200 mg, 0.89 mmol), dppf (200 mg, 0.36 mmol) and $Et_3N$ (2 mL) in MeOH (50 mL) and DMF (2 mL) was stirred under CO atmosphere (50 psi) at 80° C. overnight. The resulting mixture was cooled and filtered. A standard aqueous/EtOAc workup was followed by purification by column chromatography on silica gel (PE:EtOAc=15:1) to give product as an off-white solid (280 mg, yield 36%).

Step 3: Synthesis of methyl 2-fluoro-4-formyl-6-hydroxybenzoate

Followed procedure described in Intermediate 65, step 3 where reaction was complete after refluxing 5 min. Product was taken on crude without purification (250 mg, yield 96%).

Intermediate 84: methyl 4-formyl-2-hydroxybenzoate

Step 1: Synthesis of 4-formyl-2-methoxyphenyl trifluoromethanesulfonate

Followed the procedure described in Intermediate 82, Step 1, where addition occurred at room temperature, and reaction was run at same temperature for 1 h. Isolated product as oil (17.0 g, yield 91%).

Step 2: Synthesis of methyl 4-formyl-2-methoxybenzoate

Followed the procedure described in Intermediate 83, Step 2, to give product as a colorless solid (2.6 g, yield 76%).

Step 3: Synthesis of methyl 4-formyl-2-hydroxybenzoate

Followed procedure described in Intermediate 65, step 3 where reaction was complete after refluxing 5 min. Product was taken on crude without purification (2.2 g, yield 92%).

Intermediate 85: methyl 2-ethoxy-4-formyl-6-hydroxybenzoate

Step 1: Synthesis of ethyl 4-bromo-3,5-diethoxybenzoate

Described in Step 1 of Int. 76.

Step 2: Synthesis of (4-bromo-3,5-diethoxyphenyl)methanol

Followed the procedure described in Step 6 of Int. 76 to give a white solid (4.2 g, yield 98%).

Step 3: Synthesis of methyl 2,6-diethoxy-4-(hydroxymethyl)benzoate

Followed the procedure described in Intermediate 83, Step 2, except reaction was stirred under CO atmosphere (5 MPa) at 120° C. for 3 days. Isolated product after column as an off-white solid (1.0 g, 36%).

Step 4: Synthesis of methyl 2,6-diethoxy-4-formylbenzoate

Followed Step 7 of Intermediate 76 where reaction was refluxed 1 hour. Product (950 mg, yield 96%) was isolated after workup.

Step 5: Synthesis of methyl 2-ethoxy-4-formyl-6-hydroxybenzoate

Followed procedure described in Intermediate 65, step 3 where reaction was complete after stirring at 10° C. for 5 minutes. Isolated product after column chromatography as off-white solid (500 mg, yield 59%).

Intermediate 86: methyl 2-chloro-4-formyl-6-hydroxybenzoate

Followed the three step procedure described for preparing Intermediate 84, starting from 3-chloro-4-hydroxy-5-methoxybenzaldehyde.

Step 1: 2-chloro-4-formyl-6-methoxyphenyl trifluoromethanesulfonate 1.9 g, yield 56%.

Step 2: methyl 2-chloro-4-formyl-6-methoxybenzoate 370 mg, yield 52%.

Step 3: methyl
2-chloro-4-formyl-6-hydroxybenzoate 290 mg, yield 84%.

Intermediate 87: methyl
4-formyl-2-hydroxy-6-methoxybenzoate

Followed the procedure described for Intermediate 85, steps 3, 4, and 5.

Step 1: methyl
4-(hydroxymethyl)-2,6-dimethoxybenzoate

Isolated 750 mg, yield 20%.

Step 2: methyl 4-formyl-2,6-dimethoxybenzoate

Isolated 700 mg, yield 94%.

Step 3: methyl
4-formyl-2-hydroxy-6-methoxybenzoate

Isolated 500 mg, yield 82%.

Intermediate 88:
1-(1-methyl-1H-pyrazol-4-yl)-2-phenylethanone

Step 1: Synthesis of
N-methoxy-N,1-dimethyl-1H-pyrazole-4-carboxamide

Followed the procedure described in Step 1 of Intermediate 7, starting from 1-methyl-1H-pyrazole-4-carboxylic acid, with the following deviation: the reaction was run at 9-17° C. overnight. Isolated 4.6 g, yield 69%.

Step 2: Synthesis of
1-(1-methyl-1H-pyrazol-4-yl)-2-phenylethanone

Followed the procedure described in Step 2 of Intermediate 22, with the following deviation: crude was purified by silica gel column chromatography (PE:EtOAc=10:1) (4.0 g, yield 74%).

Intermediate 89: 3-(2-(dimethylamino)ethoxy)-4-hydroxy-5-nitrobenzaldehyde

Step 1: Synthesis of
3-(2-(dimethylamino)ethoxy)-4-methoxybenzaldehyde

To a solution of 2-(dimethylamino)ethanol (5.0 g, 56.0 mmol) and triethylamine (8.5 g, 84.0 mmol) in anhydrous DCM (50 mL) was added methanesulfonyl chloride (7.1 g, 62.0 mmol) at 0° C. under $N_2$. The mixture was stirred at 0° C. for 1 hour. The solvent was removed in vacuo (6.0 g, yield 65%), and the crude was taken up in $CH_3CN$ (100 mL). 3-hydroxy-4-methoxybenzaldehyde (5.5 g, 36.0 mmol) and potassium carbonate (13.8 g, 100.0 mol) was added and reaction was refluxed under $N_2$ overnight. An aqueous/EtOAc workup was followed, and crude was purified by silica gel column chromatography (PE:EtOAc=3:1) to give product (2.5 g, yield 31%) as yellow solid.

Step 2: Synthesis of
3-(2-(dimethylamino)ethoxy)-4-hydroxybenzaldehyde

Followed the procedure described in Intermediate 65, step 3 where the reaction was refluxed for 2 days. Column chromatography (PE:EtOAc=3:1) gave product (620 mg, yield 66%).

Step 3: Synthesis of 3-(2-(dimethylamino)ethoxy)-4-hydroxy-5-nitrobenzaldehyde

Followed procedure for Intermediate 59 to give Intermediate 89 (250 mg, 34%) as a yellow solid.

Intermediate 90:
2-phenyl-1-(tetrahydrofuran-2-yl)ethanone

Step 1: Synthesis of
N-methoxy-N-methyltetrahydrofuran-2-carboxamide

Followed the procedure described in Intermediate 10, Step 1, starting with tetrahydrofuran-2-carboxylic acid to give product (680 mg, yield: 49.7%).

Step 2: Synthesis of
2-phenyl-1-(tetrahydrofuran-2-yl)ethanone

Followed the procedure described in Intermediate 22, Step 2 to give Intermediate 90, 520 mg, yield: 63.9%.

Intermediate 91: 1-cyclopentyl-2-phenylethanone

To a solution of titanium(IV) isopropoxide (5.13 mmol, 1.46 g) in anhydrous tetrahydro-furan (10 mL) was added a solution of cyclopentylmagnesium chloride in THF (7.69 mmol) at −78° C. Reaction was warmed to −50° C. in 5 min, then maintained at that temperature for 8 min and reaction became dark-brown to black. After cooling back to −78° C., 2-phenylacetonitrile (600 mg, 5.13 mmol) was added by a syringe, and the mixture was stirred at −78° C. for 2 h. 1 N HCl aqueous solution was added to quench the reaction. The mixture was extracted with acetic acid ethyl ester (40 mL) for three times, the combined organic layer was washed with brine (30 mL), dried over $Na_2SO_4$, filtered and concentrated. The residue was purified by silica gel column chromatography to give Intermediate 91 (320 mg, yield: 66.5%) as light green oil.

Intermediate 92:
2-phenyl-1-(tetrahydrofuran-3-yl)ethanone

Step 1: Synthesis of
N-methoxy-N-methyltetrahydrofuran-3-carboxamide

Followed the procedure described in Intermediate 10, Step 1, starting with tetrahydrofuran-3-carboxylic acid to give product (0.8 g, yield 29.6%) as an oil.

Step 2: Synthesis of
2-phenyl-1-(tetrahydrofuran-3-yl)ethanone

Followed the procedure described in Intermediate 22, Step 2, where crude was purified by column chromatography (PE:EtOAc=15:1) on silica gel to give Intermediate 92 (130 mg, yield 54.6%) as an oil.

Intermediate 93:
(S)-2-phenyl-1-(tetrahydrofuran-2-yl)ethanone

Step 1: Synthesis of (S)—N-methoxy-N-methyltetrahydrofuran-2-carboxamide

Followed the procedure described in Intermediate 10, Step 1, starting with (S)-tetrahydrofuran-2-carboxylic acid to give product (1.2 g, yield 42%).

Step 2: Synthesis of (S)-2-phenyl-1-(tetrahydrofuran-2-yl)ethanone

Followed the procedure described in Intermediate 22, Step 2 with a purification by silica gel column chromatography (eluting from PE:EtOAc=20:1 to PE:EtOAc=5:1) to give Intermediate 93 (460 mg, yield 67%).

Intermediate 94:
(R)-2-phenyl-1-(tetrahydrofuran-2-yl)ethanone

Step 1: Synthesis of (R)—N-methoxy-N-methyltetrahydrofuran-2-carboxamide

Followed the procedure described in Intermediate 10, Step 1, starting with (R)-tetrahydrofuran-2-carboxylic acid to give product (1.2 g, yield 44%).

Step 2: Synthesis of (R)-2-phenyl-1-(tetrahydrofuran-2-yl)ethanone

Followed the procedure described in Intermediate 22, Step 2 with a purification by silica gel column chromatography (eluting from PE:EtOAc=20:1 to PE:EtOAc=5:1) to give Intermediate 94 (400 mg, yield 56%).

Intermediate 95:
1-cyclohexyl-2-(thiophen-3-yl)ethanone

Step 1: Synthesis of cyclohexanecarbonyl chloride

Followed the procedure described in Step 1 of Intermediate 56, starting with cyclohexanecarboxylic acid.

Step 2: Synthesis of ethyl 3-cyclohexyl-3-oxo-2-(thiophen-3-yl)propanoate

Followed the procedure described in Step 2 of Intermediate 56. Used crude from step 1 and ethyl 2-(thiophen-3-yl)acetate. Crude product was taken forward without purification.

Step 3: Synthesis of 1-cyclohexyl-2-(thiophen-3-yl)ethanone

Followed the procedure described in Step 3 of Intermediate 56.

Intermediate 96: 2-cyclohexyl-1-phenylethanone

To a suspension of Mg (735 mg, 30.5 mmol) in anhydrous THF (20 mL) was added (bromomethyl)cyclohexane (5.4 g, 30.5 mmol) at 10° C. under $N_2$ atmosphere. The resulting mixture was stirred at reflux until all of Mg was consumed. Then the resulting mixture was cooled to ambient temperature and N-methoxy-N-methylbenzamide (1.0 g, 6.1 mmol) was added and the mixture was stirred at 10° C. for 2 hours. The mixture was quenched with aqueous saturated $NH_4Cl$ (50 mL). Followed a standard aqueous/EtOAc workup and the residue was purified by column chromatography on silica gel (PE:EtOAc=20:1) to give Intermediate 96 as colorless oil (800 mg, yield 67%).

Example 179

GSNOR Assays

Various compounds were tested in vitro for their ability to inhibit GSNOR activity. GSNOR inhibitor compounds in Examples 1-87, 89-91, 93, 95-103, 105-170, 172-177 had an $IC_{50}$ of about <100 μM. GSNOR inhibitor compounds in Examples 1, 2, 4-13, 15-17, 20-23, 26, 28-39, 43-61, 63, 65, 67, 69, 71, 73, 77-81, 83-86, 95, 101-102, 105-116, 118-121, 125-139, 141-143, 146-148, 150-152, 154-156, 158-161, 163, 165, 167, 169, 170, 172-175, and 177 had an $IC_{50}$ of about <1.0 μM. GSNOR inhibitor compounds in Examples 1, 2, 4-6, 9, 13, 15-17, 20-21, 23, 29, 31-39, 43-51, 53, 55-57, 61, 63, 65, 67, 71, 73, 78-79, 81, 83, 101-102, 107-109, 111, 113, 115-116, 118-121, 125, 129-139, 141-143, 146, 148, 155-156, 158-159, 161, 163, 165, 167, 169, 172, 174, and 177 had an $IC_{50}$ of about less than 0.1 μM. GSNOR expression and purification is described in Biochemistry 2000, 39, 10720-10729.

GSNOR Fermentation:

Pre-cultures were grown from stabs of a GSNOR glycerol stock in 2XYT media containing 100 ug/ml ampicillin after an overnight incubation at 37° C. Cells were then added to fresh 2XYT (4 L) containing ampicillin and grown to an OD ($A_{600}$) of 0.6-0.9 at 37° C. before induction. GSNOR expression was induced with 0.1% arabinose in an overnight incubation at 20° C.

GSNOR Purification:

E. coli cell paste was lysed by nitrogen cavitation and the clarified lysate purified by Ni affinity chromatography on an AKTA FPLC (Amersham Pharmacia). The column was eluted in 20 mM Tris pH 8.0/250 mM NaCl with a 0-500 mM imidazole gradient. Eluted GSNOR fractions containing the Smt-GSNOR fusion were digested overnight with Ulp-1 at 4° C. to remove the affinity tag then re-run on the Ni column under the same conditions. GSNOR was recovered in the flowthrough fraction and for crystallography is further purified by Q-Sepharose and Heparin flowthrough chromatography in 20 mM Tris pH 8.0, 1 mM DTT, 10 uM $ZnSO_4$.

GSNOR Assay:

GSNO and Enzyme/NADH Solutions are made up fresh each day. The Solutions are filtered and allowed to warm to room temperature. GSNO Solution: 100 mM NaPO4 (pH 7.4), 0.480 mM GSNO. 396 μL of GSNO Solution is added to a cuvette followed by 8 μL of test compound in DMSO (or DMSO only for full reaction control) and mixed with the pipette tip. Compounds to be tested are made up at a stock concentration of 10 mM in 100% DMSO. 2 fold serial dilutions are done in 100% DMSO. 8 μL of each dilution are added to an assay so that the final concentration of DMSO in the assay is 1%. The concentrations of compounds tested range from 100 to 0.003 μM. Enzyme/NADH Solution: 100 mM NaPO4 (pH 7.4), 0.600 mM NADH, 1.0 μg/mL GSNO Reductase. 396 μL of the Enzyme/NADH Solution is added to the cuvette to start the reaction. The cuvette is placed in the Cary 3E UV/Visible Spectrophotometer and the change in 340 nm absorbance/min at 25° C. is recorded for 3 minutes. The assays are done in triplicate for each compound concentration. $IC_{50}$'s for each compound are calculated using the standard curve analysis in the Enzyme Kinetics Module of SigmaPlot.

Final assay conditions: 100 mM NaPO4, pH 7.4, 0.240 mM GSNO, 0.300 mM NADH, 0.5 µg/mL GSNO Reductase and 1% DMSO. Final volume: 800 µL/cuvette.

Example 180

Efficacy of GSNORi in Experimental Asthma

Experimental Asthma Model:

A mouse model of ovalbumin (OVA)-induced asthma is used to screen GSNOR inhibitors for efficacy against methacholine (MCh)-induced bronchoconstriction/airway hyperreactivity. This is a widely used and well characterized model that presents with an acute, allergic asthma phenotype with similarities to human asthma. Efficacy of GSNOR inhibitors are assessed using a prophylactic protocol in which GSNOR inhibitors are administered prior to challenge with MCh. Bronchoconstriction in response to challenge with increasing doses of MCh is assessed using whole body plethysmography ($P_{enh}$; Buxco). The amount of eosinophil infiltrate into the bronchoaveolar lavage fluid (BALF) is also determined as a measure of lung inflammation. The effect of GSNOR inhibitors are compared to vehicles and to Combivent (inhaled; IH) as the positive control.

Materials and Method

Allergen Sensitization and Challenge Protocol

OVA (500 µg/ml) in PBS is mixed with equal volumes of 10% (w/v) aluminum potassium sulfate in distilled water and incubated for 60 min. at room temperature after adjustment to pH 6.5 using 10 N NaOH. After centrifugation at 750×g for 5 min, the OVA/alum pellet is resuspended to the original volume in distilled water. Mice receive an intraperitoneal (IP) injection of 100 µg OVA (0.2 mL of 500 µg/mL in normal saline) complexed with alum on day 0. Mice are anesthetized by IP injection of a 0.2-mL mixture of ketamine and xylazine (0.44 and 6.3 mg/mL, respectively) in normal saline and are placed on a board in the supine position. Two hundred fifty micrograms (100 µl of a 2.5 mg/ml) of OVA (on day 8) and 125 µg (50 µl of 2.5 mg/ml) OVA (on days 15, 18, and 21) are placed on the back of the tongue of each animal.

Pulmonary Function Testing (Penh)

In vivo airway responsiveness to methacholine is measured 24 h after the last OVA challenge in conscious, freely moving, spontaneously breathing mice with whole body plethysmography using a Buxco chamber (Wilmington, N.C.). Mice are challenged with aerosolized saline or increasing doses of methacholine (5, 20 and 50 mg/mL) generated by an ultrasonic nebulizer for 2 min. The degree of bronchoconstriction is expressed as enhanced pause ($P_{enh}$), a calculated dimensionless value, which correlates with the measurement of airway resistance, impedance, and intrapleural pressure in the same mouse. $P_{enh}$ readings are taken and averaged for 4 min. after each nebulization challenge. $P_{enh}$ is calculated as follows: $P_{enh}=[(T_e/T_r-1)\times(PEF/PIF)]$, where $T_e$ is expiration time, $T_r$ is relaxation time, PEF is peak expiratory flow, and PIF is peak inspiratory flow×0.67 coefficient. The time for the box pressure to change from a maximum to a user-defined percentage of the maximum represents the relaxation time. The $T_r$ measurement begins at the maximum box pressure and ends at 40%.

Eosinophil Infiltrate in BALF

After measurement of airway hyper-reactivity, the mice are exsanguinated by cardiac puncture, and then BALF is collected from either both lungs or from the right lung after tying off the left lung at the mainstem bronchus. Total BALF cells are counted from a 0.05 mL aliquot, and the remaining fluid is centrifuged at 200×g for 10 min at 4° C. Cell pellets are resuspended in saline containing 10% BSA with smears made on glass slides. Eosinophils are stained for 5 min. with 0.05% aqueous eosin and 5% acetone in distilled water, rinsed with distilled water, and counterstained with 0.07% methylene blue.

GSNOR Inhibitors and Controls

GSNOR inhibitors are reconstituted in phosphate buffered saline (PBS), pH 7.4, at concentrations ranging from 0.00005 to 3 mg/mL. GSNOR inhibitors are administered to mice (10 mL/kg) as a single dose either intravenously (IV) or orally via gavage. Dosing is performed from 30 min. to 24 h prior to MCh challenge. Effect of GSNOR inhibitors are compared to PBS vehicle dosed in the same manner.

Combivent is used as the positive control in all studies. Combivent (Boehringer Ingelheim) is administered to the lung using the inhaler device supplied with the product, but adapted for administration to mice, using a pipette tip. Combivent is administered 48 h, 24 h, and 1 h prior to MCh challenge. Each puff (or dose) of Combivent provides a dose of 18 µg ipatropium bromide (IpBr) and 103 µg albuterol sulfate or approximately 0.9 mg/kg IpBr and 5 mg/kg albuterol.

Statistical Analyses

Area under the curve values for $P_{enh}$ across baseline, saline, and increasing doses of MCh challenge are calculated using GraphPad Prism 5.0 (San Diego, Calif.) and expressed as a percent of the respective (IV or orally administered) vehicle control. Statistical differences among treatment groups and the respective vehicle control group within each study are calculated using one-way ANOVA, Dunnetts (JMP 8.0, SAS Institute, Cary, N.C.). A p value of <0.05 among the treatment groups and the respective vehicle control group is considered significantly different.

Example 181

Mouse Pharmacokinetic (PK) Study

Experimental Model

The mouse can be used to determine the pharmacokinetics of compounds of the invention. This species is widely used to assess the bioavailability of compounds by administering both oral (PO) and intravenous (IV) test articles. Efficacy of the compounds of the invention can be compared by assessing plasma exposure in male BALB/c mice either via IV or PO administration at the times of peak activity.

Materials and Methods

IV Administration of Compounds of the Invention

Compounds of the invention can be reconstituted in a phosphate buffered saline (PBS)/10% Solutol (HS 15) clear solution resulting in a concentration of 0.2 mg/mL and administered to mice (2 mg/kg) as a single IV dose. Animals dosed via the lateral tail vein. Blood samples are collected at designated time points (0.083, 0.25, 0.5, 1, 2, 4, 8, 16, 24 hours) by cardiac puncture under isoflurane anesthesia (up to 1 mL blood per animal). The blood is collected into tubes containing Li-Heparin. The blood samples are kept on ice until centrifugation within approximately 30 minutes of collection. The plasma is transferred into labeled polypropylene tubes and frozen at −70° C. until analyzed by LC/MS/MS.

PO Administration of Compounds of the Invention

The compounds of the invention can be reconstituted in 40% Propylene Glycol/40% Propylene Carbonate/20% of a 5% Sucrose clear solution resulting in a concentration of 2 mg/mL and administered to mice (10 mg/kg) as a single oral dose via gavage. Blood samples are collected at 0.25, 0.5, 1, 2, 4, 8, 12, 16, 20 and 24 hours post dose by cardiac puncture under isoflurane anesthesia. The blood is collected in tubes containing Li-Heparin. The blood samples are kept on ice until centrifugation within approximately 30 minutes of collection. The plasma is transferred into labeled polypropylene tubes and frozen at −70° C. until analyzed by LC/MS/MS.

LC/MS/MS Analysis

Plasma samples at each timepoint can be analyzed using a LC-MS/MS with a lower limit of quantification (LLOQ) of 1 ng/mL. Plasma is analyzed to determine the amount of the compound of the invention in each sample and regression curves generated for each compounds of the invention in the relevant matrixes.

WinNonlin analysis is used for calculating PK parameters for both the IV and PO administrations:

PK parameters for IV portion—$AUC_{last}$; $AUC_{last}$; T½; Cl; Vss; $C_{max}$; MRT PK parameters for PO portion—$AUC_{last}$; $AUC_{INF}$; T½; $C_{max}$; Cl, MRT.

In addition to the above PK parameters, bioavailability (% F) can be calculated.

Example 182

Efficacy of GSNOR Inhibitors in Experimental Inflammatory Bowel Disease (IBD)

Experimental Model

An acute model of dextran sodium sulfate (DSS)-induced IBD in mice is used to explore efficacy of GSNOR inhibitors against this disease. Acute DSS-induced IBD is a widely used and well characterized model that induces pathological changes in the colon similar to those observed in the human disease. In this model and in human disease, epithelial cells within the crypts of the colon are disrupted, leading to dysfunction of the epithelial barrier and the ensuing tissue inflammation, edema, and ulceration. GSNOR inhibitor therapy may benefit IBD by restoring s-nitrosogluthathione (GSNO) levels, and thus prevent or reverse the epithelial barrier dysfunction.

Experimental IBD is induced by administration of DSS in the drinking water over several days. GSNOR inhibitors are administered daily via intravenous (IV) dosing. Effect of treatment is assessed via endoscopy and histopathology using a five point scale ranging from a score=0 (normal tissue) to a score=4 (ulcerative tissue damage and marked pathological changes). The effect of GSNOR inhibitors is compared to vehicle treated controls. The corticosteroid, prednisolone, is used as the positive control in this study and is administered daily via oral dosing. Naïve mice are also assessed as a normal tissue control.

Materials and Methods

Experimental IBD is induced by administration of 3% DSS in the drinking water on study days 0 to 5. GSNOR inhibitors are reconstituted to concentrations of 0.2 and 2 mg/ml in phosphate buffered saline (PBS), pH 7.4. Mice are treated daily via IV administration of 0.1 ml GSNOR inhibitor solution per mouse for doses of 1 and 10 mg/kg/day. GSNOR inhibitor dosing is started 2 days prior to the DSS administration and continued through the last day of the study (days −2 to 7). PBS is used as the vehicle control and is administered in the same manner as the GSNOR inhibitor. The corticosteroid, prednisolone, is used as the positive control for the study, and is administered orally at a dose of 3 mg/kg/day on each day (study days −2 to 7).

The effect of drug treatment is assessed on day 7 via endoscopy and histopathology. Mice are first anesthetized with inhaled isoflurane and subjected to endoscopy using a veterinary endoscope (Karl Storz Veterinary Endoscopy America, Inc., Goleta, Calif.). Each mouse is scored for mucosal injury using the endoscopy scoring criteria. An endoscopy score of 0 is normal, 1 is loss of vascularity, 2 is loss of vascularity and friability, 3 is friability and erosions, and 4 is ulcerations and bleeding. Following endoscopy, mice are euthanized via asphyxiation with inhaled carbon dioxide. Colon sections are then formalin-fixed, paraffin-embedded, sectioned, and stained with hematoxylin-eosin. Colon sections are examined via light microscopy and scored in a blinded fashion by a board certified veterinary pathologist with particular expertise in GI pathology. Pathological changes to the epithelium, connective tissue, and submucosa are scored based on inflammation, edema, and necrosis, and a score of 0 is normal, 1 is minimal, 2 is mild, 3 is moderate, and 4 is marked.

Example 183

Efficacy of GSNOR Inhibitors in Experimental Chronic Obstructive Pulmonary Disease (COPD)

Experimental COPD Model

An acute model of elastase-induced COPD in mice is used to explore efficacy of GSNOR inhibitors against this disease. Elastase-induced COPD is a widely used and well characterized model that induces pathological changes in the lung similar to those observed in the human disease. In this model and in human disease, airway obstruction, pulmonary inflammation, and airspace enlargement are evident. GSNOR inhibitor therapy may benefit COPD through the bronchodilatory and anti-inflammatory actions of these compounds.

Experimental COPD is induced by administration of the elastases, papain and porcine pancreatic elastase (PPE), into the lung over several days. GSNOR inhibitors are administered daily via oral dosing. Efficacy is determined by assessing the ability of GSNOR inhibitors to attenuate bronchoconstriction in response to methacholine (MCh) aerosol challenge, decrease pulmonary inflammation, and reduce airspace enlargement in the aveoli. The effect of GSNOR inhibitors are compared to vehicle treated controls. A combination of daily oral SP CXC receptor 2/receptor 1 (SP CXCR2/1) antagonist, which blocks recruitment of neutrophils and monocytes, and inhaled Flovent (fluticasone; corticosteroid), is used as the positive control in this study.

Materials and Methods

Experimental COPD is induced by administration of 80 µg papain and 20 U/mg PPE per mouse per day via intra-tracheal (IT) instillation on study days 0 to 7. GSNOR inhibitor is reconstituted to concentrations of 0.01, 0.1, and 1 mg/ml in phosphate buffered saline (PBS), pH 7.4. Mice are treated daily via oral administration (gavage) of 0.1 ml GSNORi solution per mouse for doses of 0.1, 1, and 10 mg/kg/day. PBS is used as the vehicle control and is administered via daily oral dosing. The small molecule antagonist SP CXCR2/R1 (Schering-Plough/Merck), which blocks receptors to cytokine chemoattractants for neutrophil and monocyte recruitment, is used in combination with the corticosteroid, Flovent (Glaxo), as the positive control for the study. SP CXCR2/R1 is dosed orally at 50 mg/kg/day. Flovent is dosed via inhalation at 220 µg/mouse/day. One group of mice is treated with GSNOR inhibitor, vehicle control, or positive control for 7 days (study days 8 to 14), while a second group of mice is treated with GSNOR inhibitor, vehicle control, or positive control for 14 days (study days 8 to 21).

The effect of drug treatment is assessed 7 and 14 days post-treatment by measuring attenuation of methacholine-induced bronchoconstriction (bronchodilatory effect), attenuation of pulmonary inflammation, and reduction of airspace enlargement in the alveoli (14 day post-treatment only).

Bronchodilatory Effect

In vivo airway responsiveness to methacholine is measured in conscious, freely moving, spontaneously breathing mice with whole body plethysmography using a Buxco chamber (Wilmington, N.C.). Mice are challenged with aerosolized saline or increasing doses of methacholine (5, 20, and 50 mg/ml) generated by an ultrasonic nebulizer for 2 min. The degree of bronchoconstriction is expressed as enhanced pause (Penh), a calculated dimensionless value, which correlated with the measurement of airway resistance, impedance, and intrapleural pressure in the same mouse. Penh readings are taken and averaged for 4 min. after each nebulization challenge. Penh is calculated as follows: Penh=$[(T_e/T_r-1)\times(PEF/PIF)]$, where $T_e$ is expiration time, $T_r$ is relaxation time, PEF is peak expiratory flow, and PIF is peak inspiratory flow×0.67 coefficient. The time for the box pressure to change from a maximum to a user-defined percentage of the maximum represented the relaxation time. The $T_r$ measurement began at the maximum box pressure and ended at 40%.

Anti-Inflammatory Effect

After measurement of airway hyper-reactivity, the mice are exsanguination by cardiac puncture, and then bronchoalveolar lavage fluid (BALF) is collected from the right lung after tying off the left lung at the mainstem bronchus. Total BALF cells are counted, and the remaining fluid is centrifuged at 200×g for 10 min. at 4° C. Cell pellets are resuspended in saline containing 10% bovine serum albumin (BSA) and smears are made on glass slides using cytospin. Cells are stained with Diff-Quik for white blood cell (WBC) differential counts via light microscopy. Epithelial cells are counted and subtracted from the total number of cells. The proportions of eosinophils, macrophages, neutrophils, and lymphocytes are counted using standard morphological criteria and expressed as a percentage of the total number of white blood cells (WBCs).

The ability of treatment to reduce levels of neutrophil and monocyte chemoattractants in the BALF are also assessed as additional parameters of anti-inflammatory effect. KC (keratinocyte chemoattractant), also known as GROα (growth-related oncogene alpha), and JE (MCP-1, monocyte chemoattractant protein), chemokines for neutrophil and monocyte recruitment, respectively, are measured using immunoassay.

Reduction of Airspace Enlargement

Both lungs are inflated under constant positive pressure at 25 cm water pressure with 10% buffered formaldehyde and then perfused-fixed. The fixed lungs are embedded in paraffin, stained with hematoxylin and eosin, and examined via light microscopy. Airspace enlargement is quantified morphologically by calculating the mean linear intercept (Lm) and average equivalent diameter of alveoli (D2).

It will be apparent to those skilled in the art that various modifications and variations can be made in the methods and compositions of the present invention without departing from the spirit or scope of the invention.

What is claimed is:

1. A method of treating asthma, cystic fibrosis or chronic obstructive pulmonary disease (COPD), which comprises administering to a patient in need thereof a therapeutically effective amount of a compound of Formula (I) or a pharmaceutically acceptable salt thereof:

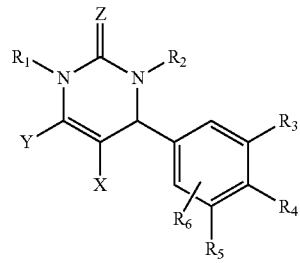

wherein
X is selected from the group consisting of aryl, substituted aryl, heteroaryl, substituted heteroaryl, cycloalkyl, substituted cycloalkyl, heterocyclyl, and substituted heterocyclyl, each having 6 members or less in the ring;
Y is selected from the group consisting of aryl, substituted aryl, heteroaryl, substituted heteroaryl, $C_4$-$C_6$ cycloalkyl, substituted $C_4$-$C_6$ cycloalkyl, heterocyclyl, and substituted heterocyclyl;
Z is selected from the group consisting of O, S and $NR_7$;
$R_1$, $R_2$ and $R_7$ are independently selected from the group consisting of hydrogen, and $C_1$-$C_6$ alkyl;
$R_3$ is selected from the group consisting of hydrogen, nitro, cyano, carboxy, carbamoyl, methylsulfonamido, fluoro, chloro, bromo, hydroxy, methylsulfonyl, and methylsulfinyl, isoxazol-4-yl, $C_1$-$C_6$ alkoxy, —C(NH)NHOH, sulfonic acid, and acetyl;
$R_4$ is selected from the group consisting of hydroxy, carboxy, and tetrazol-5-yl;
$R_5$ is selected from the group consisting of hydrogen, hydroxy, carboxy, chloro, fluoro, cyano, —O$(CH_2)_{1-6}$NMe$_2$, $C_1$-$C_6$ alkyl, —O$(CH_2)_{1-6}$OCH$_3$, —O$(CH_2)_{1-6}$OH, acetyl, CF$_3$, and $C_1$-$C_6$ alkoxy; and
$R_6$ is selected from the group consisting of hydrogen and hydroxy.

2. The method of claim 1 wherein $R_1$, $R_2$ and $R_7$ are independently selected from the group consisting of hydrogen and methyl;
$R_3$ is selected from the group consisting of hydrogen, nitro, cyano, carboxy, carbamoyl, methylsulfonamido, fluoro, chloro, bromo, methylsulfonyl, and methylsulfinyl, isoxazol-4-yl, $C_1$-$C_6$ alkoxy, —C(NH)NHOH, sulfonic acid, and acetyl;
$R_4$ is selected from the group consisting of hydroxy, carboxy, and tetrazol-5-yl;
$R_5$ is selected from the group consisting of hydrogen, hydroxy, carboxy, chloro, fluoro, cyano, —O$(CH_2)_2$NMe$_2$, $C_1$-$C_6$ alkyl, —O$(CH_2)_2$OCH$_3$, —O$(CH_2)_2$OH, acetyl, CF$_3$, methoxy, ethoxy, isopropoxy, and n-propoxy; and
$R_6$ is hydrogen.

3. The method of claim 1 wherein X is selected from the group consisting of phenyl, substituted phenyl, thiophen-yl, substituted thiophen-yl, thiazol-yl, substituted thiazol-yl, pyrazin-yl, substituted pyrazin-yl, pyridin-yl, and substituted pyridin-yl, cyclohexyl, and substituted cyclohexyl.

4. The method of claim 1 wherein X is selected from the group consisting of phenyl, thiophen-2-yl, thiophen-3-yl, thiazol-2-yl, 2-fluorophenyl, p-tolyl, m-tolyl, biphenyl-4-yl, 4-methoxyphenyl, 3-chlorophenyl, 3,4-dichlorophenyl, 3-methoxyphenyl, 3,4-dimethoxyphenyl, 4-bromophenyl, o-tolyl, 4-chlorophenyl, 2-chlorophenyl, 3-cyanophenyl, 3,4-difluorophenyl, 4-cyanophenyl, 3-carbamoylphenyl, pyrazin-2-yl, biphenyl-3-yl, 2-cyanophenyl, pyridin-4-yl, and pyridin-3-yl, 4-(dimethylamino)phenyl, 3-fluorophenyl, 3-ethylphenyl, and cyclohexyl.

5. The method of claim 1 wherein Y is selected from the group consisting of phenyl, substituted phenyl, thiophen-yl, substituted thiophen-yl, thiazol-yl, substituted thiazol-yl, pyrazin-yl, substituted pyrazin-yl, pyridin-yl, substituted pyridin-yl, furan-yl, substituted furan-yl, benzo[d][1,3]dioxol-yl, substituted benzo[d][1,3]dioxol-yl, imidazol-yl, substituted imidazol-yl, naphthalen-yl, substituted naphthalen-yl, pyrrol-yl, substituted pyrrol-yl, pyrazol-yl, substituted pyrazol-yl, tetrahydrofuran-yl, substituted tetrahydrofuran-yl, cyclopentyl, substituted cyclopentyl, cyclohexyl, and substituted cyclohexyl.

6. The method of claim 1 wherein Y is selected from the group consisting of phenyl, 3-methoxyphenyl, p-tolyl, 4-methoxyphenyl, 3,5-dichlorophenyl, 3-fluorophenyl, 4-bromophenyl, biphenyl-4-yl, 4-fluorophenyl, 4-chlorophenyl, 3-chlorophenyl, 3,4-dimethoxyphenyl, 3-fluoro-4-methoxyphenyl, 4-chloro-3-fluorophenyl, 3-chloro-4-fluorophenyl, 3,4-difluorophenyl, 3,5-difluorophenyl, 3,4-dichlorophenyl, 4-hydroxyphenyl, 2,4-difluorophenyl, furan-3-yl, 2-chlorophenyl, 3-cyanophenyl, 4-(dimethylamino)phenyl, 2-fluorophenyl, 4-morpholinophenyl, 4-aminophenyl, naphthal-2-yl, benzo[d][1,3]dioxol-5-yl, 4-cyanophenyl, naphthal-3-yl, naphthal-4-yl, 4-acetamidophenyl, thiophen-2-yl, thiophen-3-yl, 1-methyl-1H-imidazol-4-yl, naphthalene-1-yl, methyl phenylcarbamate, and naphthalene-2-yl, 4-(methanesulfonamido)phenyl, 1H-pyrrol-3-yl, 1-(phenylsulfonyl)-1H-pyrrol-3-yl, furan-2-yl, 4-(trifluoromethyl)phenyl, o-tolyl, 1-methyl-1H-pyrazol-4-yl, 1-methyl-1H-pyrazol-3-yl, 3-chloro-5-fluorophenyl, 3-hydroxyphenyl, pyrazin-2-yl, quinolin-6-yl, isoquinolin-6-yl, 1-methyl-1H-pyrazol-5-yl, tetrahydrofuran-2-yl, cyclopentyl, tetrahydrofuran-3-yl, and cyclohexyl.

7. The method of claim 1 wherein the compound of Formula (I) or a pharmaceutically acceptable salt thereof is selected from the group consisting of
4-(3-ethoxy-4-hydroxy-5-nitrophenyl)-5,6-diphenyl-3,4-dihydropyrimidin-2(1H)-one;
(S)-4-(3-ethoxy-4-hydroxy-5-nitrophenyl)-5,6-diphenyl-3,4-dihydropyrimidin-2(1H)-one;
4-(3-ethoxy-4-hydroxy-5-nitrophenyl)-6-phenyl-5-(thiophen-2-yl)-3,4-dihydropyrimidin-2(1H)-one;
4-(3-ethoxy-4-hydroxy-5-nitrophenyl)-6-phenyl-5-(thiophen-3-yl)-3,4-dihydropyrimidin-2(1H)-one;
(S)-4-(3-ethoxy-4-hydroxy-5-nitrophenyl)-6-phenyl-5-(thiophen-3-yl)-3,4-dihydropyrimidin-2(1H)-one;
4-(3-ethoxy-4-hydroxy-5-nitrophenyl)-5,6-diphenyl-3,4-dihydropyrimidine-2(1H)-thione;
4-(4-hydroxy-3-methoxy-5-nitrophenyl)-5,6-diphenyl-3,4-dihydropyrimidin-2(1H)-one;
4-(3,4-dihydroxy-5-nitrophenyl)-5,6-diphenyl-3,4-dihydropyrimidin-2(1H)-one;
4-(3-ethoxy-4-hydroxy-5-nitrophenyl)-1-methyl-5,6-diphenyl-3,4-dihydropyrimidin-2(1H)-one;
4-(3-ethoxy-4-hydroxy-5-nitrophenyl)-6-phenyl-5-(thiazol-2-yl)-3,4-dihydropyrimidin-2(1H)-one;
4-(3-ethoxy-4-hydroxy-5-nitrophenyl)-5-(2-fluorophenyl)-6-phenyl-3,4-dihydropyrimidin-2(1H)-one;
4-(3-ethoxy-4-hydroxy-5-nitrophenyl)-6-phenyl-5-p-tolyl-3,4-dihydropyrimidin-2(1H)-one;
4-(3-ethoxy-4-hydroxy-5-nitrophenyl)-6-(3-methoxyphenyl)-5-phenyl-3,4-dihydropyrimidin-2(1H)-one;
4-(3-ethoxy-4-hydroxy-5-nitrophenyl)-5-phenyl-6-p-tolyl-3,4-dihydropyrimidin-2(1H)-one;
4-(3-ethoxy-4-hydroxy-5-nitrophenyl)-6-phenyl-5-m-tolyl-3,4-dihydropyrimidin-2(1H)-one;
5-(biphenyl-4-yl)-4-(3-ethoxy-4-hydroxy-5-nitrophenyl)-6-phenyl-3,4-dihydropyrimidin-2(1H)-one;
4-(3-ethoxy-4-hydroxy-5-nitrophenyl)-5-(4-methoxyphenyl)-6-phenyl-3,4-dihydropyrimidin-2(1H)-one;
4-(3-ethoxy-4-hydroxy-5-nitrophenyl)-6-(4-methoxyphenyl)-5-phenyl-3,4-dihydropyrimidin-2(1H)-one;
5-(3-chlorophenyl)-4-(3-ethoxy-4-hydroxy-5-nitrophenyl)-6-phenyl-3,4-dihydropyrimidin-2(1H)-one;
5-(3,4-dichlorophenyl)-4-(3-ethoxy-4-hydroxy-5-nitrophenyl)-6-phenyl-3,4-dihydropyrimidin-2(1H)-one;
4-(3-ethoxy-4-hydroxy-5-nitrophenyl)-5-(3-methoxyphenyl)-6-phenyl-3,4-dihydropyrimidin-2(1H)-one;
5-(3,4-dimethoxyphenyl)-4-(3-ethoxy-4-hydroxy-5-nitrophenyl)-6-phenyl-3,4-dihydropyrimidin-2(1H)-one;
5-(4-bromophenyl)-4-(3-ethoxy-4-hydroxy-5-nitrophenyl)-6-phenyl-3,4-dihydropyrimidin-2(1H)-one;
4-(3-ethoxy-4-hydroxy-5-nitrophenyl)-6-phenyl-5-o-tolyl-3,4-dihydropyrimidin-2(1H)-one;
5-(4-chlorophenyl)-4-(3-ethoxy-4-hydroxy-5-nitrophenyl)-6-phenyl-3,4-dihydropyrimidin-2(1H)-one;
5-(2-chlorophenyl)-4-(3-ethoxy-4-hydroxy-5-nitrophenyl)-6-phenyl-3,4-dihydropyrimidin-2(1H)-one;
3-(4-(3-ethoxy-4-hydroxy-5-nitrophenyl)-2-oxo-6-phenyl-1,2,3,4-tetrahydropyrimidin-5-yl)benzonitrile;
5-(3,4-difluorophenyl)-4-(3-ethoxy-4-hydroxy-5-nitrophenyl)-6-phenyl-3,4-dihydropyrimidin-2(1H)-one;
6-(3,5-dichlorophenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-(3-fluorophenyl)-5-phenyl-3,4-dihydropyrimidin-2(1H)-one;
6-(4-bromophenyl)-4-(3-ethoxy-4-hydroxy-5-nitrophenyl)-5-phenyl-3,4-dihydropyrimidin-2(1H)-one;
6-(biphenyl-4-yl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-(4-fluorophenyl)-5-phenyl-3,4-dihydropyrimidin-2(1H)-one;
6-(4-chlorophenyl)-4-(3-ethoxy-4-hydroxy-5-nitrophenyl)-5-phenyl-3,4-dihydropyrimidin-2(1H)-one;
6-(3-chlorophenyl)-4-(3-ethoxy-4-hydroxy-5-nitrophenyl)-5-phenyl-3,4-dihydropyrimidin-2(1H)-one;
6-(3,4-dimethoxyphenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-(3-fluoro-4-methoxyphenyl)-5-phenyl-3,4-dihydropyrimidin-2(1H)-one;
4-(3-ethoxy-4-hydroxy-5-nitrophenyl)-1,3-dimethyl-5,6-diphenyl-3,4-dihydropyrimidin-2(1H)-one;
4-(4-(3-ethoxy-4-hydroxy-5-nitrophenyl)-2-oxo-6-phenyl-1,2,3,4-tetrahydropyrimidin-5-yl)benzonitrile;
6-(4-chloro-3-fluorophenyl)-4-(3-ethoxy-4-hydroxy-5-nitrophenyl)-5-phenyl-3,4-dihydropyrimidin-2(1H)-one;
6-(3-chloro-4-fluorophenyl)-4-(3-ethoxy-4-hydroxy-5-nitrophenyl)-5-phenyl-3,4-dihydropyrimidin-2(1H)-one;
6-(3,4-difluorophenyl)-4-(3-ethoxy-4-hydroxy-5-nitrophenyl)-5-phenyl-3,4-dihydropyrimidin-2(1H)-one;
6-(3,5-difluorophenyl)-4-(3-ethoxy-4-hydroxy-5-nitrophenyl)-5-phenyl-3,4-dihydropyrimidin-2(1H)-one;
6-(3,4-dichlorophenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-(4-hydroxyphenyl)-5-phenyl-3,4-dihydropyrimidin-2(1H)-one;
6-(2,4-difluorophenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-(furan-3-yl)-5-phenyl-3,4-dihydropyrimidin-2(1H)-one;

6-(2-chlorophenyl)-4-(3-ethoxy-4-hydroxy-5-nitrophenyl)-5-phenyl-3,4-dihydropyrimidin-2(1H)-one;
3-(4-(3-ethoxy-4-hydroxy-5-nitrophenyl)-2-oxo-6-phenyl-1,2,3,4-tetrahydropyrimidin-5-yl)benzamide;
3-(6-(3-ethoxy-4-hydroxy-5-nitrophenyl)-2-oxo-5-phenyl-1,2,3,6-tetrahydropyrimidin-4-yl)benzonitrile;
6-(4-(dimethylamino)phenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-(2-fluorophenyl)-5-phenyl-3,4-dihydropyrimidin-2(1H)-one;
4-(3-ethoxy-4-hydroxy-5-nitrophenyl)-6-(4-morpholinophenyl)-5-phenyl-3,4-dihydropyrimidin-2(1H)-one;
6-(4-aminophenyl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-6-phenyl-5-(pyrazin-2-yl)-3,4-dihydropyrimidin-2(1H)-one;
4-(3-ethoxy-4-hydroxy-5-nitrophenyl)-5-phenyl-6-(pyridin-2-yl)-3,4-dihydropyrimidin-2(1H)-one;
5-(biphenyl-3-yl)-4-(3-ethoxy-4-hydroxy-5-nitrophenyl)-6-phenyl-3,4-dihydropyrimidin-2(1H)-one;
6-(benzo[d][1,3]dioxol-5-yl)-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-3-methyl-5,6-diphenyl-3,4-dihydropyrimidin-2(1H)-one;
4-(6-(3-ethoxy-4-hydroxy-5-nitrophenyl)-2-oxo-5-phenyl-1,2,3,6-tetrahydropyrimidin-4-yl)benzonitrile;
4-(3-ethoxy-5-fluoro-4-hydroxyphenyl)-5,6-diphenyl-3,4-dihydropyrimidin-2(1H)-one;
4-(3-ethoxy-4-hydroxy-5-nitrophenyl)-5-phenyl-6-(pyridin-3-yl)-3,4-dihydropyrimidin-2(1H)-one;
(R)-4-(3-ethoxy-4-hydroxy-5-nitrophenyl)-5-phenyl-6-(pyridin-3-yl)-3,4-dihydropyrimidin-2(1H)-one;
(S)-4-(3-ethoxy-4-hydroxy-5-nitrophenyl)-5-phenyl-6-(pyridin-3-yl)-3,4-dihydropyrimidin-2(1H)-one;
4-(3-fluoro-4-hydroxy-5-methoxyphenyl)-5,6-diphenyl-3,4-dihydropyrimidin-2(1H)-one;
3-ethoxy-2-hydroxy-5-(2-oxo-5,6-diphenyl-1,2,3,4-tetrahydropyrimidin-4-yl)benzonitrile;
2-(4-(3-ethoxy-4-hydroxy-5-nitrophenyl)-2-oxo-6-phenyl-1,2,3,4-tetrahydropyrimidin-5-yl)benzonitrile;
4-(3-ethoxy-4-hydroxy-5-nitrophenyl)-5-phenyl-6-(pyridin-4-yl)-3,4-dihydropyrimidin-2(1H)-one;
N-(4-(6-(3-ethoxy-4-hydroxy-5-nitrophenyl)-2-oxo-5-phenyl-1,2,3,6-tetrahydropyrimidin-4-yl)phenyl)acetamide;
4-(3-ethoxy-4-hydroxy-5-nitrophenyl)-6-phenyl-5-(pyridin-4-yl)-3,4-dihydropyrimidin-2(1H)-one;
N-(3-ethoxy-2-hydroxy-5-(2-oxo-5,6-diphenyl-1,2,3,4-tetrahydropyrimidin-4-yl)phenyl)methanesulfonamide;
N-(2-hydroxy-3-methoxy-5-(2-oxo-5,6-diphenyl-1,2,3,4-tetrahydropyrimidin-4-yl)phenyl)methanesulfonamide;
3-ethoxy-2-hydroxy-5-(2-oxo-5,6-diphenyl-1,2,3,4-tetrahydropyrimidin-4-yl)benzoic acid;
4-(3-ethoxy-4-hydroxy-5-nitrophenyl)-5-phenyl-6-(thiophen-2-yl)-3,4-dihydropyrimidin-2(1H)-one;
4-(3-ethoxy-4-hydroxy-5-nitrophenyl)-5-phenyl-6-(thiophen-3-yl)-3,4-dihydropyrimidin-2(1H)-one;
4-(3-ethoxy-4-hydroxy-5-nitrophenyl)-6-(1-methyl-1H-imidazol-4-yl)-5-phenyl-3,4-dihydropyrimidin-2(1H)-one;
4-(3-ethoxy-4-hydroxy-5-nitrophenyl)-6-(naphthalen-1-yl)-5-phenyl-3,4-dihydropyrimidin-2(1H)-one;
3-ethoxy-2-hydroxy-5-(2-oxo-5,6-diphenyl-1,2,3,4-tetrahydropyrimidin-4-yl)benzamide;
methyl 4-(6-(3-ethoxy-4-hydroxy-5-nitrophenyl)-2-oxo-5-phenyl-1,2,3,6-tetrahydropyrimidin-4-yl)phenylcarbamate;
4-(3-ethoxy-4-hydroxy-5-nitrophenyl)-6-phenyl-5-(pyridin-3-yl)-3,4-dihydropyrimidin-2(1H)-one;
4-(3-ethoxy-4-hydroxy-5-nitrophenyl)-6-(naphthalen-2-yl)-5-phenyl-3,4-dihydropyrimidin-2(1H)-one;
2-hydroxy-5-(2-oxo-5,6-diphenyl-1,2,3,4-tetrahydropyrimidin-4-yl)benzoic acid;
4-(4-hydroxy-3-methoxyphenyl)-5,6-diphenyl-3,4-dihydropyrimidin-2(1H)-one;
5-(4-(dimethylamino)phenyl)-4-(3-ethoxy-4-hydroxy-5-nitrophenyl)-6-phenyl-3,4-dihydropyrimidin-2(1H)-one;
4-(2-oxo-5,6-diphenyl-1,2,3,4-tetrahydropyrimidin-4-yl)benzoic acid;
1,1'-(2-hydroxy-5-(2-oxo-5,6-diphenyl-1,2,3,4-tetrahydropyrimidin-4-yl)-1,3-phenylene)diethanone;
4-(4-hydroxy-3-nitrophenyl)-5,6-diphenyl-3,4-dihydropyrimidin-2(1H)-one;
2-hydroxy-5-(2-oxo-5,6-diphenyl-1,2,3,4-tetrahydropyrimidin-4-yl)benzonitrile;
2-ethoxy-4-(2-oxo-5,6-diphenyl-1,2,3,4-tetrahydropyrimidin-4-yl)benzoic acid;
4-(3-bromo-5-ethoxy-4-hydroxyphenyl)-5,6-diphenyl-3,4-dihydropyrimidin-2(1H)-one;
N-(4-(6-(3-ethoxy-4-hydroxy-5-nitrophenyl)-2-oxo-5-phenyl-1,2,3,6-tetrahydropyrimidin-4-yl)phenyl)methanesulfonamide;
4-(4-hydroxy-3-isopropoxy-5-nitrophenyl)-5,6-diphenyl-3,4-dihydropyrimidin-2(1H)-one;
4-(3-ethoxy-4-hydroxy-5-(methylsulfonyl)phenyl)-5,6-diphenyl-3,4-dihydropyrimidin-2(1H)-one;
4-(3-ethoxy-4-hydroxy-5-(methylsulfinyl)phenyl)-5,6-diphenyl-3,4-dihydropyrimidin-2(1H)-one;
3-ethoxy-2-hydroxy-5-(2-oxo-6-phenyl-5-(thiophen-3-yl)-1,2,3,4-tetrahydropyrimidin-4-yl)benzonitrile;
4-(3-ethoxy-4-hydroxy-5-nitrophenyl)-5-phenyl-6-(1H-pyrrol-3-yl)-3,4-dihydropyrimidin-2(1H)-one;
4-(3-ethoxy-4-hydroxy-5-nitrophenyl)-5-phenyl-6-(1-(phenylsulfonyl)-1H-pyrrol-3-yl)-3,4-dihydropyrimidin-2(1H)-one;
4-(3-ethoxy-4-hydroxy-5-nitrophenyl)-6-(4-fluorophenyl)-5-(3-methoxyphenyl)-3,4-dihydropyrimidin-2(1H)-one;
4-(3-ethoxy-4-hydroxy-5-nitrophenyl)-6-(4-fluorophenyl)-5-(thiophen-3-yl)-3,4-dihydropyrimidin-2(1H)-one;
2-hydroxy-3-nitro-5-(2-oxo-5,6-diphenyl-1,2,3,4-tetrahydropyrimidin-4-yl)benzoic acid;
4-(3-ethoxy-4-hydroxy-5-nitrophenyl)-6-(furan-2-yl)-5-phenyl-3,4-dihydropyrimidin-2(1H)-one;
2-ethoxy-4-(2-imino-5,6-diphenyl-1,2,3,4-tetrahydropyrimidin-4-yl)-6-nitrophenol;
4-(3-ethoxy-4-hydroxy-5-nitrophenyl)-5-phenyl-6-(4-(trifluoromethyl)phenyl)-3,4-dihydropyrimidin-2(1H)-one;
4-(3-ethoxy-4-hydroxy-5-nitrophenyl)-5-phenyl-6-o-tolyl-3,4-dihydropyrimidin-2(1H)-one;
4-(3-ethoxy-4-hydroxy-5-nitrophenyl)-5-(3-fluorophenyl)-6-phenyl-3,4-dihydropyrimidin-2(1H)-one;
4-(3-ethoxy-4-hydroxy-5-nitrophenyl)-6-(pyridin-3-yl)-5-(thiophen-3-yl)-3,4-dihydropyrimidin-2(1H)-one;
(Z)-2-ethoxy-4-(2-(methylimino)-5,6-diphenyl-1,2,3,4-tetrahydropyrimidin-4-yl)-6-nitrophenol;

4-(3-ethoxy-4-hydroxy-5-nitrophenyl)-6-(1-methyl-1H-pyrazol-4-yl)-5-(thiophen-3-yl)-3,4-dihydropyrimidin-2(1H)-one;
4-(3-ethoxy-4-hydroxy-5-nitrophenyl)-6-(1-methyl-1H-pyrazol-3-yl)-5-(thiophen-3-yl)-3,4-dihydropyrimidin-2(1H)-one;
4-(3-chloro-4-hydroxy-5-nitrophenyl)-5,6-diphenyl-3,4-dihydropyrimidin-2(1H)-one;
6-(3-chloro-5-fluorophenyl)-4-(3-ethoxy-4-hydroxy-5-nitrophenyl)-5-phenyl-3,4-dihydropyrimidin-2(1H)-one;
2-hydroxy-3-nitro-5-(2-oxo-5,6-diphenyl-1,2,3,4-tetrahydropyrimidin-4-yl)benzonitrile;
2-hydroxy-5-(2-oxo-5,6-diphenyl-1,2,3,4-tetrahydropyrimidin-4-yl)benzenesulfonic acid;
(S)-3-ethoxy-2-hydroxy-5-(2-oxo-6-(pyridin-3-yl)-5-(thiophen-3-yl)-1,2,3,4-tetrahydropyrimidin-4-yl)benzoic acid;
3-ethoxy-2-hydroxy-5-(2-oxo-6-(pyridin-3-yl)-5-(thiophen-3-yl)-1,2,3,4-tetrahydropyrimidin-4-yl)benzoic acid;
4-(3-fluoro-4-hydroxy-5-nitrophenyl)-5,6-diphenyl-3,4-dihydropyrimidin-2(1H)-one;
3-ethoxy-2-hydroxy-5-(2-oxo-6-(pyridin-3-yl)-5-(thiophen-3-yl)-1,2,3,4-tetrahydropyrimidin-4-yl)benzonitrile;
4-(3-ethoxy-4-hydroxy-5-nitrophenyl)-6-(3-hydroxyphenyl)-5-phenyl-3,4-dihydropyrimidin-2(1H)-one;
4-(4-hydroxy-3-nitro-5-propoxyphenyl)-5,6-diphenyl-3,4-dihydropyrimidin-2(1H)-one;
4-(3-ethoxy-4-hydroxy-5-nitrophenyl)-6-(pyrazin-2-yl)-5-(thiophen-3-yl)-3,4-dihydropyrimidin-2(1H)-one;
4-(3-ethoxy-4-hydroxy-5-nitrophenyl)-5-phenyl-6-(quinolin-6-yl)-3,4-dihydropyrimidin-2(1H)-one;
4-(3-ethoxy-4-hydroxy-5-nitrophenyl)-6-(isoquinolin-6-yl)-5-phenyl-3,4-dihydropyrimidin-2(1H)-one;
4-(3-ethoxy-4-hydroxy-5-nitrophenyl)-5-(3-methoxyphenyl)-6-(pyridin-3-yl)-3,4-dihydropyrimidin-2(1H)-one;
3-ethoxy-2-hydroxy-5-(5-(3-methoxyphenyl)-2-oxo-6-(pyridin-3-yl)-1,2,3,4-tetrahydropyrimidin-4-yl)benzoic acid;
4-(3-ethoxy-4-hydroxy-5-nitrophenyl)-6-(pyridin-4-yl)-5-(thiophen-3-yl)-3,4-dihydropyrimidin-2(1H)-one;
4-(4-hydroxy-3-(2-hydroxyethoxy)-5-nitrophenyl)-5,6-diphenyl-3,4-dihydropyrimidin-2(1H)-one;
2-hydroxy-4-(2-oxo-5,6-diphenyl-1,2,3,4-tetrahydropyrimidin-4-yl)benzoic acid;
4-(3-ethoxy-4-hydroxy-5-nitrophenyl)-6-(1-methyl-1H-pyrazol-5-yl)-5-(thiophen-3-yl)-3,4-dihydropyrimidin-2(1H)-one;
2-nitro-4-(2-oxo-5,6-diphenyl-1,2,3,4-tetrahydropyrimidin-4-yl)benzoic acid;
4-(3-ethoxy-4-hydroxy-5-nitrophenyl)-5-(3-ethylphenyl)-6-phenyl-3,4-dihydropyrimidin-2(1H)-one;
3-ethoxy-2-hydroxy-5-(6-(1-methyl-1H-pyrazol-4-yl)-2-oxo-5-(thiophen-3-yl)-1,2,3,4-tetrahydropyrimidin-4-yl)benzoic acid;
(S)-4-(3-ethoxy-4-hydroxy-5-nitrophenyl)-6-(pyridin-3-yl)-5-(thiophen-3-yl)-3,4-dihydropyrimidin-2(1H)-one;
2-chloro-4-(2-oxo-5,6-diphenyl-1,2,3,4-tetrahydropyrimidin-4-yl)benzoic acid;
(S)-3-ethoxy-2-hydroxy-5-(6-(1-methyl-1H-pyrazol-4-yl)-2-oxo-5-(thiophen-3-yl)-1,2,3,4-tetrahydropyrimidin-4-yl)benzoic acid;
(S)-4-(3-ethoxy-4-hydroxy-5-nitrophenyl)-6-(1-methyl-1H-pyrazol-3-yl)-5-(thiophen-3-yl)-3,4-dihydropyrimidin-2(1H)-one;
3-fluoro-2-hydroxy-5-(2-oxo-5,6-diphenyl-1,2,3,4-tetrahydropyrimidin-4-yl)benzoic acid;
2-fluoro-4-(2-oxo-5,6-diphenyl-1,2,3,4-tetrahydropyrimidin-4-yl)benzoic acid;
2-ethoxy-6-nitro-4-(2-oxo-5,6-diphenyl-1,2,3,4-tetrahydropyrimidin-4-yl)benzoic acid;
4-(4-hydroxy-3-nitro-5-(trifluoromethyl)phenyl)-5,6-diphenyl-3,4-dihydropyrimidin-2(1H)-one;
4-(4-hydroxy-3-(2-methoxyethoxy)-5-nitrophenyl)-5,6-diphenyl-3,4-dihydropyrimidin-2(1H)-one;
4-(4-hydroxy-3-nitro-5-propylphenyl)-5,6-diphenyl-3,4-dihydropyrimidin-2(1H)-one;
4-(2-oxo-5,6-diphenyl-1,2,3,4-tetrahydropyrimidin-4-yl)-2-(trifluoromethyl)benzoic acid;
2-fluoro-6-hydroxy-4-(2-oxo-5,6-diphenyl-1,2,3,4-tetrahydropyrimidin-4-yl)benzoic acid;
2-hydroxy-4-(6-(1-methyl-1H-pyrazol-4-yl)-2-oxo-5-(thiophen-3-yl)-1,2,3,4-tetrahydropyrimidin-4-yl)benzoic acid;
2-hydroxy-4-(2-oxo-5-phenyl-6-(pyridin-3-yl)-1,2,3,4-tetrahydropyrimidin-4-yl)benzoic acid;
2-ethoxy-6-hydroxy-4-(2-oxo-5,6-diphenyl-1,2,3,4-tetrahydropyrimidin-4-yl)benzoic acid;
4-(4-(2H-tetrazol-5-yl)phenyl)-5-phenyl-6-(pyridin-3-yl)-3,4-dihydropyrimidin-2(1H)-one;
2-chloro-6-hydroxy-4-(2-oxo-5,6-diphenyl-1,2,3,4-tetrahydropyrimidin-4-yl)benzoic acid;
4-(4-(2H-tetrazol-5-yl)phenyl)-5,6-diphenyl-3,4-dihydropyrimidin-2(1H)-one;
2-hydroxy-6-methoxy-4-(2-oxo-5,6-diphenyl-1,2,3,4-tetrahydropyrimidin-4-yl)benzoic acid;
4-(4-(2H-tetrazol-5-yl)phenyl)-6-(pyridin-3-yl)-5-(thiophen-3-yl)-3,4-dihydropyrimidin-2(1H)-one;
2-hydroxy-4-(6-(1-methyl-1H-pyrazol-4-yl)-2-oxo-5-phenyl-1,2,3,4-tetrahydropyrimidin-4-yl)benzoic acid;
(S)-2-hydroxy-4-(6-(1-methyl-1H-pyrazol-4-yl)-2-oxo-5-(thiophen-3-yl)-1,2,3,4-tetrahydropyrimidin-4-yl)benzoic acid;
4-(3-(2-(dimethylamino)ethoxy)-4-hydroxy-5-nitrophenyl)-5,6-diphenyl-3,4-dihydropyrimidin-2(1H)-one;
4-(3-ethoxy-4-hydroxy-5-nitrophenyl)-5-phenyl-6-(tetrahydrofuran-2-yl)-3,4-dihydropyrimidin-2(1H)-one;
6-cyclopentyl-4-(3-ethoxy-4-hydroxy-5-nitrophenyl)-5-phenyl-3,4-dihydropyrimidin-2(1H)-one;
4-(3-ethoxy-4-hydroxy-5-nitrophenyl)-5-phenyl-6-(tetrahydrofuran-3-yl)-3,4-dihydropyrimidin-2(1H)-one;
6-cyclohexyl-4-(3-ethoxy-4-hydroxy-5-nitrophenyl)-5-(thiophen-3-yl)-3,4-dihydropyrimidin-2(1H)-one;
4-(3-ethoxy-4-hydroxy-5-nitrophenyl)-5-phenyl-6-((S)-tetrahydrofuran-2-yl)-3,4-dihydropyrimidin-2(1H)-one;
4-(3-ethoxy-4-hydroxy-5-nitrophenyl)-5-phenyl-6-((R)-tetrahydrofuran-2-yl)-3,4-dihydropyrimidin-2(1H)-one; and
5-cyclohexyl-4-(3-ethoxy-4-hydroxy-5-nitrophenyl)-6-phenyl-3,4-dihydropyrimidin-2(1H)-one.

8. The method of claim 1 comprising administering to a patient in need thereof a therapeutically effective amount of a compound of Formula (I) or a pharmaceutically acceptable salt thereof together with a pharmaceutically accepted carrier or excipient.

* * * * *